United States Patent
Ohashi et al.

(10) Patent No.: US 6,197,768 B1
(45) Date of Patent: Mar. 6, 2001

(54) PYRIDOCARBAZOLE DERIVATIVES HAVING CGMP-PDE INHIBITORY ACTIVITY

(75) Inventors: Masayuki Ohashi; Toshiyuki Shudo; Kazumi Nishijima; Tatsuto Notsu; Akira Kikuchi; Kazutoshi Yanagibashi; Hidemitsu Nishida, all of Tokyo (JP)

(73) Assignee: Mochida Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/393,376

(22) Filed: Sep. 10, 1999

Related U.S. Application Data

(62) Division of application No. 09/000,402, filed as application No. PCT/JP97/01829 on May 29, 1997, now Pat. No. 6,018,046.

(30) Foreign Application Priority Data

May 31, 1996 (JP) .................................................. 8-160731

(51) Int. Cl.[7] ...................... A61K 31/535; A61K 31/505; A61K 31/44

(52) U.S. Cl. .................... 514/233.2; 514/256; 514/284

(58) Field of Search ................... 514/233.2, 256, 514/284

(56) References Cited

PUBLICATIONS

Harter, H.P. et al., Chimia, vol. 30, No. 2 (Feb. 1976), pp. 50–52, partially refer to compounds in formulas VII, VIII.
Henry Rapoport et al., J. Org. Chem., vol. 24, (Mar. 1959), pp. 324–327.
Rapoport et al., Chemical Abstracts, vol. 54, (13), 14247c–14248–b (1960).

*Primary Examiner*—Raymond Henley
(74) *Attorney, Agent, or Firm*—Birch, Stewart, Kolasch & Birch, LLP.

(57) ABSTRACT

The invention relates to novel pyridocarbazole derivatives having highly selective action in inhibiting cyclic GMP-phosphodiesterase (hereinafter abbreviated as cGMP-PDE), processes for producing such derivatives, agents containing at least one of such derivatives as an active ingredient for preventing and/or treating pulmonary hypertension, ischemic heart diseases or diseases against which the cGMP-PDE inhibitory action is effective, and intermediates useful for the production of pyridocarbazole derivatives.

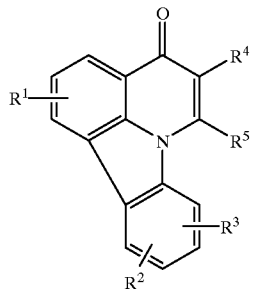

(I)

4 Claims, 6 Drawing Sheets

Example 278

Example 1, Step 3

Example 48, Step 2

Example 101, Step 6

Example 113, Step 2

Example 145, Step 1

Example 147, Step 1

Example 148, Step 1

Example 149, Step 1

Example 151, Step 1

Example 154, Step 1

Example 161, Step 1

Example 171, Step 3

Example 172, Step 1

Example 173, Step 2

Example 173, Step 3

Example 184, Step 1

Example 190, Step 1

Example 193, Step 1

Example 194, Step 1

Example 203, Step 1

Example 210, Step 1

Example 216, Step 1

Example 224, Step 1

Example 232, Step 1

Example 235, Step 4

Example 243, Step 3

Example 248, Step 4

Example 257, Step 1

Example 265, Step 2

Example 272, Step 4

Example 276, Step 4

Example 283, Step 3 ered both by the increase in cyclic GMP (hereinafter abbreviated as
PYRIDOCARBAZOLE DERIVATIVES HAVING CGMP-PDE INHIBITORY ACTIVITY This application is a divisional of application Ser. No. 09/000,402, filed on Jan. 29, 1998, now U.S. Pat. No. 6,018,046 application Ser. No. 09/000,402 is the national phase of PCT International Application No. PCT/JP97/01829 filed on May 29, 1997 under 35 U.S.C. §371. The entire contents of each of the above-identified applications are hereby incorporated by reference.

TECHNICAL FIELD

This invention relates to novel pyridocarbazole derivatives having action in inhibiting highly selective cyclic GMP-phosphodiesterase (hereinafter abbreviated as cGMP-PDE), processes for producing such derivatives, pharmaceuticals containing at least one of such derivatives as an active ingredient, in particular, agents for preventing and/or treating pulmonary hypertension, ischemic heart diseases or diseases against which the cGMP-PDE inhibition is effective, and intermediates useful for the production of pyridocarbazole derivatives.

BACKGROUND ART

The identity of vascular endothelial cell derived relaxing factors has been found to be nitric oxide (hereinafter abbreviated as NO) which, like nitroglycerin used to treat angina pectoris, manifests its vascular relaxing action as mediated by the increase in cyclic GMP (hereinafter abbreviated as cGMP). Briefly, nitrites-like relaxing factors exist endogenously and counteract catecholamine and other endogenous vasoconstricting factors to adjust the tone of blood vessels to thereby contribute to the retention of adequate blood flow. Therefore, the decrease in NO or cGMP is believed to enhance vasotonia and reduce the blood flow in tissue, eventually causing circulatory disorders or ischemic heart diseases.

Increase in vasotonia resulting from damage to coronary endothelial cells which are in the class of NO producing cells is believed to induce insufficiency in the blood flow in myocardial tissue, thereby causing anginal attacks. This results from disorders in the NO-cGMP system working as an endogenous relaxing factor. The vasodilating action of nitrites depends on the diameter of blood vessels for the degree of relaxation and because of their active site specificity (i.e., thicker coronary arteries are relaxed more intensely), nitrites have so far been in common use. However, the nitrites have a disadvantage in that their action is transient and attenuated during prolonged use. In addition, it has been pointed out that among vasodilators, adenosine enhancers such as dipyridamole which dilate narrow portions of coronary arteries to increase the coronary blood flow increase the myocardial blood flow at normal sites rather than at the lesion, thereby aggravating the ischemia (this phenomenon is generally referred to as "steal") and, hence, showing side effects such as aggravation of angina pectoris and pectoralgia.

While no effective therapeutics have been available for the various pathogenic conditions that manifest pulmonary hypertension, it has recently been reported that NO gas inhalation therapy has certain utility. Since NO gas relaxes blood vessels and lower the pulmonary arterial pressure through the increase in cGMP, it is anticipated that activation of the cGMP producing system dilates selectively pulmonary arteries in the pulmonary circulation, thereby contributing to the treatment of pulmonary hypertension. Calcium blockers and many other vasodilating drugs have so far been used in attempts to treat pulmonary hypertension, none have been commercialized since every one of them is more potent in lowering the systemic blood pressure than the pulmonary arterial pressure. An oxygen therapy has been verified to be effective in achieving improvements after its application. However, oxygen intoxication occurs as a serious side effect and the occurrence of pulmonary lesions such as pulmonary edema and fibrosis has been reported with patients who were on prolonged oxygen therapy at home. The NO gas inhalation therapy is not an exception and the NO gas used in this therapy is one of the air pollutants $NO_x$ and will easily generate $NO_2$ in the presence of oxygen, thereby potentially causing adverse effects on the airway and lungs; hence, utmost care is required in applying the NO gas and many problems are involved in its prolonged use. On the other hand, suppressing the cGMP degradation system is believed another way to maintain the concentration of cGMP, thereby allowing for selective decrease in the pulmonary arterial pressure. Briefly, an inhibitor of phosphodiesterase (hereinafter abbreviated as PDE) which is an enzyme catalyzing specific hydrolyzation of cyclic GMP holds promise as a new therapeutic free from the aforementioned side effects.

With the inhibition of PDE, cGMP increases, possibly leading to the treatment of ischemic heart diseases or pulmonary hypertension. As of today, PDE has been verified to exist in at least seven isozyme types. Of these, five types of isozymes distribute in many diverse tissues. Two isozymes are capable of selective hydrolyzation of cGMP and they are PDE type I (calmodulin-dependent PDE) and PDE type V (cGMP-PDE). On the other hand, PDE types III and IV hydrolyse cAMP selectively and PDE type II has no substrate selectivity. If the last three isozymes are inhibited, cAMP is increased to cause various obvious side effects including enhanced myocardial contraction and heart rate and depression of systemic blood pressure. Among other things, it is well known that with the inhibition of type III PDE, CAMP increases resulting in enhanced myocardial contraction. It has been reported that increased cGMP in cardiac muscle reduced myocardial contraction but the distribution of PDE type V has not been recognized in cardiac muscle. Therefore, it is anticipated that selective inhibition of PDE type V will produce selective action that is limited in the decrease in systemic blood pressure and side effects on the heart.

It has recently been found that NO releasing compounds show a inhibition of vascular smooth muscle cell proliferation with the intermediary of cGMP. For example, Garg et al. (J. Clin. Invest., 83, 1774–1777, 1989),and Nakaki et al. (Eur. J. Pharmacol., 189, 347–353, 1990) reported that the proliferation of cultured vascular smooth muscle cells isolated from aortic media in rats was suppressed by the treatment of NO releasing compounds nitroprusside, nitroglycerin, isosorbide dinitrate or 8-bromo-cGMP. Therefore, it is suggested that increased cGMP could suppress the proliferation of vascular smooth muscle cells in arteriosclerosis and post-PTCA restenosis.

The cGMP-PDE inhibitors so far disclosed in the art include pyrazolopyrimidone derivatives (see EP-A-526004), purinone derivatives (JP-A 2-88577), phenylpyrimidone derivatives (JP-A 2-295978), quinazoline derivatives (JP-A 6-192235 and JP-A 7-10843 and WO 93/12095) and phthalazine derivatives (WO 96/05176). However, there is no prior art disclosure of the fact that compounds such as the ones claimed in the present invention which have a pyridocarbazole skeleton have the cGMP-PDE inhibitory action. As for the PDE isozyme selectivity, EP-A 526004 and WO 93/12095 teach isozyme selectivity between types V and III but the selectivity has not yet been commercialized in clinical fields to demonstrate a satisfactory action.

Turning back to pyridocarbazole derivatives, their PDE inhibitory action has not yet been reported, nor are there reports that show their vasodilating action and effectiveness for pulmonary hypertension and ischemic heart diseases.

An object, therefore, of the invention is to provide novel compounds that have high isozyme selectivity and potent cGMP-PDE inhibitory action and that cause less side effects to feature high safety.

Other objects of the invention are to provide processes for producing such compounds, intermediates useful for producing them, as well as pharmaceuticals and pharmaceutical compositions containing said compounds. In particular, the invention aims at providing agents for preventing and/or treating pulmonary hypertension, ischemic heart diseases or diseases against which the cGMP-PDE inhibitory action is effective, said agents having solved at least one of the aforementioned problems with the prior art.

DISCLOSURE OF INVENTION

The present inventors conducted intensive studies with a view to obtaining drugs that are capable of potent and selective inhibition of type V PDE while featuring high safety. As a result, they found that novel pyridocarbazole derivatives and salts thereof have potent and selective type V PDE inhibiting activity and this finding has eventually led to the accomplishment of the present invention.

According to its first aspect, the invention provides compounds represented by the following general formula (I) or salts thereof or pharmaceuticals containing said compounds or salts as an active ingredient:

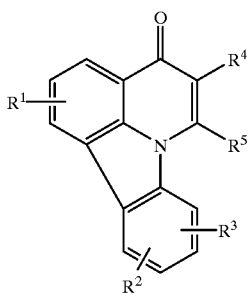

(I)

where $R^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethoxyethoxy group, an optionally protected hydroxyl group, an optionally protected mercapto group, a straight- or branched-chain alkanoyloxy group having 1–4 carbon atoms, a carbonyloxy group substituted by a phenyl group or a pyridyl group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or represented by the following general formula (XXI):

$$—O—(CH_2)_n-Z \qquad (XXI)$$

(where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6); $R^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally substituted carboxyl group, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and a pyridyl group or a straight- or branched-chain alkoxy group having 1–4 carbon atoms which may be substituted by one alkoxycarbonyl group having 1–4 carbon atoms; $R^3$ represents a hydrogen atom, a halogen atom, an optionally protected hydroxyl group or a straight- or branched-chain alkoxy group having 1–4 carbon atoms; $R^4$ represents a hydrogen atom, a halogen atom, an optionally protected carboxyl group, a phenoxy group, an anilino group, a N-methylanilino group, a 4-morpholylcarbonyl group, an alkyl group having 1 or 2 carbon atoms which may be substituted by a cyclic alkyl group having 3–6 carbon atoms, a benzyl group which may be mono- or disubstituted in the phenyl portion by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridylmethyl group which may be substituted by an alkyl group having 1–4 carbon atoms, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group, an α-hydroxybenzyl group or an alkoxycarbonyl group having 1 or 2 carbon atoms; $R^5$ represents a hydrogen atom or a methyl group; when $R^1$, $R^2$, $R^3$ and $R^5$ are a hydrogen atom at the same time, $R^4$ is not a hydrogen atom, a benzyl group, a 4-diethylaminobenzyl group or a furylmethyl group.

The preferred substituents in the compounds represented by the general formula (I) or the preferred combinations thereof are shown below but the invention is bay no means limited thereto.

Speaking of $R^1$, it is preferably substituted in 2-position and is preferably a hydroxyl group or represented by the following general formula (XXI):

—O—(CH$_2$)$_n$-Z          (XXI)

where Z represents a hydrogen atom, a carboxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a hydroxyl group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms; n is 1–4.

More preferably, $R^1$ is substituted in 2-position and is either a hydroxyl group or represented by the following general formula (XXI):

—O—(CH$_2$)$_n$-Z          (XXI)

where Z represents a hydrogen atom, a carboxyl group, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a hydroxyl group, a phenyl group, a pyridyl group, a pyrazinyl group or a pyrimidinyl group; n is 1–4.

Preferably, $R^2$ and $R^3$ are not a hydrogen atom at the same time; it is preferred that $R^2$ is substituted in 9- or 10-position and is a hydrogen atom, a halogen atom, a hydroxyl group, a trifluoromethyl group or a straight- or branched-chain alkoxy group having 1–4 carbon atoms and that $R^3$ is a hydrogen atom. Further, it is more preferred that $R^2$ is substituted in 9-position and is a halogen atom or a trifluoromethyl group and that $R^3$ is a hydrogen atom.

Preferably, $R^4$ is a hydrogen atom, an alkyl group having 1 or 2 carbon atoms, a pyrimidinylmethyl group or a pyridylmethyl group which may be substituted by a methyl group. Further, it is more preferred that $R^4$ is a methyl group, a pyrimidinylmethyl group or a pyridylmethyl group. Preferably, $R^5$ is a hydrogen atom.

The preferred combinations of the substituents are as follows: $R^1$ is substituted in 2-position and is either a hydroxyl group or represented by the following general formula (XXI):

—O—(CH$_2$)$_n$-Z          (XXI)

where Z represents a hydrogen atom, a carboxyl group, a carbamoyl group which may be mono- or disubstituted by a hydroxylmethyl group or an alkyl group having 1 or 2 alkyl groups, an alkanoyl group having 1–4 carbon atoms which may be substituted by one hydroxyl group or mercapto group, a hydroxyl group, a phenyl group, a pyridyl group, a pyrazinyl group or a pyrimidinyl group; n is 1–4; $R^2$ is a halogen atom or a trifluoromethyl group which are substituted in 9-position; $R^3$ is a hydrogen atom; $R^4$ is a methyl group, a pyrimidinylmethyl group or a pyridylmethyl group; and $R^5$ is a hydrogen atom.

According to its second aspect, the present invention provides compounds or salts thereof which are useful intermediates for the synthesis of the compounds of the general formula (I) or salts thereof, said intermediate compounds being represented by the following general formula (IV):

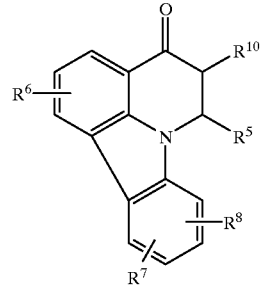

(IV)

where $R^5$ represents a hydrogen atom or a methyl group; $R^6$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, an optionally protected hydroxyl group, an optionally protected mercapto group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^7$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^8$ represents a hydrogen atom, a halogen atom, an optionally protected hydroxyl group or a straight- or branched-chain alkoxy group having 1–4 carbon atoms; $R^{10}$ represents a hydrogen atom, a halogen atom, a phenoxy group, an α-hydroxybenzyl group, an anilino group, a N-methylanilino group, a methyl group or a halogenomethyl group.

According to its third aspect, the present invention provides compounds or salts thereof which are useful intermediates for the synthesis of the compounds of the general formula (I) or salts thereof, said intermediate compounds being represented by the following general formula (VIII):

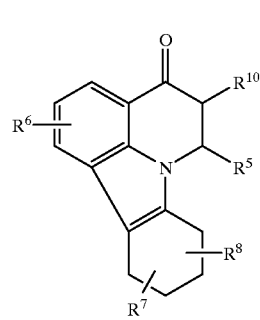

(VIII)

where $R^5$ represents a hydrogen atom or a methyl group; $R^6$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, an optionally protected hydroxyl group, an optionally protected mercapto group, a straight- or branched-chain alkyl having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^7$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^8$ represents a hydrogen atom, a halogen atom, an optionally protected hydroxyl group or a straight- or branched-chain alkoxy group having 1–4 carbon atoms; $R^{10}$ represents a hydrogen atom, a halogen atom, a phenoxy group, an α-hydroxybenzyl group, an anilino group, a N-methylanilino group, a methyl group or a halogenomethyl group.

According to its fourth aspect, the present invention provides processes (1–3) for producing said derivative compounds of the general formula (I).

Process 1

In this process, a compound represented by the following general formula (IV) or a salt thereof:

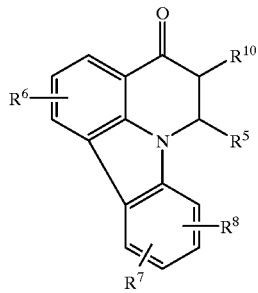

(IV)

(where $R^5$ represents a hydrogen atom or a methyl group; $R^6$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, an optionally protected hydroxyl group, an optionally protected mercapto group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^7$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^8$ represents a hydrogen atom, a halogen atom, an option ally protected hydroxyl group or a straight- or branched-chain alkoxy group having 1–4 carbon atoms; $R^{10}$ represents a hydrogen atom, a halogen atom, a phenoxy group, an α-hydroxybenzyl group, an anilino group, a N-methylanilino group, a methyl group or a halogenomethyl group) is reacted optionally, under basic conditions, with an aldehyde derivative represented by the following general formula (XIX):

$R^{12}$—CHO  (XIX)

(where $R^{12}$ represents a hydrogen atom, a methyl group, a cyclic alkyl group having 3–6 carbon atoms, a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridyl group which may be substituted by an alkyl group having 1–4 carbon atoms, a morpholyl group, a triazolyl group, a furyl group, a thienyl group, a pyrimidinyl group, a pyrazinyl group, a pyrrolyl group, an imidazolyl group, a quinolyl group, an indolyl group or a naphthyl group) and then the reaction product either in an isolated form or after dehydration to yield an enone which has the double bond subsequently isomerized in the ring, is subjected to an oxidation, either immediately or after reaction with phenol, aniline, N-methylaniline, triazole, imidazole, morpholine, etc. to derive a compound represented by the following general formula (XXII):

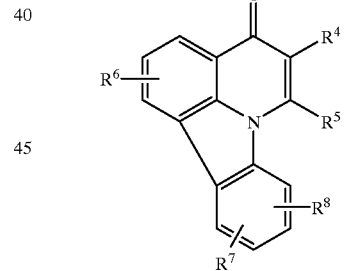

(XXII)

(where $R^4$, $R^5$, $R^6$, $R^7$ and $R^8$ have the same meanings as defined above), said compound (XXII) is optionally subjected to a substituent change and, after optional deprotection of $R^6$, reacted with a reactive halogen derivative represented by the following general formula (XX):

$R^{13}$—X  (XX)

(where X is a halogen atom, $R^{13}$ represents an alkoxycarbonyl group having 1–4 carbon atoms, a 3-carboxy-1-propenyl group, a 2,2-diethoxyethyl group, a straight- or branched-chain alkanoyl group having 1–4 carbon atoms, a carbonyl group substituted by a phenyl group or a pyridyl group, or a group: —(CH$_2$)$_n$-Z (where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6)) to yield a compound represented by the following general formula (XXIII):

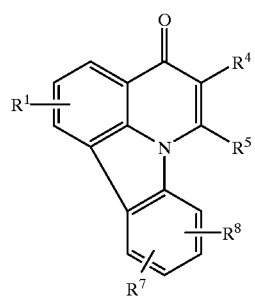

(XXIII)

(where $R^1$, $R^4$, $R^5$, $R^7$ and $R^8$ have the same meanings as defined above), which is subjected to a suitable substituent change, or alternatively, the compound represented by the general formula (XXII) is subjected to a suitable substituent change to yield a compound represented by the following general formula (XXIV):

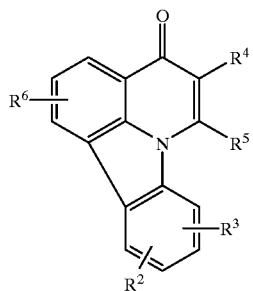

(XXIV)

(where $R^2$, $R^3$, $R^4$, $R^5$ and $R^6$ have the same meanings as defined above), which is optionally subjected to deprotection of $R^6$ and reacted with the reactive halogen derivative represented by the general formula (XX) so as to produce the compound represented by the following general formula (I) or a salt thereof:

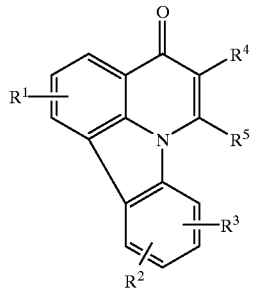

(I)

(where $R^1$, $R^2$, $R^3$, $R^4$ and $R^5$ have the same meanings as defined above).

Process 2

In this process, a compound represented by the following general formula (VIII):

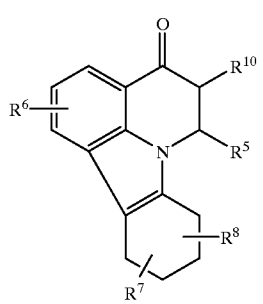

(VIII)

(where $R^5$, $R^6$, $R^7$, $R^8$ and $R^{10}$ have the same meanings as defined above) or a salt thereof is reacted optionally, under basic conditions, with an aldehyde derivative represented by the following general formula (XIX):

$R^{12}$—CHO     (XIX)

(where $R^{12}$ has the same meaning as defined above), the reaction product either in an isolated form or after dehydration to yield an enone which has the double bond subsequently isomerized in the ring, is subjected to an oxidation, either immediately or after reaction with phenol, aniline, N-methylaniline, triazole, imidazole, morpholine, etc. and, subsequently, subjected to an aromatization with an oxidizing agent to yield a compound which is optionally deprotected before it is reacted with the reactive halogen derivative represented by the following general formula (XX):

$R^{13}$—X     (XX)

(where X and $R^{13}$ have the same meanings as defined above) or subjected to a suitable substituent change so as to produce the compound represented by the following general formula (I):

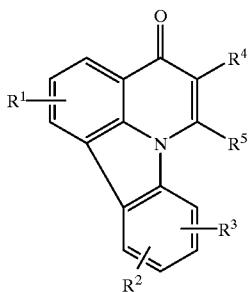

(I)

(where $R^1$, $R^2$, $R^3$, $R^4$ and $R^5$ have the same meanings as defined above) or a salt thereof.

Process 3

In this process, a compound represented by the following general formula (XIII) or a salt thereof:

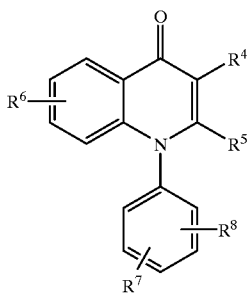

(XIII)

(where $R^4$ represents a hydrogen atom, a halogen atom, an optionally protected carboxyl group, a phenoxy group, an anilino group, a N-methylanilino group, a 4-morpholylcarbonyl group, an alkyl group having 1 or 2 carbon atoms which may be substituted by a cyclic alkyl group having 3–6 carbon atoms, a benzyl group which may be mono- or disubstituted in the phenyl portion by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridylmethyl group which may be substituted by an alkyl group having 1–4 carbon atoms, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group, an α-hydroxybenzyl group or an alkoxycarbonyl group having 1 or 2 carbon atoms; $R^5$ represents a hydrogen atom or a methyl group; $R^6$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, an optionally protected hydroxyl group, an optionally protected mercapto group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^7$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^8$ represents a hydrogen atom, a halogen atom, an optionally protected hydroxyl group or a straight- or branched-chain alkoxy group having 1–4 carbon atoms) is subjected to an aromatic carbon-carbon bond formation using palladium, optionally followed by a suitable substituent change, so as to produce the compound represented by the following general formula represented by the following general formula (I) or a salt thereof:

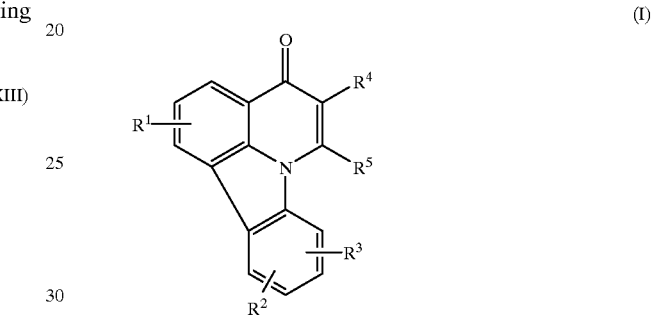

(I)

(where $R^1$, $R^2$, $R^3$, $R^4$ and $R^5$ have the same meanings as defined above).

According to its fifth aspect, the present invention provides agents for preventing or treating pulmonary hypertension which contain at least one of the compounds of the general formula (I) or salts thereof as an active ingredient.

According to its sixth aspect, the present invention provides agents for preventing or treating ischemic heart diseases which contain at least one of the compounds of the general formula (I) or salts thereof as an active ingredient.

According to its seventh aspect, the present invention provides agents for preventing or treating diseases against which the cGMP-PDE inhibitory action is effective in the presence of at least one of the compounds of the general formula (I) or salts thereof as an active ingredient.

BEST MODE FOR CARRYING OUT THE INVENTION

Figure 1:
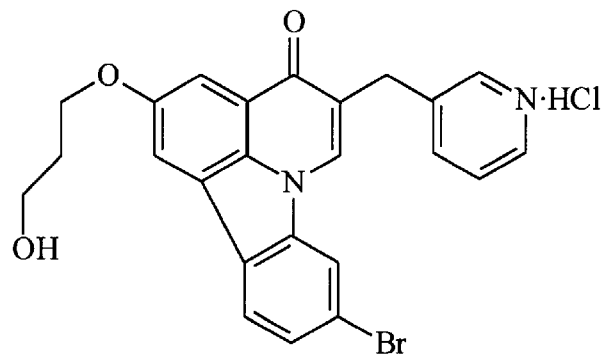
FIG. 1 shows the structural formulae of the compound synthesized in Example 278 and the intermediates obtained in several examples.
Figure 1:
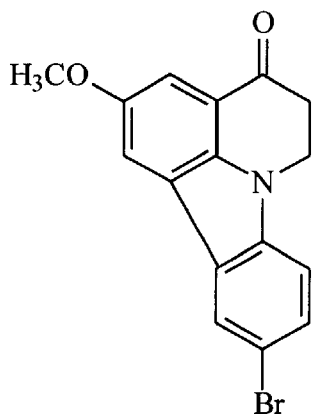
Figure 1:
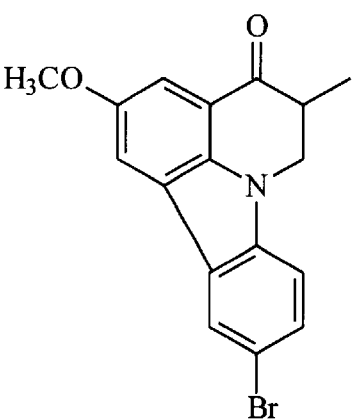
Figure 1:
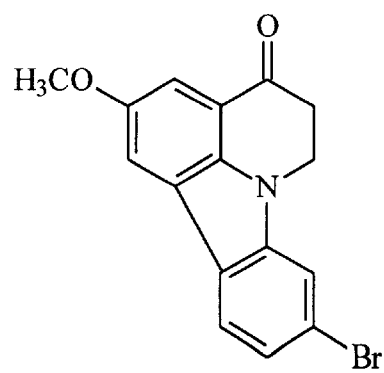
Figure 1:
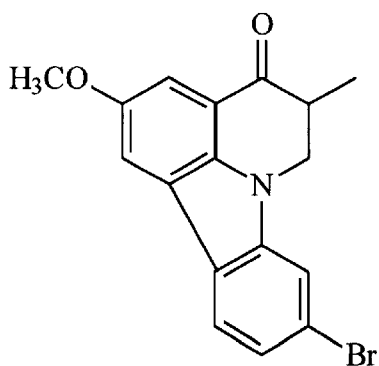
Figure 2:
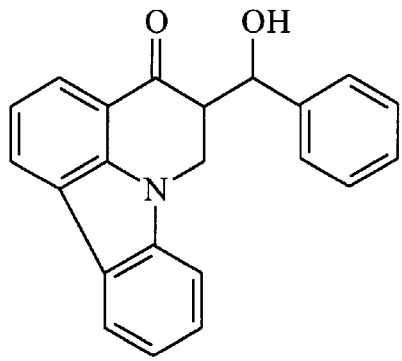
FIG. 2 shows the structural formulae of the intermediates obtained in other examples.
Figure 2:
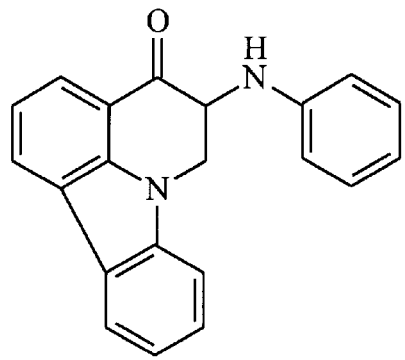
Figure 2:
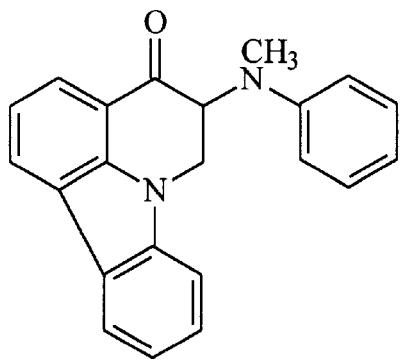
Figure 2:
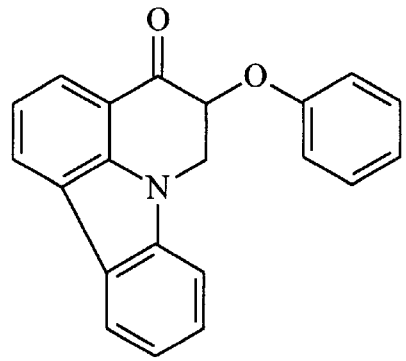
Figure 2:
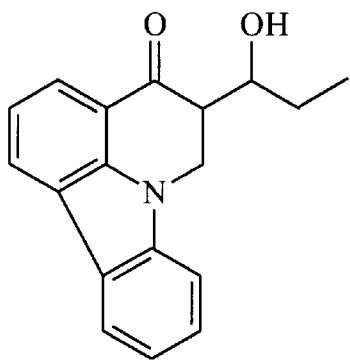
Figure 2:
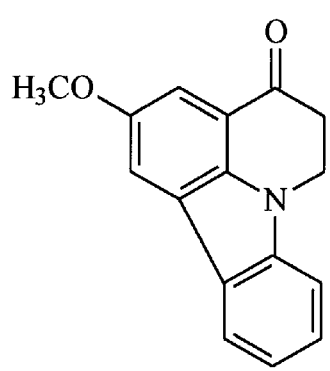
Figure 3:
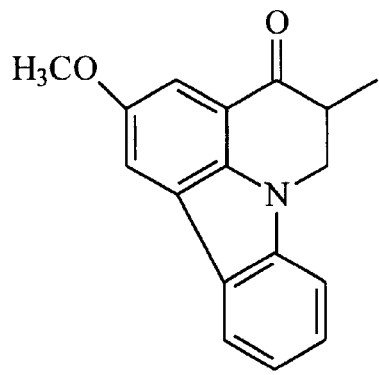
FIG. 3 shows the structural formulae of the intermediates obtained in yet other examples.
Figure 3:
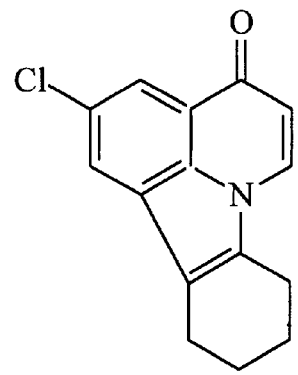
Figure 3:
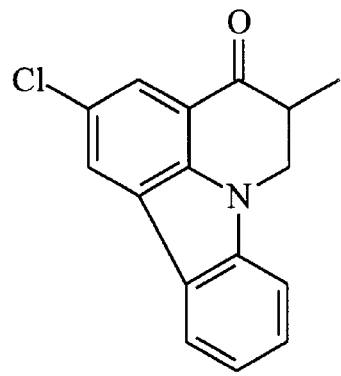
Figure 3:
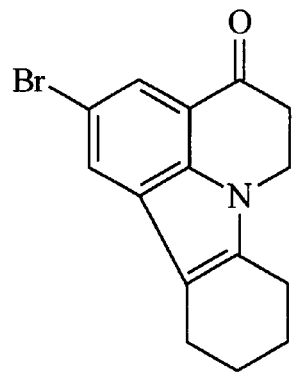
Figure 3:
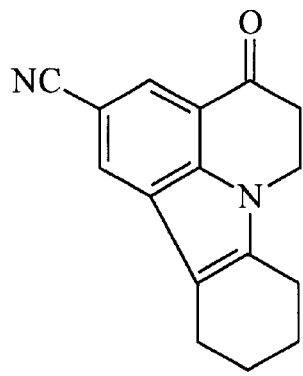
Figure 3:
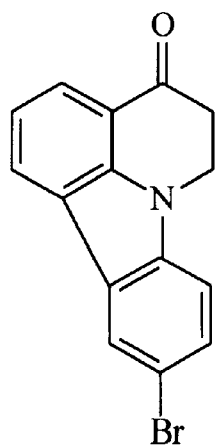
Figure 4:
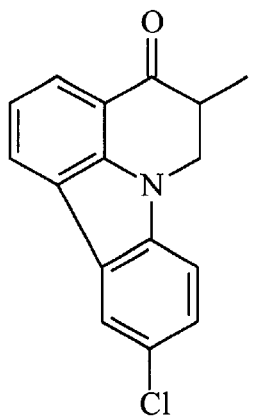
FIG. 4 shows the structural formulae of the intermediates obtained in further examples.
Figure 4:
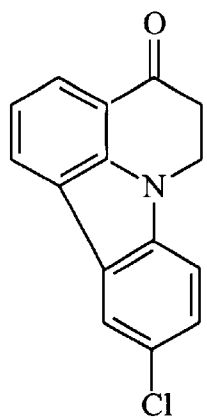
Figure 4:
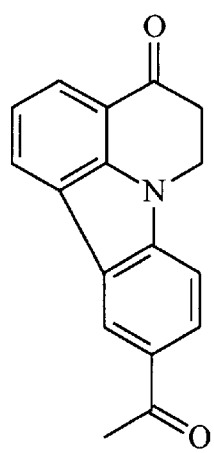
Figure 4:
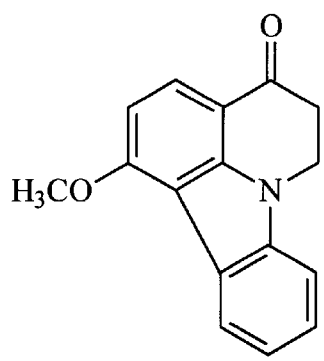
Figure 4:
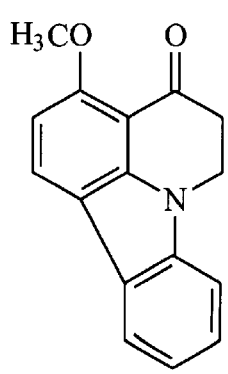
Figure 4:
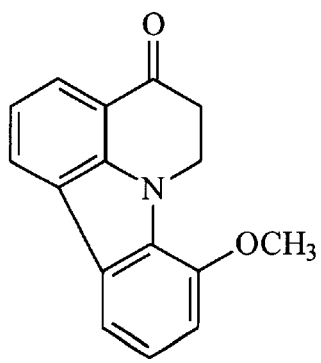
Figure 5:
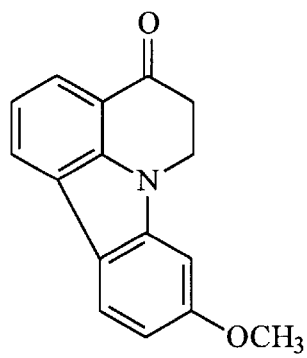
FIG. 5 shows the structural formulae of the intermediates obtained in still further examples.
Figure 5:
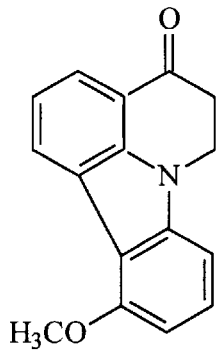
Figure 5:
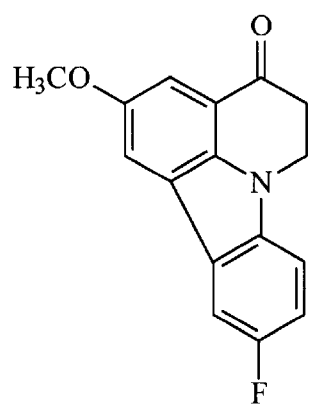
Figure 5:
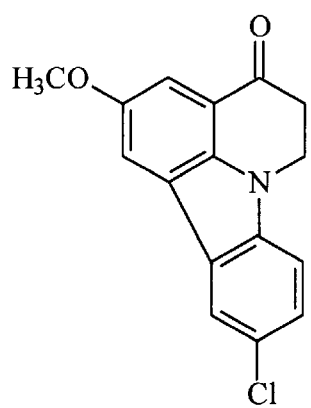
Figure 5:
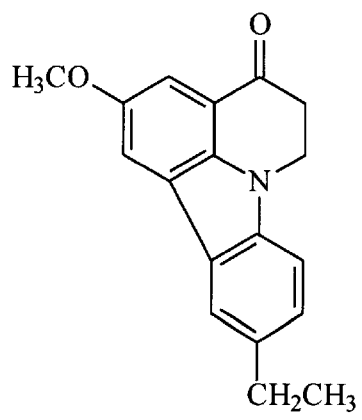
Figure 5:
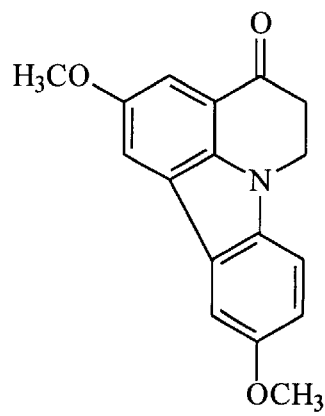
Figure 6:
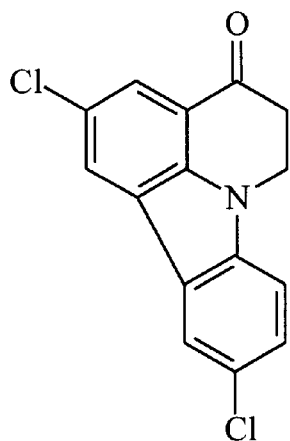
FIG. 6 shows the structural formulae of the intermediates obtained in still other examples.
Figure 6:
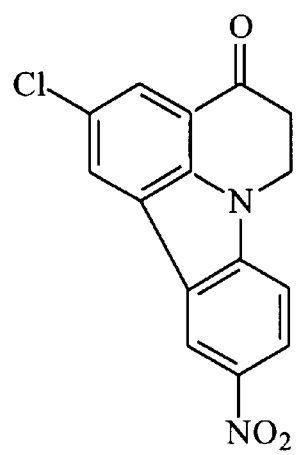
Figure 6:
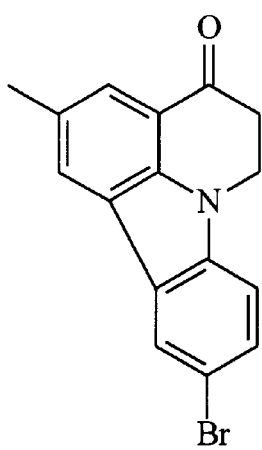
Figure 6:
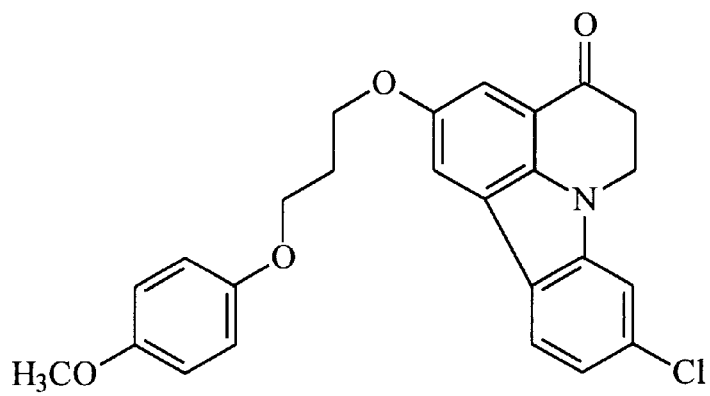

The present invention will now be described below in detail.

The pyridocarbazole derivatives which are the compounds of the invention have the respective position numbers shown in the following diagram; $R^1$ is bound in 1-, 2- or 3-position; $R^2$ or $R^3$ is bound in 8-, 9-, 10- or 11-position; $R^4$ is bound in 5-position; and $R^5$ is bound in 6-position:

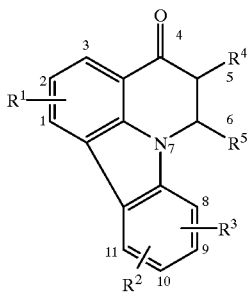

(I)

The compounds of the invention are represented by the general formula (I) set forth above. In the formula, $R^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethoxyethoxy group, an optionally protected hydroxyl group, an optionally protected mercapto group, a straight- or branched-chain alkanoyloxy group having 1–4 carbon atoms, a carbonyloxy group substituted by a phenyl group or a pyridyl group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or represented by the following general formula (XXI):

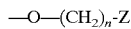 (XXI)

(where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6).

More specifically, the term "halogen atom" refers to a fluorine atom, a chlorine atom or a bromine atom; the term "alkoxycarbonyl group having 1–4 carbon atoms" refers to a methoxycarbonyl group, an ethoxycarbonyl group, a n-propoxycarbonyl group, an i-propoxycarbonyl group, a cyclopropoxycarbonyl group, a n-butoxycarbonyl group, a t-butoxycarbonyl group or the like; the term "optionally protected hydroxyl group" refers to a hydroxyl group, a trimethylsilyloxy group, a t-butyldimethylsilyloxy group, a methoxymethyloxy group or the like; the term "optionally protected mercapto group" refers to a phenylthio group, a benzylthio group or the like; the term "straight- or branched-chain alkanoyloxy group having 1–4 carbon atoms" refers to an acetoxy group, a propionyloxy group, a butyryloxy group, a pivaloyloxy group or the like; the term "carbonyloxy group substituted by a phenyl group or a pyridyl group" refers to a benzoyloxy group, a nicotinoyloxy group, an isonicotinoyloxy group or the like; the term "straight- or branched-chain alkyl group having 1–4 carbon atoms which may be substituted by one hydroxyl group" refers to a methyl group, an ethyl group, a n-propyl group, an i-propyl group, a n-butyl group, a t-butyl group, a 1-hydroxyethyl group, a 2-hydroxyethyl group, a 1-hydroxypropyl group or the like; the term "amino group which may be mono- or disubstituted by an alkyl group having 1–4 carbon atoms" refers to a methylamino group, a dimethylamino group, an ethylamino group, a diethylamino group, a n-propylamino group, a n-butylamino group or the like; the term "alkylthio group having 1–3 carbon atoms which may be monosubstituted by any group selected from the group consisting of a hydroxyl group, a carboxyl group, a phenyl group and a pyridyl group" refers to a methylthio group, an ethylthio group, a 3-hydroxypropylthio group, a carboxymethylthio group, a 3-pyridylmethylthio group or the like; the following general formula (XXI):

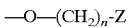 (XXI)

(where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6) refers to a methoxy group, an ethoxy group, a n-propoxy group, a n-butoxy group, a n-pentyloxy group, a n-hexyloxy group, a carboxymethyloxy group, a 2-carboxyethyloxy group, a 3-carboxypropyloxy group, a methoxymethoxy group, an ethoxymethoxy group, a 2-methoxyethoxy group, a 2-ethoxyethoxy group, a 2-(2-hydroxyethoxy)ethoxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a n-pentyloxycarbonylmethyloxy group, a n-hexyloxycarbonylmethyloxy group, a cyclopropyloxycarbonylmethyloxy group, a cyclohexyloxycarbonylmethyloxy group, a 2-(methoxycarbonyl)ethyloxy group, a 2-(ethoxycarbonyl)ethyloxy group, a 2-(n-propoxycarbonyl)ethyloxy group, a 2-(n-propoxycarbonyl)

ethyloxy group, a 2-(n-butoxycarbonyl)ethyloxy group, a 2-(t-butoxycarbonyl)ethyloxy group, a 2-(n-pentyloxycarbonyl)ethyloxy group, a 2-(n-hexyloxycarbonyl)ethyloxy group, a 2-(cyclopropyloxycarbonyl)ethyloxy group, a 2-(cyclohexyloxycarbonyl)ethyloxy group, a 3-(methoxycarbonyl)propyloxy group, a 3-(ethoxycarbonyl)propyloxy group, a 3-(n-propoxycarbonyl)propyloxy group, a 3-(i-propoxycarbonyl)propyloxy group, a 3-(n-butoxycarbonyl)propyloxy group, a 3-(t-butoxycarbonyl)propyloxy group, a 3-(n-pentyloxycarbonyl)propyloxy group, a 3-(n-hexyloxycarbonyl)propyloxy group, a 3-(cyclopropyloxycarbonyl)propyloxy group, a 3-(cyclohexyloxycarbonyl)propyloxy group, a N-hydroxymethylcarbamoylmethyloxy group, a N-methylcarbamoylmethyloxy group, a N,N-dimethylcarbamoylmethyloxy group, a N-ethylcarbamoylmethyloxy group, a N,N-diethylcarbamoylmethyloxy group, a N-n-propylcarbamoylmethyloxy group, a N-n-butylcarbamoylmethyloxy group, a 3-hydroxy-2-oxopropyloxy group, a 4-hydroxy-3-oxobutyloxy group, a 5-hydroxy-4-oxopentyloxy group, a 4-hydroxy-2-oxobutyloxy group, a 5-hydroxy-2-oxopentyloxy group, a 6-hydroxy-2-oxohexyloxy group, a 5-mercapto-2-oxopentyloxy group, a 4-carboxy-1-piperidinylcarbonylmethyloxy group, a 4-methoxycarbonyl-1-piperidinylcarbonylmethyloxy group, a 4-ethoxycarbonyl-1-piperidinylcarbonylmethyloxy group, a 4-morpholylcarbonylmethyloxy group, a 2-hydroxyethyloxy group, a 3-hydroxypropyloxy group, a 4-hydroxybutyloxy group, a 2-mercaptoethyloxy group, a 3-mercaptopropyloxy group, a 4-mercaptobutyloxy group, a 2-aminoethyloxy group, a 3-aminopropyloxy group, a 4-aminobutyloxy group, a benzyloxy group, a 2-phenethyloxy group, a 3-phenylpropyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2 -pyridylmethyloxy group, a 5-methyl-3-pyridylmethyloxy group, a 6-methyl-2-pyridylmethyloxy group, a 5-ethyl-3-pyridylmethyloxy group, a 5-t-butyl-3-pyridylmethyloxy group, a 5-methoxycarbonyl-3-pyridylmethyloxy group, a 5-ethoxycarbonyl-3-pyridylmethyloxy group, a 2-pyrazinylmethyloxy group, a 2-pyrimidinylmethyloxy group, a 4-pyrimidinylmethyloxy group, a 5-pyrimidinylmethyloxy group, a 2-furylmethyloxy group, a 3-furylmethyloxy group, a 2-thienylmethyloxy group, a 3-thienylmethyloxy group, a 3-oxadiazolylmethyloxy group, a 2-(4-methoxyphenoxy)ethyloxy group, a 3-(4-methoxyphenoxy)propyloxy group, a 3-(4-methoxyphenoxy)butyloxy group, or the like.

Preferably, $R^1$ is substituted in 2-position and it represents a hydroxyl group, a methoxy group, a carboxymethyloxy group, a 2-carboxyethyloxy group, a 3-carboxypropyloxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, a 3-aminopropyloxy group, a 4-aminobutyloxy group, a benzyloxy group, a 5-hydroxymethyl-3-pyridylmethyloxy group, a 5-acetoxymethyl-3-pyridylmethyloxy group, a 6-hydroxymethyl-2-pyridylmethyloxy group, a 6-acetoxymethyl-2-pyridylmethyloxy group, a 5-methyl-3-pyridylmethyloxy group, a 6-methyl-2-pyridylmethyloxy group, a 2-pyridylmethyloxy group, a 3-pyridylmethyloxy group, a 4-pyridylmethyloxy group, a 2-pyrazinylmethyloxy group, a 2-pyrimidinylmethyloxy group, a 4-pyrimidinylmethyloxy group, a 5-pyrimidinylmethyloxy group, etc.

More preferably, $R^1$ represents a hydroxyl group, a methoxy group, a carboxymethyloxy group, a 2-carboxyethyloxy group, a 3-carboxypropyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, a benzyloxy group, a 2-pyridylmethyloxy group, a 3-pyridylmethyloxy group, a 4-pyridylmethyloxy group, a 2-pyrazinylmethyloxy group, a 2-pyrimidinylmethyloxy group, a 4-pyrimidinylmethyloxy group, a 5-pyrimidinylmethyloxy group.

In the general formula (I), $R^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and a pyridyl group or a straight- or branched-chain alkoxy group having 1–4 carbon atoms which may be substituted by one alkoxycarbonyl group having 1–4 carbon atoms.

More specifically, the "halogen atom" refers to a fluorine atom, a chlorine atom or a bromine atom; the "optionally protected hydroxyl group" refers to a hydroxyl group, a trimethylsilyloxy group, a t-butyldimethylsilyloxy group, a methoxymethyloxy group or the like; the "optionally protected mercapto group" refers to a phenylthio group, a benzylthio group or the like; the "straight- or branched-chain alkanoyloxy group having 1–4 carbon atoms" refers to an acetoxy group, a propionyloxy group, a butyryloxy group, a pivaloyloxy group or the like; the "straight- or branched-chain alkanoyl group having 1–4 carbon atoms" refers to an acetyl group, a propionyl group, a pivaloyl group or the like; the "alkyl group having 1–4 carbon atoms" refers to a methyl group, an ethyl group, a n-propyl group, an i-propyl group, a n-butyl group, a t-butyl group or the like; the "alkylthio group having 1–3 carbon atoms which may be monosubstituted by any group selected from the group consisting of a hydroxyl group, a carboxyl group, a phenyl group and a pyridyl group" refers to a methylthio group, an ethylthio group, a 3-hydroxypropylthio group, a carboxymethylthio group, a 3-pyridylmethylthio group or the like; the "straight- or branched-chain alkoxy group having 1–4 carbon atoms which may be substituted by one alkoxycarbonyl group having 1–4 carbon atoms" refers to a methoxy group, an ethoxy group, a n-propoxy group, an i-propoxy group, a n-butoxy group, a t-butoxy group, a methoxycarbonylmethyloxy group, an ethoxycarbonylmethyloxy group, a n-propoxycarbonylmethyloxy group, an i-propoxycarbonylmethyloxy group, a n-butoxycarbonylmethyloxy group, a t-butoxycarbonylmethyloxy group, a 2-(methoxycarbonyl) ethyloxy group, a 2-(ethoxycarbonyl)ethyloxy group, a 2-(n-propoxycarbonyl)ethyloxy group, a 2-(i-propoxycarbonyl) ethyloxy group, a 2-(n-butoxycarbonyl)ethyloxy group, a 2-(t-butoxycarbonyl)ethyloxy group, a 2-(n-pentyloxycarbonyl)ethyloxy group, a 3-(methoxycarbonyl) propyloxy group, a 3-(ethoxycarbonyl)propyloxy group, a 3-(n-propoxycarbonyl)propyloxy group, a 3-(i-propoxycarbonyl)propyloxy group, a 3-(n-butoxycarbonyl) propyloxy group, a 3-(t-butoxycarbonyl)propyloxy group, or the like.

Preferably, $R^2$ is substituted in 9- or 10-position and represents a hydrogen atom, a hydroxyl group, a fluorine atom, a chlorine atom, a bromine atom, a methoxy group, an ethoxy group, a n-propoxy group, an i-propoxy group, a n-butoxy group, a t-butoxy group or a trifluoromethyl group.

More preferably, $R^2$ is substituted in 9-position and represents a chlorine atom, a bromine atom or a trifluoromethyl group.

In the general formula (I), $R^3$ represents a hydrogen atom, a halogen atom, an optionally protected hydroxyl group or a straight- or branched-chain alkoxy group having 1–4 carbon atoms. More specifically, the "halogen atom" refers to a fluorine atom, a chlorine atom, a bromine atom or the like; the "optionally protected hydroxyl group" refers to a hydroxyl group, a trimethylsilyloxy group, a t-butyldimethylsilyloxy group, a methoxymethyloxy group or the like; the "straight- or branched-chain alkoxy group having 1–4 carbon atoms" refers to a methoxy group, an ethoxy group, a n-propoxy group, an i-propoxy group, a cyclopropoxy group, a n-butoxy group, a t-butoxy group, or the like.

Preferably, $R^3$ represents a hydrogen atom, a hydroxyl group, a fluorine atom, a chlorine atom, a bromine atom, a methoxy group, an ethoxy group, a n-propoxy group, an i-propoxy group, a n-butoxy group or a t-butoxy group. More preferably, $R^3$ represents a hydrogen atom.

Preferably, $R^2$ and $R^3$ are not a hydrogen atom at the same time.

The preferred combinations of $R^2$ and $R^3$ are such that $R^2$ is substituted in 9- or 10-position and represents a hydrogen atom, a halogen atom, a hydroxyl group, a trifluoromethyl group or a straight- or branched-chain alkoxy group having 1–4 carbon atoms and $R^3$ is a hydrogen atom. More preferably, $R^2$ is a halogen atom or a trifluoromethyl group which are substituted in 9-position and $R^3$ is a hydrogen atom.

In the general formula (I), $R^4$ represents a hydrogen atom, a halogen atom, an optionally protected carboxyl group, a phenoxy group, an anilino group, a N-methylanilino group, a 4-morpholylcarbonyl group, an alkyl group having 1 or 2 carbon atoms which may be substituted by a cyclic alkyl group having 3–6 carbon atoms, a benzyl group which may be mono- or disubstituted in the phenyl portion by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridylmethyl group which may be substituted by an alkyl group having 1–4 carbon atoms, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group, an α-hydroxybenzyl group or an alkoxycarbonyl group having 1 or 2 carbon atoms.

More specifically, the "halogen atom" refers to a fluorine atom, a chlorine atom, a bromine atom or the like; the "alkyl group having 1 or 2 carbon atoms which may be substituted by a cyclic alkyl group having 3–6 carbon atoms" refers to a methyl group, an ethyl group, a cyclopropylmethyl group, a cyclohexylmethyl group or the like; the "benzyl group which may be mono- or disubstituted in the phenyl portion by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group" refers to a 2-fluorobenzyl group, a 2-chlorobenzyl group, a 2-bromobenzyl group, a 3-fluorobenzyl group, a 3-chlorobenzyl group, a 3-bromobenzyl group, a 4-fluorobenzyl group, a 4-chlorobenzyl group, a 4-bromobenzyl group, a 2-hydroxybenzyl group, a 3-hydroxybenzyl group, a 4-hydroxybenzyl group, a 2-mercaptobenzyl group, a 3-mercaptobenzyl group, a 4-mercaptobenzyl group, a 2-methoxybenzyl group, a 3-methoxybenzyl group, a 4-methoxybenzyl group, a 2-ethoxybenzyl group, a 3-ethoxybenzyl group, a 4-ethoxybenzyl group, a 2-methylthiobenzyl group, a 3-methylthiobenzyl group, a 4-methylthiobenzyl group, a 2-ethylthiobenzyl group, a 3-ethylthiobenzyl group, a 4-ethylthiobenzyl group, a 2-methoxycarbonylbenzyl group, a 3-methoxycarbonylbenzyl group, a 4-methoxycarbonylbenzyl group, a 2-ethoxycarbonylbenzyl group, a 3-ethoxycarbonylbenzyl group, a 4-ethoxycarbonylbenzyl group, a 2-t-butoxycarbonylbenzyl group, a 3-t-butoxycarbonylbenzyl group, a 4-t-butoxycarbonylbenzyl group, a 2-acetylaminobenzyl group, a 3-acetylaminobenzyl group, a 4-acetylaminobenzyl group, a 2-carboxybenzyl group, a 3-carboxybenzyl group, a 4-carboxybenzyl group, a 2-aminobenzyl group, a 3-aminobenzyl group, a 4-aminobenzyl group, a 2,3-difluorobenzyl group, a 2,4-difluorobenzyl group, a 2,5-difluorobenzyl group, a 3,4-difluorobenzyl group, a 3,5-difluorobenzyl group, a 2,3-dichlorobenzyl group, a 2,4-dichlorobenzyl group, a 2,5-dichlorobenzyl group, a 3,4-dichlorobenzyl group, a 3,5-dichlorobenzyl group, a 2,3-dibromobenzyl group, a 2,4-dibromobenzyl group, a 2,5-dibromobenzyl group, a 3,4-dibromobenzyl group, a 3,5-dibromobenzyl group, a 2,3-dihydroxybenzyl group, a 2,4-dihydroxybenzyl group, a 2,5-dihydroxybenzyl group, a 3,4-dihydroxybenzyl group, a 3,5-dihydroxybenzyl group, a 2,3-dimethoxybenzyl group, a 2,4-dimethoxybenzyl group, a 2,5-dimethoxybenzyl group, a 3,4-dimethoxybenzyl group, a 3,5-dimethoxybenzyl group, a 2,3-diethoxybenzyl group, a 2,4-diethoxybenzyl group, a 2,5-diethoxybenzyl group, a 3,4-diethoxybenzyl group, a 3,5-diethoxybenzyl group, a 2-fluoro-3-methoxybenzyl group, a 2-fluoro-4-methoxybenzyl group, a 2-fluoro-5-methoxybenzyl group, a 3-fluoro-4-methoxybenzyl group, a 3-fluoro-5-methoxybenzyl group, a 3-fluoro-2-methoxybenzyl group, a 4-fluoro-2-methoxybenzyl group, a 5-fluoro-2-methoxybenzyl group, a 4-fluoro-3-methoxybenzyl group, a 5-fluoro-3-methoxybenzyl group, or the like; the "pyridylmethyl group which may be substituted by an alkyl group having 1–4 carbon atoms" refers to a 2-pyridylmethyl group, a 3-pyridylmethyl group, a 4-pyridylmethyl group, a 5-methyl-3-pyridylmethyl group, a 6-methyl-2-pyridylmethyl group or the like; the "alkoxycarbonyl group having 1 or 2 carbon atoms" refers to a methoxycarbonyl group, an ethoxycarbonyl group or the like.

Preferably, $R^4$ represents a hydrogen atom, a methyl group, a 2-pyrimidinylmethyl group, a 4-pyrimidinylmethyl group, a 5-pyrimidinylmethyl group, a 2-pyridylmethyl group, a 3-pyridylmethyl group, a 4-pyridylmethyl group, a 5-methyl-3-pyridylmethyl group or a 6-methyl-2-pyridylmethyl group.

More preferably, $R^4$ represents a methyl group, a 5-pyrimidinylmethyl group, a 2-pyridylmethyl group, a 3-pyridylmethyl group or a 4-pyridylmethyl group.

In the general formula (I), $R^5$ represents a hydrogen atom or a methyl group, preferably a hydrogen atom.

If $R^1$, $R^2$, $R^3$ and $R^5$ in the general formula (I) are a hydrogen atom at the same time, $R^4$ is a substituent other than a hydrogen atom, a benzyl group, a 4-diethylaminobenzyl group and a furylmethyl group.

The preferred combinations of the substituents are such that $R^1$ is substituted in 2-position and represents a hydroxyl group, a carboxymethyloxy group, a 2-carboxyethyloxy group, a 3-carboxypropyloxy group, a N-hydroxymethylcarbamoylmethyloxy group, a N-ethylcarbamoylmethyloxy group, a 4-hydroxy-2-oxobutyloxy group, a 5-hydroxy-2-oxopentyloxy group, a 2-hydroxyethyloxy group, a 3-hydroxypropyloxy group, a 4-hydroxybutyloxy group, a benzyloxy group, a 2-pyridinomethyloxy group, a 3-pyridinomethyloxy group, a 4-pyridinomethyloxy group, a 2-pyrazinylmethyloxy group, a 2-pyrimidinylmethyloxy group, a 4-pyrimidinylmethyloxy group or a 5-pyrimidinylmethyloxy group; $R^2$ is a chlorine atom, a bromine atom or a trifluoromethyl group which are substituted in 9-position; $R^3$ is a hydrogen atom; $R^4$ is a methyl group, a 5-pyrimidinylmethyl group, a 2-pyridylmethyl group, a 3-pyridylmethyl group or a 4-pyridylmethyl group; and $R^5$ is a hydrogen atom.

In the general formula (IV), $R^6$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, an optionally protected hydroxyl group, an optionally protected mercapto group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms or a straight-chain alkoxy group having 1–6 carbon atoms which may be substituted by a 4-methoxyphenoxy group; $R^7$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally protected carboxyl group, a straight- or branched-chain alkanoyl group having 1–4 carbon atoms, a straight- or branched-chain alkyl group having 1–4 carbon atoms or a straight- or branched-chain alkoxy group having 1–4 carbon atoms; $R^8$ represents a hydrogen atom, a halogen atom, an optionally protected hydroxyl group or a straight- or branched-chain alkoxy group having 1–4 carbon atoms; $R^{10}$ is a hydrogen atom, a halogen atom, a phenoxy group, an α-hydroxybenzyl group, an anilino group, an N-methylanilino group, a methyl group or a halogenomethyl group. More specifically, the substituents $R^6$, $R^7$, $R^8$ and $R^{10}$ are expressed by the definitions given to the specific examples of the relevant substituents which are represented by $R^1$, $R^2$, $R^3$ and $R^4$, respectively, in the general formula (I) and which the specifically described hereinabove.

Referring to the general formula (XVI) which will be set forth later in connection with production of the claimed compounds, $R^9$ represents a hydrogen atom or a methyl group and $R^{11}$ represents a hydrogen atom or a straight- or branched-chain alkyl group having 1–4 carbon atoms; more specifically, the "straight- or branched-chain alkyl group having 1–4 carbon atoms" refers to a methyl group, an ethyl group, a n-propyl group, an i-propyl group, a n-butyl group, a t-butyl group or the like.

In the general formula (XIX), $R^{12}$ is a hydrogen atom, a methyl group, a cyclic alkyl group having 3–6 carbon atoms, a phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridyl group which may be substituted by an alkyl group having 1–4 carbon atoms, a morpholyl group, a triazolyl group, a furyl group, a thienyl group, a pyrimidinyl group, a pyrazinyl group, a pyrrolyl group, an imidazolyl group, a quinolyl group, an indolyl group or a naphthyl group.

More specifically, the "cyclic alkyl group having 3–6 carbon atoms" refers to a cyclopropyl group, a cyclohexyl group or the like; the "phenyl group which may be mono- or disubstituted by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group" refers to a 2-fluorophenyl group, a 2-chlorophenyl group, a 2-bromophenyl group, a 3-fluorophenyl group, a 3-chlorophenyl group, a 3-bromophenyl group, a 4-fluorophenyl group, a 4-chlorophenyl group, a 4-bromophenyl group, a 2-hydroxyphenyl group, a 3-hydroxyphenyl group, a 4-hydroxyphenyl group, a 2-mercaptophenyl group, a 3-mercaptophenyl group, a 4-mercaptophenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxyphenyl group, a 3-n-propoxyphenyl group, a 4-n-propoxyphenyl group, a 2-i-propoxyphenyl group, a 3-i-propoxyphenyl group, a 4-i-propoxyphenyl group, a 2-n-butoxyphenyl group, a 3-n-butoxyphenyl group, a 4-n-butoxyphenyl group, a 2-t-butoxyphenyl group, a 3-t-butoxyphenyl group, a 4-t-butoxyphenyl group, a 2-methoxycarbonylphenyl group, a 3-methoxycarbonylphenyl group, a 4-methoxycarbonylphenyl group, a 2-ethoxycarbonylphenyl group, a 3-ethoxycarbonylphenyl group, a 4-ethoxycarbonylphenyl group, a 2-t-butoxycarbonylphenyl group, a 3-t-butoxycarbonylphenyl group, a 4-t-butoxycarbonylphenyl group, a 2-acetylaminophenyl group, a 3-acetylaminophenyl group, a 4-acetylaminophenyl group, a 2-carboxyphenyl group, a 3-carboxyphenyl group, a 4-carboxyphenyl group, a 2-aminophenyl group, a 3-aminophenyl group, a 4-aminophenyl group, a 2,3-difluorophenyl group, a 2,4-difluorophenyl group, a 2,5-difluorophenyl group, a 3,4-difluorophenyl group, a 3,5-difluorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2,3-dibromophenyl group, a 2,4-dibromophenyl group, a 2,5-dibromophenyl group, a 3,4-dibromophenyl group, a 3,5-dibromophenyl group, a 2,3-dihydroxyphenyl group, a 2,4-dihydroxyphenyl group, a 2,5-dihydroxyphenyl group, a 3,4-dihydroxyphenyl group, a 3,5-dihydroxyphenyl group, a 2,3-dimethoxyphenyl group, a 2,4-dimethoxyphenyl group, a 2,5-dimethoxyphenyl group, a 3,4-dimethoxyphenyl group, a 3,5-dimethoxyphenyl group, a 2,3-diethoxyphenyl group, a 2,4-diethoxyphenyl group, a 2,5-diethoxyphenyl group, a 3,4-diethoxyphenyl group, a 3,5-diethoxyphenyl group, a 2-fluoro-3-methoxyphenyl group, a 2-fluoro-4-methoxyphenyl group, a 2-fluoro-5-methoxyphenyl group, a 3-fluoro-4-methoxyphenyl group, a 3-fluoro-5-methoxyphenyl group, a 3-fluoro-2-methoxyphenyl group, a 4-fluoro-2-methoxyphenyl group, a 5-fluoro-2-methoxyphenyl group, a 4-fluoro-3-methoxyphenyl group, a 5-fluoro-3-methoxyphenyl group, or the like; the "pyridyl group which may be substituted by an alkyl group having 1–4 carbon atoms" refers to a 2-pyridyl group, a 3-pyridyl group, a 4-pyridyl group, a 5-methyl-3-pyridyl group, a 6-methyl-2-pyridyl group, or the like. Preferably, $R^{12}$ represents a 2-pyrimidinyl group, a 4-pyrimidinyl group, a 5-pyrimidinyl group, a 2-pyridyl group, a 3-pyridyl group, a 4-pyridyl group, a 5-methyl-3-pyridyl group or a 6-methyl-2-pyridyl group. More preferably, $R^{12}$ represents a 5-pyrimidinyl group, a 2-pyridyl group, a 3-pyridyl group or a 4-pyridyl group.

Further, $R^{13}$ in the general formula (XX) represents an alkoxycarbonyl group having 1–4 carbon atoms, a 3-carboxy-1-propenyl group, a 2,2-diethoxyethyl group, a straight- or branched-chain alkanoyl group having 1–4 carbon atoms, a carbonyl group substituted by a phenyl group or a pyridyl group, or a group: —$(CH_2)_n$-Z (where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6).

More specifically, the "alkoxycarbonyl group having 1–4 carbon atoms" refers to a methoxycarbonyl group, an ethoxycarbonyl group, a n-propoxycarbonyl group, an i-propoxycarbonyl group, a cyclopropoxycarbonyl group, a n-butoxycarbonyl group, a t-butoxycarbonyl group, or the like; the "straight- or branched-chain alkanoyl group having 1–4 carbon atoms" refers to an acetyl group, a propionyl group, a butyryl group, a pivaloyl group, or the like; the "carbonyl group substituted by a phenyl group or a pyridyl group" refers to a benzoyl group, a nicotinoyl group, an isonicotinoyl group, or the like; the group: —$(CH_2)_n$-Z (where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6) refers to a methyl group, an ethyl group, a n-propyl group, an i-propyl group, a n-butyl group, a t-butyl group, a n-pentyl group, a n-hexyl group, a carboxymethyl group, a 2-carboxyethyl group, a 3-carboxypropyl group, a methoxymethyl group, an ethoxymethyl group, a 2-methoxyethyl group, a 2-ethoxyethyl group, a 2-(2-hydroxyethoxy)ethyl group, a methoxycarbonylmethyl group, an ethoxycarbonylmethyl group, a n-propoxycarbonylmethyl group, an i-propoxycarbonylmethyl group, a n-butoxycarbonylmethyl group, a t-butoxycarbonylmethyl group, a n-pentyloxycarbonylmethyl group, a n-hexyloxycarbonylmethyl group, a cyclopropyloxycarbonylmethyl group, a cyclohexyloxycarbonylmethyl group, a 2-(methoxycarbonyl)ethyl group, a 2-(ethoxycarbonyl)ethyl group, a 2-(n-propoxycarbonyl)ethyl group, a 2-(i-propoxycarbonyl)ethyl group, a 2-(n-butoxycarbonyl)ethyl group, a 2-(t-butoxycarbonyl)ethyl group, a 2-(n-pentyloxycarbonyl)ethyl group, a 2-(n-hexyloxycarbonyl)ethyl group, a 2-(cyclopropyloxycarbonyl)ethyl group, a 2-(cyclohexyloxycarbonyl)ethyl group, a 3-(methoxycarbonyl)propyl group, a 3-(ethoxycarbonyl)propyl group, a 3-(n-propoxycarbonyl)propyl group, a 3-(i-propoxycarbonyl)propyl group, a 3-(n-butoxycarbonyl)propyl group, a 3-(t-butoxycarbonyl)propyl group, a 3-(n-pentyloxycarbonyl)propyl group, a 3-(n-hexyloxycarbonyl)propyl group, a 3-(cyclopropyloxycarbonyl)propyl group, a 3-(cyclohexyloxycarbonyl)propyl group, a N-hydroxymethylcarbamoylmethyl group, a N-methylcarbamoylmethyl group, a N,N-dimethylcarbamoylmethyl group, a N-ethylcarbamoylmethyl group, a N,N-diethylcarbamoylmethyl group, a N-n-propylcarbamoylmethyl group, a N-n-butylcarbamoylmethyl group, a 3-hydroxy-2-oxopropyl group, a 4-hydroxy-3-oxobutyl group, a 5-hydroxy-4-oxopentyl group, a 4-hydroxy-2-oxobutyl group, a 5-hydroxy-2-oxopentyl group, a 6-hydroxy-2-oxohexyl group, a 5-mercapto-2-oxopentyl group, a 4-carboxy-2-piperidinylcarbonylmethyl group, a 4-methoxycarbonyl-1-piperidinylcarbonylmethyl group, a 4-ethoxycarbonyl-1-piperidinylcarbonylmethyl group, a 4-morpholylcarbonylmethyloxy group, a 2-hydroxyethyl group, a 3-hydroxypropyl group, a 4-hydroxybutyl group, a 2-mercaptoethyl group, a 3-mercaptopropyl group, a 4-mercaptobutyl group, a 2-aminoethyl group, a 3-aminopropyl group, a 4-aminobutyl group, a benzyl group, a 2-phenethyl group, a 3-phenylpropyl group, a 5-hydroxymethyl-3-pyridylmethyl group, a 5-acetoxymethyl-3-pyridylmethyl group, a 6-hydroxymethyl-2-pyridylmethyl group, a 6-acetoxymethyl-2-pyridylmethyl group, a 5-methyl-3-pyridylmethyl group, a 6-methyl-2-pyridylmethyl group, a 5-ethyl-3-pyridylmethyl group, a 5-t-butyl-3-pyridylmethyl group, a 5-methoxycarbonyl-3-pyridylmethyl group, a 5-ethoxycarbonyl-3-pyridylmethyl group, a 2-pirazinylmethyl group, a 2-pyrimidinylmethyl group, a 4-pyrimidinylmethyl group, a 5-pyrimidinylmethyl group, a 2-furylmethyl group, a 3-furylmethyl group, a 2-thienylmethyl group, a 3-thienylmethyl group, a 3-oxadiazolylmethyl group, a 2-(4-methoxyphenoxy)ethyl group, a 3-(4-methoxyphenoxy)propyl group, a 4-(4-methoxyphenoxy)butyl group, or the like.

Preferably, $R^{13}$ represents a carboxymethyl group, a 2-carboxyethyl group, a 3-carboxypropyl group, a methoxycarbonylmethyl group, an ethoxycarbonylmethyl group, a n-propoxycarbonylmethyl group, an i-propoxycarbonylmethyl group, a n-butoxycarbonyl-ethyl group, a t-butoxycarbonylmethyl group, a N-hydroxymethylcarbamoylmethyl group, a N-ethylcarbamoylmethyl group, a 4-hydroxy-2-oxobutyl group, a 5-hydroxy-2-oxopentyl group, a 2-hydroxyethyl group, a 3-hydroxypropyl group, a 4-hydroxybutyl group, a 3-aminopropyl group, a 4-aminobutyl group, a benzyl group, a 5-hydroxymethyl-3-pyridylmethyl group, a 5-acetoxymethyl-3-pyridylmethyl group, a 6-hydroxymethyl-2-pyridylmethyl group, a 6-acetoxymethyl-2-pyridylmethyl group, a 5-methyl-3-pyridylmethyl group, a 6-methyl-2-pyridylmethyl group, a 2-pyridylmethyl group, a 3-pyridylmethyl group, a 4-pyridylmethyl group, a 2-pirazinylmethyl group, a 2-pyrimidinylmethyl group, a 4-pyrimidinylmethyl group or a 5-pyrimidinylmethyl group.

More preferably, $R^{13}$ represents a carboxymethyl group, a 2-carboxyethyl group, a 3-carboxypropyl group, a N-hydroxymethylcarbamoylmethyl group, a N-ethylcarbamoylmethyl group, a 4-hydroxy-2-oxobutyl group, a 5-hydroxy-2-oxopentyl group, a 2-hydroxyethyl group, a 3-hydroxypropyl group, a 4-hydroxybutyl group, a benzyl group, a 2-pyridylmethyl group, a 3-pyridylmethyl group, a 4-pyridylmethyl group, a 2-pirazinylmethyl group, a 2-pyrimidinylmethyl group, a 4-pyrimidinylmethyl group or a 5-pyrimidinylmethyl group. Throughout the specification, the number of carbon atoms indicated for the alkoxycarbonyl group, alkanoyloxy group or alkanoyl group refers to that of carbon atoms in the corresponding alkoxy, alkyl or alkyl portion.

Aside from the protective groups specifically mentioned herein for the optionally protected substituents, the following may be mentioned: protective groups for the hydroxyl group include alkyl-type protective groups such as a methyl group, a t-butyl group, a benzyl group, a trityl group and a methoxymethyl group, silyl-type protective groups such as a trimethylsilyl group and a t-butyldimethylsilyl group, acyl-type protective groups such as a formyl group, an acetyl group and a benzoyl group, and carbonate-type protective groups such as a methoxycarbonyl group and a benzyloxycarbonyl group; protective groups for the carboxyl group include ester-type protective groups such as a methyl group, an ethyl group, a t-butyl group, a benzyl group and a methoxymethyl group; protective groups for the amino group include alkyl-type protective groups such as a benzyl group, a trityl group and a methoxymethyl group, acyl-type protective groups such as a formyl group, an acetyl group and a benzoyl group, and carbamate-type protective groups such as a t-butoxycarbonyl group and a benzyloxycarbonyl group.

The compounds of the invention may form salts with inorganic or organic acids. Examples of such salts include inorganic acid salts such as hydrochlorides, sulfates and nitrates, and organic acid salts such as acetates, oxalates, maleates, tartrates, p-toluenesulfonates and methanesulfonates. Depending on the types of the substituents used, salts may be formed with inorganic or organic bases. Examples include salts with inorganic bases such as sodium carbonate and potassium carbonate, as well as salts with organic bases such as triethylamine, diethylamine and pyridine. These salts can be obtained in the usual manner, as by mixing an equivalent amount of a compound of the invention with a solution containing an acid or base of interest and obtaining the desired salt by filtration or evaporate the solvent.

The compounds of the invention represented by the general formula (I) can be produced by processes represented by the reaction schemes to be set forth below. The compounds shown in the Reaction Schemes 1 and 2 to be set forth below, the compounds represented by the general formulae set forth herein, i.e. the general formulae (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) and (XXIV), as well as the definitions of $R^1$, $R^2$, $R^3$, $R^4$, $R^5$, $R^6$, $R^7$, $R^8$, $R^9$, $R^{10}$, $R^{11}$, $R^{12}$, $R^{13}$, X and Z are respectively the same as already discussed above. The pyridocarbazole derivatives represented by the formula (I) or salts thereof which are the compounds of the invention can be produced in accordance with Process I within the scope of Reaction Scheme 1 from compounds of the formula (II), (V) or (IX) which can easily be prepared from either documented or commercial compounds, or from salts of such compounds. The compounds of the general formula (I) can also be produced by Process 2 or 3.

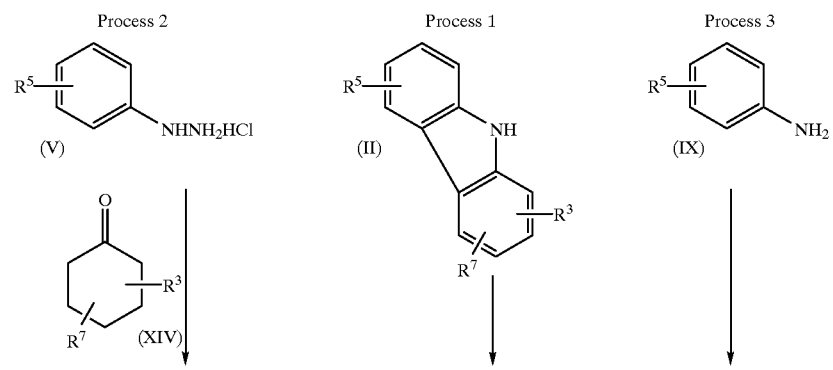

Reaction Scheme 1

-continued
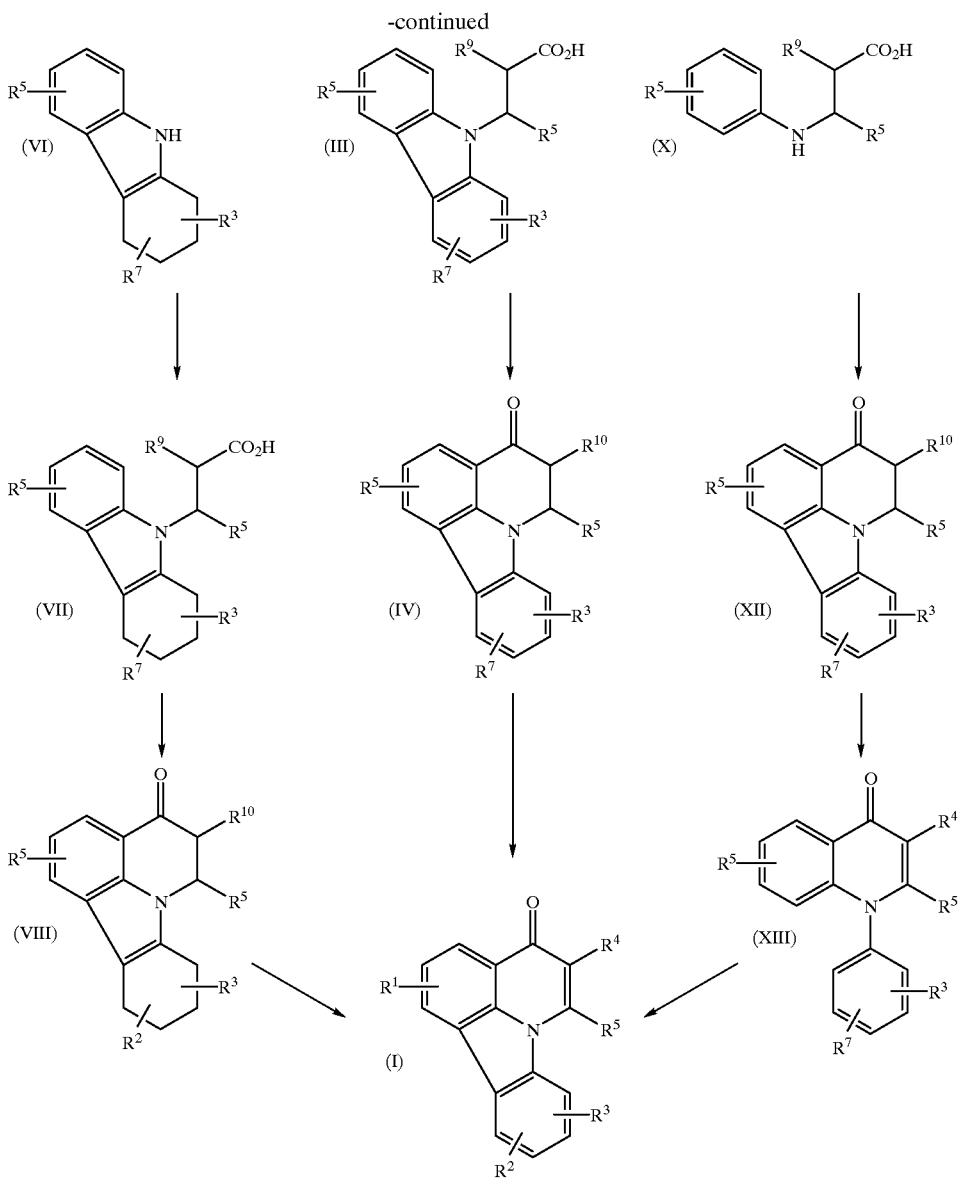
The processes for producing the compounds of the invention are described below in detail.
Process 1
A carbazole derivative represented by the general formula (II) or a salt thereof:
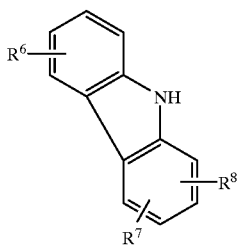
is reacted with a compound represented by the following general formula (XVI):
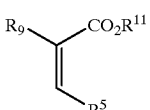
(XVI)
or the following general formula (XVII):
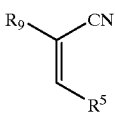
(XVII)

or the following general formula (XVIII):

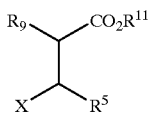

(XVIII)

and, if necessary, hydrolysis is performed to yield a compound represented by the following general formula (III):

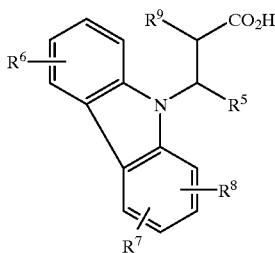

(III)

Stated more specifically, the compound of the formula (II) and the compound of the formula (XVI) or (XVII) are subjected to a Michael addition reaction in the presence or absence of copper acetate, N-benzyltrimethylammonium hydroxide (Triton B) or the like, preferably in the presence of Triton B, either without solvents or using a water, a ketone-based solvent such as acetone or methyl ethyl ketone or an ether-based solvent such as tetrahydrofuran (THF), dioxane or 1,2-dimethoxyethane (DME), preferably using acetone as a solvent at a temperature ranging from the one obtained by cooling with ice to the one where the reaction mixture is heated under reflux, preferably at room temperature for a sufficient time to ensure adequate progress of the reaction, specifically for 15 min to 1 h and, if necessary, hydrolysis is performed in either an acidic aqueous solution such as dilute hydrochloric acid or sulfuric acid or a basic aqueous solution such as dilute aqueous sodium hydroxide or potassium hydroxide, preferably in dilute aqueous hydrochloric acid or sodium hydroxide at a temperature ranging from room temperature to the one where the reaction mixture is heated under reflux, preferably at room temperature for a sufficient time to ensure adequate progress of the reaction, specifically from 15 min to 12 h; alternatively, the compound of the formula (II) and the compound of the formula (XVIII) are subjected to an addition reaction in the presence of an inorganic base such as potassium carbonate, cesium carbonate, calcium carbonate or sodium hydride or an organic base such as triethylamine, pyridine or N,N-dialkylaniline, preferably in the presence of sodium hydride using a polar solvent such as acetonitrile or dimethylformamide (DMF), a halogenated hydrocarbon solvent typified by chloroform or methylene chloride or an ether-based solvent typified by ether or tetrahydrofuran (THF), preferably using DMF as a solvent at a temperature ranging from room temperature to the one where the reaction mixture is heated under reflux, preferably at the temperature where heating under reflux is effected, for a sufficient time to ensure adequate progress of the reaction, specifically for 15 min to 3 h and, if necessary, hydrolysis is performed in either an acidic aqueous solution such as dilute hydrochloric acid or sulfuric acid or a basic aqueous solution such as dilute aqueous sodium hydroxide or potassium hydroxide, preferably in a dilute aqueous hydrochloric acid or sodium hydroxide solution at a temperature ranging from room temperature to the one where the reaction mixture is heated under reflux, preferably at room temperature for a sufficient time to ensure adequate progress of the reaction, specifically for 15 min to 12 h. By either method, the compound of the formula (III) can be produced.

Subsequently, the compound of the formula (III) is converted to an acid halide by reaction in the presence of a thionyl halide reagent such as thionyl chloride or thionyl bromide using a halogenated hydrocarbon solvent typified by chloroform or methylene chloride or an aromatic hydrocarbon-based solvent such as benzene or toluene, preferably using methylene chloride as a solvent at a temperature ranging from the one obtained by cooling with ice to the one where the reaction mixture is heated under reflux, preferably at room temperature for a sufficient time to ensure adequate progress of the reaction, specifically for 15 min to 1 h; thereafter, the resulting acid halide is subjected to Friedel-Crafts reaction in the presence of a Lewis acid such as aluminum chloride, tin chloride or zinc chloride either without solvents or using nitrobenzene, carbon disulfide or a halogenated hydrocarbon-based solvent such as methylene chloride, carbon tetrachloride or 1,2-dichloroethane, preferably using carbon disulfide or methylene chloride as a solvent at a temperature ranging from −78° C. to the one where the reaction mixture is heated under reflux, preferably at room temperature for a sufficient time to ensure adequate progress of the reaction, specifically for 15 min to 3 h; alternatively, the acid halide is subjected to reaction in the presence of trifluoroacetic anhydride using an aromatic hydrocarbon-based solvent such as benzene, toluene or xylene, preferably using toluene as a solvent at a temperature ranging from room temperature to the one where the reaction mixture is heated under reflux, preferably at the temperature where heating under reflux is effected, for a sufficient time to ensure adequate progress of the reaction, specifically for 3 h to 10 h; alternatively, the acid halide is subjected to reaction in the presence of a phosphorylating agent such as phosphorus pentoxide, polyphosphoric acid or polyphosphate ester either without solvents or optionally using an aromatic hydrocarbon-based solvent such as benzene or toluene or a halogenated hydrocarbon-based solvent such as chlorobenzene, chloroform or methylene chloride, preferably using chloroform as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; by either approach, a compound of the following general formula (IV) can be produced:

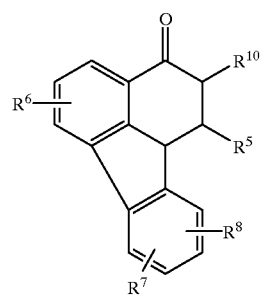

(IV)

The above-described reaction for ring closure (cyclization) has such selectivity that on account of the difference in electronic environment between the substituents $R^6$ and $R^7$ (or $R^8$) on the two benzene rings, cyclization favors the substituent which is relatively more effective electron donor. In order to achieve cyclization in the desired direction by taking advantage of this propensity, those substituents which can be changed or removed after cyclization can be used effectively. If the selectivity in cyclization is so low as to produce a mixture, purification may optionally be performed by separation through recrystallization or column chromatography.

If $R^6$, $R^7$ and $R^8$ in the compound represented by the formula (IV) are groups included within the definitions of $R^1$, $R^2$ and $R^3$ in the compound represented by the formula (I), $R^{10}$ may be changed to $R^4$ in the manner to be described below, whereby the compound of the formula (IV) is directly derivated to the compound of the formula (I) as shown in Process 1 under Reaction Scheme 1.

Subsequently, the compound represented by the formula (IV) is derivated to the compound represented by the formula (I) as set forth in Reaction Scheme 1 and the changes of substituents that are effected in the derivation are shown in Reaction Scheme 2 and described below in detail.

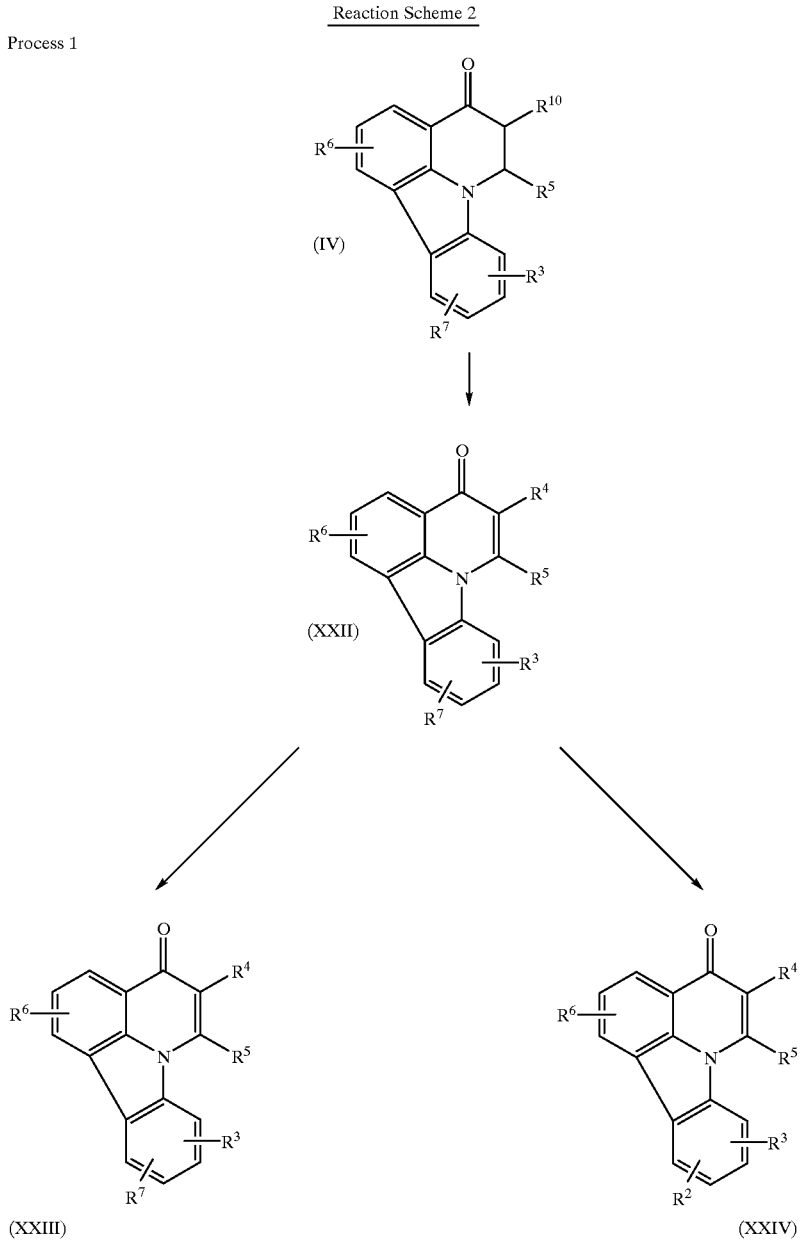

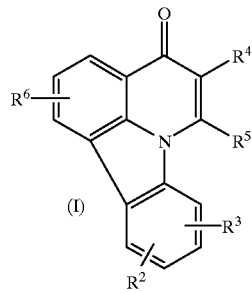

The compound of the formula (IV) is subjected to an aldole condensation reaction with aldehyde represented by $R^{12}$—CHO (XIX), optionally in the presence of an inorganic base such as potassium hydroxide, sodium hydroxide or potassium carbonate or an organic base such as piperazine, piperidine, morpholine or n-BuLi, preferably in the presence of sodium hydroxide in an alcoholic solvent such as methanol or ethanol or an ether-based solvent such as ether, THF or dioxane, preferably using ethanol as a solvent at a temperature ranging from room temperature to the one where the reaction mixture is heated under reflux, preferably at room temperature for a sufficient time to ensure adequate progress of the reaction, specifically for 3 h to 12 h. The resulting compound is not isolated but dehydrated in situ to produce an enone which has the double bond subsequently isomerized in the ring, followed by oxidation in the manner described below. Alternatively, the reaction compound is isolated and subjected to oxidation reaction (dehydrogenation) in the presence of an oxidizing agent such as chloranil, dichlorodicyanobenzoquinone (DDQ) or 5% palladium on carbon, preferably DDQ, using an aromatic hydrocarbon-based nonpolar solvent such as benzene, toluene or xylene, an ether-based solvent such as THF, DME or dioxane or an alcoholic solvent such as ethylene glycol, preferably using dioxane as a solvent at a temperature ranging from room temperature to the one where the reaction mixture is heated under reflux, preferably at room temperature for a sufficient time to ensure adequate progress of the reaction, specifically from 1 h to 12 h; alternatively, the isolated reaction product is halogenated in the presence or absence of light, azobisisobutyronitrile (AIBN) or a peroxide such as benzoyl peroxide (BPO), preferably in their absence, using a suitable halogenating agent such as chlorine gas, bromine, copper bromide, N-bromosuccinimide (NBS), N-chlorosuccinimide (NCS), trihalogenomethanesulfonyl halogenide or trichlorobromomethane, preferably copper bromide, and also using a halogenated hydrocarbon solvent such as carbon tetrachloride, chloroform or methylene chloride, an aromatic hydrocarbon-based nonpolar solvent such as benzene or toluene, acetic acid or carbon disulfide solvent or an ester-based solvent such as ethyl acetate, preferably using chloroform or ethyl acetate as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h so as to yield a reactive derivative, which is thereafter subjected to the following replacement reaction with phenol, aniline, N-methylaniline, triazole, imidazole, morpholine or the like, optionally in the presence of an inorganic base such as potassium carbonate, cesium carbonate or calcium carbonate or an organic base such as triethylamine, pyridine or N,N-dialkylaniline, preferably cesium carbonate, and also optionally using a polar solvent such as acetonitrile or dimethylformamide (DMF), a halogenated hydrocarbon solvent typified by chloroform or methylene chloride or an ether-based solvent typified by ether or tetrahydrofuran (THF), preferably without using solvents, at a temperature ranging from room temperature to the one where the reaction mixture is heated under reflux, preferably at room temperature for a sufficient time to ensure adequate progress of the reaction, specifically for 30 min to 12 h; thereafter, the reaction product is oxidized (dehydrogenated) with an oxidizing agent such as chloranil or DDQ, preferably DDQ, using an aromatic hydrocarbon-based nonpolar solvent such as benzene, toluene or xylene or an ether-based solvent such as THF, DME or dioxane, preferably using dioxane as a solvent at a temperature ranging from room temperature to the one where the reaction mixture is heated under reflux, preferably at room temperature for a sufficient time to ensure adequate progress of the reaction, specifically for 1 h to 12 h; if desired, the replacement reaction may be bypassed and the reaction derivative obtained by halogenation is directly oxidized (dehydrogenated) under the conditions described above. In either way, the compound represented by the formula (XXII) can be produced.

Subsequently, the compound of the formula (XXII) may be subjected to substituent changes as required. If $R^6$, $R^7$ or $R^8$ is a protected hydroxyl group, it is deprotected by treatment in an aqueous solution of hydrochloric acid or hydrofluoric acid, preferably in an aqueous solution of hydrochloric acid, at a temperature ranging from the one obtained by cooling with ice to the one where the reaction mixture is heated under reflux, preferably at room temperature for a sufficient time to ensure adequate progress of the reaction, specifically for 15 min to 12 h; if $R^6$, $R^7$ or $R^8$ is a methoxy group, deprotection is performed by treatment in the presence of boron tribromide, aluminum chloride or hydrobromic acid, preferably in the presence of boron tribromide, using a halogenated hydrocarbon-based solvent such as methylene chloride or chloroform or acetic acid solvent, preferably using methylene chloride as a solvent at a temperature ranging from the one obtained by cooling with ice to the one where the reaction mixture is heated under reflux, preferably at room temperature for a sufficient time to ensure adequate progress of the reaction, specifically for 3 h to 24 h; if $R^6$, $R^7$ or $R^8$ is a benzyloxy group, deprotection is performed by treatment in the presence of palladium and sodium acetate in acetic acid solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; by either method of deprotection, the compound (XXII) can be converted to a hydroxy form. The compound represented by the formula (XXII) where $R^6$ is a hydroxyl group is reacted with a reactive halogen derivative $R^{13}$—X (XX) in the presence or absence of KI using an inorganic base such as potassium carbonate, cesium carbonate or calcium carbonate or an organic base such as triethylamine, pyridine or N,N-dialkylaniline, preferably using potassium carbonate, and also using a polar solvent such as acetonitrile, dimethylformamide (DMF) or dimethyl sulfoxide (DMSO) or an ether-based solvent such as THF, dioxane or DME, preferably using DMSO as a solvent at a temperature ranging from room temperature to 80° C., preferably at room temperature for a sufficient time to ensure adequate progress of the reaction, specifically for 1 h to 12 h so as to yield a compound represented by the general formula (XXIII). The compound of (XXII) may be reacted with acetyl chloride or a bromoacetic acid ester if $R^7$ is a hydroxyl group, or with acetyl chloride if $R^8$ is a hydroxyl group.

Alternatively, the compound represented by the general formula (XXII) may have substituents changed to suitable ones to yield a compound represented by the general formula (XXIV) and if $R^6$ in this compound is a straight-chain alkyl group having 1–6 carbon atoms which may be substituted by a 4-methoxyphenoxy group, specifically exemplified by a 2-(4-methoxyphenoxy)ethyloxy group, a 3-(4-methoxyphenoxy)propyloxy group or a 4-(4-methoxyphenoxy)butyloxy group, deprotection may be performed in the presence of cerium ammonium nitrate (CAN) in acetonitrile either alone or in admixture with water, preferably using the mixture of acetonitrile and water as a solvent system, at a temperature ranging from the one obtained by cooling with ice to the one where the reaction mixture is heated under reflux, preferably at 0° C. for a sufficient time to ensure adequate progress of the reaction, specifically for 15 min to 4 h so as to derivate a compound represented by the general formula (I), specifically one in which $R^1$ is a 2-hydroxyethyloxy group, a 3-hydroxypropyloxy group, a 4-hydroxybutyloxy group or the like.

Other substituent changes that can be effected in the compound of the formula (XXII) are as follows: if $R^6$ or $R^7$ is a halogen atom, they may be changed to an amino group by reaction in the presence of copper or copper iodide in aqueous ammonia at a temperature of 150–200° C., preferably at a temperature of 180–190° C. for a sufficient time to ensure adequate progress of the reaction, specifically for 3 h to 12 h; alternatively $R^6$ or $R^7$ may be changed to a cyano group by reaction in the presence of copper cyanide in DMF at a temperature of 100–200° C., preferably at a temperature of 120–140° C. for a sufficient time to ensure adequate progress of the reaction, specifically for 1 h to 12 h.

If $R^6$ or $R^7$ is a nitro group, they may be changed to an amino group by reaction in the presence of copper using dilute sulfuric acid as a solvent at a temperature ranging from room temperature to the one where the reaction mixture is heated under reflux, preferably at 50° C. for a sufficient time to ensure adequate progress of the reaction, specifically for 30 min to 3 h.

If $R^6$ or $R^7$ is an amino group, they may be changed to a hydroxyl group by reaction in the presence of sodium nitrite using dilute sulfuric acid as a solvent at a temperature ranging from the one obtained by cooling with ice to the one where heating under reflux is effected, preferably at the temperature where heating under reflux is effected, for a sufficient time to ensure adequate progress of the reaction, specifically for 5 min to 3 h.

If $R^6$ or $R^7$ is an acetyl group, halogenation may be performed in the presence or absence of light, AIBN or a peroxide such as benzoyl peroxide (BPO), preferably in their absence using a suitable halogenating agent such as chlorine gas, bromine, copper bromide, N-bromosuccinimide (NBS), N-chlorosuccinimide (NCS), trihalogenomethanesulfonyl halogenide, trichlorobromomethane or phenyltrimethylammonium tribromide (PTT), preferably PTT, and also using a halogenated hydrocarbon solvent such as carbon tetrachloride, chloroform or methylene chloride, an aromatic hydrocarbon-based nonpolar solvent such as benzene or toluene, an ether-based solvent such as THF, dioxane or DME, acetic acid or carbon disulfide solvent, preferably using THF as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h; thereafter, the resulting halide is reacted with aniline, N-methylaniline, morpholine or the like using an inorganic base such as potassium carbonate, cesium carbonate, calcium carbonate or sodium hydrogencarbonate or an organic base such as triethylamine, pyridine or N,N-dialkylaniline, preferably using sodium hydrogencarbonate, and also using a polar solvent such as acetonitrile or dimethylformamide (DMF), a halogenated hydrocarbon solvent typified by chloroform or methylene chloride, an ether-based solvent typified by ether or THF or an alcoholic solvent such as methanol or ethanol, preferably using ethanol as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h.

If $R^6$ or $R^7$ is a halogen atom, dehalogenation may be performed in the presence of palladium using acetic acid as a solvent at a temperature ranging from room temperature to the one where the reaction mixture is heated under reflux, preferably at the temperature where heating under reflux is effected, for a sufficient time to ensure adequate progress of the reaction, specifically for 1 h to 12 h. The substituent changes described above may also be applied to $R^8$.

If necessary, the compound of (XXIII) or (XXIV) may be subjected to further substituent changes so as to produce the compound of the formula (I) or a salt thereof:

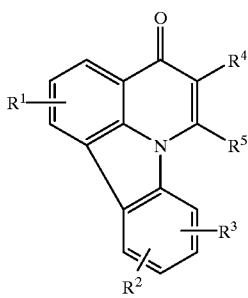

(I)

According to another method of producing the compound of the formula (I) or a salt thereof, $R^6$, $R^7$ and $R^8$ in the compound of the formula (XXII) may be changed to other substituents by the same reactions as described above to prepare the compound represented by the formula (XXIV) which is then reacted with the reactive halogen derivative of the formula (XX) in the manner already described above.

Process 2

Depending on the positions, types and number of substituents and the selectivity in ring closure (cyclization), the compound of the formula (I) may occasionally be synthesized more efficiently by Processes 2 and 3 than by Process 1.

A phenylhydrazine derivative represented by the following formula (V):

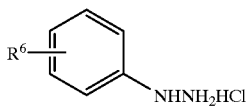

(V)

and a cyclohexanone derivative represented by the following formula (XIV) or a salt thereof:

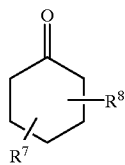

(XIV)

are subjected to the Fischer indole synthesis in the presence or absence of zinc chloride, a Lewis acid or a proton acid catalyst, preferably in their absence, using acetic acid as a solvent at a temperature ranging from room temperature to the one where the reaction mixture is heated under reflux, preferably at the temperature where heating under reflux is effected, for a sufficient time to ensure adequate progress of the reaction, specifically for 1 h to 3 h so as to yield a tetrahydrocarbazole derivative represented by the following general formula (VI):

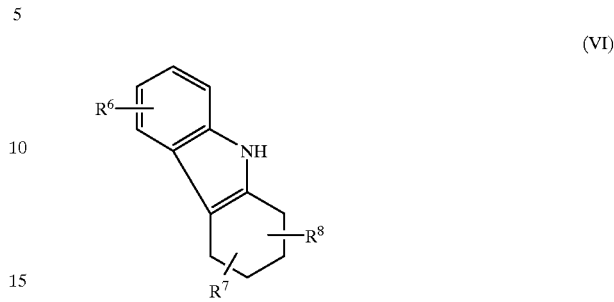

(VI)

Subsequently, in the same manner as employed to achieve transformation from the formula (II) to (III) in Process 1, the compound (VI) is derivated to the following formula (VII):

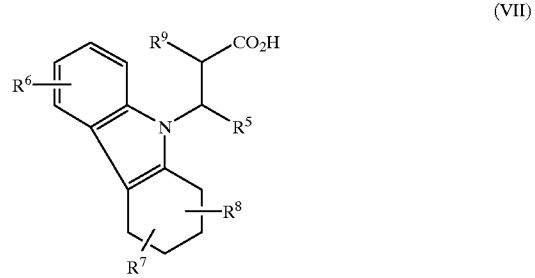

(VII)

and, subsequently, in the same manner as employed to achieve transformation from the formula (III) to (IV) in Process 1, the compound (VII) is cyclized to give an intermediate of the following formula (VIII):

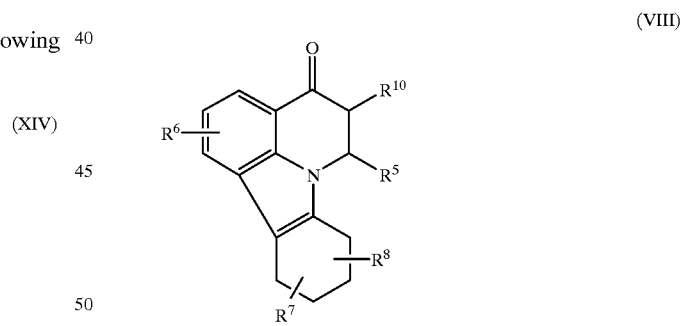

(VIII)

and the same procedure as employed to achieve transformation from the formula (IV) to (I) in Process 1 is repeated, followed by aromatization using DDQ to produce The compound represented by the following general formula (I) or a salt thereof:

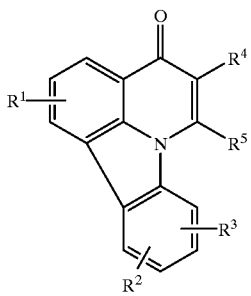
(I)

Process 3

An aniline derivative represented by the following general formula (IX) or a salt thereof:

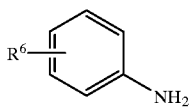
(IX)

is subjected to the same procedure as employed to achieve transformation from the formula (II) to (III) in Process 1, thereby giving an intermediate of the following formula (X):

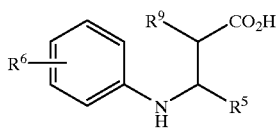
(X)

and the same procedure as employed to achieve transformation from the formula (III) to (IV) in Process 1 is repeated to perform cyclization, thereby yielding a compound of the following general formula (XI):

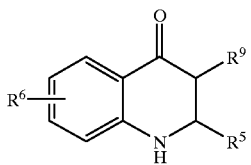
(XI)

This compound and an aryl halide represented by the following general formula (XV)

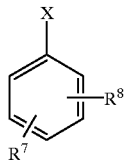
(XV)

are subjected to Ullmann reaction in the presence of a copper powder, copper oxide or an iron powder, preferably in the presence of copper oxide, using an inorganic base such as potassium hydroxide or potassium carbonate or an alkali metal reagent such as sodium alkoxide or sodium hydroxide, preferably using potassium carbonate either without solvents or using a suitable high-boiling point solvent such as DMF, DMSO, DME, dibutyl ether, xylene, decalin or 1,3-dimethyl-2-imidazolidone (DMI), preferably in the absence of solvents, at 100–200° C., preferably at 180–190° C. for a sufficient time to ensure adequate progress of the reaction, specifically for 1 h to 12 h, thereby introducing a desired substituted phenyl group to derivate a compound of the formula (XII):

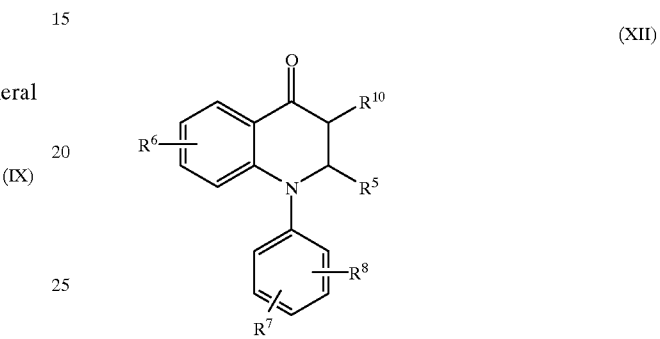
(XII)

and the same procedure as employed to achieve transformation from the formula (IV) to (I) in Process 1 is repeated to give an intermediate compound of the formula (XIII):

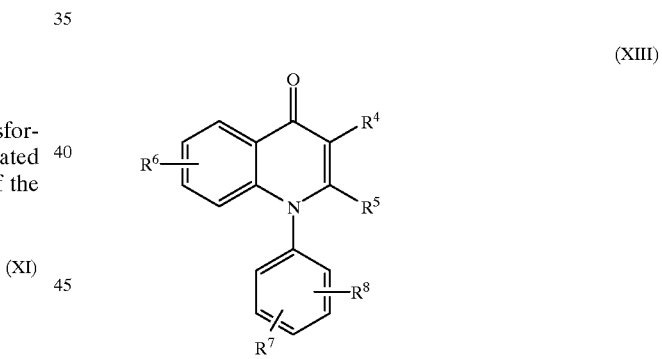
(XIII)

which is then subjected to an aromatic carbon-carbon bond formation in the presence of palladium acetate, a boron trifluoride acetic acid complex, palladium chloride or the like, preferably in the presence of palladium acetate, using a solvent such as acetic acid, trifluoroacetic acid or methanesulfonic acid, preferably using acetic acid as the solvent, at a temperature ranging from room temperature to the one where the reaction mixture is heated under reflux, preferably at the temperature where heating under reflux is effected, for a sufficient time to ensure adequate progress of the reaction, specifically for 1 h to 5 h, and the reaction product may optionally be subjected to the same reaction for substituent changes as in Process 1, thereby yielding the compound of the following general formula (I) or a salt thereof:

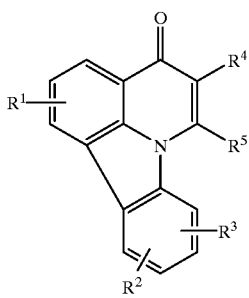

(I)

If the individual compounds synthesized by the processes described above contain reactive substituents such as a hydroxyl group, an amino group, a carboxyl group and a thiol group, they may be protected appropriately in the respective steps of reaction and later removed at appropriate stages. The methods of introducing and removing such protective groups may appropriately be selected in accordance with the types of the groups to be protected and the protective groups to be used and suitable methods may be found in the Overview in "Protective Groups in Organic Synthesis", 2nd Ed. 1991.

It should also be noted that the compounds prepared in the respective steps of each production process may have the functional groups optionally oxidized or reduced in the usual manner.

The medical terms as used in the specification are defined below.

"Pulmonary hypertension" refers to various diseases manifesting hypertension in the pulmonary artery, which include chronic bronchitis, peripheral lesions in the airway, pulmonary pneumatosis, bronchiectasis, sarcoidosis, sequelae of pulmonary tuberculosis, diffuse interstitial pneumonia, diffuse bronchiolitis, asthma, fibrosis of the lung, collagenosis, pulmonary thromboembolism, pulmonary venous obstruction, pulmonary arteritis and primary pulmonary hypertension; also included in the category of pulmonary hypertension are diseases such as cor pulmonale in a developed phase of pulmonary hypertension.

Patients manifesting pulmonary hypertension suffer from disorders in pulmonary circulation due to the obstruction of pulmonary vessels and experience cyanosis and dyspnea. They often complain of palpitation and pectoralgia, as well as coughing.

The term "ischemic heart diseases" as used herein is a generic name for the diseases that occur as the result of disorders in coronary circulation due to various causes and includes angina of effort, resting angina, unstable angina, variant angina pectoris, acute heart failure, chronic heart failure, myocardial infarction, cardiac edema and arrhythmia.

Patients with ischemic heart diseases suffer from transient or persisting anginal pains such as pectoralgia and pressure felt in the chest, which are accompanied by fatigue, dizziness, panting, vomiting and consciousness derangement. Heart failure involves dyspnea and cyanosis and, due to the marked drop in blood pressure, shocks also occur as exemplified by bradycardia, cold sweat, palor of the face, etc.

"Diseases against which the cGMP-PDE inhibitory action is effective" is a generic term for the diseases against which the increase in cGMP is believed to be effective. Aside from the diseases and symptoms mentioned in the preceding paragraphs, the diseases under consideration include arteriosclerosis, post-PTCA restenosis, thrombosis (caused by, for example, injury of vascular walls, arteriosclerosis, angitis and platelet aggregation), asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), peripheral circulatory disorders, peripheral vascular diseases, cerebral circulatory disorders (e.g. cerebral infarction), brain dysfunction, dementia, allergic diseases (e.g. atopic dermatitis and allergic rhinitis) and hypertension.

"Renal failure" refers to those pathologic and clinical symptoms which are caused by defective function of the kidneys, i.e., the decrease in glomerular filtration rate (GFR) due to various etiological factors. In chronic renal failure, some glomeruli give a sclerotic image but the progress of the sclerosis to less affected glomeruli would bring the renal failure to a developed phase.% As a result, various excreted substances will progressively accumulate in the body to cause "uremia". Polyuria and nocturia also occur due to disordered concentrating ability. If inappropriate Na and water loading accompanies renal failure, reduced GFR prevents sufficient compensation, causing edema, pulmonary edema, congestive heart failure, hypertension, etc.

EXPERIMENTS

On the pages that follow, the pharmacological action, toxicity and other features of representative compounds of the invention are described but it should be understood that the present invention will in no way be limited by the following description.

Experiment 1

PDE Inhibiting Activity

Method

On the basis of the method of Lugnier et al. (Biochem. Pharmacol., 35, 1743–1751, 1986), PDE was purified from the aorta in a dog. The canine aorta was minced and homogenized with a Waring Blender and a glass homogenizer in six volumes of a Tris-HCl buffer solution (pH 7.5, 20 mM) containing 2 mM magnesium acetate, 5 mM ethylenediaminetetraacetic acid (EDTA), 100 μg/mL of phenylmethylsulforyl fluoride and 15 mM 2-mercaptoethanol (2-ME), and centrifuged at 1200 xg for 30 min. The supernatant was separated and salted out with ammonium sulfate which was added to 45% saturation. The resulting precipitated fraction was resuspended in a Tris-HCl buffer solution (pH 7.5, 20 mM) containing 2 mM magnesium acetate and 1 mM 2-ME, dialyzed overnight and applied to a DEAE-trisacryl column (DEAE TRISACRYL M:IBF). By elution with a sodium chloride gradient (0–0.4 M), PDE types V and III were separated from the other isozymes. The supernatant fraction of 45% saturated ammonium sulfate was further mixed with ammonium sulfate to 65% saturation and salted out. The resulting precipitated fraction was similarly applied to the DEAE-trisacryl column and eluted by a sodium chloride gradient (0–0.4 M) so as to separate PDE type I.

The thus obtained PDE types V, III and I were measured for their activity in accordance with the method of Thompson et al. (Adv. Cyclic Nucleotide Res., 10, 69–72, 1979) and the method of Wells et al. (Biochim. Biophys. Acta, 384, 430–443, 1975). Specifically, a purified PDE sample was added to 50 mM Tris-HCl buffer solution (pH 7.5) containing 1 μM of substrate cGMP or cAMP (containing tritium-labelled cGMP or cAMP), 1 mM EGTA and 2 mM magnesium acetate. For PDE activity measurement, enzymatically produced 5' GMP or 5' AMP was further hydrolyzed into guanosine or adenosine with snake venom and separated from the substrate by means of an ion-exchange resin (Dowex 1-X2), followed by measuring with a scintillation counter. The activity of each test compound was determined as a percentage of the DPE activity measured when it was added as a dimethyl sulfoxide solution (DMSO) and its $IC_{50}$ (50% inhibition concentration) was calculated by the probit method. The final concentration of DMSO was adjusted to be no more than 2% in consideration of the effect on PDE activity. The results are shown in Table 1 below.

TABLE 1

PDE Inhibiting Activity

Inhibition Activity $IC_{50}$ (μM)

| Ex. No. | Type V | Type III | Type I |
|---|---|---|---|
| 2 | 0.10 | 3.6 | >30 |
| 3 | 0.0075 | >30 | >30 |
| 4 | 0.0038 | 6.8 | >30 |
| 5 | 0.0055 | 19 | >30 |
| 7 | 0.0043 | >30 | >30 |
| 15 | 0.045 | 15 | >30 |
| 18 | 0.059 | 1.9 | >30 |
| 22 | 0.11 | 11 | >30 |
| 48 | 0.10 | >100 | >100 |
| 49 | 0.10 | 198 | >300 |
| 50 | 0.0015 | >30 | >30 |
| 51 | 0.0017 | >30 | >30 |
| 52 | 0.0035 | >30 | >30 |
| 57 | 0.015 | >30 | >30 |
| 58 | 0.050 | >10 | >10 |
| 59 | 0.030 | >100 | >100 |
| 60 | 0.0009 | 15 | >30 |
| 61 | 0.0008 | >30 | >30 |
| 62 | 0.0020 | >30 | >30 |
| 63 | 0.19 | >30 | >30 |
| 64 | 0.011 | 81 | >100 |
| 66 | 0.010 | >30 | >30 |
| 76 | 0.021 | >30 | >30 |
| 82 | 0.10 | >100 | >100 |
| 83 | 0.0047 | >30 | >30 |
| 101 | 0.0047 | >30 | >30 |
| 102 | 0.0073 | 9.3 | >30 |
| 103 | 0.091 | >30 | >30 |
| 104 | 0.0032 | 3.5 | >30 |
| 105 | 0.018 | 2.4 | >30 |
| 106 | 0.088 | >30 | >30 |
| 107 | 0.021 | >30 | >30 |
| 109 | 0.067 | 14 | >30 |
| 110 | 0.0079 | 10 | >30 |
| 121 | 0.026 | >30 | >30 |
| 122 | 0.0090 | 13 | >30 |
| 155 | 0.36 | 7.3 | 48 |
| 156 | 0.20 | 5.6 | >30 |
| 193 | 0.43 | 6.9 | >100 |
| 226 | 0.060 | 12 | >30 |
| 245 | 0.042 | 3.9 | >30 |
| 264 | 0.080 | >30 | >30 |
| 277 | 0.040 | >30 | >30 |
| 283 | 0.014 | 3.6 | >30 |
| 289 | 0.017 | 2.5 | >30 |

Each of the compounds of the invention under test was found to have a marked PDE type V inhibitory action and high selectivity in enzyme inhibition.

Experiment 2

Pulmonary Arterial Pressure Lowering Action

Method

Adult mongrel dogs were anesthetized by intramuscular administration of 20 mg/kg of ketamine and intravenous administration of 20 mL/kg of physiological saline containing 5 mg/mL of α-chloralose; under artificial respiration, the aortic pressure was measured with a catheter inserted into the femoral artery and the pulmonary arterial pressure with a Swan-Ganz catheter inserted into the pulmonary artery. Anesthesia was maintained by intravenous administration of physiological saline containing 5 mg/mL of α-chloralose at a rate of 5 mL/kg per hour. Comparison was made between nitroglycerin, nifedipine and test compounds which were administered intravenously at doses of 0.01–1 mg/kg. Each test compound was dissolved in dimethylformamide (DMF) and sequentially diluted with polyethylene glycol 200 and water to give respective proportions of 20, 50 and 30% (v/v) and administered by injection into the right femoral vein in a volume of 0.3 mL/kg. The results are shown in Table 2 below, in which maximal percent decreases in the pulmonary arterial pressure and aortic pressure are listed to show the effectiveness of each test compound in lowering the pulmonary arterial pressure and the systemic blood pressure, respectively.

TABLE 2

Pulmonary Arterial Pressure Lowering Action

| Ex. No. | Dose mg/kg | Reduction in pulmonary arterial pressure, % | Reduction in systemic blood pressure, % |
|---|---|---|---|
| 3 | 0.3 | 19 | 12 |
| 50 | 0.3 | 33 | 13 |
| 60 | 0.3 | 20 | 8 |
| 102 | 0.3 | 24 | 19 |
| 105 | 0.1 | 16 | 12 |
| 109 | 0.3 | 19 | 11 |
| 110 | 0.3 | 23 | 7 |
| 193 | 0.3 | 16 | 1 |
| 279 | 0.3 | 17 | 4 |
| 285 | 0.3 | 16 | 2 |
| 291 | 0.3 | 13 | 4 |
| Nitroglycerin | 0.01 | 19 | 30 |
| Nifedipine | 0.01 | 3 | 18 |

The test compounds of the invention lowered the pulmonary arterial pressure by greater degrees than the systemic blood pressure and, hence, had selectivity for pulmonary arterial pressure. On the other hand, the two control drugs nitroglycerin and nifedipine lowered the systemic blood pressure by greater degrees than the pulmonary arterial pressure.

Experiment 3

Coronary Artery Diameter Increasing Action

Method

Adult mongrel dogs were thoracotomized under anesthesia with α-chloralose and the circumflex branch of the left coronary artery was ablated; a pair of ultrasonic crystals were attached to the tunica extima for measuring the diameter of the coronary artery whereas an electromagnetic flow probe was attached to the peripheral side to measure the coronary blood flow. Nitroglycerin, dipyridamole and each test compound were administered intravenously for comparison. Each test compound was dissolved in dimethylformamide and diluted sequentially with polyethylene glycol 200 and water to give respective proportions of 20, 50 and 30% (v/v). The results are shown in Table 3, in which the maximal changes in the diameter of the coronary artery and the coronary blood flow are expressed in terms of the ratio to the respective changes caused by 10 μg/kg of nitroglycerin.

TABLE 3

Coronary Artery Diameter Increasing Action

| Ex. No. | Dose mg/kg | Coronary artery diameter (relative to nitroglycerin) | Coronary blood flow (relative to nitroglycerin) |
|---|---|---|---|
| 155 | 1 | 1.47 | 0.79 |
| 193 | 1 | 1.44 | 1.40 |
| 278 | 1 | 1.50 | 0.04 |
| Dipyridamole | 0.03 | 0.17 | 2.66 |

Dipyridamole used as a control drug had a by far greater action in increasing the coronary blood flow (which is a measure of the dilation of small blood vessels) than the coronary artery diameter. On the other hand, the test compounds of the invention increased more of the coronary artery diameter than the coronary blood flow and it was at least comparable to nitroglycerin in selective relaxation of large coronary artery; obviously, the test compounds were in sharp contrast with dipyridamole which increased more of the coronary blood flow than the coronary artery diameter.

Experiment 4

Toxicity Test

Selected compounds of the invention were tested for their toxicity. Four weeks old male Wistar rats were perorally administered the compounds of Examples 3, 50, 102, 105, 109, 110 and 193 (to be described below) for 4 days at a daily dose of 100 mg/kg. After the end of administration, none of the animals were found to be dead until the next day and there was nothing abnormal in their body weights and general symptoms.

The four experiments described above demonstrated that the compounds of the invention had a marked PDE type V inhibitory action and an extremely high selectivity in enzyme inhibition. In addition, the compounds of the invention lowered the pulmonary arterial pressure in vivo by greater degrees than the systemic blood pressure and, hence, had selectivity for the pulmonary arterial pressure in their action. They also increased more of the coronary artery diameter than the coronary blood flow and, hence, was shown to be at least comparable to nitroglycerin (the drug of choice for treatment of angina pectoris) in selective relaxation of large coronary artery. Hence, it was suggested that the compounds of the invention had no direct effect on the heart and would not cause any "steal" nor tolerance. The compounds of the invention were also found to retard platelet aggregation. On the other hand, the compounds of the invention were shown to be low in toxicity since nothing abnormal was found in the result of the toxicity test.

Thus, the compounds of the invention having a pyridocarbazole skeleton had a marked PDE type V inhibitory action and an extremely high selectivity in enzyme inhibition and they were also found to be effective in animal models; hence, they should be effective in treating or preventing pulmonary hypertension and ischemic heart diseases. They are also useful as circulation regulators during or after surgical operation.

"Pulmonary hypertension" refers to various diseases manifesting hypertension in the pulmonary artery, which include chronic bronchitis, peripheral lesions in the airway, pulmonary pneumatosis, bronchiectasis, sarcoidosis, sequelae of pulmonary tuberculosis, diffuse interstitial pneumonia, diffuse bronchiolitis, asthma, fibrosis of the lung, collagenosis, pulmonary thromboembolism, pulmonary venous obstruction, pulmonary arteritis and primary pulmonary hypertension; also included in the category of pulmonary hypertension are diseases such as cor pulmonale in a developed phase of pulmonary hypertension.

Patients manifesting pulmonary hypertension suffer from disorders in pulmonary circulation due to the obstruction of pulmonary vessels and experience cyanosis and dyspnea. They often complain of palpitation and pectoralgia, as well as coughing. The pharmaceutical compositions of the invention are effective against these symptoms.

The term "ischemic heart diseases" as used herein is a generic name for the diseases that occur as the result of disorders in coronary circulation due to various etiological causes and includes angina of effort, resting angina, unstable angina, variant angina pectoris, acute heart failure, chronic heart failure, myocardial infarction, cardiac edema and arrhythmia.

Patients with ischemic cardiac diseases suffer from transient or persisting anginal pains such as pectoralgia and pressure felt in the chest, which are accompanied by fatigue, dizziness, panting, vomiting and consciousness derangement. Heart failure involves dyspnea and cyanosis and, due to the marked drop in blood pressure, shocks also occur as exemplified by bradycardia, cold sweat, palor of the face, etc. The pharmaceutical compositions of the invention are effective against these symptoms.

The compounds of the invention increase the cGMP level markedly and are also applicable to arteriosclerosis, post-PTCA restenosis and thrombosis (caused by, for example, injury of vascular walls, arteriosclerosis, angitis and platelet aggregation). Since all of these diseases of the coronary artery are of particular interest as etiological factors in ischemic heart diseases, the pharmaceutical compositions of the invention hold promise as highly effective agents for preventing and/or treating ischemic heart diseases.

The proliferation of vascular smooth muscle cells which is an etiological factor to the above-mentioned arteriosclerotic diseases in the coronary artery is believed to be closely involved in post-PTCA coronary restenosis and the arteriosclerotic thickening of blood vessels at other sites; hence, increased cGMP levels will contribute to retard the proliferation of vascular smooth muscle cells in arteriosclerosis and post-PTCA restenosis, potentially preventing these diseases. Several of the diseases that eventually manifest pulmonary hypertension do not actually have the complication of pulmonary hypertension in the early period of their onset as in the case of pulmonary pneumatosis and bronchitis; however, it is generally held that as hypoventilation is prolonged, the thickening of pulmonary blood vessels, the growth of arteriolar smooth muscle and other factors cause disorders in pulmonary circulation, eventually developing to irreversible pulmonary hypertension. Hence, if the pharmaceutical compositions of the invention are administered at the initial stage of those diseases in a preventive manner in order to retard the growth of vascular smooth muscle cells, it is possible to regard the subsequent onset of pulmonary hypertension.

Aside from those listed above, the "diseases against which the cGMP-PDE inhibitory action is effective" include the following against which increased cGMP levels are believed to be effective: asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), peripheral circulatory disorders, peripheral vascular diseases, cerebral circulatory disorders (e.g. cerebral infarction), brain dysfunction, dementia, allergic diseases (e.g. atopic dermatitis and allergic rhinitis) and hypertension. The pharmaceutical compositions of the invention are also applicable to these diseases, among which asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence) are worth particular mention.

"Renal failure" refers to those pathologic and, clinical symptoms which are manifested by defective function of the kidneys, i.e., the decrease in glomerular filtration rate (GFR) due to various etiological factors. In chronic renal failure, some glomeruli give a sclerotic image but the progress of the sclerosis to less affected glomeruli would bring the renal failure to developed phase. The dysfunction of glomeruli is etiologically variable in many ways but if the cGMP level is increased, the kinetics of renal blood circulation is improved to elevate the GFR and, as a result, the in vivo accumulation of various excreted substances is effectively retarded to alleviate uremia. In addition, polyuria and nocturia due to disordered concentrating ability can be alleviated. If inappropriate Na and water loading accompanies renal failure, reduced GFR prevents sufficient compensation, causing edema, pulmonary edema, congestive heart failure, hypertension, etc. These symptoms can also be alleviated. Increased cGMP levels retard the increase of mesangial cells and matrix and, hence, the sclerosis of glomeruli can effectively be retarded to slow down the progress of glomerular diseases and renal failure. Briefly, by increasing the cGMP level, the process of development from renal failure to an end-stage kidney which has heretofore been considered to be practically impossible to check by drug administration can be retarded to eventually circumvent the necessity of performing renal dialysis.

The pharmaceuticals of the invention are administered in the form of pharmaceutical compositions. The pharmaceutical compositions of the invention may contain at least one of the compounds of the invention which are represented by the general formula (I) and they are prepared by being combined with pharmaceutically acceptable vehicles. More specifically, excipients (e.g., lactose, sucrose, mannitol, crystalline cellulose and silicic acid), binders [e.g., crystalline cellulose, sugars (e.g., mannitol and sucrose), dextrin, hydroxypropyl cellulose (HPC), hydroxymethyl cellulose (HPMC), polyvinyl pyrrolidone (PVP) and macrogol], lubricants (e.g., magnesium stearate, calcium stearate and talc), coloring agents, flavoring agents, disintegrants (e.g., corn starch and carboxymethyl cellulose), antiseptics, isotonic vehicles, stabilizers (e.g., sugar and sugar alcohol), dispersants, antioxidants [e.g., ascorbic acid, butyl hydroxyanisole (BHA), propyl gallate and dl-α-tocopherol], buffering agents, preservatives (e.g., parabens, benzyl alcohol and benzalkonium chloride), fragrances (e.g., vanillin, 1-menthol and rose oil), solubilizers (e.g., cholesterol and triethanolamine), suspending or emulsifying agents, and other common suitable vehicles or solvents may be combined appropriately with the compounds of the invention into various dosage forms.

Exemplary dosage forms include tablets, capsules, granules, powders, suppositories, vaginal suppositories, syrups (e.g. oral liquids and emulsions), inhalants, external preparation, injections, etc.; these can be administered to the patient either orally or parenterally (such as by intravenous, intra-arterial, subcutaneous, intramuscular, intrarectal or intravaginal administration, or by transcutaneous or transmucomembranous absorption).

These dosage forms are typically administered in daily doses of 0.1 mg–2.5 g, preferably 0.5 mg–1.0 g, more preferably 1 mg–500 mg, per adult but these can be adjusted as appropriate for the severity of the disease or the route of administration.

Oral or parenteral administration may be performed with the entire dose given at a time or divided in 2–6 portions; alternatively, continuous administration may be performed as by intravenous drip infusion.

EXAMPLES

The following examples are provided for the purpose of further illustrating the present invention but are in no way to be taken as limiting.

NMR measurements were performed with JEOL JNM-EX270 FT-NMR (product of JEOL Ltd.) or JEOL JNM-LA300 FT-NMR (product of JEOL Ltd.; the data taken with this model are preceded by an asterisk); IR measurements with HORIBA FT-200 (product of HORIBA Ltd.); and b.p. measurements with Mettler FP-80, FP-82, FP-81HT or FP-90 (each produced by Mettler Instruments AG). In the following examples, the yield of each "title compound" is parenthesized in both absolute and relative terms.

Example 1

Synthesis of 10-bromo-2-methoxy-5-(3-pyridylmethyl)-4H-pyrido [3,2,1-jk]carbazole-4-one

[Step 1] Synthesis of 3-bromo-6-methoxycarbazole

Sodium (23.3 g) was added in small portions to anhydrous methanol (260 ml) to form a solution at room temperature. Subsequently, anhydrous dimethylformamide (1,400 ml), copper iodide (117 g) and 3,6-dibromocarbazole (100 g) were added in succession and the mixture was heated under reflux for 2 hours in an argon atmosphere. The reaction mixture was filtered through Celite while hot and left to cool, followed by addition of water (2 L) and extraction with methylene chloride. The methylene chloride layer was washed with water, 1N hydrochloric acid, water and saturated aqueous solution of sodium chloride in succession, dried over anhydrous sodium sulfate and the solvent was evaporated under reduced pressure. The residue was purified by silica gel column chromatography (eluent: hexane/methylene chloride=1:1) to obtain the title compound (33.4 g; 39%).

m.p.:149.9–151.1° C.

IR spectrum (KBr tab.) ν cm$^{-1}$:3390, 2900, 1491, 1205, 1169, 806

NMR spectrum (DMSO-d$_6$) δ ppm:11.23 (1H, s) , 8.36 (1H, s) , 7.78 (1H, d, J=2.0Hz), 7.48-7.40 (3H, m), 7.0 7 (1H, dd, J=8.8, 1.5Hz), 3.84 (3H, s)

[Step 2] Synthesis of 3-bromo-6-methoxycarbazole-N-β-propionic acid

The compound (30 g) obtained in step 1 was suspended in acetone (80 ml) and the suspension was cooled to 0° C. in an ice bath, followed by addition of methyl acrylate (25 ml) and then dropwise addition of Triton B (10 ml). The ice bath was removed and the mixture was stirred for 1 hour at room temperature and thereafter the solvent was evaporated under reduced pressure. The resulting residue was suspended in methanol (30 ml) and sodium hydroxide (10 g) dissolved in water (60 ml) was added dropwise at room temperature and the mixture was refluxed for 20 minutes. The solvent was evaporated under reduced pressure and thereafter water and ether were added to separate the mixture into the aqueous and the organic phase. The aqueous layer was rendered acidic by addition of 4 N hydrochloric acid and the resulting precipitate was dissolved in ethyl acetate; the solution was washed with water and saturated aqueous solution of sodium chloride, dried over anhydrous sodium sulfate and the solvent was evaporated under reduced pressure. The residual crude crystals were washed with hexane/ether and recovered by filtration to obtain the title compound (33.6 g; 88%).
m.p.: 149.7–152.1° C.
IR spectrum (KBr tab.) ν cm$^{-1}$:3425, 2920, 1705, 1697, 1491, 1298, 802
NMR spectrum (DMSO-d$_6$) δ ppm:8.38 (1H, d, J=1.5Hz), 7.81 (1H, d, J=2.4Hz), 7.59-7.49 (3H, m), 7.11 (1H, dd, J=8.8, 2.4Hz), 4.57 (2H, t, J=6.8Hz), 3.84 (3H, s), 2.67 (2H, t, J=6.8Hz)

[Step 3] Synthesis of 10-bromo-5,6-dihydro-2-methoxy-4H-pyrido [3,2,1-jk]carbazole-4-one The compound (24 g) obtained in step 2 was suspended in anhydrous chloroform (500 ml) and PPE (118 g) dissolved in anhydrous chloroform (350 ml) was added at room temperature and the resulting mixture was heated under reflux for 1 hour in an argon atmosphere. After allowing to cool, the mixture was poured into 1 N sodium hydroxide (500 ml) and extracted with chloroform. The chloroform layer was washed with saturated aqueous solution of sodium chloride, dried over anhydrous sodium sulfate and the solvent was evaporated under reduced pressure. The residue was purified by silica gel flash column chromatography (eluent: hexane/methylene chloride=1:3), and the crude purification product was washed with methanol and recovered by filtration to obtain the title compound (17.1 g; 75%).
m.p.: 175.2–176.1° C.
IR spectrum (KBr tab.) ν cm$^{-1}$: 2910, 1672, 1497, 1479, 797
NMR spectrum (DMSO-d$_6$) δ ppm: 8.49 (1H, s) , 8.14 (1H, d, J=2.4Hz), 7.64 (2H, bs), 7.36 (1H, d, J=2.0Hz), 4.54 (2H, t, J=7.1Hz), 3.88 (3H, s), 3.13 (2H, t, J=7.1Hz)

[Step 4] Synthesis of 10-bromo-2-methoxy-5-(3-pyridylmethyl)-4H-pyrido [3,2,1-jk]carbazole-4-one The compound (27 g) obtained in step 3 was suspended in ethanol (600 ml) and pyridine-3-aldehyde (15 ml) and sodium hydroxide (20 g) which was dissolved in water (100 ml) were added to the suspension at room temperature and the mixture was stirred for 12 hours at room temperature. About one half of the solvent was evaporated under reduced pressure and the precipitated crystals were recovered by filtration and washed with water, ethanol and ether in succession to obtain the title compound (30 g; 87%).

Example 2

Synthesis of 10-bromo-2-hydroxy-5-(3-pyridylmethyl)-4H-pyrido [3,2,1-jk]carbazole-4-one 10-bromo-2-methoxy-5-(3-pyridylmethyl)-4H-pyrido [3,2,1-jk]carbazole-4-one (10.2 g) obtained in Example 1 was suspended in anhydrous methylene chloride (1000 ml), and boron tribromide (25 g) was added dropwise at room temperature. The reaction mixture was stirred at room temperature for 12 hours, and poured into ice water (500 ml). To this mixture was added saturated aqueous solution of sodium carbonate until the termination of foaming. The crystals precipitated were recovered by filtration. The thus obtained crude crystals were washed in a mixture of methylene chloride and methanol to obtain the title compound (6.4 g, 65%).

Example 3

Synthesis of 10-bromo-2-t-butoxycarbonylmethyloxy-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (4.4 g) obtained in Example 2 was suspended in dimethyl sulfoxide (250 ml), and to the suspension was added potassium carbonate (4.5 g). The mixture was stirred at room temperature for 30 minutes, and t-butyl bromoacetate (2.1 ml) was added. The mixture was stirred at room temperature for 12 hours, and the reaction mixture was poured into ice water (300 ml) and extracted with methylene chloride. The methylene chloride layer was washed with saturated aqueous solution of sodium chloride, and dried over anhydrous sodium sulfate, and the solvent was evaporated under reduced pressure. The residue was purified by silica gel flash column chromatography (eluent: methylene chloride containing 3% methanol) to produce the title compound (3.4 g, 63%).

Example 4

Synthesis of 10-bromo-2-i-propoxycarbonylmethyloxy-5- (3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (3.6 g) obtained in Example 2 was suspended in dimethyl sulfoxide (200 ml), and to the suspension was added potassium carbonate (2.5 g), and the mixture was stirred at room temperature for 30 minutes. i-propyl bromoacetate (1.4 ml) was added, and the mixture was stirred at room temperature for 12 hours. The reaction mixture was poured into ice water (300 ml) and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: methylene chloride containing 3% methanol), and the crude product was washed with ether and a small amount of methanol in succession, and recovered by filtration to obtain the title compound (2.6 g, 59%).

Example 5

Synthesis of 10-bromo-2-ethoxycarbonylmethyloxy-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (13.9 g) obtained in Example 2 was suspended in dimethyl sulfoxide (500 ml), and to the suspension was added potassium carbonate (9.5 g), and the mixture was stirred at room temperature for 30 minutes. Ethyl bromoacetate (4.2 ml) was added, and the mixture was stirred at room temperature for 12 hours. The reaction mixture was poured into ice water (500 ml) and precipitated crystals were recovered by filtration. The thus obtained crude crystals were purified by silica gel flash column chromatography (eluent: methylene chloride containing 3% methanol), and the crude product was re-precipitated from chloroform-hexane and recovered by filtration to obtain the title compound (9.0 g, 53%).

Example 6

Synthesis of 10-bromo-2-carboxymethyloxy-5-(3-pyridylmethyl)-4H-pyrido [3,2,1-jk]carbazole-4-one 10-bromo-2-ethoxycarbonylmethyloxy-5-(3-pyridylmethyl)-4H-pyrido [3,2,1-jk]carbazole-4-one (2 g) obtained in Example 5 was suspended in ethanol (100 ml), and to the suspension was added 1N aqueous solution of sodium hydroxide (20 ml), and the mixture was stirred at room temperature for 12 hours. After evaporate the solvent under reduced pressure, 4N sodium hydroxide and methylene chloride were added to the residue for phase separation. To the aqueous layer was added 4N hydrochloric acid to a pH of 6, and the precipitated crystals were recovered by filtration to obtain the title compound (1.8 g, 96%).

Example 7

Synthesis of 10-bromo-2-n-propoxycarbonylmethyloxy-5-(3-pyridylmethyl)-4H-pyrido [3,2,1-jk]carbazole-4-one The procedure of Example 3 was repeated by using 10-bromo-2-hydroxy-5-(3-pyridylmethyl)-4H-pyrido [3,2,1-jk]carbazole-4-one (250 mg) and n-propyl bromoacetate (0.1 ml) to obtain the title compound (170 mg, 55%).

Example 8

Synthesis of 10-bromo-2-(1-ethoxycarbonyl-1-methylethyloxy)-5-(3-pyridylmethyl)-4H-pyrido[3,2,1-jk]carbazole-4-one The procedure of Example 3 was repeated by using 10-bromo-2-hydroxy-5-(3-pyridylmethyl)-4H-pyrido [3,2,1-jk]carbazole-4-one (500 mg) and ethyl α-bromoisobutyrate (0.22 ml) to obtain the title compound (470 mg, 74%).

Example 14

Synthesis of 10-bromo-2-n-pentyloxycarbonylmethyloxy-5-(3-pyridylmethyl)-4H-pyrido [3,2,1-jk]carbazole-4-one 10-bromo-2-carboxymethyloxy-5-(3-pyridylmethyl)-4H-pyrido [3,2,1-jk]carbazole-4-one (300 mg) obtained in Example 6 was suspended in anhydrous benzene (10 ml), and to the suspension was added thionyl chloride (0.95 ml) at room temperature. The mixture was heated under reflux in an argon atmosphere for 3 hours and allowed to cool. The solvent was evaporated under reduced pressure, and after adding anhydrous benzene (5 ml), the solvent was evaporated again. The resulting residue was dissolved in anhydrous methylene chloride (3 ml), and the solution was added dropwise to a solution of 1-pentanol (0.065 ml) and triethylamine (0.18 ml) dissolved in methylene chloride (30 ml) in an ice bath, and the solution was stirred for 20 minutes. Water was added to the reaction mixture, and the mixture was extracted with methylene chloride. The methylene chloride layer was repeatedly washed with saturated aqueous solution of sodium chloride, and dried over anhydrous sodium sulfate. The residual crude crystals were washed with ether, and recovered by filtration to obtain the title compound (200 mg, 58%).

Example 17

Synthesis of 10-bromo-2- (3-carboxy-1-trans-propenyloxy)-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (400 mg) obtained in Example 2 was suspended in dimethyl sulfoxide (30 ml), and to the suspension was added potassium carbonate (0.3 g), and the mixture was stirred at room temperature for 30 minutes. Ethyl 4-bromocrotonate (0.15 ml) was added and the mixture was stirred at room temperature for 12 hours. The reaction mixture was poured into ice water (300 ml), and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent: ethyl acetate). The resulting crude crystals were suspended in ethanol (20 ml), and 1N aqueous solution of sodium hydroxide (5 ml) was added to the suspension followed by stirring at room temperature for 12 hours. The solvent was evaporated under reduced pressure and the residue was extracted with water and ethyl acetate. 1N hydrochloric acid was added to the aqueous layer to a pH of 7, and the precipitated crystals were recovered by filtration to obtain the title compound (50 mg, 10%).

Example 18

Synthesis of 10-bromo-5-(3-pyridylmethyl)-2-(3-pyridylmethyloxy)-4H-pyrido [3,2,1-jk]carbazole-4-one 10-bromo-2-hydroxy-5-(3-pyridylmethyl)-4H-pyrido [3,2,1-jk]carbazole-4-one (3.9 g) obtained in Example 2 was suspended in dimethyl sulfoxide (230 ml), and to the suspension was added potassium carbonate (4.0 g), and the mixture was stirred at room temperature for 30 minutes. 3-picolylchloride hydrochloride (1.9 g) was added and the mixture was stirred at room temperature for 12 hours. The reaction mixture was poured into ice water (500 ml), and the precipitated crystals were recovered by filtration to obtain the title compound (2.9 g, 61%).

Example 22

Synthesis of 2-benzyloxy-10-bromo-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (2.0 g) obtained in Example 2 was suspended in a mixed solvent of anhydrous dimethylformamide (64 ml) and anhydrous tetrahydrofuran (120 ml), and sodium hydride(60%, 260 mg) was added to the suspension in an ice bath. Benzylbromide (400 mg) was added dropwise and the mixture was stirred at room temperature for 12 hours. A small amount of methanol was added to the reaction mixture, and the mixture was extracted with ethyl acetate. The ethyl acetate layer was washed with 1N aqueous solution of sodium hydroxide and saturated aqueous solution of sodium chloride in succession, dried over anhydrous sodium sulfate, and the solvent was evaporated under reduced pressure. The residue was purified by silica gel column chromatography (eluent: methylene chloride containing 3% methanol) to produce the title compound (1.7 g, 67%).

Example 24

Synthesis of 2-(5-acetoxymethyl-3-pyridylmethyloxy)-10-bromo-5-(3-pyridylmethyl)-4H-pyrido [3,2,1-jk]carbazole-4-one

[Step 1] Synthesis of dimethyl pyridine-3,5-dicarboxylate

Pyridine-3,5-dicarboxylic acid (8.3 g) was suspended in anhydrous methanol (60 ml), and thionyl chloride (11 ml) was added dropwise at room temperature. The mixture was heated under reflux for 1.5 hours in an argon atmosphere and allowed to cool. The solvent was evaporated under reduced pressure, and extracted with water-ethyl acetate. The ethyl acetate layer was washed with saturated aqueous solution of sodium hydrogencarbonate and saturated aqueous solution of sodium chloride, and dried over anhydrous sodium sulfate. The solvent was evaporated under reduced pressure to obtain the title compound (7.5 g, 78%).

m.p.: 83.5–84.5° C.

IR spectrum (KBr tab.) ν cm$^{-1}$: 1734, 1603, 1315, 1269, 1240, 995, 746

NMR spectrum (*DMSO-d$_6$) δ ppm: 9.30 (2H, s), 8.66 (1H, s), 3.93 (6H, s)

[Step 2] Synthesis of pyridine-3,5-dimethanol monoacetate

The compound (11.9 g) produced in step 1 was dissolved in anhydrous ether (300 ml), and cooled to 0° C. in an ice bath. Lithium aluminium hydride (6 g) was added in small portions and the temperature was gradually increased, and the mixture was stirred at room temperature for 12 hours. The mixture was cooled again in an ice bath, and methanol (400 ml) was added, and the solvent was evaporated under reduced pressure. The residue was purified by silica gel column chromatography (eluent: chloroform containing 3% methanol), and the crude purification product was crystallized in a hexane-ether mixed solution to produce crude crystals. The resulting crystals (3.4 g) were suspended in pyridine (10 ml), and acetyl chloride (1.8 ml) was added dropwise at room temperature. After the dropwise addition, the solvent was evaporated under reduced pressure, and the residue was purified by silica gel column chromatography (eluent: chloroform containing 3% methanol). The crude purification product was washed with methanol and recovered by filtration to obtain the title compound (1 g, 23%).

m.p.: 152.2-130.9° C.

IR spectrum (KBr tab.) ν cm$^{-1}$: 3305, 2740, 2700, 1747, 1566, 1230, 1072

NMR spectrum (*DMSO-d$_6$) δ ppm: 8.79 (1H, s), 8.74 (1H, s), 8.37 (1H, s), 5.25 (2H, s), 4.68 (2H, s), 2.11 (3H, s)

[Step 3] Synthesis of 3-acetoxymethyl-5-chloromethyl pyridine

The compound (500 mg) obtained in step 2 was suspended in anhydrous benzene (8 ml), and thionyl chloride (0.2 ml) was added dropwise at room temperature. The mixture was stirred at room temperature for 15 minutes. The solvent was evaporated under reduced pressure to obtain the title compound (540 mg; 83%).

IR spectrum (neat) ν cm$^{-1}$: 3396, 3367, 1716, 1633, 1562, 1385, 1227, 1057

NMR spectrum (*DMSO-d$_6$) δ ppm: 8.76 (1H, d, J=1.8Hz), 8.70 (1H, d, J=1.8Hz), 8.16 (1H, s), 5.20 (2H, s), 4.90 (2H, s), 2.10 (3H, s)

[Step 4] Synthesis of 2-(5-acetoxymethyl-3-pyridylmethyloxy)-10-bromo-5-(3-pyridylmethyl)-4H-pyrido [3,2,1-jk]carbazole-4-one The procedure of Example 18 was repeated by using 10-bromo-2-hydroxy-5-(3-pyridylmethyl)-4H-pyrido [3,2,1-jk]carbazole-4-one (400 mg) and the compound (280 mg) produced in step 3 to obtain the title compound (480 mg, 86%).

Example 25

Synthesis of 10-bromo-2-(5-hydroxymethyl-3-pyridylmethyloxy)-5-(3-pyridylmethyl)-4H-pyrido [3,2,1-jk]carbazole-4-one 2- (5-acetoxymethyl-3-pyridylmethyloxy)-10-bromo-5-(3-pyridylmethyl)-4H-pyrido [3,2,1-jk]carbazole-4-one (200 mg) obtained in Example 24 was suspended in methanol (10 ml), and to the suspension was added an aqueous solution of sodium hydroxide (a solution prepared by dissolving 85 mg of sodium hydroxide in 0.8 ml of water), and the mixture was stirred at room temperature for 1 hour. The crystals precipitated were washed with methanol and ether in succession, and recovered by filtration to obtain the title compound (180 mg, 97%).

Example 26

Synthesis of 10-bromo-2-(3-hydroxypropyloxy)-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (0.6 g) obtained in Example 2 was suspended in dimethyl sulfoxide (40 ml), and to the suspension was added potassium carbonate (0.8 g), and the mixture was stirred at room temperature for 30 minutes. 3-bromo-1-propanol (0.3 ml) was added and the mixture was stirred at room temperature for 12 hours. The reaction mixture was poured into ice water (500 ml), and extracted with ethyl acetate. The ethyl acetate layer was washed with saturated aqueous solution of sodium chloride, washed with anhydrous sodium sulfate, and the solvent was evaporated under reduced pressure. The residue was purified by silica gel flash column chromatography (eluent: methylene chloride containing 3% methanol) to produce the title compound (0.25 g, 37%).

Example 32

Synthesis of 10-bromo-2-(4-hydroxy-2-oxobutyloxy)-5-(3-pyridylmethyl)-4H-pyrido [3,2,1-jk]carbazole-4-one

[Step 1] Synthesis of ethyl 4-chloroacetoacetate ethylene acetal

Ethyl 4-chloroacetoacetate (5 g), ethylene glycol (17 ml) and tosylic acid (0.1 g) were added to benzene, and the mixture was heated under reflux in an argon atmosphere for 16 hours (in this process, water was compulsorily removed from the reaction system by using deansteak apparatus), and allowed to cool. After adding water to the reaction mixture, the reaction mixture was extracted with ethyl acetate. The ethyl acetate layer was washed with saturated aqueous solution of sodium chloride, washed with anhydrous sodium sulfate, and the solvent was evaporated under reduced pressure. The residue was purified by silica gel flash column chromatography (eluent: hexane/ethyl acetate=20:1) to produce the title compound (2.0 g, 32%).

IR spectrum (neat) ν cm$^{-1}$: 2983, 2900, 1736, 1207, 1101, 1032

NMR spectrum (*CDCl$_3$) δ ppm: 4.17 (2H, q, J=7.0Hz), 4.08 (4H, s), 3.75 (2H, s), 2.85 (2H, s), 1.28 (3H, t, J=7.0Hz)

[Step 2] Synthesis of 4-chloro-1-butanol-3-one ethylene acetal

The compound (1.41 g) produced in step 1 was dissolved in anhydrous tetrahydrofuran (50 ml), and lithium aluminium hydride (0.26 g) was added in small portions to the solution in an ice bath, and the mixture was stirred for 1 hour. To the solution was added in small portions saturated aqueous solution of ammonium chloride until the end of foaming. After adding water, the reaction mixture was extracted with ethyl acetate. The ethyl acetate layer was washed with saturated aqueous solution of sodium chloride, washed with anhydrous sodium sulfate, and the solvent was evaporated under reduced pressure to obtain the title compound (1.0 g, 92%).

IR spectrum (neat) ν cm$^{-1}$: 2966, 2895, 1641, 1431, 1119, 1039

NMR spectrum (*CDCl$_3$) δ ppm: 4.10 (4H, s), 3.82-3.75 (2H, m), 3.54 (2H, s), 2.44-2.41 (1H, m), 2.12 (2H, t, J=5.6Hz)

[Step 3] Synthesis of 4-chloro-1-butanol-3-one

The compound (0.25 g) produced in step 2 was dissolved in tetrahydrofuran (10 ml), and 4N hydrochloric acid (5 ml) was added to the solution. The solution was heated to 50° C. in a water bath, stirred for 16 hours, and extracted with ether. The ethyl acetate layer was washed with saturated aqueous solution of sodium chloride, washed with anhydrous sodium sulfate, and the solvent was evaporated under reduced pressure. The residue was purified by silica gel column chromatography (eluent: hexane/ethyl acetate=2:1) to produce the title compound (20 mg, 12%).

IR spectrum (neat) ν cm$^{-1}$: 2939, 2895, 1732, 1398, 1051, 770

NMR spectrum (*CDCl$_3$) δ ppm: 4.14 (2H, s), 3.95-3.89 (2H, m), 2.87 (2H, t, J=5.4Hz), 2.23-2.21 (1H, m)

[Step 4] Synthesis of 10-bromo-2-(4-hydroxy-2-oxobutyloxy)-5-(3-pyridylmethyl)-4H-pyrido [3,2,1-jk] carbazole-4-one The procedure of Example 26 was repeated by using 10-bromo-2-hydroxy-5-(3-pyridylmethyl)-4H-pyrido [3,2,1-jk]carbazole-4-one (40 mg) and the compound (15 mg) produced in step 4 to obtain the title compound (81 mg, 29%).

Example 33

Synthesis of 10-bromo-2-ethoxy-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (0.3 g) obtained in Example 2 was suspended in dimethyl sulfoxide (20 ml), and to the suspension was added potassium carbonate (0.2 g), and the mixture was stirred at room temperature for 30 minutes. Ethyl iodide (0.13 ml) was added and the mixture was stirred at 80° C. in a hot water bath for 6 hours. The reaction mixture was poured into ice water, and extracted with ethyl acetate. The ethyl acetate layer was washed with saturated aqueous solution of sodium chloride, washed with anhydrous sodium sulfate, and the solvent was evaporated under reduced pressure. The residue was purified by silica gel flash column chromatography (eluent: ethyl acetate) to obtain the title compound (0.16 g, 45%).

Example 34

Synthesis of 10-bromo-2-butoxy-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (0.3 g) obtained in Example 2 was suspended in dimethyl sulfoxide (30 ml), and to the suspension was added potassium carbonate (0.2 g), and the mixture was stirred at room temperature for 30 minutes. 1-iodobutane (0.1 ml) was added and the mixture was stirred at room temperature for 12 hours. The reaction mixture was poured into ice water, and extracted with ethyl acetate. Thie ethyl acetate layer was washed with saturated aqueous solution of sodium chloride, washed with anhydrous sodium sulfate, and the solvent was evaporated under reduced pressure. The residue was purified by silica gel flash column chromatography (eluent: ethyl acetate) to obtain the title compound (0.25 g, 73%).

Example 38

Synthesis of 2-acetoxy-10-bromo-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (200 mg) obtained in Example 2 was suspended in pyridine (5 ml), and to the suspension was added acetic anhydride (0.14 ml), and the mixture was stirred at room temperature for 2 hours. A small amount of methanol was added dropwise to the reaction mixture, and the solvent was evaporated under reduced pressure. The residual crude crystals were washed with methanol and ether in succession to produce the title compound (100 mg; 46%).

Example 39

Synthesis of 10-bromo-2-(2-oxobutyloxy)-5-(3-pyridylmethyl) -4H-pyrido [3,2,1-jk]carbazole-4-one 10-bromo-2-hydroxy-5-(3-pyridylmethyl)-4H-pyrido [3,2,1-jk]carbazole-4-one (0.3 g) obtained in Example 2 was suspended in dimethyl sulfoxide (20 ml), and to the suspension was added potassium carbonate (0.2 g), and the mixture was stirred at room temperature for 30 minutes. 1-bromo-2-butanone (0.1 ml) was added and the mixture was stirred at room temperature for 12 hours. The reaction mixture was poured into ice water, and the precipitated crystals were recovered by filtration. The resulting crude crystals were washed with methanol and ethanol in succession to obtain the title compound (192 mg, 55%).

Example 41

Synthesis of 10-bromo-2-(2-hydroxypentyloxy)-5-(3-pyridylmethyl)-4H-pyrido [3,2,1-jk]carbazole-4-one 10-bromo-2-(2-oxopentyloxy)-5-(3-pyridylmethyl)-4H-pyrido [3,2,1-jk]carbazole-4-one (400 mg) obtained in Example 40 was suspended in anhydrous methanol (20 ml), and to the suspension was added in small portions sodium boron hydride (92 mg) in an ice bath, and the mixture was stirred at room temperature for 12 hours. The solvent was evaporated under reduced pressure and the residue was extracted by adding water and methylene chloride. The methylene chloride layer was washed with saturated aqueous solution of sodium chloride, dried over anhydrous sodium sulfate, and the solvent was evaporated under reduced pressure. The residue was purified by silica gel flash column chromatography (eluent: methylene chloride containing 4% methanol) to obtain the title compound (140 mg; 28%).

Example 43

Synthesis of 10-bromo-2-(N-ethylcarbamoylmethyloxy)-5-(3-pyridylmethyl)-4H-pyrido [3,2,1-jk]carbazole-4-one 10-bromo-2-carboxymethyloxy-5-(3-pyridylmethyl)-4H-pyrido [3,2,1-jk]carbazole-4-one (300 mg) obtained in Example 6 was suspended in anhydrous benzene (10 ml), and to the suspension was added thionyl chloride (1 ml). The mixture was heated under reflux in an argon atmosphere for 3 hours. The solvent was evaporated under reduced pressure. The resulting residue was added to a mixed solution of 1 N sodium hydroxide (0.6 ml) and ethylamine (70% aqueous solution; 5 ml) at room temperature. The precipitated crystals were washed with water, methanol and ethanol in succession to obtain the title compound (130 mg; 43%).

Example 44

Synthesis of 10-bromo-2-(4-morpholinocarbonylmethyloxy)-5-(3-pyridylmethyl)-4H-pyrido [3,2,1-jk]carbazole-4-one 10-bromo-2-carboxymethyloxy-5-(3-pyridylmethyl)-4H-pyrido [3,2,1-jk]carbazole-4-one (1 g) obtained in Example 6 was suspended in anhydrous benzene (30 ml), and to the suspension was added thionyl chloride (3 ml). The mixture was heated under reflux in an argon atmosphere for 3 hours. The solvent was evaporated under reduced pressure. The resulting residue was added to a mixed solution of morpholine (0.2 ml) and triethylamine (0.3 ml) dissolved in anhydrous methylene chloride (50 ml) at room temperature. The mixture was stirred for 30 minutes and extracted with water and ethyl acetate. The ethyl acetate layer was washed with saturated aqueous solution of sodium chloride, dried over anhydrous sodium sulfate, and the solvent was evaporated under reduced pressure. The residual crude crystals were recrystallized from ethanol to obtain the title compound (260 mg, 51%).

Example 46

Synthesis of 10-bromo-2- (4-carboxy-1-piperidinocarbonylmethyloxy)-5-(3-pyridylmethyl)-4H-pyrido [3,2,1-jk]carbazole-4-one 10-bromo-2-(4-ethoxycarbonyl-1-piperidinocarbonylmethyloxy)-5-(3-pyridylmethyl)-4H-pyrido [3,2,1-jk]carbazole-4-one (250 mg) obtained in Example 45 was suspended in ethanol (30 ml), and to the suspension was added 1 N aqueous solution of sodium hydroxide (8 ml) and the mixture was stirred for 90 minutes at room temperature. After evaporate the solvent under reduced pressure, water and ethyl acetate were added to extract the mixture. The aqueous layer was adjusted to pH 6 by adding 1 N hydrochloric acid, and the mixture was extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent: methylene chloride/methanol=5:1). The crude purification product was washed with ether and recovered by filtration to obtain the title compound (100 mg, 42%).

Example 47

Synthesis of 10-bromo-2-(N-hydroxymethylcarbamoylmethyloxy)-5-(3-pyridylmethyl)-4H-pyrido [3,2,1-jk]carbazole-4-one 10-bromo-2-hydroxy-5-(3-pyridylmethyl)-4H-pyrido [3,2,1-jk]carbazole-4-one (250 mg) obtained in Example 2 was suspended in dimethyl sulfoxide (20 ml), and to the suspension was added potassium carbonate (213 mg). The mixture was stirred at room temperature for 30 minutes, and N-hydroxymethyl-2-chloroacetamide (130 mg) and potassium iodide (1 grain) were added and the mixture was stirred for 36 hours at room temperature. The reaction mixture was poured into ice water and extracted with ethyl acetate. The ethyl acetate layer was washed with saturated aqueous solution of sodium chloride, dried over anhydrous sodium sulfate, and the solvent was evaporated under reduced pressure. The residue was washed with hot methanol to obtain the title compound (116 mg, 38%).

Example 48

Synthesis of 10-bromo-2-methoxy-5-methyl-4H-pyrido [3,2,1-jk]carbazole-4-one

[Step 1] Synthesis of 3-bromo-6-methoxycarbazole-N-α-methyl-β-propionic acid 3-bromo-6-methoxycarbazole (20 g) produced in Example 1, step 1 was dissolved in anhydrous tetrahydrofuran (200 ml), and to the solution were added methyl methacrylate (77.6 ml), then Triton B (0.7 ml). The mixture was heated under reflux in an argon atmosphere for 2 hours, and the solvent was evaporated under reduced pressure. The resulting residue was suspended in methanol (60 ml), and sodium hydroxide (6.4 g) dissolved in water (80 ml) was added dropwise at room temperature, and the mixture was stirred at room temperature for 12 hours. The solvent was evaporated under reduced pressure, and water and ether were added for phase separation. The aqueous layer was rendered acidic by addition of 4N hydrochloric acid, and ethyl acetate was added for further phase separation. The ethyl acetate layer was washed with water and saturated aqueous solution of sodium chloride, dried over anhydrous sodium sulfate, and the solvent was evaporated under reduced pressure. The residual crude crystals were washed with hexane and ether and recovered by filtration to obtain the title compound (25.0 g, 95%).

m.p.: 183.4–186.0° C.

IR spectrum (KBr tab.) ν cm$^{-1}$: 3420, 2950, 1697, 1491, 800

NMR spectrum (DMSO-$d_6$) δ ppm: 8.38 (1H, s), 7.80 (1H, s), 7.57-7.49 (3H, m), 7.15-7.08 (1H, m), 4.58 (1 H, m), 4.34 (1H, m), 3.84 (3H, s), 3.07-2.88 (1H, m), 1.04 (3H, d, J=6.4Hz)

[Step 2] Synthesis of 10-bromo-5,6-dihydro-2-methoxy-5-methyl-4H-pyrido [3,2,1-jk]carbazole-4-one The compound (30 g) obtained in step 1 was suspended in toluene (1200 ml), and diphosphorus pentaoxide (20 g) was added to the suspension. The mixture was heated under reflux in an argon atmosphere for 12 hours (during which diphosphorus pentaoxide (20 g) was supplemented twice). After allowing to cool, the reaction mixture was poured into ice water (1000 ml), filtered through Celite to remove the floating material, and extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent: hexane/ethyl acetate=5:1), and the crude purification product was recrystallized from ethanol and recovered by filtration to obtain the title compound (16.0 g, 56%).

m.p.: 163.8–166.6° C.

IR spectrum (KBr tab.) ν cm$^{-1}$: 1687, 1672, 1497, 1479, 1444, 1194, 797

NMR spectrum (DMSO-$d_6$) δ ppm: 8.47 (1H, s), 8.12 (1H, d, J=1.5Hz), 7.76-7.58 (2H, m), 7.36 (1H, d, J=1.5Hz), 4.77 (1H, dd, J=11.8, 6.5Hz), 4.06 (1H, dd, J=11.8, 11.8Hz), 3.87 (3H, s), 3.32-3.23 (1H, m), 1.28 (3H, d, J=6.5Hz)

[Step 3] Synthesis of 10-bromo-2-methoxy-5-methyl-4H-pyrido [3,2,1-jk]carbazole-4-one The compound (5.9 g) obtained in step 2 was dissolved in anhydrous dioxane (400 ml), and DDQ (5.8 g) was added at room temperature. The mixture was heated under reflux in an argon atmosphere for 23 hours (during which DDQ (2 g) was supplemented twice). After allowing to cool, the reaction mixture was added to 1N aqueous solution of sodium hydroxide (500 ml), and extracted with ethyl acetate. The ethyl acetate layer was washed with 1N aqueous solution of sodium hydroxide and saturated aqueous solution of sodium chloride in succession, dried over anhydrous sodium sulfate, and the solvent was evaporated under reduced pressure. The resulting crude crystals were washed with methanol (60 ml) at an elevated temperature and recovered by filtration to obtain the title compound (4.8 g, 82%).

Example 49

Synthesis of 10-bromo-2-hydroxy-5-methyl-4H-pyrido [3,2,1-jk]carbazole-4-one 10-bromo-2-methoxy-5-methyl-4H-pyrido[3,2,1-jk]carbazole-4-one (4.8 g) obtained in Example 48 was suspended in anhydrous methylene chloride (400 ml), and boron tribromide (25 g) was added dropwise to the suspension at room temperature. The mixture was stirred at room temperature for 12 hours and the reaction mixture was poured into ice water (1500 ml) and the crystals precipitated were recovered by filtration. The resulting crude crystals were washed with ether, and recovered by filtration to obtain the title compound (4.6 g, constant amount).

Example 50

Synthesis of 10-bromo-2-t-butoxycarbonylmethyloxy-5-methyl-4H-pyrido [3,2,1-jk]carbazole-4-one 10-bromo-2-hydroxy-5-methyl-4H-pyrido[3,2,1-jk] carbazole-4-one (250 mg) obtained in Example 49 was suspended in dimethyl sulfoxide (10 ml), and potassium carbonate (210 mg) was added to the suspension. The mixture was stirred at room temperature for 30 minutes and t-butyl bromoacetate (0.13 ml) was added to the mixture. The mixture was stirred for 2.5 hours at room temperature, and the reaction mixture was poured into ice water (50 ml) and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel column chromatography (eluent: methylene chloride containing 2% methanol), and the crude purification product was washed with ether and recovered by filtration to obtain the title compound (130 mg, 39%).

Example 51

Synthesis of 10-bromo-5-methyl-2-i-propoxy-carbonylmethyloxy-5-(3-pyridylmethyl)-4H-pyrido [3,2,1-jk]carbazole-4-one 10-bromo-2-hydroxy-5-methyl-4H-pyrido[3,2,1-jk] carbazole-4-one (250 mg) obtained in Example 49 was suspended in dimethyl sulfoxide (10 ml), and potassium carbonate (210 mg) was added to the suspension. The mixture was stirred at room temperature for 30 minutes and i-propyl bromoacetate (0.12 ml) and potassium iodide (1 grain) were added in succession, and the mixture was stirred at room temperature for 12 hours. The reaction mixture was poured into ice water (50 ml) and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: ethyl acetate), and the crude purification product was washed with ether and recovered by filtration to obtain the title compound (220 mg, 67%).

Example 52

Synthesis of 10-bromo-2-ethoxycarbonylmethyloxy-5-methyl-4H-pyrido [3,2,1-jk]carbazole-4-one 10-bromo-2-hydroxy-5-methyl-4H-pyrido[3,2,1-jk] carbazole-4-one (400 mg) obtained in Example 49 was suspended in dimethyl sulfoxide (10 ml), and potassium carbonate (0.34 g) was added to the suspension. The mixture was stirred at room temperature for 30 minutes and ethyl bromoacetate (0.16 ml) was added. The mixture was stirred at room temperature for 12 hours, and the reaction mixture was poured into ice water (50 ml). The crystals precipitated were recovered by filtration. The resulting crude crystals were washed with water, ethanol and ether in succession, and recovered by filtration to obtain the title compound (360 mg, 71%).

Example 53

Synthesis of 10-bromo-2-carboxymethyloxy-5-methyl-4H-pyrido [3,2,1-jk]carbazole-4-one 10-bromo-2-ethoxycarbonylmethyloxy-5-methyl-4H-pyrido [3,2,1-jk]carbazole-4-one (200 mg) obtained in Example 52 was suspended in a mixed solution of ethanol (10 ml) and methylene chloride (10 ml), and 1N aqueous solution of sodium hydroxide (1 ml) was added to the suspension. The mixture was stirred at room temperature for 90 minutes, and the solvent was evaporated under reduced pressure. To the residue was added water and 1N hydrochloric acid to pH 1, and the crystals precipitated were recovered by filtration to obtain the title compound (170 mg, 91%).

Example 54

Synthesis of 10-bromo-5-methyl-2-(3-pyridylmethyloxy)-4H-pyrido [3,2,1-jk]carbazole-4-one 10-bromo-2-hydroxy-5-methyl-4H-pyrido[3,2,1-jk] carbazole-4-one (350 mg) obtained in Example 49 was suspended in dimethyl sulfoxide (14 ml), and potassium carbonate (440 mg) was added to the suspension. The mixture was stirred at room temperature for 30 minutes and 3-picolylchloride hydrochloride (190 mg) was added to the mixture. The mixture was stirred at room temperature for 12 hours, and the reaction mixture was poured into ice water (500 ml). The crystals precipitated were recovered by filtration. The resulting crude crystals were washed with methanol and ether in succession, and recovered by filtration to obtain the title compound (270 mg, 60%).

Example 55

Synthesis of 10-bromo-2-(4-hydroxybutyloxy)-5-methyl-4H-pyrido [3,2,1-jk]carbazole-4-one 10-bromo-2-hydroxy-5-methyl-4H-pyrido[3,2,1-jk] carbazole-4-one (250 mg) obtained in Example 49 was suspended in dimethyl sulfoxide (10 ml), and potassium carbonate (210 mg) was added to the suspension. The mixture was stirred at room temperature for 30 minutes and 4-chloro-1-butanol (0.09 ml) was added to the mixture. The mixture was stirred at 80° C. in a hot water bath for 14 hours, and the reaction mixture was poured into ice water (500 ml) and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel column chromatography (eluent: methylene chloride containing 4% methanol) to obtain the title compound (80 mg, 26%).

Example 56

Synthesis of 2-acetoxy-10-bromo-5-methyl-4H-pyrido [3,2,1-jk]carbazole-4-one 10-bromo-2-hydroxy-5-methyl-4H-pyrido[3,2,1-jk] carbazole-4-one (200 mg) obtained in Example 49 was suspended in pyridine (6 ml), and acetic anhydride (0.18 ml)

was added to the suspension. The mixture was stirred at room temperature for 40 minutes and a small amount of methanol was added dropwise to the reaction mixture. The solvent was evaporated under reduced pressure, and the residue was washed with ethanol and ether in succession to obtain the title compound (160 mg, 70%).

Example 57

Synthesis of 10-bromo-2-(2-oxopentyloxy)-5-methyl-4H-pyrido [3,2,1-jk]carbazole-4-one 10-bromo-2-hydroxy-5-methyl-4H-pyrido[3,2,1-jk] carbazole-4-one (250 mg) obtained in Example 49 was suspended in dimethyl sulfoxide (10 ml), and potassium carbonate (210 mg) was added to the suspension. The mixture was stirred at room temperature for 30 minutes and 1-bromo-2-pentanone (188 mg) was added to the mixture. The mixture was stirred at room temperature for 12 hours, and the reaction mixture was poured into ice water (500 ml), and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: methylene chloride containing 2% methanol) to obtain the title compound (150 mg, 48%).

Example 58

Synthesis of 10-bromo-2-methoxy-4H-pyrido [3,2,1-jk]carbazole-4-one 10-bromo-5,6-dihydro-2-methoxy-4H-pyrido[3,2,1-jk] carbazole-4-one (3.6 g) obtained in Example 1, step 3 was dissolved in anhydrous dioxane (300 ml), and DDQ (3.0 g) was added at room temperature. The mixture was heated under reflux in an argon atmosphere for 5 hours. After allowing to cool, the reaction mixture was added to 1N aqueous solution of sodium hydroxide (500 ml), and extracted with ethyl acetate. The ethyl acetate layer was washed with 1N aqueous solution of sodium hydroxide and saturated aqueous solution of sodium chloride in succession, dried over anhydrous sodium sulfate, and the solvent was evaporated under reduced pressure. The residue was purified by silica gel column chromatography (eluent: methylene chloride containing 3% methanol) to obtain the title compound (2.9 g, 79%).

Example 59

Synthesis of 10-bromo-2-hydroxy-4H-pyrido [3,2,1-jk]carbazole-4-one 10-bromo-2-methoxy-4H-pyrido[3,2,1-jk]carbazole-4-one (3.2 g) obtained in Example 58 was suspended in anhydrous methylene chloride (500 ml), and boron tribromide (25 g) was added dropwise at room temperature. The mixture was stirred at room temperature for 12 hours and the reaction mixture was poured into ice water (1 L) and the crystals precipitated were recovered by filtration. The methylene chloride layer of the filtrate was washed with saturated aqueous solution of sodium chloride, dried over anhydrous sodium sulfate, and the solvent was evaporated under reduced pressure. The two types of crystals thus obtained were combined, and the above-described procedure was repeated. The reaction mixture was poured into ice water (1 L), and the crystals precipitated were recovered by filtration. The crude crystals obtained were washed with a mixed solution of chloroform and methanol at an elevated temperature and recovered by filtration to obtain the title compound (2.4 g, 78%).

Example 60

Synthesis of 10-bromo-2-t-butoxycarbonylmethyloxy-4H-pyrido [3,2,1-jk] carbazole-4-one i0-bromo-2-hydroxy-4H-pyrido[3,2, 1-jk]carbazole-4-one (2.5 g) obtained in Example 59 was suspended in dimethyl sulfoxide (120 ml), and potassium carbonate (2.2 g) was added to the suspension. The mixture was stirred at room temperature for 30 minutes and t-butyl bromoacetate (1.4 ml) was added to the mixture. The mixture was stirred at room temperature for 12 hours, and the reaction mixture was poured into ice water (900 ml), and the crystals precipitated were recovered by filtration. The crude crystals were purified by silica gel flash column chromatography (eluent: methylene chloride containing 2% methanol) to obtain the title compound (1.9 g, 68%).

Example 61

Synthesis of 10-bromo-2-i-propoxycarbonylmethyloxy-4H-pyrido [3,2,1-jk] carbazole-4-one 10-bromo-2-hydroxy-4H-pyrido[3,2,1-jk]carbazole-4-one (3 g) obtained in Example 59 was suspended in dimethyl sulfoxide (120 ml), and potassium carbonate (2.6 g) was added to the suspension. The mixture was stirred at room temperature for 30 minutes and i-propyl bromoacetate (1.4 ml) and potassium iodide (1 grain) were added in succession to the mixture. The mixture was stirred at room temperature for 12 hours, and the reaction mixture was poured into ice water (500 ml), and the crystals precipitated were recovered by filtration. The crude crystals were purified by silica gel flash column chromatography (eluent: methylene chloride containing 1% methanol) to obtain the title compound (2.0 g, 51%).

Example 62

Synthesis of 10-bromo-2-ethoxycarbonylmethyloxy-4H-pyrido [3,2,1-jk]carbazole-4-one 10-bromo-2-hydroxy-4H-pyrido[3,2,1-jk]carbazole-4-one (400 mg) obtained in Example 59 was suspended in dimethyl sulfoxide (10 ml), and potassium carbonate (0.34 g) was added to the suspension. The mixture was stirred at room temperature for 30 minutes and ethyl bromoacetate (0.15 ml) was added to the mixture. The mixture was stirred at room temperature for 12 hours, and the reaction mixture was poured into ice water (50 ml), and the crystals precipitated were recovered by filtration. The crude crystals obtained were washed with water, ethanol and ether in succession, and recovered by filtration to obtain the title compound (410 mg, 84%).

Example 63

Synthesis of 10-bromo-2-carboxymethyloxy-4H-pyrido [3,2,1-jk]carbazole-4-one 10-bromo-2-ethoxycarbonylmethyloxy-4H-pyrido[3,2,1-jk]carbazole-4-one (200 mg) obtained in Example 62 was suspended in a mixed solution of ethanol (10 ml) and methylene chloride (10 ml), and 1N aqueous solution of sodium hydroxide (1 ml) was added to the suspension. The mixture was stirred at room temperature for 10 minutes, and the solvent was evaporated under reduced pressure. To the residue was added water and 1N hydrochloric acid to pH 1, and the crystals precipitated were recovered by filtration to obtain the title compound (160 mg, 84%).

Example 64

Synthesis of 10-bromo-2-(3-pyridylmethyloxy)-4H-pyrido [3,2,1-jk]carbazole-4-one 10-bromo-2-hydroxy-4H-pyrido[3,2,1-jk]carbazole-4-one (300 mg) obtained in Example 59 was suspended in dimethyl sulfoxide (20 ml), and potassium carbonate (400 mg) was added to the suspension. The mixture was stirred at room temperature for 30 minutes and 3-picolylchloride hydrochloride (180 mg) was added and the mixture was, stirred at room temperature for 12 hours. The reaction mixture was poured into ice water (100 ml), and the precipitated crystals were recovered by filtration. The resulting crude crystals were washed with methanol and ether in succession, and recovered by filtration to obtain the title compound (200 mg, 52%).

Example 70

Synthesis of 10-bromo-2-(5-hydroxymethyl-3-pyridylmethyloxy)-4H-pyrido [3,2,1-jk]carbazole-4-one 2-(5-acetoxymethyl-3-pyridylmethyloxy)-10-bromo-4H-pyrido [3,2,1-jk]carbazole-4-one (200 mg) obtained in Example 69 was suspended in methanol (12 ml), and a solution of sodium hydroxide (100 mg) in water (0.8 ml) was added to the suspension. The mixture was stirred at room temperature for 1 hour, and the precipitated crystals were washed with methanol and ether in succession, and recovered by filtration to obtain the title compound (170 mg, 93%).

Example 71

Synthesis of 2-(6-acetoxymethyl-2-pyridylmethyloxy) -10-bromo-4H-pyrido [3,2,1-jk]carbazole-4-one

[Step 1] Synthesis of pyridine-2,6-dimethanol monoacetate

Pyridine-2,6-dimethanol (5 g) was suspended in pyridine (10 ml), and acetyl chloride (2.56 ml) was added dropwise at room temperature. The mixture was stirred at room temperature for 20 minutes, and the solvent was evaporated under reduced pressure. The residue was purified by silica gel column chromatography (eluent: chloroform/methanol=9:1) to obtain the title compound (2 g, 31%).
IR spectrum (neat) ν $cm^{-1}$: 1741, 1599, 1462, 1377, 12 28, 1074, 793
NMR spectrum (*DMSO-$d_6$) δ ppm: 7.82 (1H, t, J=7.7Hz), 7.41 (1H, d, J=7.7Hz), 7.26 (1H, d, J=7.7Hz), 5.4 5 (1H, t, J=5.8Hz), 5.10 (2H, s), 4.55 (2H, d, J=5.8Hz), 2.12 (3H, s)
[Step 2] Synthesis of 2-acetoxymethyl-6-chloromethylpyridine
The compound (1.9 g) produced in step 1 was suspended in anhydrous benzene (10 ml), and thionyl chloride (0.77 ml) was added dropwise at room temperature. The mixture was stirred for 20 minutes and the solvent was evaporated under reduced pressure. The residue was washed with ether to obtain the title compound (1.29 g, 62%).
IR spectrum (neat) ν $cm^{-1}$: 2953, 1743, 1595, 1460, 13 75, 1227, 1057
NMR spectrum (*DMSO-$d_6$) δ ppm: 7.88 (1H, t, J=7.6Hz), 7.50 (1H, d, J=7.6Hz), 7.39 (1H, d, J=7.6Hz), 5.14 (2H, s), 4.78 (2H, s), 2.13 (3H, s)
[Step 3] Synthesis of 2-(6-acetoxymethyl-2-pyridylmethyloxy)-10-bromo-4H-pyrido [3,2,1-jk] carbazole-4-one
The procedure of Example 64 was repeated by using 10-bromo-2-hydroxy-4H-pyrido[3,2,1-jk]carbazole-4-one (400 mg) and the compound (280 mg) produced in step 3 to obtain the title compound (480 mg, 79%).

Example 73

Synthesis of 10-bromo-2- (5-methoxycarbonyl-2-pyridylmethyloxy)-4H-pyrido [3,2,1-jk]carbazole-4-one

[Step 1] Synthesis of methyl 6-bromomethylnicotinate
methyl 6-methylnicotinate (1 g) was dissolved in carbon tetrachloride (100 ml), and N-bromosuccinimide (1.3 g) was added. The mixture was heated under reflux in an argon atmosphere for 8 hours, and allowed to cool. The precipitated crystals were removed by filtration, and the solvent was evaporated from the filtrate under reduced pressure. The residue was purified by silica gel column chromatography (eluent: hexane/methylene chloride=1:3) to obtain the title compound (540 mg, 35%).
m.p.: 75.2–76.3° C.
IR spectrum (KBr tab.) ν $cm^{-1}$: 1728, 1713, 1595, 1435, 1286, 1124, 1103
NMR spectrum (*DMSO-$d_6$) δ ppm: 9.05 (1H, s), 8.34-8.30 (1H, m), 7.71 (1H, d, J=7.9Hz), 4.77 (2H, s), 3.89 (3H, s),
[Step 2] Synthesis of 10-bromo-2-(5-methoxycarbonyl-2-pyridylmethyloxy)-4H-pyrido [3,2,1-jk]carbazole-4-one
The procedure of Example 64 was repeated by using 10-bromo-2-hydroxy-4H-pyrido[3,2,1-jk]carbazole-4-one (250 mg) and the compound (220 mg) produced in step 1 to obtain the title compound (250 mg, 67%).

Example 74

Synthesis of 10-bromo-2-(5-methyl-3-pyridylmethyloxy)-4H-pyrido [3,2,1-jk]carbazole-4-one Lutidine (1 g) was dissolved in carbon tetrachloride (100 ml), and N-bromosuccinimide (1.3 g) was added. The mixture was heated under reflux in an argon atmosphere for 5 hours, and allowed to cool. The precipitated crystals were removed by filtration. The procedure of Example 64 was repeated by using the thus obtained filtrate and 10-bromo-2-hydroxy-4H-pyrido[3,2,1-jk]carbazole-4-one (100 mg) to obtain the title compound (20 mg, 15%).

Example 75

Synthesis of 10-bromo-2-pyrazylmethyloxy-4H-pyrido [3,2,1-jk]carbazole-4-one

Pyrazine-2-carboxylic acid (2 g) was suspended in a mixed solvent of anhydrous methanol (100 ml) and anhydrous tetrahydrofuran (50 ml), and trimethylsilyldiazomethane-hexane solution (10 ml) was added to the suspension in an ice bath. The mixture was stirred at room temperature for 12 hours, and the solvent was evaporated under reduced pressure. The thus obtained residue was suspended in anhydrous tetrahydrofuran (15 ml), and lithium aluminium hydride (530 mg) was slowly added to the suspension at room temperature. After stirring for 2 hours, saturated aqueous solution of sodium hydrogencarbonate was added to the reaction mixture until the termination of foaming. The mixture was extracted with ether. The ether layer was washed with saturated aqueous solution of sodium chloride, and dried over anhydrous sodium sulfate, and the solvent was evaporated under reduced pressure. The residue was purified by silica gel column chromatography (eluent: methylene chloride/methanol=10:1). The resulting compound (200 mg) was suspended in anhydrous benzene (10 ml), and thionyl chloride (an excessive amount) was added dropwise at room temperature, and the mixture was stirred for 20 minutes. The solvent was evaporated under reduced pressure. The procedure of Example 64 was repeated by using the thus obtained residue, and the title compound (40 mg, 10%) was obtained from 10-bromo-2-hydroxy-4H-pyrido [3,2,1-jk]carbazole-4-one (300 mg).

Example 79

Synthesis of 10-bromo-2-(4-hydroxybutyloxy)-4H-pyrido [3,2,1-jk]carbazole-4-one 10-bromo-2-hydroxy-4H-pyrido[3,2,1-jk]carbazole-4-one (250 mg) obtained in Example 59 was suspended in dimethyl sulfoxide (12 ml), and potassium carbonate (220 mg) was added to the suspension. The mixture was stirred at room temperature for 30 minutes and 4-chrolo-1-butanol (0.096 ml) and potassium iodide (1 grain) were added to the mixture. The mixture was stirred at 80° C. in a hot water bath for 24 hours, and the reaction mixture was poured into ice water (100 ml), and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: methylene chloride/methanol=20:1) to obtain the title compound (160 mg, 52%).

Example 83

Synthesis of 10-bromo-2-(2-oxopentyloxy)-4H-pyrido [3,2,1-jk]carbazole-4-one 10-bromo-2-hydroxy-4H-pyrido[3,2,1-jk]carbazole-4-one (250 mg) obtained in Example 59 was suspended in dimethyl sulfoxide (10 ml), and potassium carbonate (210 mg) was added to the suspension. The mixture was stirred at room temperature for 30 minutes and 1-bromo-2-pentanone (170 mg) was added to the mixture. The mixture was stirred at room temperature for 3 hours, and the reaction mixture was poured into ice water and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent: methylene chloride containing 2% methanol) to obtain the title compound (130 mg, 41%).

Example 84

Synthesis of 10-bromo-2-methoxy-5-(2-pyridylmethyl)-4H-pyrido [3,2,1-jk]carbazole-4-one 10-bromo-5,6-dihydro-2-methoxy-4H-pyrido[3,2,1-jk] carbazole-4-one (0.7 g) obtained in Example 1, step 3 was suspended in ethanol (30 ml), and pyridine-2-aldehyde (0.7 g) and sodium hydroxide (0.3 g) dissolved in water (5 ml) were added at room temperature. The mixture was stirred at room temperature for 12 hours, and approximately half of the solvent was evaporated under reduced pressure. The precipitated crystals were recovered by filtration, and washed with water, ethanol and ether in succession to obtain the title compound (0.56 g, 61%).

Example 85

Synthesis of 10-bromo-2-hydroxy-5-(2-pyridylmethyl)-4H-pyrido [3,2,1-jk]carbazole-4-one 10-bromo-2-methoxy-5-(2-pyridylmethyl)-4H-pyrido [3,2,1-jk]carbazole-4-one (0.54 g) obtained in Example 84 was suspended in anhydrous methylene chloride (30 ml), and boron tribromide (5 ml) was added dropwise at room temperature. The mixture was stirred at room temperature for 12 hours, and the reaction mixture was poured into ice wacer, and to this mixture was added saturated aqueous solution of sodium carbonate until the termination of foaming. The crystals precipitated were recovered by filtration, and the resulting crude crystals were washed with a mixed solution of methylene chloride and methanol to obtain the title compound (0.173 g, 33%).

Example 86

Synthesis of 10-bromo-2-1-butoxycarbonylmethyloxy-5-(2-pyridylmethyl)-4H-pyrido [3,2,1-jk]carbazole-4-one 10-bromo-2-hydroxy-5-(2-pyridylmethyl)-4H-pyrido [3,2,1-jk]carbazole-4-one (190 mg) obtained in Example 85 was suspended in dimethyl sulfoxide (10 ml), and potassium carbonate (130 mg) was added. After stirring the mixture at room temperature for 30 minutes, t-butyl bromoacetate (110 mg) was added, and the mixture was stirred at room temperature for 12 hours. The reaction mixture was poured into ice water and extracted with methylene chloride. The methylene chloride layer was washed with saturated aqueous solution of sodium chloride, dried over anhydrous sodium sulfate, and the solvent was evaporated under reduced pressure. The residue was purified by silica gel flash column chromatography (eluent: methylene chloride containing 3% methanol) to obtain the title compound (88 mg, 36%).

Example 95

Synthesis of 10-bromo-2-methoxy-5-(1H-1,2,4-triazole-1-ylmethyl)-4H-pyrido [3,2,1-jk]carbazole-4-one 10-bromo-2-methoxy-5-methyl-4H-pyrido[3,2,1-jk] carbazole-4-one (400 mg) obtained in Example 48 was suspended in anhydrous benzene, and N-bromosuccinimide (312 mg) and 2,2'-azobisisobutylonitrile (1 grain) were added to the suspension. The mixture was heated under reflux in an argon atmosphere, and allowed to cool, and the solvent was evaporated under reduced pressure. The residue was added to a suspension of 1,2,4-triazole (94 mg) and cesium carbonate (443 mg) in anhydrous acetonitrile (20 ml), and the mixture was stirred at room temperature for 12 hours. The solvent was evaporated under reduced pressure, and the residue was extracted by adding water and methylene chloride. The methylene chloride layer was washed with saturated aqueous solution of sodium chloride, and dried over anhydrous sodium sulfate, and the solvent was evaporated under reduced pressure. The residue was purified by silica gel flash column chromatography (eluent: methylene chloride containing 3% methanol) to obtain the title compound (60 mg, 12%).

Example 97

Synthesis of 2-acetoxy-10-bromo-5-(1H-1,2,4-triazole-1-ylmethyl)-4H-pyrido [3,2,1-jk]carbazole-4-one 10-bromo-2-hydroxy-5-(1H-1,2,4-triazole-1-ylmethyl)-4H-pyrido [3,2,1-jk]carbazole-4-one (30 mg) obtained in Example 96 was suspended in pyridine (0.8 ml), and acetic anhydride (0.021 ml) was added, and the mixture was stirred at room temperature for 3 hours. After adding dropwise a small amount of ethanol to the reaction mixture, the solvent was evaporated under reduced pressure. The residue was washed with ethanol and ether in succession to obtain the title compound (24 mg, 72%).

Example 98

Synthesis of 10-bromo-5-ethoxycarbonyl-2-methoxy-4H-pyrido [3,2,1-jk]carbazole-4-one

[Step 1] Synthesis of diethyl 3-bromo-6-methoxycarbazole-N-methylenemalonate 3-bromo-6-methoxycarbazole (2.5 g) produced in Example 1, step 1 and diethyl ethoxymethylenemalonate (9.16 ml) were dissolved in xylene, and the solution was heated under reflux in an argon atmosphere for 120 hours, and allowed to cool. The solvent was evaporated under reduced pressure and the residue was purified by silica gel column chromatography (eluent: chloroform) to obtain the title compound (2 g, 50%).
m.p.: 95.6–97.6° C.
IR spectrum (KBr tab.) ν cm$^{-1}$: 1716, 1705, 1491, 1246, 1221, 791
NMR spectrum (DMSO-d$_6$) δ ppm: 8.50 (1H, d, J=2.0Hz), 8.43 (1H, s), 7.89 (1H, d, J=2.6Hz), 7.65 (1H, dd, J=8.9, 2.0Hz), 7.54-7.41 (2H, m), 7.14 (1H, dd, J=8.9, 2.6Hz), 4.29 (2H, q, J=7.1Hz), 4.00 (2H, q, J=7.1Hz), 3.87 (3H, s), 1.31 (3H, t, J=7.1Hz), 0.9 (3H, t, J=7.1Hz)

[Step 2] Synthesis of 10-bromo-5-ethoxycarbonyl-2-methoxy-4H-pyrido [3,2,1-jk]carbazole-4-one The compound (1.9 g) obtained in step 1 was added to polyphosphoric acid (140 g), and the mixture was heated to 80° C. in a hot water bath and stirred for 11 hours. After allowing to cool, the mixture was poured into ice water and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: chloroform) to obtain the title compound (650 mg, 38%).

Example 99

Synthesis of 10-bromo-5-carboxy-2-methoxy-4H-pyrido [3,2,1-jk]carbazole-4-one 10-bromo-5-ethoxycarbonyl-2-methoxy-4H-pyrido[3,2,1-jk]carbazole-4-one (400 mg) obtained in Example 98 was suspended in ethanol (10 ml), and 1N sodium hydroxide (3 ml) was added. The mixture was stirred at room temperature for 12 hours, and the solvent was evaporated under reduced pressure. To tne residue was added IN hydrochloric acid to pH 1, and the crystals precipitated were recovered by filtration, and washed with ethanol and ether to obtain the title compound (310 mg, 83%).

Example 100

Synthesis of 10-bromo-2-methoxy-5-(4-morpholinocarbonyl)-4H-pyrido [3,2,1-jk]carbazole-4-one 10-bromo-5-carboxy-2-methoxy-4H-pyrido[3,2,1-jk]carbazole-4-one (180 mg) obtained in Example 99 was suspended in anhydrous benzene (10 ml), and thionyl chloride (0.71 ml) was added. The mixture was heated under reflux in an argon atmosphere for 5 hours, and the solvent was evaporated under reduced pressure. The resulting residue was added to a mixed solution of morpholine (0.098 ml) and triethylamine (0.157 ml) dissolved in anhydrous methylene chloride (10 ml) at room temperature. After stirring for 2 hours, the mixture was extracted by adding water and methylene chloride. The methylene chloride layer was washed with saturated aqueous solution of sodium chloride, and dried over anhydrous sodium sulfate, and the solvent was evaporated under reduced pressure. The residue was washed with ethanol and ether in succession to obtain the title compound (165 mg, 77%).

Example 101

Synthesis of 9-bromo-2-methoxy-5-(3-pyridylmethyl)-4H-pyrido [3,2,1-jk]carbazole-4-one

[Step 1] Synthesis of 4'-bromo-2'-nitrophenylbenzoquinone 4-bromo-2-nitroaniline (10 g) was suspended in a mixed solution of conc. hydrochloric acid (120 ml) and water (22 ml), and the suspension was heated on a hot water bath for dissolution of the content. After the complete dissolution, the solution was cooled to 10° C., and stirred for 30 minutes. Sodium nitrite (5.3 g) dissolved in water (15 ml) was added dropwise to the solution maintained at a temperature not exceeding 10° C., and the insoluble content was separated by using glass wool filter. The filtrate was slowly added dropwise to the suspension of sodium hydrogen carbonate (56.8 g) and benzoquinone (5.6 g) in water (56.7 ml), and the crystals precipitated were recovered by filtration. The resulting crude crystals were washed with ethanol and recovered by filtration to obtain the title compound (8.6 g, 60%).
m.p.: 164.1–168.7° C.
IR spectrum (KBr tab.) ν cm$^{-1}$: 1664, 1651, 1603, 1524, 1354, 1101, 918
NMR spectrum (*DMSO-d$_6$) δ ppm: 8.40 (1H, d, J=2.0Hz), 8.14 (1H, dd, J=8.1, 2.0Hz), 7.59 (1H, d, J=8.1H z), 7.13 (1H, s), 7.03 (2H, s)

[Step 2] Synthesis of 2'-amino-4'-bromophenylhydroquinone

The compound (8.5 g) obtained in step 1 was suspended in 3N hydrochloric acid (213 ml), and tin chloride dihydrate (25 g) was added to the suspension. The mixture was heated to 90° C. on a hot water bath, stirred for 2 hours, allowed to cool, and poured into water (300 ml). 3N aqueous solution of sodium hydroxide was added to the mixture and adjusted to pH 7, and the mixture was extracted with ethyl acetate. The ethyl acetate layer was washed with saturated aqueous solution of sodium chloride, and dried over anhydrous sodium sulfate, and the solvent was evaporated under reduced pressure. The resulting crude purification product was washed with ether and recovered by filtration to obtain the title compound (4.8 g, 61%).
m.p.: 203.4–206.5° C.
IR spectrum (KBr tab.) ν cm$^{-1}$: 3388, 1616, 1506, 1479, 1406, 1244, 1211, 779

NMR spectrum (*DMSO-d$_6$) δ ppm: 8.87 (1H, s),8.80 (1H, s), 6.90 (1H, d, J=2.0Hz), 6.84 (1H, d, J=8.5Hz), 6.74 (1H, d, J=2.0Hz), 6.71 (1H, d, J=1.4Hz), 6.5 8 (1H, dd, J=8.5, 3.0Hz), 6.46 (1H, d, J=3.0Hz),4. 87 (2H, s)

[Step 3] Synthesis of 2-bromo-6-hydroxycarbazole

The compound (14 g) obtained in step 2 was dissolved in methanol, and silica gel (90 g) was added to the solution. The solvent was evaporated under reduced pressure, and the residue was stirred at 90° C. on a hot water bath for 10 hours, and extracted with methanol. The silica gel used for the reaction was separated by filtration, and the solvent was evaporated from the filtrate under reduced pressure. The residue was purified by silica gel column chromatography (eluent: hexane/ethyl acetate=1:1) to obtain the title compound (5.0 g, 38%).
m.p.: 248.4–252.2° C.
IR spectrum (KBr tab.) ν cm$^{-1}$: 3402, 1608, 1583, 1458, 1178, 812, 609
NMR spectrum (*DMSO-d$_6$) δ ppm: 11.06 (1H, s),9.02 (1H, s), 7.95 (1H, d, J=8.2Hz), 7.58 (1H, d, J=1.7Hz), 7.42 (1H, d, J=2.4Hz), 7.31 (1H, d, J=8.7Hz),7.2 0 (1H, dd, J=8.2, 1.7Hz),6.92 (1H, dd, J=8.7, 2.4Hz)

[Step 4] Synthesis of 2-bromo-6-methoxycarbazole

The compound (6 g) obtained in step 3 was dissolved in acetone (180 ml), and potassium hydroxide (1.3 g) was added to the solution at room temperature. Dimethyl sulfate (2.2 ml) was then added dropwise to the solution. After stirring at room temperature for 2 hours, the solvent was evaporated under reduced pressure and the residue was extracted with water and ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: hexane/ethyl acetate=4:1) to obtain the title compound (3.2 g, 51%).
m.p.: 138.6–142.6° C.
IR spectrum (KBr tab.) ν cm$^{-1}$: 3336, 1495, 1219, 1201, 804
NMR spectrum (*DMSO-d$_6$) δ ppm: 11.19 (1H, s), 8.04 (1H, d, J=8.3Hz), 7.69 (1H, d, J=2.5Hz), 7.61 (1H, d, J=1.7Hz), 7.40 (1H, d, J=8.7Hz), 7.23 (1H, dd, J=8.3, 1.7Hz), 7.04 (1H, dd, J=8.7, 2.5Hz), 3.83 (3H, s)

[Step 5] Synthesis of 2-bromo-6-methoxycarbazole-N-β-propionic acid

The compound (2.8 g) obtained in step 4 was suspended in acetone (50 ml), and to the suspension were added dropwise methyl acrylate (1.8 ml), then Triton B (0.6 ml) at room temperature. After stirring for 40 minutes, the solvent was evaporated under reduced pressure. The resulting residue was dissolved in methanol (50 ml), and to the solution was added dropwise sodium hydroxide (0.9 g) dissolved in water (10 ml) at room temperature, and the mixture was stirred at room temperature for 70 minutes. The solvent was evaporated under reduced pressure, and the residue was adjusted to pH 3 by adding 1N hydrochloric acid and extracted with ethyl acetate. The ethyl acetate layer was washed with saturated aqueous solution of sodium chloride, and dried over anhydrous sodium sulfate, and the solvent was evaporated under reduced pressure. The residue was washed with hexane and recovered by filtration to obtain the title compound (3.2 g, 91%).
m.p.: 169.0–171.9° C.
IR spectrum (KBr tab.) ν cm$^{-1}$: 1693, 1489, 1483, 1290, 1225, 1209, 874
NMR spectrum (*DMSO-d$_6$) δ ppm: 12.39 (1H, s), 8.08 (1H, d, J=8.2Hz), 7.86 (1H, d, J=1.6Hz), 7.74 (1H, d, J=2.6Hz), 7.55 (1H, d, J=8.9Hz), 7.29 (1H, dd, J=8.2, 1.6Hz), 7.12 (1H, dd, J=8.9, 2.6Hz), 4.58 (2H, t, J=6.8Hz), 3.85 (3H, s), 2.71 (2H, t, J=6.8Hz)

[Step 6] Synthesis of 9-bromo-5,6-dihydro-2-methoxy-4H-pyrido [3,2,1-jk]carbazole-4-one The compound (2.9 g) obtained in step 5 was suspended in anhydrous chloroform (100 ml), and to the suspension was added PPE (21.6 g) dissolved in anhydrous chloroform (100 ml) at room temperature. The mixture was heated under reflux in an argon atmosphere for 1 hour, allowed to cool, poured into water (300 ml), and extracted with chloroform. The chloroform layer was washed with saturated aqueous solution of sodium chloride, and dried over anhydrous sodium sulfate, and the solvent was evaporated under reduced pressure. The residue was purified by silica gel column chromatography (eluent: hexane/ethyl acetate=9:1) to obtain the title compound (1.7 g, 63%).
m.p.: 174.9–178.8° C.
IR spectrum (KBr tab.) ν cm$^{-1}$: 1666, 1479, 1298, 1223, 1201, 1032, 797
NMR spectrum (*DMSO-d$_6$) δ ppm: 8.17 (1H, d, J=8.4Hz), 8.10 (1H, d, J=2.4Hz), 7.95 (1H, d, J=1.8Hz), 7.40 (1H, dd, J=8.4, 1.8Hz), 7.36 (1H, d, J=2.4H z), 4.56 (2H, t, J=7.1Hz), 3.88 (3H, s), 3.12 (2 H, t, J=7.1Hz)

[Step 7] Synthesis of 9-bromo-2-methoxy-5-(3-pyridylmethyl)-4H-pyrido [3,2,1-jk]carbazole-4-one The compound (3.7 g) obtained in step 6 was suspended in ethanol (210 ml), and to the suspension were added pyridine-3-aldehyde (1.7 ml) and sodium hydroxide (3.6 g) dissolved in water (20 ml) at room temperature. The mixture was stirred at room temperature for 12 hours, and approximately half of the solvent was evaporated under reduced pressure. The crystals precipitated were recovered by filtration, and washed with water, ethanol and ether in succession to obtain the title compound (4.2 g, 90%).

Example 102

Synthesis of 9-bromo-2-hydroxy-5-(3-pyridylmethyl)-4H-pyrido [3,2,1-jk]carbazole-4-one 9-bromo-2-methoxy-5-(3-pyridylmethyl)-4H-pyrido [3,2,1-jk]carbazole-4-one (700 mg) obtained in Example 101 was suspended in anhydrous methylene chloride (70 ml), and to the suspension was added dropwise a solution of boron tribromide in methylene chloride (1M; 10 ml) at room temperature. The reaction mixture was stirred at room temperature for 12 hours, and poured into ice water (100 ml). To this mixture was added saturated aqueous solution of sodium carbonate until the termination of foaming. The crystals precipitated were recovered by filtration. The thus obtained crude crystals were washed with ethanol and ether in succession to obtain the title compound (450 mg, 67%).

Example 103

Synthesis of 9-bromo-2-t-butoxycarbonyl-methyloxy-5-(3-pyridylmethyl)-4H-pyrido [3,2,1-jk] carbazole-4-one 9-bromo-2-hydroxy-5-(3-pyridylmethyl)-4H-pyrido [3,2, 1-jk]carbazole-4-one (200 mg) produced in Example 102 was suspended in dimethyl sulfoxide (8 ml). After adding potassium carbonate (136 mg), the mixture was stirred at room temperature for 30 minutes, and t-butyl bromoacetate (0.09 ml) was added. After stirring at room temperature for 2 hours, the reaction mixture was poured into ice water (20 ml) and the crystals precipitated were recovered by filtration. The thus obtained crude crystals were washed with water, ethanol and ether in succession and recovered by filtration to obtain the title compound (144 mg, 56%).

Example 104

Synthesis of 9-bromo-2-carboxymethyloxy-5-(3-pyridylmethyl)-4H-pyrido [3,2,1-jk]carbazole-4-one 9-bromo-2-t-butoxycarbonylmethyloxy-5-(3-pyridylmethyl)-4H-pyrido [3,2,1-jk]carbazole-4-one (57 mg) produced in Example 103 was dissolved in acetic acid (0.5 ml) and 48% HBr (0.5 ml), and the solution was stirred at 60° C. for 1 hour and allowed to cool. Saturated aqueous solution of sodium hydrogencarbonate was added to pH 7, and the crystals precipitated were recovered by filtration, washed with water, ethanol and ether in succession, and recovered by filtration to obtain the title compound (40 mg, 79%).

Example 105

Synthesis of 9-bromo-5-(3-pyridylmethyl)-2-(3-pyridylmethyloxy)-4H-pyrido [3,2,1-jk]carbazole-4-one 9-bromo-2-hydroxy-5-(3-pyridylmethyl)-4H-pyrido [3,2,1-jk]carbazole-4-one (200 mg) produced in Example 102 was suspended in dimethyl sulfoxide (8 ml). After adding potassium carbonate (204 mg), the mixture was stirred at room temperature for 30 minutes, and 3-picolylchloride (0.09 ml) was added. After stirring at room temperature for 12 hours, the reaction mixture was poured into ice water (20 ml) and the crystals precipitated were recovered by filtration. The thus obtained crude crystals were washed with water, ethanol and ether in succession and recovered by filtration to obtain the title compound (177 mg, 72%).

Example 107

Synthesis of 9-bromo-2-(5-hydroxymethyl-3-pyridylmethyloxy)-5-(3-pyridylmethyl)-4H-pyrido [3,2,1-jk]carbazole-4-one 2-(5-acetoxymethyl-3-pyridylmethyloxy)-9-bromo-5-(3-pyridylmethyl)-4H-pyrido [3,2,1-jk]carbazole-4-one (200 mg) produced in Example 106 was suspended in methanol (10 ml), and to the suspension was added a solution of sodium hydroxide (85 mg) in water (0.8 ml). The mixture was stirred at room temperature for 10 minutes, and the crystals precipitated were recovered by filtration, and washed with methanol and ether in succession to obtain the title compound (170 mg, 92%).

Example 108

Synthesis of 9-bromo-5-(3-pyridylmethyl)-2-(5-pyrimidylmethyloxy)-4H-pyrido [3,2,1-jk]carbazole-4-one

[Step 1] Synthesis of 5-pyrimidine ethanol

Pyrimidine-5-carboxyaldehyde (400 mg) prepared by the procedure described in Syn. Commun. 24: 253, 1994 was dissolved in anhydrous methanol (8 ml), and to the solution was added in small portions sodium boron hydride (210 mg) in an ice bath, and the mixture was stirred for 30 minutes. The solvent was evaporated under reduced pressure, and the residue was extracted with water and ethyl acetate. The ethyl acetate layer was washed with saturated aqueous solution of sodium chloride, and dried over anhydrous sodium sulfate, and the solvent was evaporated under reduced pressure to obtain the title compound (250 mg, 61%).
IR spectrum (neat) v cm$^{-1}$: 1651, 1570, 1443, 1408, 10 36, 725
NMR spectrum (*CDCl$_3$) δ ppm: 9.17 (1H, s), 8.77 (2H, s), 7.27 (1H, s), 4.79 (2H, s)

[Step 2] Synthesis of 5-pyrimidyl methylchloride

The compound (270 mg) obtained in step 1 was suspended in anhydrous methylene chloride (10 ml), and thionyl chloride (10 ml) was added to the suspension at room temperature. The mixture was stirred at room temperature for 2 hours, and the solvent was evaporated under reduced pressure to obtain the title compound (310 mg, 99%).
IR spectrum (neat) v cm$^{-1}$: 1626, 1589, 1537, 1431, 1410, 1041, 687
NMR spectrum (*DMSO-d$_6$) δ ppm: 9.18 (1H, s), 8.91 (2H, s), 4.86 (2H, s)

[Step 3] Synthesis of 9-bromo-5-(3-pyridylmethyl)-2-(5-pyrimidylmethyloxy)-4H-pyrido [3,2,1-jk]carbazole-4-one The procedure of Example 105 was repeated by using 9-bromo-2-hydroxy-5-(3-pyridylmethyl)-4H-pyrido[3,2,1-jk]carbazole-4-one (250 mg) and 5-pyrimidylmethyl chloride (120 mg) produced in step 2 to obtain the title compound (200 mg, 65%).

Example 109

Synthesis of 9-bromo-2-(N-ethylcarbamoylmethyloxy)-5-(3-pyridylmethyl)-4H-pyrido [3,2,1-jk]carbazole-4-one The procedure of Example 105 was repeated by using 9-bromo-2-hydroxy-5-(3-pyridylmethyl)-4H-pyrido[3,2,1-jk]carbazole-4-one (300 mg) and N-ethyl-2-chloroacetamide (153 mg) to obtain the title compound (230 mg, 63%).

Example 110

Synthesis of 9-bromo-2-(3-hydroxypropyloxy)-5-(3-pyridylmethyl)-4H-pyrido [3,2,1-jk]carbazole-4-one 9-bromo-2-hydroxy-5-(3-pyridylmethyl)-4H-pyrido [3,2,1-jk]carbazole-4-one (400 mg) produced in Example 102 was suspended in dimethyl sulfoxide (40 ml). After adding potassium carbonate (540 mg), the mixture was stirred at room temperature for 30 minutes, and 3-bromo-1-propanol (0.3 ml) was added. After stirring at room temperature for 12 hours, the reaction mixture was poured into ice water (100 ml) and the crystals precipitated were recovered by filtration. The thus obtained crude crystals were washed with water, ethanol and ether in succession and recovered by filtration to obtain the title compound (177 mg, 72%).

Example 112

Synthesis of 2-(3-aminopropyloxy)-9-bromo-5-(3-pyridylmethyl)-4H-pyrido [3,2,1-jk]carbazole-4-one 9-bromo-2-(3-N-phthalimidopropyloxy)-5-(3-pyridylmethyl)-4H-pyrido [3,2,1-jk]carbazole-4-one (50 mg) produced in Example 111 was suspended in methanol (0.8 ml), and hydrazine monohydrate (8.45 mg) was added to the suspension. The mixture was heated under reflux in an argon atmosphere for 90 minutes, and allowed to cool. Water (1 ml) was added, and the solvent was evaporated under reduced pressure, and the residue was extracted by adding water and ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: methylene chloride/methanol=10:1) to obtain the title compound (39 mg, 67%).

Example 113

Synthesis of 9-bromo-2-methoxy-5-methyl-4H-pyrido [3,2,1-jk]carbazole-4-one

[Step 1] Synthesis of 2-bromo-6-methoxycarbazole-N-α-methyl-β-propionic acid 2-bromo-6-methoxycarbazole (4 g) produced in Example 101, step 4 was dissolved in anhydrous tetrahydrofuran (32 ml), and to the solution were added methyl methacrylate (12.4 ml) and then Triton B (1.12 ml). The mixture was heated under reflux in an argon atmosphere for 1 hour, and the solvent was evaporated under reduced pressure. The resulting residue was suspended in methanol (40 ml), and sodium hydroxide (1 g) dissolved in water (13 ml) was added dropwise to the solution at room temperature, and the mixture was heated under reflux for 4 hours. The solvent was evaporated under reduced pressure, and water and ether were added for phase separation. The aqueous layer was rendered acidic by addition of 1N hydrochloric acid, and ethyl acetate was added for extraction. The ethyl acetate layer was washed with saturated aqueous solution of sodium chloride, dried over anhydrous sodium sulfate, and the solvent was evaporated under reduced pressure. The residue was washed with hexane and recovered by filtration to obtain the title compound (4.0 g, 95%).

NMR spectrum (*DMSO-$d_6$) δ ppm: 12.39 (1H, bs), 8.07 (1 H, d, J=8.3Hz), 7.82 (1H, d, J=1.6Hz), 7.73 (1H, d, J=2.4Hz), 7.53 (1H, d, J=8.9Hz), 7.27 (1H, dd, J=8.3, 1.6Hz), 7.09 (1H, dd, J=8.9, 2.4Hz), 4.61- 4.54 (1H, m), 4.38-4.31 (1H, m), 3.84 (3H, s), 3.02-2.95 (1H, m), 1.08 (3H, d, J=7.0Hz)

[Step 2] Synthesis of 9-bromo-5,6-dihydro-2-methoxy-5-methyl-4H-pyrido [3,2,1-jk]carbazole-4-one The compound (4.0 g) obtained in step 1 was suspended in anhydrous chloroform (130 ml), and PPE (28.6 g) dissolved in anhydrous chloroform (130 ml) was added to the suspension. The mixture was heated under reflux in an argon atmosphere for 1 hour, allowed to cool, poured into water (200 ml), and extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent: hexane/ethyl acetate=9:1) to obtain the title compound (2.7 g, 71%).

m.p.: 201.1–204.4° C.

IR spectrum (KBr tab.) ν cm$^{-1}$: 1659, 1477, 1462, 1308, 1225, 1032, 866

NMR spectrum (DMSO-$d_6$) δ ppm: 8.17 (1H, d, J=8.3Hz), 8.09 (1H, d, J=2.3Hz), 7.94 (1H, d, J=1.3Hz), 7.41-7.36 (2H, m), 4.81 (1H, dd, J=12.0, 6.6Hz), 4.10 (1H, dd, J=12.0, 12.0Hz), 3.38 (3H, s), 3.32-3.25 (1H, m), 1.28 (3H, d, J=6.6Hz)

[Step 3] Synthesis of 9-bromo-2-methoxy-5-methyl-4H-pyrido [3,2,1-jk]carbazole-4-one The compound (2.7 g) obtained in step 2 was dissolved in anhydrous dioxane (150 ml), and DDQ (2.67 g) was added at room temperature. The mixture was heated under reflux in an argon atmosphere for 9 hours (during which DDQ (2 g) was supplemented) and allowed to cool. The reaction mixture was added to 1N aqueous solution of sodium hydroxide (300 ml), and extracted with ethyl acetate. The ethyl acetate layer was washed with saturated aqueous solution of sodium chloride, dried over anhydrous sodium sulfate, and the solvent was evaporated under reduced pressure. The resulting crude crystals were washed with ethanol at an elevated temperature and recovered by filtration to obtain the title compound (1.7 g, 63%).

Example 114

Synthesis of 9-bromo-2-hydroxy-5-methyl-4H-pyrido [3,2,1-jk]carbazole-4-one 9-bromo-2-methoxy-5-methyl-4H-pyrido[3,2,1-jk]carbazole-4-one (1.6 g) produced in Example 113 was suspended in anhydrous methylene chloride (120 ml), and a solution of boron tribromide in methylene chloride (1M, 28 ml) was added dropwise at room temperature. After stirring at room temperature for 3 hours, the reaction mixture was poured into ice water (100 ml) and the crystals precipitated were recovered by filtration. The thus obtained crude crystals were washed with ethanol and ether in succession to obtain the title compound (1.5 g, 98%).

Example 115

Synthesis of 9-bromo-5-methyl-2-(3-pyridylmethyloxy)-4H-pyrido [3,2,1-jk]carbazole-4-one 9-bromo-2-hydroxy-5-methyl-4H-pyrido[3,2,1-jk]carbazole-4-one (250 mg) produced in Example 114 was suspended in dimethyl sulfoxide (10 ml), and potassium carbonate (315 mg) was added to the suspension. After stirring at room temperature for 30 minutes, 3-picolylchloride (137 mg) was added to the suspension. After stirring at room temperature for 12 hours, the reaction mixture was poured into ice water (100 ml) and the crystals precipitated were recovered by filtration. The thus obtained crude crystals were washed with water, ethanol and ether in succession, and recovered by filtration to obtain the title compound (250 mg, 78%).

Example 116

Synthesis of 9-bromo-2-methoxy-4H-pyrido [3,2,1-jk]carbazole-4-one 9-bromo-5,6-dihydro-2-methoxy-4H-pyrido[3,2,1-jk]carbazole-4-one (1.0 g) obtained in Example 101, step 6 was dissolved in anhydrous dioxane (40 ml), and DDQ (1.45 g) was added at room temperature. The mixture was heated under reflux in an argon atmosphere for 3 hours and allowed to cool. The reaction mixture was added to 1N aqueous solution of sodium hydroxide (150 ml), and extracted with ethyl acetate. The ethyl acetate layer was washed with saturated aqueous solution of sodium chloride, dried over anhydrous sodium sulfate, and the solvent was evaporated under reduced pressure. The resulting crude crystals were washed with ethanol and recovered by filtration to obtain the title compound (0.7 g, 70%).

Example 117

Synthesis of 9-bromo-2-hydroxy-4H-pyrido [3,2,1-jk]carbazole-4-one 9-bromo-2-methoxy-4H-pyrido[3,2,1-jk]carbazole-4-one (650 mg) produced in Example 116 was suspended in anhydrous methylene chloride (50 ml), and a solution of boron tribromide in methylene chloride (1M, 12 ml) was added dropwise at room temperature. The mixture was heated under reflux for 14 hours, and the reaction mixture was poured into 1N aqueous solution of sodium hydroxide (100 ml), and the crystals precipitated were recovered by filtration. The thus obtained crude crystals were washed with ethanol and ether in succession to obtain the title compound (380 mg, 61%).

Example 119

Synthesis of 9-bromo-2-carboxymethyloxy-4H-pyrido [3,2,1-jk]carbazole-4-one 9-bromo-2-t-butoxycarbonylmethyloxy-4H-pyrido[3,2,1-jk]carbazole-4-one (120 mg) produced in Example 118 was dissolved in acetic acid (5 ml) and 48% HBr (5 ml), and the solution was stirred at room temperature for 12 hours. The reaction mixture was poured into water and the crystals precipitated were recovered by filtration, and washed with water, ethanol and ether in succession to obtain the title compound (96 mg, 92%).

Example 121

Synthesis of 5-benzyl-9-bromo-2-methoxy-4H-pyrido [3,2,1-jk]carbazole-4-one 9-bromo-5,6-dihydro-2-methoxy-4H-pyrido[3,2,1-jk]carbazole-4-one (200 mg) obtained in Example 101, step 6 was suspended in ethanol (12 ml), and benzaldehyde (103 mg) and sodium hydroxide (190 mg) dissolved in water (1 ml) were added to the suspension. The mixture was stirred at room temperature for 12 hours, and approximately half of the solvent was evaporated under reduced pressure. The crystals precipitated were recovered by filtration, and washed with water, ethanol and ether in succession to obtain the title compound (217 mg, 87%).

Example 122

Synthesis of 5-benzyl-9-bromo-2-hydroxy-4H-pyrido [3,2,1-jk]carbazole-4-one 5-benzyl-9-bromo-2-methoxy-4H-pyrido[3,2,1-jk]carbazole-4-one (137 mg) produced in Example 121 was dissolved in acetic acid (7 ml) and 48% HBr (7 ml), and the solution was stirred at room temperature for 30 hours. The reaction mixture was poured into water and the crystals precipitated were recovered by filtration, and washed with water, ethanol and ether in succession to obtain the title compound (77 mg, 58%).

Example 123

Synthesis of 9-bromo-2-methoxy-5-(5-methyl-3-pyridylmethyl)-4H-pyrido [3,2,1-jk]carbazole-4-one 9-bromo-5,6-dihydro-2-methoxy-4H-pyrido[3,2,1-jk]carbazole-4-one (300 mg) obtained in Example 101, step 6 was suspended in ethanol (18 ml), and 5-methylnicotinic aldehyde (176 mg) prepared in accordance with the procedure described in J.O.C., 53, 3513 (1988) and sodium hydroxide (291 mg) dissolved in water (1.5 ml) were added to the suspension. The mixture was stirred at room temperature for 12 hours, and approximately half of the solvent was evaporated under reduced pressure. The crystals precipitated were recovered by filtration, and washed with water, ethanol and ether in succession to obtain the title compound (312 mg, 79%).

Example 124

Synthesis of 9-bromo-2-hydroxy-5-(5-methyl-3-pyridylmethyl)-4H-pyrido [3,2,1-jk]carbazole-4-one 9-bromo-2-methoxy-5-(5-methyl-3-pyridylmethyl)-4H-pyrido [3,2,1-jk]carbazole-4-one (302 mg) produced in Example 123 was suspended in anhydrous methylene chloride (80 ml), and boron tribromide (0.33 ml) was added dropwise at room temperature. After stirring at room temperature for 3 hours, the reaction mixture was poured into ice water (100 ml) and saturated aqueous solution of sodium hydrogencarbonate was added thereto until the termination of foaming. The crystals precipitated were recovered by filtration. The thus obtained crude crystals were washed with ethanol and ether in succession to obtain the title compound (227 mg, 78%).

Example 125

Synthesis of 9-bromo-2-methoxy-5-(5-pyrimidylmethyl) -4H-pyrido [3,2,1-jk]carbazole-4-one 9-bromo-5,6-dihydro-2-methoxy-4H-pyrido[3,2,1-jk]carbazole-4-one (300 mg) obtained in Example 101, step 6 was suspended in ethanol (17 ml), and pyrimidine-5-carboxyaldehyde (157 mg) prepared by the procedure described in Syn. Commun. 24, 253 (1994) and sodium hydroxide (291 mg) dissolved in water (1.7 ml) were added to the suspension at room temperature. The mixture was stirred at room temperature for 12 hours, and approximately half of the solvent was evaporated under reduced pressure. The crystals precipitated were recovered by filtration, and the residue was purified by alumina flash column chromatography (eluent: methylene chloride containing 4% methanol) to obtain the title compound (300 mg, 79%).

Example 126

Synthesis of 9-bromo-2-hydroxy-5-(5-pyrimidylmethyl)-4H-pyrido [3,2,1-jk]carbazole-4-one 9-bromo-2-methoxy-5-(5-pyrimidylmethyl)-4H-pyrido [3,2,1-jk]carbazole-4-one (260 mg) produced in Example 125 was suspended in anhydrous methylene chloride (16 ml), and boron tribromide (3.7 ml) was added dropwise at room temperature. After stirring at room temperature for 3 hours, the reaction mixture was poured into ice water and saturated aqueous solution of sodium hydrogencarbonate was added thereto until the termination of foaming. The crystals precipitated were recovered by filtration. The thus obtained crude crystals were washed with ethanol and ether in succession to obtain the title compound (250 mg, 99%).

Example 145

Synthesis of 5-benzoyl-4H-pyrido[3,2,1-jk] carbazole-4-one

[Step 1] Synthesis of 5,6-dihydro-5-(α-hydroxybenzyl)-4H-pyrido [3,2,1-jk]carbazole-4-one 5,6-dihydro-4H-pyrido[3,2,1-jk]carbazole-4-one (4 g) prepared by the procedure described in J.O.C., 24, 324 (1959) was dissolved in anhydrous tetrahydrofuran (160 ml). n-butyl lithium (solution in hexane, 15 ml) was added dropwise to the solution cooled in an acetone-dry ice bath, and the mixture was stirred for 30 minutes. Benzaldehyde (2 ml) dissolved in anhydrous tetrahydrofuran (80 ml) was gradually added dropwise to the solution cooled in an acetone-dry ice bath, and the mixture was stirred for 90 minutes. Saturated aqueous solution of ammonium chloride of an adequate amount was added to the reaction mixture, and the mixture was heated to room temperature, and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: hexane/ethyl acetate=5:1) to obtain the title compound (852 mg, 14%).
m.p.: 158.5–160.0° C.
IR spectrum (KBr tab.) ν cm$^{-1}$: 3433, 1678, 1448, 1221, 748, 710
NMR spectrum (DMSO-d$_6$) δ ppm: 8.41 (1H, d, J=7.6Hz), 8.23 (1H, d, J=7.9Hz), 7.79 (1H, d, J=7.6Hz), 7.59-7.22 (9H, m), 5.75 (1H, d, J=4.3Hz), 5.38 (1H, t, J=4.3Hz), 4.62 (1H, dd, J=12.4, 8.6Hz), 4.34 (1H, dd, J=12.4, 6.4Hz), 3.46-3.43 (1H, m)

[Step 2] Synthesis of 5-benzoyl-4H-pyrido[3,2,1-jk]carbazole-4-one

The procedure of Example 48, step 3 was repeated, and the title compound (83 mg, 11%) was obtained from the compound (700 mg) produced in step 1.

Example 146

Synthesis of 5-(α-hydroxybenzyl)-4H-pyrido [3,2,1-jk]carbazole-4-one 5-benzoyl-4H-pyrido[3,2,1-jk]carbazole-4-one (80 mg) produced in Example 145 was dissolved in anhydrous tetrahydrofuran (80 ml), and lithium aluminium tri-t-butoxyhydride (76 mg) was added to the solution in an ice bath, and the mixture was stirred for 30 minutes. Saturated aqueous solution of ammonium chloride of an adequate amount was added to the reaction mixture, and the mixture was heated to room temperature, and extracted with ethyl acetate. The ethyl acetate layer was washed with saturated aqueous solution of sodium chloride, and dried over anhydrous sodium sulfate, and the solvent was evaporated under reduced pressure. The residual crude crystals were re-precipitated from hexane and ethyl acetate to obtain the title compound (35 mg, 44%).

Example 147

Synthesis of 5-anilino-4H-pyrido[3,2,1-jk] carbazole-4-one

[Step 1] Synthesis of 5-anilino-5,6-dihydro-4H-pyrido [3,2,1-jk]carbazole-4-one

Copper bromide (II) (2.4 g) was dissolved in ethyl acetate, and the solution was heated under reflux in an argon atmosphere. To the solution was added dropwise 5,6-dihydro-4H-pyrido[3,2,1-jk]carbazole-4-one (2 g) prepared by the procedure described in J.O.C., 24, 324 (1959), dissolved in chloroform (20 ml), and the mixture was heated under reflux in an argon atmosphere for 3 hours, and allowed to cool. Floating materials were removed by filtration, and the filtrate was extracted with water and ethyl acetate.

The ethyl acetate layer was washed with saturated aqueous solution of sodium chloride, and dried over anhydrous sodium sulfate, and the solvent was evaporated under reduced pressure. The thus obtained residue was added to aniline, and the mixture was heated to 60° C. in a hot water bath, stirred for 30 minutes, and allowed to cool. 1N hydrochloric acid was added and the reaction mixture was extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: hexane/methylene chloride=1:1) to obtain the title compound (215 mg, 14%).
m.p.: 149.7–152.0° C.
IR spectrum (KBr tab.) ν cm$^{-1}$: 3342, 1693, 1601, 1500, 1319, 744
NMR spectrum (DMSO-d$_6$) δ ppm: 8.44 (1H, dd, J=7.6, 1.0Hz), 8.26 (1H, d, J=7.6Hz), 7.82 (1H, dd, J=7.6, 1.0Hz), 7.76 (1H, d, J=8.3Hz), 7.58-7.52 (1H, m), 7.38-7.27 (2H, m), 7.14-7.08 (2H, m), 6.83 (2H, d, J=7.9Hz), 6.61 (1H, t, J=7.3Hz), 6.16 (1H, d, J=6.9Hz), 5.09-4.92 (2H, m), 4.44-4.30 (1H, m)

[Step 2] Synthesis of 5-anilino-4H-pyrido[3,2,1-jk]carbazole-4-one

The procedure of Example 48, step 3 was repeated, and the title compound (16 mg, 16%) was obtained from the compound (100 mg) produced in step 1.

Example 148

Synthesis of 5-(N-methylanilino)-4H-pyrido [3,2,1-jk]carbazole-4-one

[Step 1] Synthesis of 5,6-dihydro-(N-methylanilino)-4H-pyrido [3,2,1-jk]carbazole-4-one The procedure of Example 147, step 1 was repeated, and the title compound (552 mg, 52%) was obtained from 5,6-dihydro-4H-pyrido [3,2,1-jk]carbazole-4-one (1 g) and N-methylaniline (1.06 g).
m.p.: 139.4–143.1° C.
IR spectrum (KBr tab.) ν cm$^{-1}$: 1682, 1597, 1504, 1344, 1223, 748
NMR spectrum (DMSO-d$_6$) δ ppm: 8.45-8.42 (1H, m), 8.26 (1H, d, J=7.9Hz), 7.83 (1H, dd, J=7.6, 0.7Hz), 7.73 (1H, d, J=8.3Hz), 7.61-7.26 (3H, m), 7.19 (2H, dd, J=8.6, 7.3Hz), 6.99-6.89 (2H, m), 6.73-6.64 (1H, m), 5.74 (1H, dd, J=12.5, 7.6Hz), 4.95 (1H, dd, J=11.9, 7.6Hz), 4.69-4.53 (1H, m), 3.00 (3H, s)

[Step 2] Synthesis of 5-(N-methylanilino)-4H-pyrido[3,2,1-jk]carbazole-4-one

The procedure of Example 48, step 3 was repeated, and the title compound (26 mg, 7%) was obtained from the compound (400 mg) produced in step 1.

Example 149

Synthesis of 5-phenoxy-4H-pyrido[3,2,1-jk] carbazole-4-one

[Step 1] Synthesis of 5,6-dihydro-5-phenoxy-4H-pyrido [3,2,1-jk]carbazole-4-one

The procedure of Example 147, step 1 was repeated, and the title compound (183 mg, 8.7%) was obtained from 5, 6-dihydro-4H-pyrido[3,2,1-jk]carbazole-4-one (2 g) and phenol (0.72 g).
m.p.: 163.9–165.0° C.
IR spectrum (KBr tab.) ν cm$^{-1}$: 1678, 1599, 1498, 1246, 1223, 744
NMR spectrum (DMSO-d$_6$) δ ppm: 8.47 (1H, dd, J=7.6, 0.7Hz), 8.27 (1H, d, J=7.6Hz), 7.87-7.82 (1H, m), 7.75 (1H, d, J=8.3Hz), 7.63-7.50 (1H, m), 7.41-7.27 (4H, m), 7.11 (2H, d, J=7.9Hz), 7.00 (1H, t, J=7.3Hz), 5.78 (1H, dd, J=8.3, 5.6Hz), 5.04 (1H, dd, J=12.5, 5.6Hz), 4.71 (1H, dd, J=12.5, 8.3Hz)

[Step 2] Synthesis of 5-phenoxy-4H-pyrido[3,2,1-jk]carbazole-4-one

The procedure of Example 48, step 3 was repeated, and the title compound (12 mg, 12%) was obtained from the compound (100 mg) produced in step 1.

Example 150

Synthesis of 5-bromo-4H-pyrido[3,2,1-jk]carbazole-4-one

Copper bromide (II) (2.4 g) was dissolved in ethyl acetate, and the solution was heated under reflux in an argon atmosphere. To the solution was added dropwise 5,6-dihydro-4H-pyrido [3,2,1-jk]carbazole-4-one (2 g) prepared by the procedure described in J.O.C., 24, 324 (1959), dissolved in chloroform (20 ml), and the mixture was heated under reflux in an argon atmosphere for 3 hours, and allowed to cool. Floating materials were removed by filtration, and the filtrate was extracted with water and ethyl acetate. The ethyl acetate layer was washed with saturated aqueous solution of sodium chloride, and dried over anhydrous sodium sulfate, and the solvent was evaporated under reduced pressure. The procedure of Example 48, step 3 was repeated by using the resulting residue (100 mg), and there was obtained the title compound (18 mg, 18%).

Example 151

Synthesis of 5-(1-hydroxypropyl)-4H-pyrido [3,2,1-jk]carbazole-4-one

[Step 1] Synthesis of 5,6-dihydro-5-(1-hydroxypropyl)-4H-pyrido [3,2,1-jk]carbazole-4-one 5,6-dihydro-4H-pyrido[3,2,1-jk]carbazole-4-one (800 mg) prepared by the procedure described in J.O.C., 24, 324 (1959) was dissolved in anhydrous tetrahydrofuran (30 ml). n-butyl lithium (solution in hexane, 3 ml) was added dropwise to the solution cooled in an acetone-dry ice bath, and the mixture was stirred for 30 minutes. Propionaldehyde (0.29 ml) dissolved in anhydrous tetrahydrofuran (15 ml) was gradually added dropwise to the solution cooled in an acetone-dry ice bath, and the mixture was stirred for 90 minutes. Saturated aqueous solution of ammonium chloride of an adequate amount was added to the reaction mixture, and the mixture was heated to room temperature, and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: hexane/ethyl acetate=4:1) to obtain the title compound as a diastereomer (450 mg, 45%).
m.p.: 107.8° C. (dec)
IR spectrum (KBr tab.) ν cm$^{-1}$: 3466, 2958, 1655, 1597, 1483, 1219, 756
NMR spectrum (DMSO-d$_6$) δ ppm: 8.39 (1H, d, J=7.6Hz), 8.23 (1H, d, J=7.9Hz), 7.84-7.65 (2H, m), 7.60-7.49 (1H, m), 7.38-7.21 (2H, m), 5.50-4.93 (1H, m), 4.72-4.50 (2H, m), 4.20-3.89 (1H, m), 3.29-2.99 (1H, m), 1.62-1.29 (2H, m), 0.99-0.79 (3H, m)

[Step 2] Synthesis of 5-(1-hydroxypropyl)-4H-pyrido[3,2,1-jk]carbazole-4-one

The procedure of Example 48, step 3 was repeated, and the title compound (20 mg, 8%) was obtained from the compound (250 mg) produced in step 1.

Example 154

Synthesis of 2-methoxy-5-(3-pyridylmethyl)-4H-pyrido [3,2,1-jk]carbazole-4-one

[Step 1] Synthesis of 5,6-dihydro-2-methoxy-4H-pyrido [3,2,1-jk]carbazole-4-one

The procedure of Example 1, steps 1, 2 and 3 was repeated to obtain the title compound from 3-bromocarbazole prepared by the procedure described in Kogyo Kagaku Zasshi (Journal of Industrial Chemistry) 70, 63 (1967).
m.p.: 127.7–129.6° C.
IR spectrum (KBr tab.) ν cm$^{-1}$: 1653, 1479, 1460, 1392, 1140, 746

NMR spectrum (DMSO-d$_6$) δ ppm: 8.22 (1H, d, J=7.3Hz), 8.07 (1H, d, J=2.4Hz), 7.64 (1H, d, J=8.3Hz), 7.52 (1H, dd, J=8.3, 7.3Hz), 7.34 (1H, d, J=2.4Hz), 7.28-7.19 (1H, m), 4.54 (2H, t, J=7.0Hz), 3.89 (3H, s), 3.13 (2H, t, J=7.0Hz)

[Step 2] Synthesis of 2-methoxy-5-(3-pyridylmethyl)-4H-pyrido [3,2,1-jk]carbazole-4-one The procedure of Example 1, step 4 was repeated, and the title compound (1.64 g, 61%) was obtained from the compound (2 g) produced in step 1.

Example 161

Synthesis of 2-methoxy-5-methyl-4H-pyrido [3,2,1-jk]carbazole-4-one

[Step 1] Synthesis of 5,6-dihydro-2-methoxy-5-methyl-4H-pyrido [3,2,1-jk]carbazole-4-one The procedure of Example 1, step 1 was repeated to obtain 3-methoxycarbazole from 3-bromocarbazole prepared by the procedure described in Kogyo Kagaku Zasshi (Journal of Industrial Chemistry) 70, 63 (1967), and the procedure of Example 48, steps 1 and 2 was repeated to obtain the title compound.
m.p.: 164.8–168.2° C.
IR spectrum (KBr tab.) ν cm$^{-1}$: 1653, 1460, 1201, 1092, 1032, 746
NMR spectrum (DMSO-d$_6$) δ ppm: 8.22 (1H, d, J=7.8Hz), 8.07 (1H, d, J=2.4Hz), 7.64 (1H, d, J=8.3Hz), 7.58-7.47 (1H, m), 7.34 (1H, d, J=2.4Hz), 7.33-7.23 (1H, m), 4.78 (1H, dd, J=11.8, 6.7Hz), 4.17-4.02 (1H, m), 3.89 (3H, s), 3.33-3.31 (1H, m), 1.30 (3H, d, J=6.7Hz)

[Step 2] Synthesis of 2-methoxy-5-methyl-4H-pyrido[3,2,1-jk]carbazole-4-one

The procedure of Example 48, step 3 was repeated, and the title compound (1.45 g, 73%) was obtained from the compound (2 g) produced in step 1.

Example 171

Synthesis of 2-chloro-4H-pyrido[3,2,1-jk]carbazole-4-one

[Step 1] Synthesis of 6-chloro-1,2,3,4-tetrahydrocarbazole 4-chlorophenylhydrazine hydrochloride (25 g) was suspended in acetic acid (120 ml), and cyclohexanone (14.5 ml) was added. The mixture was heated under reflux for 2 hours and cooled to 0° C. The precipitated crystals were recovered by filtration, and washed with water and ethanol. The crude product was recrystallized from methanol to obtain the title compound (12.4 g, 43%).
m.p.: 146.3–146.4° C.
IR spectrum (KBr tab.) ν cm$^{-1}$: 3406, 2939, 1470, 1439, 1057, 800, 592
NMR spectrum (DMSO-d$_6$) δ ppm: 10.84 (1H, s), 7.33 (1H, d, J=2.1Hz), 7.21 (1H, d, J=8.5Hz), 6.96 (1H, dd, J=8.5, 2.1Hz), 2.73-2.57 (4H, m), 1.84-1.76 (4H, m)

[Step 2] Synthesis of 6-chloro-1,2,3,4-tetrahydrocarbazole-N-β-propionic acid

The compound (10 g) produced in step 1 was suspended in acetone (50 ml), and the suspension was cooled in an ice bath, and to the suspension were added methyl acrylate (8.8 ml) and then Triton B (2 ml). After stirring for 1 hour, the solvent was evaporated under reduced pressure. The thus obtained residue was suspended in methanol (20 ml), and sodium hydroxide (4.3 g) dissolved in water (50 ml) was added dropwise to the suspension at room temperature. The mixture was heated under reflux for 20 minutes. The solvent was evaporated under reduced pressure, and water and ether were added for phase separation. The aqueous layer was rendered acidic by addition of 4N hydrochloric acid, and the precipitate formed was dissolved in ethyl acetate. The solution was washed with water and saturated aqueous solution of sodium chloride in succession, dried over anhydrous sodium sulfate, and the solvent was evaporated under reduced pressure. The residual crude crystals was washed with hexane and ether to obtain the title compound (10.1 g, 75%).

m.p.: 158.1–159.1° C.
IR spectrum (KBr tab.) ν cm$^{-1}$: 2935, 1711, 1471, 1446, 1290, 957, 797
NMR spectrum (DMSO-d$_6$) δ ppm: 12.4 (1H, s), 7.43-7.37 (2H, m), 7.03 (1H, dd, J=8.9, 2.0Hz), 4.27 (2H, t, J=5.4Hz), 2.73 (2H, t, J=5.4Hz), 2.64-2.56 (4H, m), 1.86-1.75 (4H, m)

[Step 3] Synthesis of 2-chloro-8,9,10,11-tetrahydro-4H-pyrido [3,2,1-jk]carbazole-4-one The compound (10 g) obtained in step 2 was suspended in anhydrous toluene (200 ml), and diphosphorus pentaoxide (51 g) was added to the suspension. The mixture was heated under reflux in an argon atmosphere for 3 hours. After allowing to cool, the reaction mixture was added to water, and the insoluble content was removed by filtration through Celite. The filtrate was extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent: ethyl acetate) to obtain the title compound (1.47 g, 16%).

m.p.: 255.7–258.2° C. IR spectrum (KBr tab.) ν cm$^{-1}$: 2929, 1614, 1595, 1554, 1489, 1277, 1207, 824
NMR spectrum (DMSO-d$_6$) δ ppm: 8.33 (1H, d, J=7.8Hz), 7.93 (1H, d, J=1.7Hz), 7.75 (1H, d, J=1.7Hz), 6.21 (1H, d, J=7.8Hz), 2.93-2.80 (2H, m), 2.72-2.61 (2H, m), 1.93-1.80 (4H, m)

[Step 4] Synthesis of 2-chloro-4H-pyrido[3,2,1-jk]carbazole-4-one

The compound (0.8 g) obtained in step 3 was dissolved in anhydrous dioxane (20 ml), and DDQ (1.48 g) was added at room temperature. The mixture was heated under reflux in an argon atmosphere for 6 hours. After allowing to cool, the reaction mixture was added to 1N sodium hydroxide, and extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent: methylene chloride/ethyl acetate=2:1) to obtain the title compound (320.mg, 41%).

Example 172

Synthesis of 2-chloro-5-methyl-4H-pyrido [3,2,1-jk]carbazole-4-one

[Step 1] Synthesis of 2-chloro-5,6-dihydro-5-methyl-4H-pyrido [3,2,1-jk]carbazole-4-one The procedure of Example 48, steps 1 and 2 was repeated, and the title compound was obtained from 3-chlorocarbazole prepared by the procedure described in Rec. Trav. Chim., 73, 197 (1954).

m.p.: 155.2–159.2° C.
IR spectrum (KBr tab.) ν cm$^{-1}$: 2931, 1680, 1446, 1136, 746
NMR spectrum (DMSO-d$_6$) δ ppm: 8.51 (1H, d, J=2.0Hz), 8.31-8.22 (1H, m), 7.73-7.64 (2H, m), 7.58 (1H, t, J=7.1Hz), 7.31 (1H, t, J=7.1Hz), 4.85 (1H, dd, J=12.2, 6.6Hz), 4.21-4.08 (1H, m), 3.42-3.26 (1 H, m), 1.31 (3H, d, J=6.9Hz)

[Step 2] Synthesis of 2-chloro-5-methyl-4H-pyrido[3,2,1-jk]carbazole-4-one

The procedure of Example 171, step 4 was repeated, and the title compound (9 mg, 20%) was obtained from the compound (45 mg) produced in step 1.

Example 173

Synthesis of 2-cyano-4H-pyrido[3,2,1-jk]carbazole-4-one

[Step 1] Synthesis of 6-bromo-1,2,3,4-tetrahydrocarbazole-N-β-propionic acid

The procedure of Example 171, steps 1 and 2 was repeated to synthesize the title compound from 4-bromophenylhydrazine hydrochloride and methyl acrylate.

m.p.: 167.0° C. (dec)
IR spectrum (KBr tab.) ν cm$^{-1}$: 2935, 1711, 1470, 1288, 1263, 793
NMR spectrum (DMSO-d$_6$) δ ppm: 12.38 (1H, bs), 7.51 (1H, d, J=2.0Hz), 7.38 (1H, d, J=8.5Hz), 7.15 (1H, dd, J=8.5, 2.0Hz), 4.27 (2H, t, J=7.1Hz), 2.76-2.64 (2H, m), 2.62-2.51 (4H, m), 1.85-1.75 (4H, m)

[Step 2] Synthesis of 2-bromo-5,6,8,9,10,11-hexahydro-4H-pyrido [3,2,1-jk]carbazole-4-one The compound (170 g) obtained in step 1 was suspended in anhydrous toluene (3 L), and diphosphorus pentaoxide (750 g) was added to the suspension. The mixture was heated under reflux in an argon atmosphere for 5 hours. After allowing to cool, the reaction mixture was added to water, and the insoluble content was removed by filtration through Celite. The filtrate was extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent: ethyl acetate) to obtain the title compound (30 g, 19%).

m.p.: 153.3° C. (dec)
IR spectrum (KBr tab.) ν cm$^{-1}$: 2929, 1676, 1489, 1417, 1367, 1186, 1126
NMR spectrum (DMSO-d$_6$) δ ppm: 7.84 (1H, d, J=1.5Hz), 7.43 (1H, d, J=1.5Hz), 4.31 (2H, t, J=7.0Hz), 3.02 (2H, t, J=7.0Hz), 2.81-2.57 (4H, m), 1.99-1.77 (4H, m)

[Step 3] Synthesis of 2-cyano-5,6,8,9,10,11-hexahydro-4H-pyrido [3,2,1-jk]carbazole-4-one The compound (20 g) obtained in step 2 was suspended in anhydrous dimethylformamide (30 ml), and copper cyanide (25 g) was added to the suspension. The mixture was stirred in an oil bath at 120 to 140° C. in an argon atmosphere for 5 hours. After allowing to cool, the reaction mixture was added to an aqueous solution of ethylenediamine (400 ml), and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent: ethyl acetate) to obtain the title compound (12 g, 73%).

m.p.: 222.5° C. (dec)
IR spectrum (KBr tab.) ν cm$^{-1}$: 2929, 2214, 1691, 1502, 887
NMR spectrum (DMSO-d$_6$) δ ppm: 8.17 (1H, s), 7.68 (1H, s), 4.38 (2H, t, J=6.8Hz), 3.06 (2H, t, J=6.8Hz), 2.83-2.62 (4H, m), 1.95-1.71 (4H, m)

[Step 4] Synthesis of 2-cyano-4H-pyrido[3,2,1-jk]carbazole-4-one

The compound (2 g) obtained in step 3 was dissolved in anhydrous dioxane (250 ml), and DDQ (6.53 g) was added at room temperature. The mixture was heated under reflux in an argon atmosphere for 12 hours. After allowing to cool, the reaction mixture was added to 1N sodium hydroxide, and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent: methylene chloride containing 2% ethyl acetate) to obtain the title compound (1 g, 51%).

Example 174

Synthesis of 2-carbamoyl-4H-pyrido[3,2,1-jk] carbazole-4-one 2-cyano-4H-pyrido[3,2,1-jk]carbazole-4-one (880 mg) produced in Example 173 was suspended in ethylene glycol monoethylether (88 ml), and 1N aqueous solution of sodium hydroxide (5.3 ml) was added to the suspension. The mixture was heated under reflux in an argon atmosphere for 4 hours, and allowed to cool. The reaction mixture was added to 2N aqueous solution of sodium hydroxide, and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: ethyl acetate) to obtain the title compound (180 mg, 20%).

Example 175

Synthesis of 2-carboxy-4H-pyrido[3,2,1-jk] carbazole-4-one 2-carbamoyl-4H-pyrido[3,2,1-jk]carbazole-4-one (350 mg) produced in Example 174 was suspended in conc. nitric acid (13 ml), and sodium nitrite (1.84 g) was added to the suspension in an ice bath. The mixture was stirred at room temperature for 12 hours, and water was added to the reaction mixture. The crystals precipitated were recovered by filtration, and washed with methanol and ether in succession to obtain the title compound (300 mg, 85%).

Example 176

Synthesis of 2-methoxycarbonyl-4H-pyrido [3,2,1-jk]carbazole-4-one 2-carboxy-4H-pyrido[3,2,1-jk]carbazole-4-one (500 mg) produced in Example 175 was suspended in tetrahydrofuran (100 ml), and methanol (several drops) was added to the suspension. Trimethylsilyldiazomethane (2M hexane solution, 1 ml) was added dropwise at room temperature, and the mixture was stirred for 90 minutes. The solvent was evaporated under reduced pressure, and the residue was purified by silica gel flash column chromatography (eluent: ethyl acetate) to obtain the title compound (250 mg, 48%).

Example 177

Synthesis of 2-hydroxymethyl-4H-pyrido [3,2,1-jk] carbazole-4-one 2-methoxycarbonyl-4H-pyrido[3,2,1-jk]carbazole-4-one (300 mg) produced in Example 176 was suspended in anhydrous methylene chloride (100 ml), and diisobutylaluminium hydride (1M solution in methylene chloride, 4.3 ml) was added dropwise to the suspension in an acetone-dry ice bath. The mixture was stirred at room temperature for 1 hour, and methanol and water was added to the reaction mixture. The floating materials formed were separated by filtration, and the filtrate was distilled under reduced pressure to remove the solvent. The residue was purified by silica gel flash column chromatography (eluent: ethyl acetate) to obtain the title compound (70 mg, 26%).

Example 178

Synthesis of 2-bromo-5-(3-pyridylmethyl)-4H-pyrido [3,2,1-jk]carbazole-4-one

[Step 1] Synthesis of 2-bromo-5-(3-pyridylmethyl)-8,9,10,11-tetrahydrocarbazole-4-one The procedure of Example 1, step 4 was repeated, and the title compound (5.52 g, 86%) was produced from 2-bromo-5,6,8,9,10,11-hexahydro-4H-pyrido [3,2,1-jk]carbazole-4-one (5 g) and pyridine-3-aldehyde (5 g).

m.p.: 326.0° C. (dec)

IR spectrum (KBr tab.) ν $cm^{-1}$: 2941, 1612, 1589, 1572, 1493, 1294

NMR spectrum ($CDCl_3$) δ ppm: 8.58 (1H, d, J=1.5Hz), 8.47 (1H, dd, J=4.9, 1.5Hz), 8.22 (1H, d, J=1.5H z), 7.84 (1H, d, J=1.5Hz), 7.75-7.66 (1H, m), 7.63 (1H, s), 7.22 (1H, dd, J=8.3, 4.9Hz), 3.92 (2H, s), 2.82-2.68 (4H, m), 2.05-1.89 (4H, m)

[Step 2] Synthesis of 2-bromo-5-(3-pyridylmethyl)-4H-pyrido [3,2,1-jk]carbazole-4-one The procedure of Example 171, step 4 was repeated, and the title compound (12 mg, 1%) was produced from the compound (3g) produced in step 1.

Example 179

Synthesis of 2-amino-5-(3-pyridylmethyl)-4H-pyrido [3,2,1-jk]carbazole-4-one 2-bromo-5-(3-pyridylmethyl)-4H-pyrido[3,2,1-jk] carbazole-4-one (555 mg) produced in Example 178, copper (20 mg), and copper iodide (10 mg) were suspended in aqueous ammonia (28%, 30 ml) in a pressure-resistant microbomb, and the suspension was heated to 180 to 190° C. in an oil bath and stirred for 8 hours. The reaction mixture was then allowed to cool and brought back to normal pressure, and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: ethyl acetate), and the crude purification product was recrystallized from ethanol to obtain the title compound (120 mg; 26%).

Example 184

Synthesis of 10-bromo-5-(3-pyridylmethyl)-4H-pyrido [3,2,1-jk]carbazole-4-one

[Step 1] Synthesis of 10-bromo-5,6-dihydro-4H-pyrido[3,2,1-jk]carbazole-4-one

The procedure of Example 1, steps 2 and 3 was repeated to obtain the title compound from 3-bromocarbazole prepared by the procedure described in Kogyo Kagaku Zasshi (Journal of Industrial Chemistry) 70, 63, (1967).

m.p.: 134.3 (dec)

IR spectrum (KBr tab.) ν $cm^{-1}$: 1626, 1597, 1487, 1219, 797, 746

NMR spectrum (DMSO-$d_6$) δ ppm: 8.55-8.41 (2H, m), 7.81 (1H, dd, J=7.8, 1.0Hz), 7.73-7.62 (2H, m), 7.33 (1H, t, J=7.6Hz), 4.60 (2H, t, J=7.1Hz), 3.14 (2H, t, J=7.1Hz)

[Step 2] Synthesis of 10-bromo-5-(3-pyridylmethyl)-4H-pyrido [3,2,1-jk]carbazole-4-one The procedure of Example 1, step 4 was repeated, and the title compound (4.65 g, 90%) was obtained from the compound (4 g) produced in step 1.

Example 190

Synthesis of 10-chloro-5-methyl-4H-pyrido [3,2,1-jk]carbazole-4-one

[Step 1] Synthesis of 10-chloro-5,6-dihydro-5-methyl-4H-pyrido [3,2,1-jk]carbazole-4-one The procedure of Example 48, steps 1 and 2 was repeated, and the title compound was obtained from 3-chlorocarbazole prepared by the procedure described in Rec. Trav. Chim., 73, 197 (1954).

m.p.: 146.2–151.7° C.

IR spectrum (KBr tab.) $\nu$ cm$^{-1}$: 1682, 1597, 1485, 1335, 1228, 1215, 746

NMR spectrum (DMSO-d$_6$) $\delta$ ppm: 8.45 (1H, d, J=7.6Hz), 8.37 (1H, d, J=2.1Hz), 7.82 (1H, d, J=7.6Hz), 7.7 1 (1H, d, J=8.8Hz), 7.56 (1H, dd, J=8.8, 2.1Hz), 7.33 (1H, t, J=7.6Hz), 4.84 (1H, dd, J=12.2, 6.7Hz), 4.22-4.08 (1H, m), 3.46-3.24 (1H, m), 1.30 (3H, d, J=6.7Hz)

[Step 2] Synthesis of 10-chloro-5-methyl-4H-pyrido[3,2,1-jk]carbazole-4-one

The procedure of Example 48, step 3 was repeated, and the title compound (1 g, 67%) was obtained from the compound (1.5 g) produced in step 1.

Example 193

Synthesis of 10-chloro-4H-pyrido[3,2,1-jk]carbazole-4-one

[Step 1] Synthesis of 10-chloro-5,6-dihydro-4H-pyrido [3,2,1-jk]carbazole-4-one

The procedure of Example 1, steps 2 and 3 was repeated, and the title compound was obtained from 3-chlorocarbazole prepared by the procedure described in Rec. Trav. Chim., 73, 197 (1954).

m.p.: 144.3–147.9° C.

IR spectrum (KBr tab.) $\nu$ cm$^{-1}$: 1682, 1489, 1346, 1333, 1219, 798

NMR spectrum (DMSO-d$_6$) $\delta$ ppm: 8.52-8.38 (2H, m), 7.81 (1H, dd, J=7.8, 1.0Hz), 7.73 (1H, d, J=8.8Hz), 7.57 (1H, dd, J=8.8, 2.4Hz), 7.33 (1H, t, J=7.1H z), 4.61 (2H, t, J=7.1Hz), 3.14 (2H, t, J=7.1Hz)

[Step 2] Synthesis of 10-chloro-4H-pyrido[3,2,1-jk]carbazole-4-one

The procedure of Example 58 was repeated, and the title compound (1 g, 34.0%) was obtained from the compound (3 g) produced in step 1.

Example 194

Synthesis of 10-acetyl-5-(3-pyridylmethyl)-4H-pyrido [3,2,1-jk]carbazole-4-one

[Step 1] Synthesis of 10-acetyl-5,6-dihydro-4H-pyrido [3,2,1-jk]carbazole-4-one

The procedure of Example 1, steps 2 and 3 was repeated, and the title compound was obtained from 3-acetylcarbazole prepared by the procedure described in Rec. Trav. Chim., 66, 533 (1947).

m.p.: 192.1–196.2° C.

IR spectrum (KBr tab.) $\nu$ cm$^{-1}$: 1678, 1657, 1485, 1213, 804

NMR spectrum (DMSO-d$_6$) $\delta$ ppm: 8.96 (1H, s), 8.55 (1H, d, J=7.3 Hz), 8.17 (1H, d, J=8.8Hz), 7.83 (1H, d, J=7.8Hz), 7.77 (1H, d, J=8.8Hz), 7.43-7.34 (1H, m), 4.67 (2H, t, J=7.1Hz), 3.16 (2H, t, J=7.1Hz), 2.70 (3H, s)

[Step 2] Synthesis of 10-acetyl-5-(3-pyridylmethyl)-4H-pyrido [3,2,1-jk]carbazole-4-one The procedure of Example 1, step 4 was repeated, and the title compound (580 mg, 43%) was obtained from the compound (1 g) produced in step 1.

Example 195

Synthesis of 10-carboxy-5-(3-pyridylmethyl)-4H-pyrido [3,2,1-jk]carbazole-4-one

Sodium hydroxide (300 mg) was dissolved in water (15 ml), and bromine (0.1 ml) was added dropwise to the solution in an ice bath. The solution was diluted with dioxane (14 ml). 10-acetyl-5- (3-pyridylmethyl) -4H-pyrido [3,2,1-jk]carbazole-4-one (190 mg) produced in Example 194 was dissolved in dioxane (30 ml), and the solution that had been prepared as described above was added dropwise to this solution in an ice bath. After stirring for 5 minutes, sodium sulfite (70 mg) dissolved in water (10 ml) was added to the solution, and ether was added for phase separation. The aqueous layer was adjusted to pH 7 by adding 1N hydrochloric acid, and the crystals precipitated were recovered by filtration and washed with methanol and acetone in succession to obtain the title compound (67 mg, 35%).

Example 198

Synthesis of 5-benzyl-10-(4-morpholinoacetyl)-4H-pyrido [3,2,1-jk]carbazole-4-one 10-acetyl-5-benzyl-4H-pyrido[3,2,1-jk]carbazole-4-one (100 mg) produced in Example 196 was suspended in anhydrous tetrahydrofuran (10 ml), and to the suspension was added phenyltrimethylammonium tribromide (170 mg). The mixture was heated under reflux in an argon atmosphere for 3 hours, allowed to cool, and extracted with ethyl acetate. The ethyl acetate layer was washed with saturated aqueous solution of sodium chloride, and dried over anhydrous sodium sulfate, and the solvent was evaporated under reduced pressure. The thus obtained residue was suspended in ethanol (10 ml), and morpholine (30 gl) and sodium hydrogencarbonate (30 mg) were added. The mixture was heated under reflux in an argon atmosphere for 1 hour, allowed to cool, and extracted with water and ethyl acetate. The ethyl acetate layer was washed with saturated aqueous solution of sodium chloride, and dried over anhydrous sodium sulfate, and the solvent was evaporated under reduced pressure. The residue was purified by silica gel flash column chromatography (eluent: methylene chloride/methanol=20:1) to obtain the title compound (12 mg, 9.6%).

Example 199

Synthesis of 5-benzyl-10-(1-hydroxyethyl)-4H-pyrido [3,2,1-jk]carbazole-4-one 10-acetyl-5-benzyl-4H-pyrido[3,2,1-jk]carbazole-4-one (150 mg) produced in Example 196 was suspended in methanol (15 ml), and 1N sodium hydroxide (1 drop) was added. The mixture was cooled in an ice bath, and sodium boron hydride (161 mg) was gradually added. After stirring the mixture at room temperature for 1 hour, a small amount of saturated sodium hydrogencarbonate was added to the reaction mixture, and the solution was extracted with ethyl acetate. The ethyl acetate layer was washed with saturated aqueous solution of sodium chloride, and dried over anhydrous sodium sulfate, and the solvent was evaporated under reduced pressure. The residual crude crystals were washed with a mixed solvent of ether and hexane to obtain the title compound (126 mg, 83%).

Example 203

Synthesis of 1-methoxy-5-(3-pyridylmethyl)-4H-pyrido [3,2,1-jk]carbazole-4-one

[Step 1] Synthesis of 5,6-dihydro-1-methoxy-4H-pyrido [3,2,1-jk]carbazole-4-one

The procedure of Example 1, steps 2 and 3 was repeated, and the title compound was obtained from 4-methoxycarbazole prepared by the procedure described in J. Heterocyclic Chem., 25, 907, (1988).
m.p.: 133.5–136.7° C.
IR spectrum (KBr tab.) ν cm$^{-1}$: 1670, 1601, 1363, 1259, 746
NMR spectrum (DMSO-d$_6$) δ ppm: 8.14 (1H, d, J=7.9Hz), 7.81 (1H, d, J=8.3Hz), 7.65 (1H, d, J=8.3Hz), 7.52-7.46 (1H, m), 7.28 (1H, t, J=7.9Hz), 6.91 (1H, d, J=8.3Hz), 4.55 (2H, t, J=7.0Hz), 4.12 (3H, s), 3.07 (2H, t, J=7.0Hz)

[Step 2] Synthesis of 1-methoxy-5-(3-pyridylmethyl)-4H-pyrido [3,2,1-jk]carbazole-4-one The procedure of Example 1, step 4 was repeated, and the title compound (1.2 g, 89%) was obtained from the compound (1 g) produced in step 1.

Example 210

Synthesis of 3-methoxy-5-(3-pyridylmethyl)-4H-pyrido [3,2,1-jk]carbazole-4-one

[Step 1] Synthesis of 5,6-dihydro-3-methoxy-4H-pyrido [3,2,1-jk]carbazole-4-one

The procedures of Example 101, step 4, and Example 1, steps 2 and 3 were repeated, and the title compound was obtained from commercially available 2-hydroxycarbazole.
m.p.: 148.9–150.7° C.
IR spectrum (KBr tab.) ν cm$^{-1}$: 1674, 1601, 1585, 1250, 1174, 1122, 1099, 754
NMR spectrum (DMSO-d$_6$) δ ppm: 8.30 (1H, d, J=8.7Hz), 8.10 (1H, dd, J=7.6, 1.0Hz), 7.58 (1H, d, J=7.9Hz), 7.50-7.39 (1H, m), 7.24 (1H, td, J=7.9, 1.0Hz), 6.94 (1H, d, J=8.7Hz), 4.49 (2H, t, J=7.1Hz), 3.91 (3H, s), 3.00 (2H, t, J=7.1Hz)

[Step 2] Synthesis of 3-methoxy-5-(3-pyridylmethyl)-4H-pyrido [3,2,1-jk]carbazole-4-one The procedure of Example 1, step 4 was repeated, and the title compound (1.61 g, 79%) was obtained from the compound (1.5 g) produced in step 1.

Example 216

Synthesis of 8-methoxy-5-(3-pyridylmethyl)-4H-pyrido [3,2,1-jk]carbazole-4-one

[Step 1] Synthesis of 5,6-dihydro-8-methoxy-4H-pyrido [3,2,1-jk]carbazole-4-one

The procedure of Example 1, steps 2 and 3 was repeated, and the title compound was obtained from 1-methoxycarbazole prepared by the procedure described in J.C.S. Perkin I, 235, (1988).
m.p.: 177.5–180.3° C.
IR spectrum (KBr tab.) ν cm$^{-1}$: 1682, 1576, 1441, 1292, 1257, 770
NMR spectrum (DMSO-d$_6$) δ ppm: 8.37 (1H, dd, J=7.6, 1.0Hz), 7.87-7.76 (2H, m), 7.30 (1H, t, J=7.6Hz), 7.23 (1H, t, J=7.9Hz), 7.12 (1H, dd, J=7.9, 1.0Hz), 4.85 (2H, t, J=7.0Hz), 3.99 (3H, s), 3.13 (2H, d, J=7.0Hz)

[Step 2] Synthesis of 8-methoxy-5-(3-pyridylmethyl)-4H-pyrido [3,2,1-jk]carbazole-4-one The procedure of Example 1, step 4 was repeated, and the title compound (1.54 g, 76%) was obtained from the compound (1.5 g) produced in. step 1.

Example 224

Synthesis of 9-methoxy-5-(3-pyridylmethyl)-4H-pyrido [3,2,1-jk]carbazole-4-one

[Step 1] Synthesis of 5,6-dihydro-9-methoxy-4H-pyrido [3,2,1-jk]carbazole-4-one

The procedures of Example 101, step 4, and Example 1, steps 2 and 3 were repeated, and the title compound was obtained from commercially available 2-hydroxycarbazole.
m.p.: 115.4–117.5° C.
IR spectrum (KBr tab.) ν cm$^{-1}$: 1680, 1630, 1475, 1356, 1223, 1082, 743
NMR spectrum (DMSO-d$_6$) δ ppm: 8.27 (1H, d, J=7.6Hz), 8.09 (1H, d, J=8.7Hz), 7.68 (1H, d, J=7.6Hz), 7.28-7.22 (2H, m), 6.89 (1H, dd, J=8.7, 2.1Hz), 4.56 (2H, t, J=7.0Hz), 3.90 (3H, s), 3.12 (2H, t, J=7.0Hz),

[Step 2] Synthesis of 9-methoxy-5-(3-pyridylmethyl)-4H-pyrido [3,2,1-jk]carbazole-4-one The procedure of Example 1, step 4 was repeated, and the title compound (1.52g, 74%) was obtained from the compound (1.52 g) produced in step 1.

Example 232

Synthesis of 11-methoxy-5- (3-pyridylmethyl)-4H-pyrido [3,2,1-jk]carbazole-4-one

[Step 1] Synthesis of 5,6-dihydro-11-methoxy-4H-pyrido [3,2,1-jk]carbazole-4-one The procedure of Example 1, steps 2 and 3 was repeated, and the title compound was obtained from 4-methoxycarbazole prepared by the procedure described in J. Heterocyclic Chem., 25, 907, (1988).
m.p.: 177.8–180.7° C.
IR spectrum (KBr tab.) ν cm$^{-1}$: 1670, 1489, 1458, 1346, 1273, 746
NMR spectrum (DMSO-d$_6$) δ ppm: 8.31 (1H, dd, J=6.6, 1.0Hz), 7.74 (1H, dd, J=7.6, 1.0Hz), 7.55-7.46 (1H, m), 7.34-7.23 (2H, m), 6.87 (1H, d, J=8.3Hz), 4.57 (2H, t, J=7.1Hz), 4.05 (3H, s), 3.13 (2H, t, J=7.1Hz)

[Step 2] Synthesis of 11-methoxy-5-(3-pyridylmethyl)-4H-pyrido [3,2,1-jk]carbazole-4-one The procedure of Example 1, step 4 was repeated, and the title compound (230 mg, 78%) was obtained from the compound (220 mg) produced in step 1.

Example 235

Synthesis of 10-fluoro-2-methoxy-5-(3-pyridylmethyl)-4H-pyrido [3,2,1-jk]carbazole-4-one

[Step 1] Synthesis of 6-fluoro-1,2,3,4-tetrahydrocarbazole

The procedure of Example 171, step 1 was repeated, and the title compound (126 g, 83%) was obtained from commercially available 4-fluorophenylhydrazine (130 g).
m.p.: 107.6° C. (dec)
IR spectrum (KBr tab.) ν cm$^{-1}$: 3408, 2931, 1583, 1483, 1446, 795
NMR spectrum (CDCl$_3$) δ ppm: 7.66 (1H, bs), 7.17 (1H, d d, J=8.9, 4.3Hz), 7.09 (1H, dd, J=9.6, 2.6Hz), 6.88-6.80 (1H, m), 2.74-2.64 (4H, m), 1.96-1.82 (4H, m)

[Step 2] Synthesis of 3-fluorocarbazole

The compound (1 g) produced in step 1 was dissolved in xylene (6 ml), and chloranil (1.3 g) was added. The mixture was heated under reflux in an argon atmosphere for 3 hours and allowed to cool. The reaction mixture was decanted, and the insoluble content was removed by filtration, and the filtrate was concentrated under reduced pressure. The residue was purified by silica gel flash column chromatography (eluent: hexane/ethyl acetate=15:1) to obtain the title compound (232 mg, 24%).
m.p.: 203.2° C. (dec)
IR spectrum (KBr tab.) ν cm$^{-1}$: 3419, 1585, 1497, 1169, 746
NMR spectrum (DMSO-d$_6$) δ ppm: 11.29 (1H, bs), 8.13 (1H, d, J=7.8Hz), 7.95 (1H, dd, J=9.5, 2.7Hz), 7.53-7.37 (3H, m) 7.30-7.11 (2H, m)

[Step 3] Synthesis of 3-bromo-6-fluorocarbazole

The compound (13.5 g) produced in step 2 was dissolved in dimethylformamide (200 ml), and N-bromosuccinimide (14.2 g) dissolved in dimethylformamide (136 ml) was added dropwise to the solution in an ice bath. The mixture was stirred for 15 minutes, and the reaction mixture was poured into ice water, and extracted with ethyl acetate. The ethyl acetate layer was washed with saturated aqueous solution of sodium chloride, and dried over anhydrous sodium sulfate, and the solvent was evaporated under reduced pressure. The residue was purified by silica gel column chromatography (eluent: hexane/ethyl acetate=8:1) to obtain the title compound (16.8 g, 87%).
m.p. 158.0° C. (dec)
IR spectrum (KBr tab.) ν cm$^{-1}$: 3410, 1489, 1443, 1161, 8810, 571
NMR spectrum (DMSO-d$_6$) δ ppm: 11.48 (1H, s), 8.40 (1H, d, J=2.0Hz), 8.03 (1H, dd, J=9.5, 2.7Hz), 7.55-7.45 (3H, m), 7.32-7.24 (1H, m)

[Step 4] Synthesis of 5,6-dihydro-10-fluoro-2-methoxy-4H-pyrido [3,2,1-jk]carbazole-4-one The procedure of Example 1, steps 1, 2 and 3 was repeated to obtain the title compound from the compound produced in step 3.
m.p.: 166.8–169.4° C.
IR spectrum (KBr tab.) ν cm$^{-1}$: 1672, 1483, 1290, 1190, 1124, 854, 783
NMR spectrum (DMSO-d$_6$) δ ppm: 8.09 (1H, d, J=2.4Hz), 8.07 (1H, d, J=2.4Hz), 7.66 (1H, dd, J=8.8, 4.4H z), 7.42-7.35 (2H, m), 4.54 (2H, t, J=7.1Hz), 3.8 8 (3H, s), 3.13 (2H, t, J=7.1Hz)

[Step 5] Synthesis of 10-fluoro-2-methoxy-5-(3-pyridylmethyl)-4H-pyrido [3,2,1-jk]carbazole-4-one The procedure of Example 1, step 4 was repeated to obtain the title compound (2.28 g, 86%) from the compound (2 g) produced in step 4.

Example 238

Synthesis of 2-butyryloxy-10-fluoro-5-(3-pyridylmethyl)-4H-pyrido [3,2,1-jk]carbazole-4-one 10-fluoro-2-hydroxy-5-(3-pyridylmethyl)-4H-pyrido [3,2,1-jk]carbazole-4-one (150 mg) produced in Example 236 was suspended in pyridine (12 ml), and n-butyryl chloride (74 gl) was added dropwise to the suspension in an ice bath. After stirring for 50 minutes, the solvent was evaporated under reduced pressure. The residue was washed with ether to obtain the title compound (126 mg, 70%).

Example 243

Synthesis of 10-chloro-2-methoxy-5-(3-pyridylmethyl)-4H-pyrido [3,2,1-jk]carbazole-4-one

[Step 1] Synthesis of 3-methoxycarbazole

The procedure of Example 1, step 1 was repeated to obtain the title compound (76 g, 82%) from 3-bromocarbazole (116 g) prepared by the procedure described in Kogyo Kagaku Zasshi (Journal of Industrial Chemistry), 70, 63, (1967).
m.p.: 153.2–154.3° C.
IR spectrum (KBr tab.) ν cm$^{-1}$: 3406, 1497, 1460, 1171, 1034, 820, 748
NMR spectrum (DMSO-d$_6$) δ ppm: 11.03 (1H, s), 8.09 (1H, d, J=7.8Hz), 7.67 (1H, d, J=2.3Hz), 7.45-7.31 (3H, m), 7.13-7.08 (1H, m), 7.02 (1H, dd, J=8.8, 2.3Hz), 3.84 (3H, s)

[Step 2] Synthesis of 3-chloro-6-methoxycarbazole

The procedure of Example 235, step 3 was repeated, and the title compound (6.4 g, 17%) was obtained from the compound (33 g) produced in step 1 and N-chlorosuccinimide (23.5 g).
m.p.: 152.1–154.9° C.
IR spectrum (KBr tab.) ν cm$^{-1}$: 3415, 1491, 1462, 1223, 1205, 1169, 814
NMR spectrum (DMSO-d$_6$) δ ppm: 11.21 (1H, s), 8.21 (1H, d, J=2.0Hz), 7.75 (1H, d, J=2.4Hz), 7.47-7.32 (3H, m), 7.05 (1H, dd, J=8.8, 2.4Hz), 3.84 (3H, s)

[Step 3] Synthesis of 10-chloro-5,6-dihydro-2-methoxy-4H-pyrido [3,2,1-jk]carbazole-4-one The procedure of Example 1, steps 2 and 3 was repeated to obtain the title compound from the compound produced in step 2.
m.p.: 162.2–168.2° C.
IR spectrum (KBr tab.) ν cm$^{-1}$: 1672, 1495, 1479, 1288, 1200, 798
NMR spectrum (DMSO-d$_6$) δ ppm: 8.36 (1H, d, J=2.4Hz), 8.14 (1H, d, J=2.3Hz), 7.68 (1H, d, J=8.6Hz), 7.54 (1H, dd, J=8.6, 2.3Hz), 7.37 (1H, d, J=2.4Hz), 4.55 (2H, t, J=7.0Hz), 3.88 (3H, s), 3.13 (2H, t, J=7.0Hz)

[Step 4] Synthesis of 10-chloro-2-methoxy-5-(3-pyridylmethyl)-4H-pyrido [3,2,1-jk]carbazole-4-one The procedure of Example 1, step 4 was repeated to obtain the title compound (850 mg, 69%) from the compound (950 mg) produced in step 3.

Example 248

Synthesis of 10-ethyl-2-methoxy-5-(3-pyridylmethyl)-4H-pyrido [3,2,1-jk]carbazole-4-one

[Step 1] Synthesis of 4-acetyl-4'-methoxydiphenylamine p-aminoacetophenone (1 g), 4-iodoanisole (3.46 g), and potassium carbonate (2.04 g) and copper (25 mg) were added to dibutylether (11 ml), and the mixture was heated under reflux in an argon atmosphere for 8 hours and allowed to cool. The insoluble content was removed by filtration, and the filtrate was distilled to remove the solvent under reduced pressure. The residue was purified by silica gel flash column chromatography (eluent: hexane/ethyl acetate=3:1) to obtain the title compound (368 mg, 21%).
m.p.: 116.5–120.9° C.
IR spectrum (KBr tab.) ν cm$^{-1}$: 3307, 1649, 1587, 1508, 1279, 1244, 833
NMR spectrum (*DMSO-d$_6$) δ ppm: 8.58 (1H, s), 7.77 (2H, d, J=8.8Hz), 7.13 (2H, d, J=8.8Hz), 6.94 (2H, d, J=8.8Hz), 6.88 (2H, d, J=8.8Hz), 3.75 (3H, s), 2.43 (3H, s)

[Step 2] Synthesis of 3-acetyl-6-methoxycarbazole

The compound (100 mg) produced in step 1 was dissolved in acetic acid (5 ml), and palladium diacetate (186 mg) was added. The mixture was heated under reflux in an argon atmosphere for 10 minutes, and allowed to cool. The insoluble content was removed by filtration, and the filtrate was extracted with water and ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent:hexane/ethyl acetate=3:1) to obtain the title compound (34 mg, 34%).

m.p.: 203.6–207.7° C.

IR spectrum (KBr tab.) υ cm$^{-1}$: 1659, 1630, 1495, 1269, 1219, 1028

NMR spectrum (*DMSO-d$_6$) δ ppm: 11.52 (1H, s), 8.86 (1H, d, J=1.5 Hz), 7.99 (1H, dd, J=8.6, 1.5 Hz), 7.87 (1H, d, J=2.4 Hz), 7.50 (1H, d, J=8.6 Hz), 7.44 (1H, d, J=8.7 Hz), 7.07 (1H, dd, J=8.7, 2.4 Hz), 3.87 (3H, s), 2.67 (3H, s)

[Step 3] Synthesis of 3-ethyl-6-methoxycarbazole

The compound (6.24 g) produced in step 2 was suspended in acetic acid (460 ml), and 10% palladium carbon (4.6 g) and sodium acetate (10.3 g) were added. The mixture was heated under reflux in a hydrogen atmosphere for 90 minutes, and allowed to cool. The insoluble content was removed by filtration, and the filtrate was poured into water and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent:hexane/ ethyl acetate=7:1) to obtain the title compound (6.24 g, 66%).

m.p.: 87.5–91.2° C.

IR spectrum (KBr tab.) υ cm$^{-1}$: 3404, 2958, 1497, 1468, 1209, 1149, 1032

NMR spectrum (*DMSO-d$_6$) δ ppm: 10.88 (1H, bs), 7.92–7.88 (1H, m), 7.64 (1H, d, J=2.5 Hz), 7.38–7.33 (2H, m), 7.20 (1H, dd, J=8.5, 1.5 Hz), 6.98 (1H, dd, J=8.5, 2.5 Hz), 3.83 (3H, s), 2.75 (2H, q, J=7.5 Hz), 1.27 (3H, t, J=7.5 Hz)

[Step 4] Synthesis of 5,6-dihydro-10-ethyl-2-methoxy-4H-pyrido[3,2,1-jk]carbazole-4-one The procedure of Example 1, steps 2 and 3 was repeated by using the compound produced in step 3 to obtain the title compound.

m.p.: 109.3–110.3° C.

IR spectrum (KBr tab.) υ cm$^{-1}$: 2964, 1676, 1500, 1485, 1300, 1227, 1082

NMR spectrum (*DMSO-d$_6$) δ ppm: 8.05–8.03 (2H, m), 7.54 (1H, d, J=8.3 Hz), 7.38 (1H, dd, J=8.3, 1.7 Hz), 7.30 (1H, d, J=2.2 Hz), 4.50 (2H, t, J=7.1 Hz), 3.88 (3H, s), 3.11 (2H, t, J=7.1 Hz), 2.78 (2H, q, J=7.6 Hz), 1.28 (3H, t, J=7.6 Hz)

[Step 5] Synthesis of 10-ethyl-2-methoxy-5-(3-pyridylmethyl)-4H-pyrido[3,2,1-jk]carbazole-4-one The procedure of Example 1, step 4 was repeated by using the compound (400 mg) produced in step 4 to obtain the title compound (507 mg, 96%).

Example 253

Synthesis of 2-hydroxy-10-methoxy-5-(3-pyridylmethyl)-4H-pyrido[3,2,1-jk]carbazole-4-one 2-benzyloxy-10-methoxy-5-(3-pyridylmethyl)-4H-pyrido[3,2,1-jk]carbazole-4-one (470 mg) obtained in Example 252 was dissolved in acetic acid. To the solution were added sodium acetate (259 mg) and palladium carbon (116 mg), and the mixture was heated under reflux in a hydrogen atmosphere for 3 hours. The reaction mixture was filtered, and the filtrate was distilled to remove the solvent under reduced pressure. To the residue was added an aqueous solution of sodium hydrogencarbonate until the termination of foaming. The mixture was extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent:methylene chloride/methanol=20:1) to obtain the title compound (257 mg, 62%).

Example 257

Synthesis of 2,10-dimethoxy-5-(3-pyridylmethyl)-4H-pyrido[3,2,1-jk]carbazole-4-one

[Step 1] Synthesis of 5,6-dihydro-2,10-dimethoxy-4H-pyrido[3,2,1-jk]carbazole-4-one The procedure of Example 1, steps 1, 2 and 3 was repeated by using commercially available 3,6-dibromocarbazole.

m.p.: 136.7–140.4° C.

IR spectrum (KBr tab.) υ cm$^{-1}$: 1670, 1486, 1458, 1215, 1130, 1076, 771

NMR spectrum (DMSO-d$_6$) δ ppm: 8.07 (1H, d, J=2.4 Hz), 7.82 (1H, d, J=2.4 Hz), 7.56 (1H, d, J=8.7 Hz), 7.31 (1H, d, J=2.4 Hz), 7.15 (1H, dd, J=8.7, 2.4 Hz), 4.48 (2H, t, J=7.1 Hz), 3.88 (3H, s), 3.86 (3H, s), 3.11 (2H, t, J=7.1 Hz)

[Step 2] Synthesis of 2,10-dimethoxy-5-(3-pyridylmethyl)-4H-pyrido[3,2,1-jk]carbazole-4-one The procedure of Example 1, step 4 was repeated by using the compound (1 g) produced in step 1 to obtain the title compound (1 g, 77%).

Example 264

Synthesis of 2,10-dichlor-4H-pyrido[3,2,1-jk]carbazole-4-one

[Step 1] Synthesis of N-(4-chlorophenyl)-β-alanine p-chloroaniline (200 g) was suspended in water (100 ml) and acrylic acid (54.1 ml) was added to the suspension. The mixture was heated under reflux for 2 hours in a nitrogen atmosphere. After allowing to cool, 2 N aqueous solution of sodium hydroxide (500 ml) was added, and the mixture was extracted with ether. The aqueous layer was adjusted to pH 3 with 1 N hydrochloric acid and extracted with ethyl acetate. The ethyl acetate layer was washed with saturated aqueous solution of sodium chloride, dried over anhydrous sodium sulfate, and the solvent was evaporated under reduced pressure. The title compound (137.3g, 87%) was obtained without further purification.

m.p.: 119.0–121.0° C.

IR spectrum (KBr tab.) υ cm$^{-1}$: 1707, 1599, 1508, 1435, 1329, 1219, 816

NMR spectrum (*DMSO-d$_6$) δ ppm: 7.08 (2H, d, J=8.9 Hz), 6.56 (2H, d, J=8.9 Hz), 5.83 (1H, bs), 3.21 (2H, t, J=6.8 Hz), 2.50–2.45 (2H, m)

[Step 2] Synthesis of 6-chloro-2,3-dihydro-4(1H)-quinolinone

The compound (137 g) obtained in step 1 was added to polyphosphoric acid (2147 g) and the mixture was heated at 120 to 130° C. for 1 hour with stirring in an oil bath. The reaction mixture was poured into ice water (4 L) and extracted with ethyl acetate. The ethyl acetate layer was washed with saturated aqueous solution of sodium chloride, dried over anhydrous sodium sulfate, and the solvent was evaporated under reduced pressure. The residue was purified by silica gel column chromatography (eluent:hexane/ethyl acetate 1:2) to obtain the title compound (83.5 g, 66%).

m.p.: 124.8–129.8° C.

IR spectrum (KBr tab.) υ cm⁻¹: 3348, 1648, 1613, 1512, 1398, 1294, 1167, 814

NMR spectrum (*DMSO-d$_6$) δ ppm: 7.49 (1H, d, J=2.6 Hz), 7.29 (1H, dd, J=9.6, 2.6 Hz), 7.02 (1H, s), 6.80 (1H, d, J=9.6 Hz), 3.46–3.41 (2H, m), 2.56–2.54 (2H, m)

[Step 3] Synthesis of 6-chloro-1-(4-chlorophenyl)-2,3-dihydro-4(1H)-quinolinone

The compound (9.02 g) obtained in step 2,1-chloro-4-iodobenzene (23.7 g), copper oxide (II) (1.04 g) and potassium carbonate (6.87 g) were mixed, and the mixture was heated at 180 to 190° C. for 6 hours with stirring in an oil bath in an argon atmosphere. The reaction mixture was poured into ice water and extracted with ether. Insoluble content was removed by filtration and the ether layer was washed with saturated aqueous solution of sodium chloride, dried over anhydrous sodium sulfate, and the solvent was evaporated under reduced pressure. The residue was purified by silica gel column chromatography (eluent:hexane/methylene chloride=1:2) to obtain the title compound (5.3 g, 36%).

m.p.: 142.8–149.5° C.

IR spectrum (KBr tab.) υ cm⁻¹: 1677, 1490, 1475, 1209, 1166, 825

NMR spectrum (*DMSO-d$_6$) δ ppm: 7.82 (1H, d, J=8.6 Hz), 7.67 (2H, d, J=2.7 Hz), 7.41–7.39 (1H, m), 7.37–7.36 (1H, m), 7.33 (1H, dd, J=9.1, 2.7 Hz), 6.62 (1H, d, J=9.1 Hz), 3.90 (2H, t, J=6.9 Hz), 2.80 (2H, t, J=6.9 Hz)

[Step 4] Synthesis of 6-chloro-1-(4-chlorophenyl)- 4(1H)-quinolinone

The compound (1 g) obtained in step 3 was dissolved in ethylene glycol (10 ml). To the solution was added 5% palladium carbon (200 mg) and the mixture was heated under reflux for 30 minutes in an argon atmosphere. After allowing to cool, the insoluble content was removed by filtration and the filtrate was distilled to remove the solvent under reduced pressure. The residue was purified by silica gel column chromatography (eluent:hexane/ethyl acetate= 1:1) to obtain the title compound (120 mg, 12%).

m.p.: 236.3–237.5° C.

IR spectrum (KBr tab.) υ cm⁻¹: 1632, 1587, 1493, 1471, 1293, 825

NMR spectrum (DMSO-d$_6$) δ ppm: 8.14 (1H, d, J=2.6 Hz), 8.02 (1H, d, J=7.6 Hz), 7.75–7.72 (2H, m), 7.67–7.63 (3H, m), 7.05 (1H, d, J=9.2 Hz), 6.22 (1H, d, J=7.6 Hz)

[Step 5] Synthesis of 2,10-dichlor-4H-pyrido[3,2,1-jk]carbazole-4-one 6-chloro-1-(4-chlorophenyl)-4(1H)-quinolinone (2 g) obtained in step 4 was dissolved in acetic acid (150 ml) and to the solution were added a boron tribromide-acetic acid complex (44 ml) and palladium diacetate (6.28 g). The mixture was heated under reflux for 1 hour in an argon atmosphere and allowed to cool. The insoluble content was removed by filtration and the solution was extracted with water and ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent:hexane/ethyl acetate=1:2) to obtain the title compound (40 mg, 2%).

Example 265

Synthesis of 5-benzyl-2,10-dichloro-4H-pyrido[3,2, 1-jk]carbazole-4-one

[Step 1] Synthesis of 3,6-dichlorocarbazole

The procedure of Example 243, step 2 was repeated by using commercially available carbazole (50 g) to obtain the title compound (29 g, 41%).

m.p.: 206.5–208.6° C.

IR spectrum (KBr tab.) υ cm⁻¹: 3406, 1477, 1464, 1286, 1078, 810, 571

NMR spectrum (DMSO-d$_6$) δ ppm: 11.59 (1H, s), 8.30 (2H, d, J=2.0 Hz), 7.52 (2H, d, J=8.7 Hz), 7.42 (2H, dd, J=8.7, 2.0 Hz)

[Step 2] Synthesis of 2,10-dichloro-5,6-dihydro-4H-pyrido[3,2,1-jk]carbazole-4-one The procedure of Example 1, steps 2 and 3 was repeated by using the compound produced in step 1 to obtain the title compound.

m.p.: 248.5–252.1° C.

IR spectrum (KBr tab.) υ cm⁻¹: 1683, 1495, 1470, 1323, 1213, 791

NMR spectrum (DMSO-d$_6$) δ ppm: 8.59 (1H, d, J=2.0 Hz), 8.42 (1H, d, J=2.3 Hz), 7.77–7.73 (2H, m), 7.61 (1H, dd, J=8.6, 2.0 Hz), 4.62 (2H, t, J=7.0 Hz), 3.16 (2H, t, J=7.0 Hz)

[Step 3] Synthesis of 5-benzyl-2,10-dichloro-4H-pyrido [3,2,1-jk]carbazole-4-one The procedure of Example 90 was repeated by using the compound (500 mg) produced in step 2 to obtain the title compound (508 mg, 81%).

Example 271

Synthesis of 5-(4-aminobenzyl)-2,10-dichlor-5-(3-pyridylmethyl)-4H-pyrido[3,2,1-jk]carbazole-4-one The compound (1.5 g) obtained in Example 270 was suspended in a mixed solvent of tetrahydrofuran (500 ml) and water (200 ml) and hydrobromic acid (48%, 200 ml) was added to the suspension. The mixture was heated under reflux for 39 hours in an argon atmosphere and allowed to cool. After evaporate approximately half of the solvent under reduced pressure, the residue was adjusted to pH 7 by addition of 1 N sodium hydroxide. The crystals precipitated were recovered by filtration, and washed with methanol and ether in succession to obtain the title compound (860 mg, 74%).

Example 272

Synthesis of 2-chloro-10-nitro-5-(3-pyridylmethyl)-4H-pyrido[3,2,1-jk]carbazole-4-one

[Step 1] Synthesis of 3-chlorocarbazole-N-β-propionitrile 3-chlorocarbazole (3 g) prepared by the procedure described in Rec. Trav. Chim., 73: 197, 1954 was suspended in acrylonitrile (7.06 ml) and to the suspension was added dropwise Triton B (0.1 ml) in an ice bath. After stirring for 15 minutes, an adequate amount of ethanol was added. The precipitated crystals were recovered by filtration to obtain the title compound (3.7 g, 98%).

m.p.: 164.7–166.3° C.

IR spectrum (KBr tab.) υ cm⁻¹: 1473, 1456, 1275, 1200, 806, 744

NMR spectrum (DMSO-d$_6$) δ ppm: 8.29 (1H, d, J=2.3 Hz) 8.22 (1H, d, J=7.9 Hz), 7.79–7.73 (2H, m), 7.51–7.50 (2H, m), 7.28–7.22 (1H, m), 4.76 (2H, t, J=6.6 Hz), 3.04 (2H, t, J=6.6 Hz)

[Step 2] Synthesis of 3-chloro-6-nitrocarbazole-N-β propionitrile

The compound (3.5 g) obtained in step 1 was dissolved in nitrobenzene (31 ml) and to the solution was added fuming sulfuric acid (1.25 ml), and the mixture was stirred for 1 hour at room temperature. The crystals were recovered by filtration and washed with methanol and ether in succession to obtain the title compound (2.67 g, 65%).

m.p.: 326.2° C. (dec)

IR spectrum (KBr tab.) $\upsilon$ cm$^{-1}$: 1510, 1479, 1336, 1321, 1296, 1097

NMR spectrum (DMSO-d$_6$) $\delta$ ppm: 9.30 (1H, d, J=2.3 Hz), 8.61 (1H, d, J=2.0 Hz) 8.40 (1H, d, J=9.1, 2.3Hz), 7.98 (1H, d, J=9.1 Hz),7.91 (1H, d, J=8.8 Hz), 7.63 (1H, d, J=8.8, 2.0 Hz) 4.87 (2H, t, J=6.6 Hz), 3.10 (2H, t, J=6.6 Hz)

[Step 3] Synthesis of 3-chloro-6-nitrocarbazole-N-$\beta$ propionic acid

The compound (3 g) obtained in step 2 was suspended in ethanol (40 ml) and 2 N sodium hydroxide (40 ml) was added to the suspension. The mixture was heated under reflux for 9 hours in an argon atmosphere and allowed to cool. After evaporate the solvent under reduced pressure, water and ether were added for phase separation. The aqueous layer was rendered acidic by addition of 4 N hydrochloric acid. The resulting precipitate was recovered by filtration and washed with methanol and ether in succession to obtain the title compound (2.1 g, 66%).

m.p.: 325.8° C. (dec)

IR spectrum (KBr tab.) $\upsilon$ cm$^{-1}$: 1713, 1508, 1477, 1338, 1323, 1298, 814

NMR spectrum (DMSO-d$_6$) $\delta$ ppm: 12.42 (1H, bs), 9.27 (1H, d, J=2.3 Hz), 8.58 (1H, d, J=2.0 Hz), 8.37 (1H, dd, J=9.2, 2.3 Hz), 7.87(1H, d, J=9.2 Hz), 7.81 (1H, d, J=8.8 Hz), 7.60 (1H, dd, J=8.8, 2.0 Hz), 4.72 (2H, t, J=6.6 Hz), 2.80 (2H, t, J=6.6 Hz)

[Step 4] Synthesis of 2-chloro-5,6-dihydro-10-nitro-4H-pyrido[3,2,1-jk]carbazole-4-one The compound (200 mg) obtained in step 3 was suspended in anhydrous methylene chloride (2.5 ml) and to the suspension were added thionyl chloride (0.1 ml) and anhydrous dimethylformamide (1 drop) in an ice bath. The mixture was heated under reflux for 2 hours in an argon atmosphere and allowed to cool. The solvent was evaporated under reduced pressure. The resulting residue was suspended in anhydrous methylene chloride (2 ml) and the suspension was cooled in an dry ice-acetone bath. After adding aluminium chloride (167 ml), the suspension was heated to room temperature. The reaction mixture was poured into ice water and extracted with ethyl acetate. The ethyl acetate layer was washed with saturated aqueous solution of sodium chloride, dried over anhydrous sodium sulfate, and the solvent was evaporated under reduced pressure. The residue was purified by silica gel flash column chromatography (eluent:methylene chloride containing 3% methanol) to obtain the title compound (94 mg, 50%).

m.p.: 360.0° C. (dec)

IR spectrum (KBr tab.) $\upsilon$ cm$^{-1}$: 1686, 1603, 1510, 1329, 1302, 750

NMR spectrum (DMSO-d$_6$) $\delta$ ppm: 9.36 (1H, d, J=2.4 Hz), 8.82 (1H, d, J=1.7 Hz), 8.46 (1H, d d, J=9.0, 2.4 Hz), 7.90 (1H, d, J=9.0 Hz), 7.80 (1H, d, J=1.7 Hz), 4.73 (2H, t, J=7.1 Hz), 3.20 (2H, t, J=7.1 Hz)

[Step 5] Synthesis of 2-chloro-10-nitro-5-(3-pyridylmethyl)-4H-pyrido[3,2,1-jk]carbazole-4-one The procedure of Example 1, step 4 was repeated by using the compound (3 g) produced in step 4 to obtain the title compound (2.3 g, 59%).

Example 273

Synthesis of 10-amino-2-chloro-5-(3-pyridylmethyl)-4H-pyrido[3,2,1-jk]carbazole-4-one 2-chloro-10-nitro-5-(3-pyridylmethyl)-4H-pyrido[3,2,1-jk]carbazole-4-one (1.86 g) obtained in Example 272 was dissolved in conc. sulfuric acid (11 ml) and copper (995 mg) was added to the solution. The mixture was heated to 50 ° C. in a hot water bath and stirred for 30 minutes. After allowing to cool, the reaction mixture was poured into ice water, then the solution was adjusted to pH 10 with 1 N aqueous solution of sodium hydroxide. The precipitated crystals were recovered by filtration, and washed with water and ether in succession to obtain the title compound (1.37 g, 80%).

Example 274

Synthesis of 2-chloro-10-hydroxy-5-(3-pyridylmethyl)-4H-pyrido[3,2,1-jk]carbazole-4-one 10-amino-2-chloro-5-(3-pyridylmethyl)-4H-pyrido[3,2,1-jk]carbazole-4-one (300 mg) obtained in Example 273 was dissolved in a mixed solvent of conc. sulfuric acid (14.6 ml) and water (20 ml) and sodium nitrite (63 mg) dissolved in water (1 ml) was added dropwise in an ice bath. A mixed solvent of conc. sulfuric acid (20 ml) and water (15 ml) was heated under reflux in an argon atmosphere. After adding dropwise thereto the solution previously prepared, the mixture was stirred for 5 minutes and allowed to cool. The mixture was adjusted to pH 9 with 1 N aqueous solution of sodium hydroxide, and extracted with ethyl acetate. The ethyl acetate layer was washed with saturated aqueous solution of sodium chloride, dried over anhydrous sodium sulfate, and the solvent was evaporated under reduced pressure. The residue was washed with methanol and ether in succession to obtain the title compound (213 mg, 71%).

Example 276

Synthesis of 10-bromo-2-methyl-5-(3-pyridylmethyl)-4H-pyrido[3,2,1-jk]carbazole-4-one

[Step 1] Synthesis of 6-methyl-1,2,3,4-tetrahydrocarbazole

The procedure of Example 171, step 1 was repeated by using p-tolylhydrazine hydrochloride (25 g) to obtain the title compound (27 g, 93%).

m.p.: 147.3–150.6° C.

IR spectrum (KPr tab.) $\upsilon$ cm$^{-1}$: 3396, 2929, 1589, 1439, 1315, 797, 596

NMR spectrum (DMSO-d$_6$) $\delta$ ppm: 10.45 (1H, s), 7.12 (1H, s), 7.11 (1H, d, J=7.8 Hz), 6.78 (1H, dd, J=7.8, 1.5 Hz), 2.69–2.65 (2H, m), 2.60–2.50 (2H, m), 2.34 (3H, s), 1.81–1.78 (4H, m)

[Step 2] Synthesis of 3-methylcarbazole

The compound 20 g) obtained in step 1 was dissolved in xylene (500 ml) and 10% palladium carbon (6 g) was added to the solution. The mixture was heated under reflux for 5 hours in an argon atmosphere. The reaction mixture was filtered while hot and the filtrate was distilled to remove the solvent under reduced pressure. The residue was purified by silica gel flash column chromatography (eluent: hexane/ethyl acetate=20:1) to obtain the title compound (7.5 g, 38%).

m.p.: 206.2–209.5° C.

IR spectrum (KBr tab.) $\upsilon$ cm$^{-1}$: 3408, 1462, 1242, 806, 748, 729, 573

NMR spectrum (DMSO-d$_6$) δ ppm: 11.09 (1H, s), 8.05 (1H, d, J=7.8 Hz), 7.89 (1H, s), 7.44 (1H, d, J=8.3 Hz), 7.38–7.32 (2H, m), 7.20 (1H, dd, J=8.3, 1.5 Hz), 7.11 (1H, t, J=6.8 Hz), 2.46 (3H, s)

[Step 3] Synthesis of 3-bromo-6-methylcarbazole

The procedure of Example 235, step 3 was repeated by using the compound (2 g) produced in step 2 to obtain the title compound (1.85 g, 64%).

m.p.: 211.7–212.69° C.

IR spectrum (KBr tab.) υ cm$^{-1}$: 3394, 1491, 1444, 1296, 1240, 812, 569

NMR spectrum (DMSO-d$_6$) δ ppm: 11.29 (1H, bs), 8.29 (1H, d, J=2.0 Hz), 7.95 (1H, d, J=1.2 Hz), 7.54–7.35 (3H, m), 7.24 (1H, dd, J=8.3, 1.2 Hz), 2.45 (3H, s)

([Step 4] Synthesis of 10-bromo-5,6-dihydro-2-methyl-4H-pyrido[3,2,1-jk]carbazole-4-one The procedure of Example 1, steps 2 and 3 was repeated by using the compound produced in step 3 to obtain the title compound.

m.p.: 201.7–204.4° C.

IR spectrum (KBr tab.) υ cm$^{-1}$: 1670, 1597, 1498, 1477, 1281, 1221, 791

NMR spectrum (CDCl$_3$) δ ppm: 8.17 (1H, d, J=1.6 Hz), 7.98 (1H, s), 7.77–7.76 (1H, m), 7.59 (1H, dd, J=8.5, 1.6 Hz), 7.26 (1H, s), 4.46 (2H, t, J=7.1 Hz), 3.15 (2H, t, J=7.1 Hz), 2.55 (3H, s)

[Step 5] Synthesis of 10-bromo-2-methyl-5-(3-pyridylmethyl)-4H-pyrido[3,2,1-jk]carbazole-4-one The procedure of Example 1, step 4 was repeated by using the compound (2 g) produced in step 4 to obtain the title compound (120 mg, 47%).

Example 278

Synthesis of 9-bromo-2-(3-hydroxyoropyloxy)-5-(3-pyridylmethyl)-4H-pyrido[3,2,1-jk]carbazole-4-one hydrochloride 9-bromo-2-(3-hydroxypropyloxy)-5-(3-pyridylmethyl)-4H-pyrido[3,2,1-jk]carbazole-4-one (300 mg) obtained in Example 110 was suspended in methanol (10 ml) and a solution of hydrogen chloride in methanol (5 ml) was added on an ice bath. The mixture, was stirred for 5 minutes. The solvent was evaporated under reduced pressure, and the resulting crude crystals were washed with ether to obtain the title compound (320 mg, 98%).

m.p.: 201.1–204.2° C.

IR spectrum (KBr tab.) υ cm$^{-1}$: 3369, 1578, 1508, 1464, 1389

NMR spectrum (*DMSO-d$_6$) δ ppm: 9.21 (1H, s), 8.95 (1H, s), 8.76 (1H, d, J=5.5 Hz), 8.54 (1H, d, J=8.1 Hz), 8.38 (1H, d, J=1.6 Hz), 8.28–8.19 (2H, m), 7.95 (1H, dd, J=8.1, 5.5 Hz), 7.65 (1H, dd, J=8.3, 1.6 Hz), 7.53 (1H, d, J=1.6 Hz), 4.22 (2H, t, J=6.3 Hz), 4.06 (2H, s), 3.62 (2H, t, J=6.1 Hz), 2.07–1.89 (2H, m)

Example 279

Synthesis of 9-bromo-2-(3-hydroxypropyloxy)-5-(3-pyridylmethyl)-4H-pyrido[3,2,1-jk]carbazole-4-one methanesulfonate 9-bromo-2-(3-hydroxypropyloxy)-5-(3-pyridylmethyl)-4H-pyrido[3,2,1-jk]carbazole-4-one (250 mg) obtained in Example 110 was suspended in methanol (200 ml) and to the suspension was added a solution of methanesulfonic acid (57 mg) in methanol (5 ml) at room temperature. The mixture was stirred for 30 minutes. The solvent was evaporated under reduced pressure, and the resulting crude crystals were washed with a small amount of methanol and ether in succession to obtain the title compound (270 mg, 89%).

m.p.: 243.9–250.7° C.

IR spectrum (KBr tab.) υ cm$^{-1}$: 3388, 1572, 1510, 1209, 1192, 1055

NMR spectrum (*DMSO-d$_6$) δ ppm: 9.19 (1H, s), 8.96–8.91 (1H, m), 8.75 (1H, d, J=5.5 Hz), 8.50 (1H, d, J=8.1 Hz) 8.40 (1H, d, J=1.4 Hz), 8.27 (1H, d, J=2.2 Hz), 8.24 (1H, d, J=8.3 Hz), 7.96–7.89 (1H, m), 7.67 (1H, dd, J=8.3, 1.4 Hz), 7.54 (1H, d, J=2.2 Hz), 4.22 (2H, t, J=6.3 Hz), 4.06 (2H, s), 3.62 (2H, t, J=6.1 Hz), 2.32 (3H, s), 2.02–1.88 (2H, m)

Example 280

Synthesis of 9-bromo-2-(3-hydroxyoropyloxy)-5-(3-pyridylmethyl)-4H-pyrido[3,2,1-jk]carbazole-4-one nitrate 9-bromo-2-(3-hydroxypropyloxy)-5-(3-pyridylmethyl)-4H-pyrido[3,2,1-jk]carbazole-4-one (50 mg) obtained in Example 110 was suspended in methanol (100 ml) and to the suspension was added a solution of nitric acid (11 mg) in methanol (5 ml) at room temperature. The mixture was stirred for 30 minutes. The solvent was evaporated under reduced pressure, and the resulting crude crystals were washed with a small amount of methanol and ether in succession to obtain the title compound (47 mg, 83%).

m.p.: 200. 2–202.4° C.

IR spectrum (KBr tab.) υ cm$^{-1}$: 3371, 1572, 1462, 1385, 1333

NMR spectrum (*DMSO-d$_6$) δ ppm: 9.18 (1H, s), 8.93 (1H, s), 8.75 (1H, d, J=5.7 Hz), 8.51 (1H, d, J=7.9 Hz), 8.39 (1H, d, J=1.5 Hz), 8.27 (1H, d, J=2.2 Hz), 8.24 (1H, d, J=8.4 Hz), 7.97–7.88 (1H, m), 7.67 (1H, dd, J=8.4, 1.5 Hz), 7.54 (1H, d, J=2.2 Hz), 4.22 (2H, t, J=6. 4 Hz), 4.06 (2H, s), 3.62 (2H, t, J=6.1 Hz), 2.03–1.88 (2H, m)

Example 281

Synthesis of 9-bromo-2-(3-hydroxypropyloxy)-5-(3-pyridylmethyl)-4H-pyrido[3,2,1-jk]carbazole-4-one sulfate 9-bromo-2-(3-hydroxypropyloxy)-5-(3-pyridylmethyl)-4H-pyrido[3,2,1-jk]carbazole-4-one (50 mg) obtained in Example 110 was suspended in methanol (100 ml) and to the suspension was added a solution of sulfuric acid (6×10$^{-3}$ ml) in methanol (5 ml) at room temperature. The mixture was stirred for 30 minutes. The solvent was evaporated under reduced pressure, and the resulting crude crystals were washed with a small amount of methanol and ether in succession to obtain the title compound (49 mg, 81%).

m.p.: >300° C.

IR spectrum (KBr tab.) υ cm$^{-1}$: 3388, 1564, 1512, 1389, 1225, 1188, 1059

NMR spectrum (*DMSO-d$_6$) δ ppm: 9.18 (1H, s), 8.96–8.90 (1H, m), 8.75 (1H, d, J=5.7 Hz), 8.51 (1H, d, J=8.3 Hz), 8.40 (1H, d, J=1.4 Hz), 8.27 (1H, d, J=2.1 Hz), 8.24 (1H, d, J=8.2 Hz), 7.97–7.89 (1H, m), 7.68 (1H, dd, J=8.2, 1.4 Hz), 7.54 (1H, d, J=2.1 Hz), 4.22 (2H, t, J=6.3 Hz), 4.06 (2H, s), 3.62 (2H, t, J=6.2 Hz), 2.02–1.89 (2H, m)

Example 282

Synthesis of 9-bromo-2-(3-hydroxypropyloxy)-5-(3pyridylmethyl)-4H-pyrido[3,2,1-jk]carbazole-4-one maleate 9-bromo-2-(3-hydroxypropyloxy)-5-(3-pyridylmethyl)-4H-pyrido[3,2,1-jk]carbazole-4-one (50 mg) obtained in Example 110 was suspended in methanol (100 ml) and to the suspension was added a solution of maleic acid (2.5 mg) in methanol (5 ml) at room temperature. The mixture was heated under reflux with stirring for 30 minutes and allowed to cool. The solvent was evaporated under reduced pressure, and the resulting crude crystals were washed with a small amount of methanol and ether in succession to obtain the title compound (50 mg, 80%).

m.p.: 188.4–191.4° C.

IR spectrum (KBr tab.) υ cm$^{-1}$: 3365, 1595, 1576, 1510, 1462, 1389

NMR spectrum (*DMSO-d$_6$) δ ppm: 9.17 (1H, s), 8.71–8.65 (1H, m), 8.49–8.40 (2H, m), 8.28–8.21 (2H, m), 7.90 (1H, d, J=8.3 Hz), 7.65 (1H, dd, J=8.3, 1.0 Hz), 7.56 (1H, d, J=2.0 Hz), 7.44–7.36 (1H, m), 6.22 (2H, s), 4.23 (2H, t, J=6.5 Hz), 3.9 1 (2H, s), 3.62 (2H, t, J=6.5 Hz), 2.00–1.89 (2H, m)

Example 283

Synthesis of 9-chloro-2-(3-hydroxypropyloxy)-5-(3-pyridylmethyl)-4H-pyrido[3,2,1-jk]carbazole-4-one

[Step 1] Synthesis of 2-chloro-6-[3-(4-methoxyphenoxy)propyloxy]carbazole 2-chloro-6-hydroxycarbazole (14.2 g) prepared by the procedure described in Justus Liebigs Ann. Chem., 617, 54 (1958) was dissolved in methanol (140 ml) and to the solution was added 2 N solution of potassium hydroxide in methanol (36.7 ml). The mixture was stirred for 5 minutes at room temperature. After evaporate the solvent under reduced pressure, toluene (40 ml) was added and the solvent was evaporated again under reduced pressure. The resulting crystals were suspended in toluene (53 ml). To the suspension were added 3-(4-methoxyphenoxy)propylbromide (18.0 g) prepared by the procedure described in Kokai Tokkyo Koho JP-A 02193942, dissolved in toluene (18 ml), then 18-crown-6 (1.9 g) dissolved in toluene (18 ml). The mixture was heated under reflux for 1 hour and allowed to cool. 0.001 N hydrochloric acid (120 ml) was added, and the mixture was extracted with ethyl acetate. The ethyl acetate layer was washed with saturated aqueous solution of sodium chloride, dried over anhydrous sodium sulfate, and the solvent was evaporated under reduced pressure. The residue was dissolved in acetone, and re-precipitated from methanol/water (1:1), then dissolved in methylene chloride. After adding silica gel, the solvent was evaporated under reduced pressure, and the residue was eluted from the silica gel as the adsorbent with a solution of hexane/methylene chloride (1:1). The solvent was evaporated under reduced pressure to obtain the title compound (15.7g, 56%).

m.p.: 137.1–138.7° C.

IR spectrum (KBr tab.) υ cm$^{-1}$: 3396, 1508, 1456, 1294, 1201, 1031, 823

NMR spectrum (*DMSO-d$_6$) δ ppm: 11.21 (1H, s), 8.12 (1H, d, J=2.3 Hz), 7.73 (1H, d, J=2.3 Hz), 7.47 (1H, d, J=1.8 Hz), 7.40 (1H, d, J=8.7 Hz), 7.12 (1H, dd, J=8.3, 1.8 Hz), 7.06 (1H, dd, J=8.7, 2.3 Hz), 6.95–6.82 (4H, m), 4.21 (2H, t, J=6.2 Hz), 4.11 (2H, t, J=6.1 Hz), 3.69 (3H, s), 2.25–2.13 (2H, m)

[Step 2] Synthesis of 2-chloro-6-[3-(4-methoxyphenoxy)propyloxy]carbazole-N-β-propionic acid The compound (15.7 g) obtained in step 1 was dissolved in acetone (630 ml), and to the solution were added dropwise methyl acrylate (4.6 g) and then Triton B (3.7 ml) on an ice bath. After stirring for 1 hour, the solvent was evaporated under reduced pressure. The resulting residue was suspended in methanol (94 ml), and sodium hydroxide (3.3 g) dissolved in water (4.4 ml) was added dropwise to this suspension, and the mixture was stirred at 60° C. for 30 minutes on a hot water bath. After evaporate the solvent under reduced pressure, the residue was decanted with ether and 1 N hydrochloric acid and ethyl acetate were added to the resulting crystals for phase separation. The ethyl acetate layer was washed with saturated aqueous solution of sodium chloride, dried over anhydrous sodium sulfate, and the solvent was evaporated under reduced pressure to obtain the title compound (17.6 g, 94%).

m.p.: 126.7°130.7° C.

IR spectrum (KBr tab.) υ cm$^{-1}$: 2937, 1699, 1514, 1489, 1238, 1072, 822

NMR spectrum (*DMSO-d$_6$) δ ppm: 12.34 (1H, bs), 8.12 (1H, d, J=8.4 Hz), 7.77 (1H, d, J=2.5 Hz), 7.71 (1H, d, J=1.6 Hz), 7.54 (1H, d, J=8.9 Hz), 7.20–7.18 (2H, m), 6.97–6.80 (4H, m), 4.58 (2H, t, J=6.7 Hz) 4.22 (2H, t, J=6.2 Hz), 4.11 (2H, t, J=6.2 Hz), 3.69 (3H, s), 2.71 (2H, t, J=6.7 Hz), 2.26–2.13 (2H, m)

[Step 3] Synthesis of 9-chloro-5,6-dihydro-2-[3-(4-methoxyphenoxy)propyloxy]-4H-pyrido[3,2,1-jk]carbazole-4-one The compound (14.6 g) obtained in step 2 was suspended in anhydrous chloroform (400 ml), and to the suspension was added PPE (83.2 g) dissolved in anhydrous chloroform (400 ml), and the mixture was heated under reflux for 1.5 hours in an argon atmosphere and allowed to cool. The mixture was poured into water and extracted with methylene chloride. The methylene chloride layer was washed with saturated aqueous solution of sodium chloride, dried over anhydrous sodium sulfate, and the solvent was evaporated under reduced pressure. The residue was crystallized from acetone/methanol (1:1) and recovered by filtration. The crude crystals were dissolved in chloroform while hot and re-precipitated from methanol to obtain the title compound (6.3 g, 38%).

m.p.: 156.3–159.0° C.

IR spectrum (KBr tab.) υ cm$^{-1}$: 2953, 1680, 1506, 1443, 1228, 1065, 818

NMR spectrum (*DMSO-d$_6$) δ ppm: 8.20 (1H, d, J=8.3 Hz), 8.11 (1H, d, J=2.2 Hz), 7.80 (1H, d, J=1.7 Hz), 7.3 5 (1H, d, J=2.2 Hz), 7.25 (1H, dd, J=8.3, 1.7 Hz), 6.94–6.77 (4H, m), 4.54 (2H, t, J=7.0 Hz), 4.24 (2H, t, J=6.1 Hz), 4.10 (2H, t, J=6.1 Hz), 3.67 (3H, s), 3.10 (2H, t, J=7.0 Hz), 2.24–2.12 (2H, m)

[Step 4] Synthesis of 9-chloro-2-[3-(4-methoxyphenoxy)propyloxy]-5-(3-pyridylmethyl)-4H-pyrido[3,2,1-jk]carbazole-4-one The compound (6.3 g) obtained in step 3 was suspended in ethanol (410 ml) and to the suspension were added pyridine-3-aldehyde (2.5 g) and sodium hydroxide (4.6 g) dissolved in water (25 ml). The mixture was stirred for 15 minutes at 60° C. on a hot water bath. After evaporate the solvent under reduced pressure, the crystals were washed with water. The resulting crude crystals were dissolved in an aqueous solution of hot acetonitrile (hot acetonitrile:water= 20:1), and re-precipitated from water to obtain the title compound (6.7 g, 87%).

m.p.: 157.0–160.9° C.

IR spectrum (KBr tab.) υ cm$^{-1}$: 3431, 2933, 1605, 1508, 1462, 1232, 1064

NMR spectrum (*DMSO-d$_6$) δ ppm: 9.10 (1H, s), 8.66–8.60 (1H, m), 8.42–8.35 (1H, m), 8.25 (1H, d, J=1.8

Hz), 8.22 (1H, d, J=8.2 Hz), 8.19 (1H, d, J=2.2 Hz), 7.79–7.70 (1H, m), 7.53 (1H, d, J=2.2 Hz), 7.47 (1H, dd, J=8.2, 1.8 Hz), 7.32–7.23 (1H, m), 6.95–6.78 (4H, m), 4.29 (2H, t, J=6.2 Hz), 4.11 (2H, t, J=6.1 Hz), 3.86 (2H, s), 3.66 (3H, s), 2.28–2.14 (2H, m)

[Step 5] Synthesis of 9-chloro-2-(3-hydroxypropyloxy)-5-(3-pyridylmethyl)-4H-pyrido[3,2,1-jk]carbazole-4-one The compound (3.7 g) obtained in step 4 was suspended in an aqueous solution of acetonitrile (400 ml, acetonitrile:water=4:1), and to the suspension was added dropwise slowly CAN (11.5 g) dissolved in an aqueous solution of acetonitrile (40 ml, acetonitrile:water=4:1) on an ice bath. After stirring for 15 minutes, 1 N aqueous solution of sodium hydroxide was added. The precipitated crystals were recovered by filtration and washed with a small amount of water. The crude crystals were added to ethyl acetate. After stirring for 3 hours, the insoluble content was removed by filtration and the filtrate was washed with 10% aqueous solution of sodium sulfite, 1N aqueous solution of sodium hydroxide and saturated aqueous solution of sodium chloride in succession, dried over anhydrous sodium sulfate, and the solvent was evaporated under reduced pressure. The resulting crystals were washed with ether and recovered by filtration to obtain the title compound (1.3 g, 46%).

m.p.: 213.9–220.8° C.

IR spectrum (KBr tab.) υ cm$^{-1}$: 3429, 1597, 1506, 1462, 1389, 1234, 1065

NMR spectrum (*DMSO-d$_6$) δ ppm: 9.15 (1H, s), 8.66–8.60 (1H, m), 8.42–8.35 (1H, m), 8.35–8.18 (3H, m), 7.80–7.73 (1H, m), 7.54 (1H, d, J=2.2 Hz), 7.51 (1H, dd, J=8.3, 1.8 Hz), 7.33–7.24 (1H, m), 4.63 (1H, t, J=5.0 Hz), 4.22 (2H, t, J=6.4 Hz), 3.88 (2H, s), 3.69–3.55 (2H, m), 2.03–1.88 (2H, m)

Example 284

Synthesis of 9-chloro-2-(3-hydroxypropyloxy)-5-(3-pyridylmethyl)-4H-pyrido[3,2,1-jk]carbazole-4-one hydrochloride The procedure of Example 278 was repeated by using the compound (60 mg) produced in Example 283 to obtain the title compound (55 mg, 85%).

m.p.: 199.3–202.7° C.

IR spectrum (KBr tab.) υ cm$^{-1}$: 3396, 1605, 1578, 1510, 1462, 1390, 1066

NMR spectrum (*DMSO-d$_6$) δ ppm: 9.20 (1H, s), 8.92 (1H, s), 8.73 (1H, d, J=5.3 Hz), 8.48 (1H, d, J=8.1 Hz), 8.30 (1H, d, J=8.3 Hz), 8.30–8.22 (2H, m), 7.94–7.85 (1H, m), 7.58–7.47 (2H, m), 4.22 (2H, t, J=6.3 Hz), 4.05 (2H, s), 3.62 (2H, t, J=6.1 Hz), 2.02–1.88 (2H, m)

Example 285

Synthesis of 9-chloro-2-(3-hydroxypropyloxy)-5-(3-pyridylmethyl)-4H-pyrido[3,2,1-jk]carbazole-4-one methanesulfonate The procedure of Example 279 was repeated by using the compound (780 mg) produced in Example 283 to obtain the title compound (696 mg, 73%).

m.p.: 215.7–221.6° C.

IR spectrum (KBr tab.) υ cm$^{-1}$: 3431, 1605, 1510, 1462, 1390, 1211, 1039

NMR spectrum (*DMSO-d$_6$) δ ppm: 9.18 (1H, s), 8.9 2 (1H, s), 8.74 (1H, d, J=5.3 Hz) 8.48 (1H, d, J=9 Hz), 8.31 (1H, d, J=8.4 Hz), 8.30–8.22 (2H, m), 7.91 (1H, dd, J=7.9, 5.3 Hz), 7.60–7.51 (2H, m), 4.22 (2H t, J=6.5 Hz), 4.05 (2H, s), 3.62 (2H, t, J=6.2 Hz), 2.31 (3H, s), 2.00–1.89 (2H, m)

Example 286

Synthesis of 9-fluoro-2-(3-hydroxypropyloxy)-5-(3-pyridylmethyl)-4H-pyrido[3,2,1-jk]carbazole-4-one The procedure of Example 283, steps 1, 2, 3, 4 and 5 was repeated by using commercially available 4-fluoro-2-nitroaniline to obtain the title compound.

m.p.: 204.5–208.7° C.

IR spectrum (KBr tab.) υ cm$^{-1}$: 1593, 1574, 1512, 1464, 1205, 1097, 847

NMR spectrum (*DMSO-d$_6$) δ ppm: 9.09 (1H, s), 8.63 (1H, d, J=2.2 Hz), 8.40–8.38 (1H, m), 8.29 (1H, dd, J=8.5, 5.3 Hz), 8.19 (1H, d, J=2.0 Hz), 8.05 (1H, dd, J=9.5, 2.2 Hz), 7.80–7.71 (1H, m), 7.50 (1H, d, J=2.0 Hz), 7.38–7.22 (2H, m), 4.62 (1H, t, J=5.1 Hz), 4.22 (2H, t, J=6.2 Hz), 3.89 (2H, s), 3.71–3.57 (2H, m), 2.05–1.88 (2H, m)

Example 287

Synthesis of 9-fluoro-2-(3-hydroxypropyloxy)-5-(3-pyridylmethyl)-4H-pyrido[3,2,1-jk]carbazole-4-one methanesulfonate The procedure of Example 279 was repeated by using the compound (700 mg) produced in Example 286 to obtain the title compound (750 mg, 87%).

m.p.: 198.5–203.6° C.

IR spectrum (KBr tab.) υ cm$^{-1}$: 3032, 1593, 1514, 1464, 1392, 1201, 1039

NMR spectrum (*DMSO-d$_6$) δ ppm: 9.13 (1H, s), 8.95 (1H, s), 8.77 (1H, d, J=5.2 Hz), 8.55 (1H, d, J=8.1 Hz), 8.31 (1H, dd, J=8.7, 5.4 Hz), 8.21 (1H, d, J=2.2 Hz), 8.01 (1H, dd, J=9.5, 2.2 Hz), 8.00–7.91 (1H, m), 7.48 (1H, d, J=2.2 Hz), 7.41–7.29 (1H, m), 4.21 (2H, t, J=6.2 Hz), 4.07 (2H, s), 3.62 (2H, t, J=6.2 Hz), 2.34 (3H, s), 2.01–1.88 (2H, m)

Example 288

Synthesis of 2-(3-hydroxypropyloxy)-5-(3-pyridylmethyl)-4H-pyrido[3,2,1-jk]carbazole-4-one The procedure of Example 105 was repeated by using the compound (100 mg) produced in Example 155 and 3-bromo-1-propanol (83 ml) to obtain the title compound (82 mg, 69%).

m.p.: 72.5–78.6° C.

IR spectrum (KBr tab.) υ cm$^{-1}$: 3400, 1568, 1510, 1458, 1335, 1309

NMR spectrum (*DMSO-d$_6$) δ ppm: 9.15 (1H, s), 8.68–8.61 (1H, m), 8.38 (1H, dd, J=4.7, 1.6 Hz), 8.28 (1H, d, J=7.5 Hz), 8.21 (1H, d, J=2.2 Hz), 8.10 (1H, d, J=8.3 Hz), 7.82–7.73 (1H, m), 7.70 –7.61 (1H, m), 7.53 (1H, d, J=2.2 Hz), 7.51–7.42 (1H, m), 7.28 (1H, dd, J=7.7, 4.9 Hz), 4.63 (1H, t, J=5.1 Hz), 4.23 (2H, t, J=6.3 Hz), 3.91 (2H, s), 3.68–3.54 (2H, m), 2.02–1.88 (2H, m)

Example 289

Synthesis of 2-(3-hydroxypropyloxy)-5-(3-pyridylmethyl)-9-trifluoromethyl-4H-pyrido[3,2,1-jk]carbazole-4-one The procedure of Example 283, steps 1, 2, 3, 4 and 5 was repeated by using commercially available 4-trifluoromethyl-2-nitroaniline to obtain the title compound.

m.p.: 194.2–198.0° C.

IR spectrum (KBr tab.) υ cm⁻¹: 3213, 1605, 1574, 1471, 1389, 1346, 1321, 1161, 1117

NMR spectrum (*DMSO-d$_6$) δ ppm: 9.32 (1H, s), 8.70–8.64 (1H, m), 8.61 (1H, s), 8.51 (1H, d, J=8.5 Hz), 8.42–8.33 (2H, m), 7.82 (1H, d, J=8.5 Hz), 7.83–7.75 (1H, m), 7.63 (1H, d, J=2.2 Hz), 7.29 (1H, dd, J=8.0, 4.7 Hz), 4.62 (1H, t, J=5.0 Hz), 4.2 5 (2H, t, J=6.4 Hz), 3.90 (2H, s), 3.69–3.58 (2H, m), 2.03–1.90 (2H, m)

Example 290

Synthesis of 2-(3-hydroxyoropyloxy)-5-(3-pyridylmethyl)-9-trifluoromethyl-4H-pyrido[3,2,1-jk]carbazole-4-one hydrochloride The procedure of Example 278 was repeated by using the compound (60 mg) produced in Example 289 to obtain the title compound (57 mg, 89%).

m.p.: 185.6–189.3° C.

IR spectrum (KBr tab.) υ cm⁻¹: 3429, 1651, 1574, 1470, 1346, 1319, 1119

NMR spectrum (*DMSO-d$_6$) δ ppm: 9.36 (1H, s), 8.88 (1H, s), 8.67 (1H, d, J=5.5 Hz), 8.58 (1H, s), 8.54 (1H, d, J=7.7 Hz), 8.41 (1H, d, J=2.0 Hz), 8.40–8.32 (1H, m), 7.89–7.75 (2H, m), 7.63 (1H, d, J=2.0 Hz), 4.25 (2H, t, J=6.2 Hz), 4.04 (2H, s), 3.62 (2H, t, J=6.2 Hz), 2.04–1.89 (2H, m)

Example 291

Synthesis of 2-(3-hydroxypropyloxy)-5-(3-pyridylmethyl)-9-trifluoromethyl-4H-pyrido[3,2,1-jk]carbazole-4-one methanesulfonate The procedure of Example 279 was repeated by using the compound (600 mg) produced in Example 289 to obtain the title compound (683 mg, 94%).

m.p.: 204.2–211.1° C.

IR spectrum (KBr tab.) υ cm⁻¹: 3402, 1620, 1574, 1471, 1319, 1207, 1057

NMR spectrum (*DMSO-d$_6$) δ ppm: 9.36 (1H, s), 8.9 0 (1H, s), 8.75–8.74 (1H, m), 8.57 (1H, s), 8.54 (1H, d, J=7.9 Hz), 8.46–8.37 (2H, m), 7.92–7.77 (2H, m), 7.62 (1H, d, J=2.2 Hz), 4.25 (2H, t, J=6.6 Hz), 4.05 (2H, s), 3.62 (2H, t, J=6.2 Hz), 2.30 (3H, s), 2.01–1.90 (2H, m)

Examples in which the compounds were synthesized according to the respective processes described in other examples are enumerate in Table 4.

TABLE 4

| | |
|---|---|
| Compounds synthesized by the process of Example 1, step 1 | Example 185, Example 188, Example 252, Example 255 |
| Compounds synthesized by the process of Example 1, step 4 | Example 127, Example 128, Example 129, Example 130, Example 131, Example 133, Example 135, Example 136, Example 137, Example 138, Example 139, Example 140, Example 141, Example 142, Example 143, Example 144 |
| Compounds synthesized by the process of Example 2 | Example 132, Example 155, Example 186, Example 204, Example 211, Example 217, Example 225, Example 233, Example 236, Example 244, Example 249, Example 258, Example 269 |
| Compounds synthesized by the process of Example 3 | Example 10, Example 12, Example 13, Example 159 |
| Compounds synthesized by the process of Example 5 | Example 157, Example 206, Example 219, Example 227, Example 245, Example 250, Example 254 |
| Compounds synthesized by the process of Example 6 | Example 9, Example 11, Example 134, Example 158, Example 160 |
| Compounds synthesized by the process of Example 14 | Example 15, Example 16 |
| Compounds synthesized by the process of Example 18 | Example 19, Example 20, Example 21, Example 23, Example 251, |
| Compounds synthesized by the process of Example 26 | Example 27, Example 28, Example 29, Example 30, Example 31 |
| Compounds synthesized by the process of Example 34 | Example 35, Example 36, Example 37 |
| Compounds synthesized by the process of Example 38 | Example 156, Example 205, Example 212, Example 218, Example 226, Example 234, Example 237, Example 259 |
| Compounds synthesized by the process of Example 39 | Example 40, Example 42 |
| Compound synthesized by the process of Example 44 | Example 45 |
| Compound synthesized by the process of Example 48 | Example 152 |
| Compound synthesized by the process of Example 49 | Example 162 |
| Compound synthesized by the process of Example 52 | Example 164 |
| Compound synthesized by the process of Example 53 | Example 165 |
| Compounds synthesized by the process of Example 56 | Example 163, Example 183, Example 209, Example 215, Example 222, Example 230, Example 241 |
| Compounds synthesized by the process of Example 58 | Example 169, Example 187, Example 200, Example 207, Example 213, Example 220, Example 228, Example 239 |
| Compounds synthesized by the process of Example 59 | Example 170, Example 189, Example 208, Example 214, Example 221, Example 229, Example 240, Example 247, Example 261, Example 263 |
| Compounds synthesized by the process of Example 62 | Example 223, Example 231 |
| Compounds synthesized by the process of Example 64 | Example 65, Example 66, Example 67, Example 68, Example 69, Example 76, Example 77, Example 78 |
| Compound synthesized by the process of Example 70 | Example 72 |
| Compounds synthesized by the process of Example 79 | Example 80, Example 81 |
| Compounds synthesized by the process of Example 84 | Example 87, Example 90, Example 92, Example 94, Example 196, Example 260 |
| Compounds synthesized the process of Example 85 | Example 88, Example 91, Example 93, Example 96 |
| Compounds synthesized by the process of Example 86 | Example 89 |
| Compounds synthesized by the process of Example 95 | Example 153, Example 166, Example 191, Example 192 |
| Compound synthesized by the process of Example 96 | Example 167 |
| Compound synthesized by the process of Example 97 | Example 168 |
| Compounds synthesized | Example 106, Example 111 |

TABLE 4-continued

| | |
|---|---|
| by the process of Example 105 | |
| Compounds synthesized by the process of Example 115 | Example 118, Example 120 |
| Compound synthesized by the process of Example 171, step 4 | Example 180 |
| Compounds synthesized by the process of Example 179 | Example 181, Example 182 |
| Compounds synthesized by the process of Example 195 | Example 197, Example 201 |
| Compound synthesized by the process of Example 198 | Example 202 |
| Compound synthesized by the process of Example 238 | Example 242 |
| Compound synthesized by the process of Example 243, step 3 | Example 246 |
| Compound synthesized by the process of Example 253 | Example 256 |
| Compound synthesized by the process of Example 257, step 1 | Example 262 |
| Compound synthesized by the process of Example 264 | Example 275 |
| Compounds synthesized by the process of Example 265, step 3 | Example 266, Example 267, Example 268, Example 270 |
| Compound synthesized by the process of Example 276, step 4 | Example 277 |

The data on physical properties of the compounds in Examples 1 to 277 are shown in Table 5. The structural formulae of the compounds in Examples 1 to 277 and 279 to 291 are shown in Tables 6 to 17, and the structural formulae of the compound in Example 278 and intermediates produced in several examples are shown in the Drawings.

TABLE 5

| EX. No. | IR (KBr, cm-1) | NMR(ppm) (*:300MHz, non-mark: 270MHz) | M.P. (°.C) |
|---|---|---|---|
| 1 | 1578, 1504, 1475, 1419, 1329 | *DMSO-d6: 9.07(1H, s), 8.63(1H, d, J=1.9 Hz), 8.50(1H, d, J=2.2Hz), 8.38(1H, dd, J=4.6, 1.9Hz), 8.18(1H, d, J=2.2Hz), 8.00 (1H, d, J=8.7Hz), 7.80~7.75(2H, m), 7.53(1H, d, J=2.2Hz), 7.30~7.26(1H, m), 3.93(3H,s), 3.88(2H, s) | 240.9–243.5 |
| 2 | 3292, 1568, 1502, 1390, 1319, 795, 716 | *DMSO-d6: 10.16(1H, bs), 9.08(1H, s), 8.63(1H, s), 8.52(1H, d, J=1.9Hz), 8.39 (1H, bs), 8.04~8.00(2H, m), 7.80~7.75 (2H, m), 7.49(1H, d, J =2.2Hz), 7.28(1H, dd, J=7.6, 4.9Hz), 3.88(2H, s) | 345.8 (dec.) |
| 3 | 3429,1649, 1605, 1578, 1504, 1423, 1329, 1155 | *DMSO-d6: 9.14(1H,s),8.63(1H,s), 8.58 (1H, d, J=1.9Hz), 8.39~8.37(1H, m), 8.30 (1H, d, J=2.3Hz), 8.07(1H, d, J=8.9Hz), 7.85~7.74(2H, m), 7.52(1H, d, J=2.3Hz), 7.30~7.23(1H, m), 4.87(2H, s), 3.89 (2H, s), 1.44(9H, s) | 183.0–185.0 |
| 4 | 3500, 3000, 1741, 1603, 1504, 1325, 1225 | *DMSO-d6: 9.12(1H, s), 8.65~8.62(1H, m), 8.56(1H, d, J=1.9Hz), 8.38(1H, dd, J= 4.8, 1.5Hz), 8.30(1H, d, J=2.3Hz), 8.05 (1H, d, J=8.7Hz), 7.84~7.80(1H, m), 7.76 (1H, d, J=7.9Hz), 7.52(1H, d, J=2.3Hz), 7.28(1H, dd, J=7.9, 4.8Hz), 5.07~4.96 (3H,m), 3.89(2H, s) 1.24~1.18(6H,m) | 171.3–173.0 |
| 5 | 3500, 1747, 1605, 1578, 1504, 1327 | DMSO-d6: 9.14(1H, s), 8.63~8.58(2H, m), 8.39~8.37(1H, m), 8.32(1H, d, J=2.0Hz), 8.07(1H, d, J=8.8Hz), 7.83(1H d d,J= 8.8, 2.0Hz), 7.78~7.74(1H m), 7.54(1H d, J=2.0Hz), 7.30~7.25(1H, m), 5.00(2 H, s), 4.20(2H, q, J=7.1Hz), 3.89(2H, s) 1.23(3H, t J=7.1Hz) | 222.9 (dec.) |
| 6 | 3500, 1653, 1599,1506, 1473, 1325 | DMSO-d6: 9.15(1H, s), 8.62~8.60(2H, m), 8.38~8.32(2H, m), 8.08(1H,d,J=8.8Hz), 7.83(1H, dd, J=8.8, 2.0Hz), 7.76(1H, d, J=7.8Hz), 7.53(1H, d, J=2.0Hz), 7.28 (1H, dd, J=7.8, 4.9Hz), 4.90(2H, s), 3.90 (2H, s) | 226.7 (dec.) |
| 7 | 1738, 1608, 1502, 1471, 1439, 804, 712 | *DMSO-d6: 9.15(1H1s),8.63(1H.d, J=1.6 Hz), 8.59(1H, d, J=1.9Hz), 8.39~8.37 (1H, m), 8.34(1H, d, J=2.3Hz), 8.07(1H, d, J=8.7Hz), 7.8A(1H, dd, J=8.7, 1.9Hz), 7.78~7.73(1H, m), 7.55(1H, d, J=2.3Hz), 7.30~7.25(1H.m), 5.03(2H, s), 4.11(2H, t,J=6.6Hz), 3.89(2H, s), 1.64~1.57(2H m), 0.86(3H, t, J=7.5Hz) | 177.0–179.3 |

TABLE 5-continued

| EX. No. | IR (KBr, cm-1) | NMR(ppm) (*:300MHz, non-mark: 270MHz) | M.P. (° .C) |
|---|---|---|---|
| 8 | 3000, 1720, 1605, 1470, 1333,1142 | *DMSO-d6: 9.16(1H, s), 8.62(1H, d, J=1.6 Hz), 8.60(1H, d, J=1.9Hz), 8.38(1H, dd, J=4.6, 1.6Hz), 8.22(1H, d, J=2.2Hz)18.0 8(1H, d, J=8.7Hz), 7.84(1H, dd, J=8.7, 1.9Hz), 7.78~7.74(1H, m), 7.50(1H, d, J=2 2Hz), 7.28(1H, dd, J=7.9, 4.9Hz), 4.21 (2H, q, J=7.1Hz), 3.88(2H, s), 1.60(6H, s) 1.20(3H, t, J=7.1Hz) | 163.2– 168.4 |
| 9 | 3500, 1595, 1578, 1470, 1333,1147 | *DMSO-d6: 13.20(1H, bs), 9.17(1H, s), 8.65(1H, s), 8.59(1H, d, J=1.9Hz), 8.42~ 8.40(1H, m),8.24(1H, d, J=2.2Hz), 8.08 (1H, d, J=8.7Hz), 7.86~7.80(2H, m), 7.54 (1H, d, J=2.2Hz), 7.33(1H, dd, J=7.7, 4.7 Hz), 3.90(2H, s), 1.59(6H, s) | 249.4– 251.2 |
| 10 | 2900, 1716, 1649, 1605, 1508, 1327, 869 | *DMSO-d6: 9.04(1H, s), 8.63(1H, d, J=1.6 Hz), 8.46(1H, d, J=1.5Hz), 8.38(1H, dd, J=4.7, 1.5Hz), 8.15~8.12(1H, m), 7.98 (1H, d, J=8.7Hz), 7.78~7.75(2H, m), 7.48 (1H, d, J=2.2Hz), 7.28(1H, dd, J=7.7, 4.7 Hz), 4.16~4.06(4H, m), 3.87(2H, s), 2.55~ 2.51(2H, m), 2.09~2.04(2H, m), 1.19 (3H, t, J=7.2Hz) | 159.6- 163 8 |
| 11 | 3412, 1647, 1576, 1508, 1329, 715 | *DMSO-d6: 9.11(1H, s), 8.61(1H, d, J=1.6 Hz), 8.53(1H, d, J=1.9Hz), 8.36(1H, dd, J=4.6, 1.6Hz), 8.26(1H, d, J=2.2Hz), 8.0 4(1H, d, J=8.7Hz), 7.82~7.73(2H, m), 7.53 (1H, d, J=2.2Hz), 7.29~7.27(1H.m), 4.15(2H, t, J=6.4Hz), 3.88(2H, s), 2.38~ 2.36(2H, m), 2.02~1.98(2H, m) | 300.0 (dec.) |
| 12 | 1767, 1597, 1579, 1508, 1338, 1188 | *DMSO-d6: 9.15(1H, s), 8.62(1H, d, J= 1.5Hz), 8.55(1H, d, J=1.8Hz), 8.37(1H, dd, J=4.7, 1.5Hz), 8.31(1H, d, J=2.4Hz), 8.06 (1H, d, J=8.7Hz), 7.83(1H, dd, J=8.7, 1.8Hz), 7.78~7.72(1H, m), 7.57(1H, d, J=2.4 Hz), 7.34~7.25(6H, m), 5.21(2H, s), 5.10(2H s), 3.88(2H, s) | 254.0 (dec.) |
| 13 | 1759, 1603, 1574, 1504, 1325, 1225, 1174 | *DMSO-d6: 9.14(1H, s), 8.65~8.53(2H, m), 8.36(1H, dd, J=4.6, 1.4Hz), 8.32(1H, d, 2.3Hz), 8.06(1H, d, J=8.8Hz), 7.82(1H, dd, J=8.8, 2.0Hz), 7.74(1H, d, J=7.8Hz) 7.54(1H, d, J=2.3Hz), 7.26(1H, dd, J=7.8, 4.6Hz), 5.02(2H, s), 3.88(2H, s), 3.71 (3H, s) | 270.3 (dec.) |
| 14 | 2929, 1740, 1603, 1504, 1327, 1201, 1173 | *DMSO-d6: 9.16(1H, s), 8.63(1H, s), 8.60~ 8.58(1H, m), 8.39~8.37(1H, m), 8.34 (1H, d, J=2.2Hz), 8.08(1H, d, J=8.6Hz), 7.86~7.83(1H, m), 7.77~7.74(1H, m), 7.55(1H, d, J=2.2Hz), 7.28(1H, dd, J=7.8, 4.9Hz), 5.03(2H, s), 4.13(2H, t, J=6.4Hz), 3.89(2H, s), 1.60~1.50(2H, m), 1.19~ 1.16(4H, m), 0.72(3H, t, J=6.8Hz) | 129.8– 133.3 |
| 15 | 2939, 1751, 1601, 1581, 1473, 1340, | *DMSO-d6: 9.16(1H, s), 8.63(1H, s), 8.60~ 8.59(1H, m), 8.39~8.37(1H, m), 8.35~ 8.34(1H, m), 8.08(1H, d, J=8.6Hz), 7.86~ 7.83(1H m), 7.77~7.75(1H, m), 7.55~ 7.52(1H, m), 7.31~7.25(1H, m), 5.00 (2H, s), 4.80~4.75(1H, m), 3.90(2H, s), 1.77~1.75(2H, m), 1.67~1.55(2H, m), 1.44~ 1.17(6H, m) | 142.4– 145.5 |
| 16 | 2920, 1751, 1605, 1578, 1504, 1327, 716 | *DMSO-d6: 9.13(1H, s), 8.61(1H, s), 8.56~ 8.54(1H, m), 8.40~8.29(2H, m), 8.05 (1H, d, J=8.6Hz), 7.85~7.60(2H, m), 7.53 (1H, d, J=2.2Hz), 7.25(1H, dd, J=8.1, 4.6 Hz), 5.01(2H, s), 4.23(2H, t, J=5.8Hz), 3.88(2H, s), 2.58~2.48(2H, m), 2.17(6H, s) | 74.8– 78.8 |
| 17 | 1718, 1603, 1504, 1327, 798 | *DMSO-d6: 12.30(1H, bs), 9.17(1H, s), 8.63 (1H, d, J=2.0Hz), 8.63(1H, d, J=1.6Hz), 8.41(1H, d, J=2.2Hz), 8.38(1H, dd, J=4.6 1.6Hz), 8.08(1H, d, J=8.7Hz), 7.85(1H, dd, J=8.7, 2.0Hz), 7.78~7.74(1H, m), 7.67(1H, d, J=2.2Hz), 7.30~7.26(1H, m) 6.87(1H, d, J=6.2Hz), 5.18~5.10(1H, m), 3.90(2H, s), 3.22(2H, dd, J=7.1, 1.6Hz) | 161.5– 164.9 |
| 18 | 3402, 1647, 1591, 1576, | *DMSO-d6: 9.13(1H, s), 8.75(1H, d, J=1.6 Hz), 8.63(1H, d, J=1.6Hz), 8.57(1H, dd, | |

TABLE 5-continued

| EX. No. | IR (KBr, cm-1) | NMR(ppm) (*:300MHz, non-mark: 270MHz) | M.P. (° .C) |
|---|---|---|---|
| | 1506, 1471, 1331, 712 | J=4 9, 1.6Hz), 8.55(1H, d, J=1.9Hz), 8.38 (1H, dd, J=4.9, 1.6Hz), 8.36(1H, d, J=2.2 Hz), 8.06(1H, d, J=8.9Hz), 7.96~7.94 (1H, m), 7.83(1H, dd, J=8.9, 1.9Hz), 7.78~ 7.74(1H, m) , 7.70(1H, d, J=2.2Hz), 7.46 (1H, dd, J=7.9, 4.9Hz), 7.28(1H, dd, J=7.9, 4.9Hz), 5.36(2H, s), 3.89(2H, s) | 181.0- 183.2 |
| 19 | 3000, 1601, 1579, 1502, 1331, 1232, | *DMSO-d6: 9.12(1H, s), 8.65~8.57(3H, m), 8.54(1H, d, J=1.8Hz), 8.41~8.36(2H, m), 8.05(1H, d, J=8.7Hz), 7.81(1H, dd, J= 8.7, 1.8Hz), 7.77~7.74(1H, m), 7.65~ 7.64(1H, m), 7.54~7.50(2H, m), 7.30~7.25 (1H, m), 5.39(2H, s), 3.88(2H, s) | 239.0 (dec.) |
| 20 | 3000, 1593, 1578, 1504, 1473, 1327 | *DMSO-d6: 9.14(1H, s), 8.63~8.57(3H, m), 8.40~8.36(2H, m), 8.07(1H, d, J=8.9 Hz), 7.86~1.81(2H, m), 7.76(1H, d, J=7.9 Hz), 7.66(1H, d, J=2.3Hz), 7.59(1H, d, J= 7.6Hz), 7.42~7.32(1H, m), 7.30~7.27 (1H m), 5.39(2H, s), 3.89(2H, s) | 193.4 (dec.) |
| 21 | 3450, 1740, 1647, 1608, 1504, 1277, | *DMSO-d6: 9.32(1H, d, J=1.6Hz), 9.17(1H, s), 8.92(1H, dd, J=4.9, 1.6Hz), 8.63(1H, d, J=1.8Hz) , 8.57~8.50(2H, m), 8.49 (1H, d, J=1.6Hz), 8.37(1H, m), 8.09~8.04 (2H, m), 7.83(1H, dd, J=8.7, 1.8Hz), 7.76 (1H, d, J=8.0Hz), 7.68(1H, dd, J=8.1, 4.9 Hz), 7.27(1H, dd, J=8.0, 4.9Hz), 3.89(2H s) | 153.6– 160.9 |
| 22 | 1603, 1578; 1502, 1329, 729 | DMSO-d6: 9.13(1H, s), 8.63(1H, d, J=1.8 Hz), 8.55(1H, d, J=2.0Hz), 8.38(1H, dd, J= 4.6, 1.8Hz), 8.35(1H, d, J=2.0Hz), 8.06 (1H, d, J=8.8Hz), 7.82(1H, dd, J=8.8, 2.0 Hz), 7.76(1H, d, J=7.8Hz), 7.66(1H, d, J= 2.0Hz), 7.54~7.51(2H, m), 7.45~7.32 (3H, m), 7.23(1H, dd, J=7.8, 4.6Hz), 5.31 (2H, s), 3.89(2H, s) | 181.6– 185.0 |
| 23 | 1687, 1597, 1578, 1506, 1329, 1230, 970 | *DMSO-d6: 9.15(1H, s), 8.62(1H, d, J=1.9 (9Hz), 8.59(1H, d, J=1.9Hz), 8.38~8.36 (2H, m), 8.09~8.06(3H, m), 7.83(1H, dd, J32 8.7, 1.9Hz), 7.77~7.70(2H, m), 7.63~ 7.58(3H, m), 7.29~7.25(1H, m), S.84(2H, s), 3.89(2H, s) | 241.9 (dec.) |
| 24 | 1728, 1603, 1504, 1331, 1248, 1232 | *DMSO-d6: 9.14(1H, s), 8.72(1H, bs), 8.64 (1H, s), 8.59(1H, s), 8.55(1H, d, J=1.9 Hz), 8.39~8.36(2H, m), 8.10~7.94(2H, m), 7.87~7.73(2H, m), 7.71(1H, d, J=2.2 Hz), 7.31~7.25(1H, m), 5.38(2H, s), 5.16 (2H, s), 3.90(2H, s), 2.07(3H, s) | 140.6– 144.1 |
| 25 | 1599, 1578, 1506, 1327, 1028, 714 | *DMSO-d6: 9.15(1H, s), 8.64~8.60(2H, m), 8.56(1H.d, J=1.9Hz), 8.51(1H, d, J=1.4 Hz), 8.38~8.37(2H, m), 8.07(1H, d, J= 8.7Hz), 7.92~7.86(1H, m), 7.83(1H, dd, J=8.7, 1.9Hz), 7.75(1H, dd, J=7.9, 1.6Hz), 7.70(1H, d, J=2.2Hz), 7.32~7.25(1H, m), 5.37(2H.s) 4.57(2H, s), 3.90(2H, s) | 186.3– 191.4 |
| 26 | 3500, 3000, 1601, 1579, 1504, 1329 | *DMSO-d6: 9.12(1H, s), 8.63(1H, d, J=1.9 Hz), 8.55(1H, d, J=1.6Hz), 8.39~8.37 (1H, m), 8.26(1H, d, J=2.2Hz), 8.05(1H, d, J=9.7Hz), 7.83~7.75(2H, m), 7.55(1H, d, J=2.2Hz), 7.30~7.26(1H, m), 4.62(1H, t, J=5.4Hz), 4.22(2H, t, J=6.4Hz), 3.89 (2H, s), 3.63~3.59(2H, m), 1.99~1.92(2H, m) | 213.4– 220.8 |
| 27 | 3500, 3000, 1597, 1500, 1329, 1227 | *DMSO-d6: 9.11(1H, s), 8.68~8.60(1H, m), 8.54(1H, d, J=1.6Hz), 8.45~8.35(1H, m), 8.24(1H, d, J=2.2Hz), 8.04(1H, d, J= 8.7Hz), 7.88~7.76(2H, m), 7.54(1H, d, J= 2.2Hz), 7.31~7.27(1H, m), 4.52~4.48 (1H, m), 4.16(2H, t, J=6.5Hz), 3.89(2H, s), 3.51~3.47(2H, m), 1.86~1.81(2H, m) 1.67~1.60(2H, m) | 161.7– 166.6 |
| 28 | 3500, 3000, 1593, 1578, 1506, 1335, 764 | *DMSO-d6: 9.13(1H, s), 8.63(1H, d, J=1.9 Hz), 8.56(1H, d, J=1.9Hz), 8.39~8.37 (1H, m), 8.27(1H, d, J=2.3Hz), 8.06(1H, d, J=8.6Hz), 7.82(1H, dd, J=8.6, 1.9Hz), 7.78~ 7.75(1H, m), 7.56(1H d, J=2.3Hz), 7.30~7.25(1H, m), 4.40(1H, bs), 4.15(2H, | 186.7– 189.4 |

TABLE 5-continued

| EX. No. | IR (KBr, cm-1) | NMR(ppm) (*:300MHz, non-mark: 270MHz) | M.P. (° .C) |
|---|---|---|---|
| | | t, J=6.5Hz), 3.89(2H, s), 3.45~3.43 (2H, m), 1.85~1.75(2H, m), 1.53~1.50 (4H, m) | |
| 29 | 2935, 2927, 1589, 1578, 1508, 1331, 1228 | *DMSO-d6: 9.08(1H, s), 8.61(1H, d, J=1.9 Hz), 8.51(1H, d, J=1.9Hz), 8.37~8.35 (1H, m), 8.21(1H, d, J=2.2Hz), 8.01(1H, d, J=8.7Hz), 7.80~7.73(2H, m), 7.50(1H, d, J=2.2Hz), 7.28~7.26(1H, m), 4.37(1H, t, J=5.2Hz), 4.11(2H, t, J=6.5Hz), 3.87 (2H, s), 3.40~3.38(2H, m), 1.78~1.76(2H, m), 1.47~1.38(6H, m) | 175.1– 178.4 |
| 30 | 3433, 1591, 1572, 1508, 1327, 1115, 714 | *DMSO-d6: 9.11(1H, s), 8.65~8.62(1H, m), 8.53(1H, d, J=1.9Hz), 8.39~8.37(1H, m), 8.26(1H, d, J=2.3Hz), 8.05(1H, d, J= 8.7Hz), 7.83~7.75(2H, m), 7.56(1H, d, J= 2.3Hz), 7.28(1H, dd, J=7.9, 4.9Hz), 4.69~ 4.66(1H, m), 4.29~4.26(2H, m), 3.89 (2H, s), 3.85~3.82(2H, m), 3.57~3.52 (4H, m) | 123.9– 128.9 |
| 31 | 2927, 1647, 1605, 1578, 1508, 1329, 797 | DMSO-d6: 9.12(1H, s), 8.63(1H, s), 8.58 (1H, d, J=1.7Hz), 8.40~8.35(1H, m), 8.29(1H, d, J=2.0Hz), 8.06(1H, d, J=8.9Hz), 7.84~7.75(2H, m), 7.56(1H, d, J=2.0Hz), 7.30~7.26(1H, m), 4.71~4.67(1H, m), 3.95~3.80(4H, m), 3.47~3.30(2H, m), 1.07(6H, s) | 112.7– 113.9 |
| 32 | 1716, 1564, 1508, 1327, 1049, 716 | *DMSO-d6: 9.16(1H, s), 8.63(1H, s), 8.57 (1H, s), 8.39~8.27(2H, m), 8.08(1H, d, J=8.4Hz), 7.86~7.74(2H, m), 7.54(1H, d, J=1.6Hz), 7.28(1H, dd, J=7.6, 4.6Hz), 5.09(2H, s), 4.80(1H.t, J=4.9Hz), 3.89 (2H, s), 3.75~3.69(2H, m), 2.72~2.68(2H, m) | 211.7– 214.7 |
| 33 | 3500, 3000, 1603, 1578, 1504, 1468, 1331 | *DMSO-d6: 9.14(1H, s), 8.63(1H, d, J=1.9 Hz), 8.56(1H, s), 8.39~8.37(1H, m), 8.26 (1H, d, J=1.6Hz), 8.07(1H, d, J=8.7Hz), 7.84~7.74(2H, m), 7.55(1H, d, J=1.6Hz), 7.28(1H, dd, J=7.9, 4.9Hz), 4.21(2H, q, J=7.0Hz), 3.89(2H, s), 1.42(3H, t, J=7.0Hz) | 180.3– 182.8 |
| 34 | 3000, 1603, 1578, 1504, 1466, 1329 | DMSO-d6: 9.08(1H, s), 8.63(1H, d, J=1.5 Hz), 8.51(1H, d, J=1.5Hz), 8.38(1H, dd, J= 4.4, 1.5Hz), 8.21(1H, d, J=2.0Hz), 8.02 (1H, d, J=8.8Hz), 7.81~74(2H, m), 7.5 1(1H, d, J=2.0Hz), 7.28(1H, dd, J=7.8, 8.44Hz), 4.15~4.10(2H, m), 3.88(2H, s), 1.81~ 1.73(2H, m), 1.54~1.45(2H, m), 0.97 (3H, t, J=7.3Hz) | 168.1– 176.2 |
| 35 | 3100, 1649, 1603, 1578, 1504, 1328, 1115, 797 | DMSO-d6: 9.09(1H, s), 8.63(1H, d, J=1.5 Hz), 8.51(1H, d, J=2.0Hz), 8.39~8.37(1H, m), 8.23(1H, d, J=1.9Hz), 8.03(1H, d, J= 8.8Hz), 7.82~7.75(2H.m), 7.55(1H, d, J=1.9Hz), 7.29(1H, dd, J=7.6, 4.6Hz), 4.27 (2H, t, J=4.4Hz), 3.89(2H, s) 3.75(2H, t, J=4.4Hz), 3.35(3H, s) | 155.0– 159.7 |
| 36 | 1595, 1579, 1506, 1470, 1335, 1230, 1119 | *DMSO-d6: 9.10(1H.s), 8.62(1H, s).8.52 (1H, d, J=1.9Hz), 8.38~8.34(1H, m), 8.25(1H, d, J=2.3Hz), 8.03(1H, d, J=8.7Hz), 7.82~7.75(2H, m), 7.55(1H, d, J=2.3Hz), 7.28(1H, dd, J=7.7, 4.7Hz), 4.25(2H, m), 3.88(2H, s), 3.77(2H, m), 3.53(2H, q, J= 7.1Hz), 1.14(3H, t, J=7.1Hz) | 174.9– 177.0 |
| 37 | 2972, 1649, 1599, 1578, 1508, 1335, 800, 712 | *DMSO-d6: 9.15(1H, s), 8.63(1H, d, J=2.2 Hz), 8.58(1H, d, J=1.9Hz), 8.40~8.36 (1H, m), 8.34(1H, d, J=2.3Hz), 8.07(1H, d, J=8.7Hz), 7.83(1H, dd, J=8.7, 1.9Hz), 7.79~7.74(1H, m), 7.59(1H, d, J=2.3Hz), 7.30~7.26(1H, m), 4.90(1H, t, J=5.2Hz), 4.15(2H, d, J=5.2Hz), 3.89(2H, s), 3.78~ 3.55(4H, m), 1.19~1.14(6H, m) | 150.2– 154.1 |
| 38 | 1761, 1605, 1578, 1500, 1329, 1211 | DMSO-d6: 9.22(1H, s), 8.64(1H, s), 8.59 (1H.s), 8.42~8.38(2H, m), 8.12(1H, d, J= 8.8Hz), 7.88~7.86(2H, m), 7.78~7.75 (1H, m), 7.31~7.26(1H, m), 3.91(2H, s), 2.38(3H, s) | 127.7– 134.0 |
| 39 | 2950, 1724, 1599, 1578, | *DMSO-d6: 9.10(1H, s), 8.63(1H, s), 8.53 (1H, s), 8.38(1H, d, J=4.2Hz), 8.23(1H, | 204.5 (dec.) |

TABLE 5-continued

| EX. No. | IR (KBr, cm-1) | NMR(ppm) (*:300MHz, non-mark: 270MHz) | M.P. (° .C) |
|---|---|---|---|
| | 1506, 1327, 798 | d, J=2.0Hz), 8.03(1H, d, J=8.7Hz), 7.82~7.74(2H, m), 7.49(1H, d, J=2.0Hz), 7.28 (1H, dd, J=7.8, 4.2Hz), 5.05(2H, s), 3.88 (2H, s), 2.60(2H, q, J=7.5Hz), 1.01(3H, t, J–7.5Hz) | |
| 40 | 1718, 1599, 1578, 1506, 1329 | *DMSO-d6: 9.15(1H, s), 8.63(1H, d, J=1.4 Hz), 8.58(1H; d, J=1.9Hz), 8.38(1H, dd, J=4.9, 1.4Hz), 8.28(1H, d, J=2.3Hz), 8.07 (1H, d, J=8.8Hz), 7.83(1H, dd, J=8.8, 1.9 Hz), 7.74~7.70(1H, m), 7.51(1H, d, J=2.3 Hz), 7.28(1H, dd, J=7.6, 4.9Hz), 5.06 (2H, 5), 3.89(2H, s), 2.58~2.53(2H, m), 1.60~1.53(2H, m), 0.90(3H, t, J=7.3Hz) | 212.6 (dec.) |
| 41 | 3435, 2951, 1599, 1578, 1508, 1331 | *DMSO-d6: 9.13(1H, s), 8.63(1H, s), 8.58~8.57(1H, m), 8.39~8.37(1H, m), 8.29~8.27(1H, m ), 8.06(1H, d, J=8.6Hz), 7.83~7.80(1H, m), 7.76(1H, d, J=7.9Hz), 7.58~7.55(1H, m), 7.30~7.26(1H, m), 4.94 (1H, d, J=5.1Hz), 4.02~4.00(2H, m), 3.94~3.82(3H, m), 1.51~1.47(4H, m), 0.94~0.90(3H, m) | 180.0–184.9 |
| 42 | 3431, 1713, 1601, 1578, 1504, 1473, 1325 | *DMSO-d6: 9.12(1H, s), 8.61(1H, s), 8.55 (1H, d, J=1.9Hz), 8.43~8.31(1H, m), 8.25(1H, d, J=2.4Hz), 8.05(1H, d, J=8.7Hz), 7.83~7.73(2H, m), 7.49(1H, d, J=2.4Hz), 7.26(1H, dd, J=7.6, 4.6Hz), 5.33(2H, s), 3.87(2H, s), 1.20(9H, s) | 238.7–240.0 |
| 43 | 3400, 3000, 1662, 1576, 1506, 1325 | *DMSO-d6: 9.10(1H, s), 8.61~8.60(1H, m), 8.52(1H, d, J=1.6Hz), 8.37~8.35(1H, m), 8.28~8.23(2H, m), 8.03(1H, d, J=8.7 Hz), 7.81~7.73(2H, m), 7.59(1H, d, J=2.2 Hz), 7.26(1H, dd, J=7.6, 4.9Hz), 4.64(2H, s), 3.87(2H, s), 3.21~3.12(2H, m), 1.04 (3H, t, J=7.2Hz) | 309.8 (dec.) |
| 44 | 3435, 1660, 1649, 1576, 1506, 1327, 1117, 795 | *DMSO-d6: 9.11(1H, s), 8.61(1H, d, J=2.5 Hz), 8.54(1H, d, J=1.5Hz), 8.36(1H, dd, J=4.7, 1.5Hz), 8.25(1H, d, J=2.2Hz), 8.04 (1H, d, J=8.7Hz), 7.81~7.72(2H, m), 7.56 (1H, d, J=2.2Hz), 7.26(1H, dd, J=7.7, 4.7Hz), 5.06(2H, s), 3.87(2H, s), 3.64~3.45(8H, m) | 150.2–153.1 |
| 45 | 2930, 1726, 1653, 1603, 1327, 1180, 1039 | *DMSO-d6: 9.15(1H, s), 8.62(1H, s), 8.58 (1H, d, J=1.9Hz), 8.39~8.37(1H, m), 8.28 (1H, d, J=2.2Hz), 8.07(1H, d, J=8.7Hz), 7.83(1H, dd, J=8.7, 1.9Hz), 7.78~7.73 (1H, m), 7.57(1H, d, J=2.2Hz), 7.32~7.25 (1H, m), 5.06(2H, m), 4.24~4.03(3H, m), 3.92~3.83(3H, m), 3.26~3.08(1H, m), 2.88~2.58(2H, m), 1.97~1.81(2H, m), 1.72~1.55(1H, m), 1.49~1.34(1H, m), 1.19(3H, t, J=7.1Hz) | 107.0–114.5 |
| 46 | 1718, 1653, 1560, 1508, 1323, 1205 | *DMSO-d6: 12.32(1H, bs), 9.15(1H, s), 8.63(1H, d, J=1.6Hz), 8.58(1H, d, J=1.9Hz), 8.38~8.37(1H, m), 8.28(1H, d, J=2.3Hz), 8.97(1H, d, J=8.7Hz), 7.83(1H, dd, J= 8.7, 1.9Hz), 7.81~7.74(1H, m), 7.57(1H, d, J=2.3Hz), 7.30~7.25(1H, m), 5.06(2H, s), 4.23~4.13(1H, m), 3.95~3.79(3H, m), 3.25~3.10(1H, m), 2.88~2.71(1H, m), 2.55~2.54(1H, m), 1.96~1.79(2H, m), 1.70~1.53(1H, m), 1.49~1.32(1H, m) | 156.0–164.4 |
| 47 | 3365, 1676, 1643, 1601, 1506, 1327, 797 | *DMSO-d6: 9.14(1H, s), 8.89~8.81(1H, m), 8.63(1H, s), 8.56(1H d, J=1.9Hz), 8.41~8.36(1H, m), 8.32(1H, d, J=2.2Hz), 8.07 (1H, d, J=8.5Hz), 7.83(1H, dd, J=8.5, 1.9Hz), 7.76(1H, d, J=7.8Hz), 7.63(1H, d, J=2.2Hz), 7.28(1H, dd, J=7.8, 4.7Hz), 5.72~5.68(1H, m), 4.71(2H, s), 4.62~4.58(2H, m), 3.89(2H, s) | 217.9–221.6 |
| 48 | 3055, 1647, 1597, 1581, 1508, 1477, 1331 | DMSO-d6: 8.94(1H, s), 8.58~8.50(1H, m), 8.26(1H, d, J=1.8Hz), 8.05(1H, d, J= 8.8Hz), 7.80(1H, dd, J=8.8, 2.0Hz), 7.60(1H, d, J=1.8Hz), 3.96(3H, s), 2.12(3H, s) | 301.1 (dec.) |
| 49 | 3115, 1560, 1446, 1327, 1282, 1159 | *DMSO-d6: 8.91(1H, s), 8.52(1H, d, J=2.0 Hz), 8.05~7.99(2H, m), 7.77(1H, dd, J= 8.7, 2.0Hz), 7.52(1H, d, J=2.2Hz), 2.10 | 325.2 (dec.) |

TABLE 5-continued

| EX. No. | IR (KBr, cm-1) | NMR(ppm) (*:300MHz, non-mark: 270MHz) | M.P. (° .C) |
|---|---|---|---|
| | | (3H, s) | |
| 50 | 3498, 3000, 1745, 1647, 1601, 1329, 1145, 849 | *DMSO-d6: 8.96(1H, s), 8.58(1H, d, J=2.0 Hz), 8.30(1H, d, J=2.3Hz), 8.07(1H, d, J= 8.6Hz), 7.81(1H, dd, J=8.6, 2.0Hz), 7.55 (1H, d, J=2.3Hz), 4.89(2H, s), 2.11(3H, s), 1.45(9H, s) | 196.4– 198.1 |
| 51 | 3500, 3000, 1747, 1601, 1504, 1232 | *DMSO-d6: 8.96(1H, s), 8.58(1H, d, J=1.9 Hz), 8.32(1H, d, J=2.3Hz), 8.07(1H, d, J= 8.7Hz), 7.82(1H, dd, J=8.7, 1.9Hz), 7.57 (1H, d, J=2.3Hz), 5.05~4.98(3H, m), 2.12(3H, s), 1.24~1.22(6H, m) | 184.1– 187.4 |
| 52 | 3000, 1751, 1599, 1504, 1338, 1188 | DMSO-d6: 8.92(1H, s), 8.54(1H, s), 8.28 (1H, d, J=1.5Hz), 8.03(1H, d, J=8.8Hz), 7.78(1H, d, J=8.8Hz), 7.56(1H, d, J=1.5Hz), 5.00(2H, s), 4.21(2H, q, J=7.0Hz), 2.11 (3H, s), 1.24(3H, t, J=7.0Hz) | 188.6 (dec.) |
| 53 | 3500, 1749, 1560, 1506, 1327, 1188, 1159 | DMSO-d6: 8.92(1H, s), 8.55(1H, d, J=2.0 Hz), 8.27(1H, d, J=2.4Hz), 8.03(1H, d, J= 8.8Hz), 7.79(1H, dd, J=8.8, 2.0Hz), 7.53 (1H, d, J=2.4Hz), 4.91(2H, s), 2.11(3H, s) | 304.0 (dec.) |
| 54 | 3000, 1601, 1579, 1502, 1325, 1286 | *DMSO-d6: 8.91(1H, s), 8.77(1H, d, J= 1.1Hz), 8.59~8 57(1H, m), 8.51(1H, d, J=1.3 Hz), 8.32(1H, d, J=2.0Hz), 8.05~7.95 (2H, m), 7.79(1H, dd, J=8.4, 1.3Hz), 7.70 (1H, d, J=2.0Hz), 7.47(1H, d, J=7.9, 4.9 Hz), 5.36(2H, s), 2.09(3H, s) | 248.0 (dec.) |
| 55 | 1601, 1579, 1504, 1325, 1047 | *DMSO-d6: 8.95(1H, s), 8.56~8.55(1H, m), 8.27(1H, d, J=2.0Hz), 8.06(1H, d.J= 8.7Hz), 7.82~7.79(1H, m), 7.59(1H, d, J= 2.0Hz), 4.50(1H, d, J=5.2Hz), 4.18(2H, t, J=6.5Hz), 3.53~3.47(2H, m) , 2.12(3H, s), 1.92~1.79(2H, m), 1.69~1.57(2H, m) | 106.7– 109.5 |
| 56 | 1757, 1605, 1504, 1331, 1217, 1200 | DMSO-d6: 9.04(1H, s), 8.60~8.56(1H, m), 8.41(1H, d, J=2.0Hz), 8.11(1H, d, J=8.3 Hz), 7.91(1H, d, J=2.0Hz), 7.87~7.84 (1H, m) , 2.38(3H, s), 2.13(3H, s) | 331.3 (dec.) |
| 57 | 3000, 1732, 1578, 1508, 1325 | *DMSO-d6: 8.92(1H, s), 8.54(1H, d, J=1.9 Hz), 8.24(1H, d, J=2.3Hz), 8.03(1H, d, J= 8.7Hz), 7.79(1H, dd, J=8.7, 1.9Hz), 7.52 (1H, d, J=2.3Hz), 5.05(2H, s), 2.58~2.53 (2H, m), 2.09(3H, s), 1.60~1.53(2H, m), 0.89(3H, t, J=7.3Hz) | 208.2– 211.9 |
| 58 | 1651, 1608, 1498, 1325, 816, 731 | *DMSO-d6: 8.90(1H, d, J=7.7Hz), 8.54(1H, d, J=2.0Hz), 8.24(1H, d, J=2.2Hz), 8.07 (1H, d, J=8.7Hz), 7.79(1H, dd, J=8.7, 2.0 Hz), 7.55(1H, d, J=2.2Hz), 6.35(1H, d, J= 7.7Hz), 3.94(3H, s) | 250.2– 254.5 |
| 59 | 3000, 1649, 1599, 1500, 1423, 1184, 829 | *DMSO-d6: 10.18(1H, s), 8.90(1H, d, J=7.6 Hz), 8.54(1H, d, J=2.0Hz), 8.08(1H, d, J=8.7Hz), 8.02(1H, d, J=2.2Hz), 7.78(1H, dd, J=8.7, 2.0Hz), 7.49(1H, d, J=2.2Hz), 6.33(1H, d, J=7.6Hz) | 360.0< |
| 60 | 3020, 1757, 1641, 1500, 1321, 1254, 814 | *DMSO-d6: 8.94(1H, d, J=7.6Hz), 8.58(1H, d, J=2.1Hz), 8.31(1H, d, J=2.4Hz), 8.10 (1H, d, J=8.7Hz), 7.82(1H, dd, J=8.7, 2.1Hz), 7.52(1H, d, J=2.4Hz), 6.37(1H, d, J= 7.6Hz), 4.89(2H, s), 1.49(9H, s) | 209.2– 211.8 |
| 61 | 3000, 1757, 1605, 1500, 1321, 1198, 814 | *DMSO-d6: 8.95(1H, d, J=7.7Hz), 3.59(1H, d, J=1.9Hz), 8.34(1H, d, J=2.3Hz), 8.12 (1H, d, J=8.6Hz), 7.83(1H, dd, J=8.6, 1.9 Hz), 7.54(1H, d, J=2.3Hz), 6.38(1H, d, J= 7.7Hz), 5.07~4.99(3H, m), 1.26~1.22 (6H, m) | 190.6– 192.6 |
| 62 | 3100, 1755, 1606, 1500, 1321, 1194, 816 | DMSO-d6: 8.94(1H, d, J=7.8Hz), 8.58(1H, d, J=2.0Hz), 8.33(1H, d, J=2.4Hz), 8.11 (1H, d, J=8.8Hz), 7.82(1H, dd, J=8.8, 2.0 Hz), 7.55(1H, d, J=2.4Hz), 6.38(1H, d, J= 7.8Hz), 5.03(2H, s), 4.21(2H, q, J=7.1Hz), 1.23(3H, t, J=7.1Hz) | 189.8 (dec.) |
| 63 | 3500, 1755, 1570, 1508, 1466, 1200, 822 | DMSO-d6: 13.13(1H, bs), 8.94(1H, d, J=7.6 6Hz), 8.60(1H, d, J=2.0Hz), 8.32(1H, d, J=2.4Hz), 8.11(1H, d, J=8.5Hz), 7.82(1H, dd, J=8.5, 2.0Hz), 7.53(1H, d, J=2.4Hz), 6.38(1H, d, J=7.6Hz), 4.92(2H, s) | 300.0< |
| 64 | 1649, 1612, 1500, 1317, | *DMSO-d6: 8.93(1H, d, J=7.7Hz), 8.77(1H, d, J=1.9Hz), 8.59~8.57(1H, m), 8.54 | 229.3– 233.5 |

TABLE 5-continued

| EX. No. | IR (KBr, cm-1) | NMR(ppm) (*:300MHz, non-mark: 270MHz) | M.P. (° .C) |
|---|---|---|---|
| | 816 | (1H, d, J=1.9Hz), 8.35(1H, d, J=2.2Hz), 8.10(1H, d, J=8.8Hz), 7.99~7.95(1H, m), 7.81(1H, dd, J=8.8, 1.9Hz), 7.70(1H, d, J=2.2Hz), 7.47(1H, dd, J=7.9, 4.9Hz), 6.37 (1H, d, J=7.7Hz), 5.38(2H, s) | |
| 65 | 3000, 1649, 1616, 1504, 1387, 1192, 812 | *DMSO-d6: 8.93(1H, d, J=7.7Hz), 8.63~8.61(1H, m), 8.56(1H, d, J=1.9Hz), 8.40 (1H, d, J=2.3Hz), 8.10(1H, d, J=8.7Hz), 7.90~7.79(2H, m), 7.66(1H, d, J=2.3Hz), 7.62~7.60(1H, m), 7.40~7.36(1H, m), 6.37(1H, d, J=7.7Hz), 5.40(2H, s) | 260.9–263.1 |
| 66 | 1649, 1614, 1500, 1323, 1186, 816 | DMSO-d6: 8.93(1H, d, J=7.3Hz), 8.55(1H, d, J=2.1Hz), 8.36(1H, d, J=2.2Hz), 8.10 (1H, d, J=8.5Hz), 7.80(1H, dd, J=8.5, 2.1 Hz), 7.67(1H, d, J=2.2Hz), 7.56~7.46(2H, m), 7.43~7.37(3H, m), 6.37(1H, d, J=7.3Hz), 5.32(2H, s) | 203.2 (dec.) |
| 67 | 1650, 1606, 1502, 1323, 1190, 818 | *DMSO-d6: 8.93(1H, d, J=7.6Hz), 8.57~8.53(2H, m), 0.28(1H, d, J=2.0Hz), 8.10 (1H, d, J=8.7Hz), 7.82~7.73(2H, m), 7.58 (1H, d, J=2.0Hz), 7.43(1H, d, J=8.1HZ), 7.29~7.25(1H, m), 6.37(1H, d, J=7.6Hz), 4.57(2H, t, J=6.5Hz), 3.30(2H, t, J=6.5Hz) | 117.5–121.5 |
| 68 | 3000, 1649, 1601, 1506, 1327, 1194, 825 | *DMSO-d6: 8.94(1H, d, J=7.7Hz), 8.57(1H, d, J=1.9Hz), 8.51~8.50(1H, m), 8.42 (1H, dd, J=4.6, 1.4Hz), 8.30(1H, d, J=2.2Hz), 8.11(1H, d, J=8.7Hz), 7.81(1H, dd, J=8.7, 1.9Hz), 7.73~7.70(1H, m), 7.57(1H, d, J=2.2Hz), 7.33(1H, dd, J=7.9, 4.6Hz), 6.37(1H, d, J=7 7Hz), 4.18(2H, t, J=6.2 Hz), 2.85(2H, t, J=7.3Hz), 2.17~2.12 (2H, m) | 165.8–168.4 |
| 69 | 1743, 1595, 1508, 1244, 820 | *DMSO-d6: 8.95(1H, d, J=7.7Hz), 8.74~8.71(1H, m), 8.60~8.54(2H, m), 8.38~8.36(1H, m), 8.13~8.07(1H, m), 7.97~7.96 (1H, m), 7.85~7.80(1H, m), 7.72~7.70 (1H, m), 6.38(1H, d, J=7.7Hz), 5.39(2H, s), 5.16(2H, s), 2.08(3H, s) | 181.2–185.4 |
| 70 | 3500, 1647, 1601, 1504, 1471, 1325, 822 | *DMSO-d6: 8.96(1H, d, J=7.7Hz), 8.64(1H, s), 8.57(1H, d, J=1.6Hz), 8.51(1H, s), 8.39(1H, d, J=2.2Hz), 8.12(1H, d, J=8.7Hz), 7.90(1H, s), 7.82(1H, dd, J=8.7, 1.6Hz), 7.72(1H, d, J=2.2Hz), 6.39(1H, d, J=7.7Hz), 5.39(2H, s), 4.58(2H, s) | 206.0–208.6 |
| 71 | 1736, 1645, 1612, 1321, 1273, 818, 785 | *DMSO-d6: 8.94(1H, d, J=7.6Hz), 8.56(1H, d, J=1.9Hz), 8.41(1H, d, J=2.2Hz), 8.11 (1H, d, J=8.7Hz), 7.90(1H, dd, J=7.9, 7.6Hz), 7.81(1H, dd, J=8.7, 1.9Hz), 7.67 (1H, d, J=2.2Hz), 7.56(1H, d, J=7.9Hz), 7.40 (1H, d, J=7.6Hz), 6.37(1H, d, J=7.6Hz), 5.39(2H, s), 5.18(2H, s), 2.14(3H, s) | 204.6–207.8 |
| 72 | 1643, 1606, 1556, 1506, 1319, 818 | *DMSO-d6: 8.92(1H, d, J=7.6Hz), 8.55(1H, d, J=1.9Hz), 8.39(1H, d, J=2.3Hz), 8.09 (1H, d, J=8.7Hz), 7.88~7.86(1H, m), 7.81 (1H, dd, J=8.7, 1.9Hz), 7.65(1H, d, J=2.3 Hz), 7.46~7.43(2H, m), 6.36(1H, d, J=7.6Hz), 5.49(1H, t, J=5.9Hz), 5.36(2H, s), 4.61(2H, d, J=5.9Hz) | 244.0–247.2 |
| 73 | 1718, 1601, 1502, 812 | *DMSO-d6: 9.13~9.12(1H, m), 8.95(1H, d, J=7.6Hz), 8.59(1H, d, J=1.9Hz), 8.44 (1H, d, J=2.4Hz), 8.39~8.36(1H, m), 8.12 (1H, d, J=8.7Hz), 7.83(1H, dd, J=8.7, 1.9 Hz), 7.77(1H, d, J=8.7Hz), 7.68(1H, d, J=2.4Hz), 6.38(1H, d, J=7.6Hz), 5.52(2H, s), 3.90(3H, s) | 257.7 (dec.) |
| 74 | 1645, 1608, 1591, 1504, 1325, 822 | *DMSO-d6: 8.96(1H, d, J=7.6Hz), 8.57~8.56(2H, m), 8.42(1H, s), 8.38(1H, d, J=2.2 Hz), 8.12(1H, d, J=8.7Hz), 7.83(1H, dd, J=8.7, 1.4Hz), 7.78(1H, s), 7.71(1H, d, J=2.2Hz), 6.39(1H, d, J=7.6Hz), 5.35(2H, s) 2.34(3H, s) | 242.0–245.2 |
| 75 | 1649, 1606, 1506, 1387, 1325, 1190, 822 | *DMSO-d6: 8.96(1H, d, J=7.6Hz), 8.92(1H, s), 8.72(1H, d, J=2.4Hz), 8.67(1H, d, J=2.4Hz), 8.58(1H, d, J=1.6Hz), 8.43(1H, d, J=2.3Hz), 8.12(1H, d, J=8.7Hz), 7.85~7.81(1H, m), 7.74(1H, d, J=2.3Hz), 6.39 | 267.0 (dec.) |

TABLE 5-continued

| EX. No. | IR (KBr, cm-1) | NMR(ppm) (*:300MHz, non-mark: 270MHz) | M.P. (° .C) |
|---|---|---|---|
| | | (1H, d, J=7.6Hz), 5.50(2H, s) | |
| 76 | 3076, 1653, 1614, 1506, 1470, 1194, 818 | *DMSO-d6: 9.72(1H, s), 8.96(1H, d, J=7.7 Hz), 8.58~8.57(1H, m), 8.40~8.38(1H, m), 8.12(1H, d, J=8.6Hz), 7.85~7.82(1H, m), 7.76(1H, m), 6.40(1H, d, J=7.7Hz), 5.59(2H, s) | 250.0 (dec.) |
| 77 | 2933, 2781, 1649, 1610, 1504, 1325, 818 | *DMSO-d6: 8.86(1H, d, J=7.9Hz), 8.48(1H, d, J=1.9Hz), 8.19(1H, d, J=1.9Hz), 8.04 (1H, d, J=8.7Hz), 7.76(1H, dd, J=8.7, 1.9Hz), 7.50~7.49(1H, m), 6.33(1H, d, J=7.9 Hz), 4.04~3.95(2H, m), 2.92~2.83 (1H, m), 2.69~2.58(1H, m), 2.18(3H, s), 2.13~2.08(1H, m), 1.99~1.45(6H, m) | 149.3– 154.8 |
| 78 | 2765, 1647, 1608, 1504, 1464, 820 | *DMSO-d6: 8.92(1H, d, J=7.7Hz), 8.56(1H, d, J=1.9Hz), 8.27(1H, d, J=2.3Hz), 8.09 (1H, d, J=8.7Hz), 7.82~7.78(1H, m), 7.55(1H, d, J=2.3Hz), 6.36(1H, d, J=7.7Hz) 4.19(2H, t, J=6.4Hz), 2.46(2H, t, J=7.1 Hz), 2.20(6H, s), 2.00~1.91(2H, m) | 128.8– 129.2 |
| 79 | 1597, 1504, 1321, 1190, 820 | *DMSO-d6: 8.93(1H, d, J=7.6Hz), 8.56(1H, d, J=1.9Hz), 8.28(1H, d, J=2.0Hz), 8.10 (1H, d, J=8.8Hz), 7.81(1H, dd, J=8.8, 1.9 Hz), 7.56(1H, d, J=2.0Hz), 6.37(1H, d, J= 7.6Hz), 4.53~4.49(1H, m), 4.18(2H, t, J=6.4Hz), 3.51~3.49(2H, m), 1.92~1.78 (2H, m), 1.70~1.57(2H, m) | 89.8– 92.9 |
| 80 | 3367, 2939, 2866, 1597, 1504, 1321 1192 | DMSO-d6: 8.85(1H, d, J=7.6Hz), 8.47(1H, d, J=1.8Hz), 8.16(1H, d, J=2.1Hz), 8.03 (1H, d, J=8.6Hz), 7.75(1H, dd, J=8.6, 1.8 Hz), 7.48(1H, d, J=2.1Hz), 6.33(1H, d, J= 7.6Hz), 4.45~4.42(1H, m), 4.15~4.10 (2H, m), 3.50~3.40(2H, m), 1.84~1.79(2H, m), 1.54~1.51(4H, m) | 145.3– 150.9 |
| 81 | 2935, 2927, 1589, 1502, 1323, 1190, 818 | *DMSO-d6: 8.91(1H, d, J=7.9Hz), 8.54(1H, d, J=1.9Hz), 8.25(1H, d, J=2.2Hz), 8.09 (1H, d, J=8.7Hz), 7.81(1H, dd, J=8.7, 1.9Hz), 7.54(1H, d, J=2.2Hz), 6.36(1H, d, J= 7.9Hz), 4.39(1H, t, J=5.2Hz), 4.15(2H, t, J=6.4Hz), 3.43~3.39(2H, m), 1.81~ 1.79(2H, m), 1.51~1.42(6H, m) | 106.9– 110.8 |
| 82 | 1765, 1651, 1608, 1504, 1323, 1203, 820 | *DMSO-d6: 9.00(1H, d, J=7.8Hz), 8.57(1H, d, J=2.0Hz), 8.40(1H, d, J=2.0Hz), 8.13 (1H, d, J=8.3Hz), 7.88~7.83(2H, m), 6.43 (1H, d, J=7.8Hz), 2.39(3H, s) | 286.2 (dec.) |
| 83 | 3000, 1720, 1610, 1504, 1321, 822 | *DMSO-d6: 8.93(1H, d, J=7.7Hz), 8.57(1H, d, J=1.8Hz), 8.27(1H, d, J=2.3Hz), 8.10 (1H d, J=8.7Hz), 7.81(1H, dd, J=8.7, 1.8 Hz), 7.51(1H, d, J=2.3Hz), 6.36(1H, d, J= 7.7Hz), 5.06(2H, s), 2.55(2H, t, J=7.5Hz), 1.60~1.52(2H, m), 0.89(3H, t J=7.5Hz) | 199.7– 203.5 |
| 84 | 1605, 1597, 1506, 1475, 1435, 1340 | DMSO-d6: 9.06(1H, s), 8.56(1H, d, J=2.0 Hz), 8.44(1H, d, J=3.9Hz), 8.26(1H, d, J= 2.2Hz), 8.09(1H, d, J=8.8Hz), 7.79(1H, dd, J=8.8, 2.0Hz), 7.70~7.64(1H, m), 7.56 (1H, d, J=2.2Hz), 7.37(1H, d, J=7.8Hz), 7.21~7.16(1H, m), 4.04(2H, s), 3.94(3H, s) | 218.9 (dec.) |
| 85 | 1605, 1498, 1394, 1338, 804 | DMSO-d6: 10.14(1H, bs), 9.03(1H, s), 8.53 (1H, d, J=2.0Hz), 8.44(1H, d, J=4.4Hz), 8.08(1H, d, J=8.8Hz), 8.01(1H, d, J=2.0 Hz), 7.77(1H, dd, J=8.8, 2.0Hz), 7.70~7.64 (1H, m), 7.49(1H, d, J=2.0Hz), 7.36(1 H, d, J=7.8Hz), 7.21~7.17(1H, m), 4.02 (2H, s) | 329.5 (dec.) |
| 86 | 3003, 1743, 1734, 1603, 1502, 1153, 843 | *DMSO-d6: 9.10(1H, s), 8.61(1H, d, J=1.9 Hz), 8.47~8.42(1H, m), 8.33(1H, d, J=2.3 Hz), 8.13(1H, d, J=8.7Hz), 7.82(1H, dd, J=8.7, 1.9Hz), 7.70~7.64(1H, m), 7.52 (1H, d, J=2.3Hz), 7.37(1H, d, J=7.6Hz), 7.23~7.15(1H, m), 4.88(2H, s), 4.04(2H, s), 1.44(9H, s) | 187.4– 188.2 |
| 87 | 3000, 1599, 1578, 1473, 1325, 1282, 1153 | DMSO-d6: 9.11(1H, s), 8.55(1H d, J=2.0 Hz), 8.45~8.41(2H, m), 8.24(1H, d, J= 2.4Hz), 8.04(1H, d, J=8.8Hz), 7.83~7.79 (1H, m), 7.55(1H, d, J=2.4Hz), 7.37~7.35 (2H, m), 3.94(3H, s), 3.90(2H, s) | 225.6– 226.5 |
| 88 | 1643, 1606, | *DMSO-d6: 10.16(1H, s), 9.12(1H, s), 8.54 | 301.1 |

TABLE 5-continued

| EX. No. | IR (KBr, cm-1) | NMR(ppm) (*:300MHz, non-mark: 270MHz) | M.P. (° .C) |
|---|---|---|---|
| | 1597, 1578, 1466, 1329, 1277, 798 | (1H, d, J=1.9Hz), 8.45~8.41(2H, m), 8.02~8.06(2H, m), 7.79(1H, dd, J=8.7, 1.9Hz), 7.49(1H, d, J=1.9Hz), 7.35~7.39 (2H, m), 3.88(2H, s) | (dec.) |
| 89 | 2978, 1751, 1603, 1504, 1327, 1153, 800 | *DMSO-d6: 9.15(1H, s), 8.60(1H, d, J=1.9 Hz), 8.43(2H, d, J=5.8Hz), 8.32(1H, d, J=2.4Hz), 8.07(1H, d, J=8.6Hz), 7.84(1H, dd, J=8.6, 1.9Hz), 7.52(1H, d, J=2.4Hz), 7.36(2H, d, J=5.8Hz), 4.88(2H, s), 3.90 (2H, s), 1.44(9H, s) | 149.6– 150.8 |
| 90 | 3000, 1601, 1504, 1473, 1433, 1336, 1228 | DMSO-d6: 9.01(1H, s), 8.50(1H, d, J=2.0 Hz), 8.19(1H, d, J=2.2Hz), 8.01(1H, d, J= 8.8Hz), 7.77(1H, dd, J=8.8, 2.0Hz), 7.54 (1H, d, J=2.2Hz), 7.39~7.37(2H1m), 7.30~ 7.23(2H, m), 7.18~7.13(1H, m), 3.93 (3H, s), 3.88(2H, s) | 324.6 (dec.) |
| 91 | 3323, 1574, 1448, 1421, 1390, 1325 | DMSO-d6: 10.14(1H, bs), 9.04(1H, s), 8.53(1H, d, J=1.6Hz), 8.05(1H, d, J=8.6Hz), 8.01(1H, d, J=2.4Hz), 7.78(1H, dd, J=8.6, 1.6Hz), 7.50(1H, d, J=2.4Hz), 7.37(2H, d, J=7.3Hz),.7.26(2H, dd, J=7.3, 5.9Hz), 7.17(1H, d, J=5.9Hz), 3.87(2H, s) | 315.2 (dec.) |
| 92 | 3000, 1603, 1504, 1473, 1336, 1248, 1228 | DMSO-d6: 9.02(1H, s), 8.57(1H, d, J=2.0 Hz), 8.26(1H, d, J=2.4Hz), 8.07(1H, d, J= 8.8Hz), 7.80(1H, dd, J=8.8, 2.0Hz), 7.58 (1H, d, J=2.4Hz), 7.29(2H, d, J=8.8Hz), 6.82(2H, d, J=8.8Hz), 3.95(3H, s), 3.82 (2H, s), 3.69(3H, s) | 190.2– 194.2 |
| 93 | 3305, 1578, 1564, 1510, 1448, 1327, 1234 | *DMSO-d6: 10.12(1H, s), 9.13(1H, s), 8.96(1H, s), 8.54(1H, d, J=1.8Hz), 8.07~8.01 (2H, m), 7.78(1H, dd, J=9.0, 1.8Hz), 7.50(1H, d, J=2.2Hz), 7.16~7.14(2H, m), 6.66~6.63(2H, m), 3.75(2H, s) | 300.0 (dec.) |
| 94 | 3100, 1649, 1601, 1504, 1333, 735 | DMSO-d6: 9.02(1H, s), 8.58(1H, d, J=2.0 Hz), 8.28(1H, d, J=2.0Hz), 8.09(1H, d, J= 8.5Hz), 7.80(1H, dd, J=8.5, 2.0Hz), 7.60 (1H, d, J=2.0Hz), 7.52~7.49(1Hm), 6.34 (1H, dd, J=2.7, 2.4Hz), 6.12(1H, d, J= 2.7Hz), 3.96(3H, s), 3.92(2H, s) | 154.9– 159.4 |
| 95 | 3000, 1597, 1508, 1338, 1273, 1020 | DMSO-d6: 9.30(1H, s), 8.60~8.59(2H, m), 8.29(1H, d, J=2.2Hz), 8.11(1H, d, J= 8.8Hz), 7.93(1H, d, J=1.0Hz), 7.86~7.83 (1H, m), 7.58(1H, d, J=2.2Hz), 5.32(2H, s) | 272.1 (dec.) |
| 96 | 3300, 1581; 1506, 1450, 1421, 1327, 1273 | DMSO-d6: 10.24(1H, s), 9.26(1H, s), 8.60~ 8.56(2H, m), 8.09(1H, d, J=8.8Hz), 8.04(1H, m), 7.93(1H, s), 7.83~7.80(1H, m), 7.49(1H, d, J=1.0Hz), 5.30(2H, s) | 300.0 (dec.) |
| 97 | 3000, 1768, 1605, 1506, 1329, 1198, 1147 | DMSO-d6: 9.37(1H, s), 8.62~8.58(2H, m), 8.47~8.43(1H, m), 8.15(1H, d, J=8.3Hz), 7.94~7.79(3H, m), 5.32(2H, s), 2.38 (3H, s) | 244.3 (dec.) |
| 98 | 1728, 1680, 1657, 1554, 1502, 1230, 1155 | *DMSO-d6: 9.47(1H, s), 8.55(1H, d, J= 1.9Hz), 8.30(1H, d, J=8.7Hz), 8.23(1H, d, J=2.2Hz), 7.81(1H, dd, J=8.7, 1.9Hz), 7.6 (1H, d, J=2.2Hz), 4.31(2H, q, J=7.1Hz), 3.90(3H, s), 1.35(3H, t, J=7.1Hz) | 240.4– 249.4 |
| 99 | 1718, 1547, 1473, 806 | DMSO-d6: 14.79(1H, s), 9.93(1H, s), 8.63(1H, d, J=1.9Hz), 8.52(1H, d, J=8.5Hz), 8.42(1H, d, J=2.3Hz), 7.88(1H, dd, J=8.5, 1.9Hz), 7.72(1H, d, J=2.3Hz), 4.01(3H, s) | 333.7 (dec.) |
| 100 | 1606, 1473, 1319, 1238, 802 | *DMSO-d6: 9.24(1H, s), 8.60(1H, d, J=2.0 Hz), 8.31(1H, d, J=2.2Hz), 8.20(1H, d, J= 8.7Hz), 7.82(1H, dd, J=8.7, 2.0Hz), 7.62 (1H, d, J=2.2Hz), 3.98(3H, s), 3.69~3.64 (4H, m), 3.62~3.53(2H, m), 3.40~3.31 (2H, m) | 317.4 (dec.) |
| 101 | 1603, 1508, 1468, 1425, 1385, 802 | *DMSO-d6: 9.18(1H, s), 8.67~8.62(1H, m), 8.48~8.44(1H, m), 8.39(1H, d, J=4.9 Hz), 8.25~8.23(2H, m), 7.77(1H, d, J= 7.9Hz), 7.65(1H, d, J=8.1Hz), 7.58(1H, d, J= 2.4Hz), 7.28(1H, dd, J=7.9, 4.9Hz), 3.95 (3H, s), 3.89(2H, s) | 280.5– 285.3 |
| 102 | 3307, 1576, 1572, 1512, 1448, 1392, 901 | *DMSO-d6: 10.13(1H, s), 9.11(1H, s), 8.61 (1H, s), 8.41(1H, d, J=1.7Hz), 8.37~ 8.35(1H, m), 8.18(1H, d, J=8.3Hz), 7.96(1H, d, J=2.2Hz), 7.78~7.72(1H, m), 7.64~ | 355.0 (dec.) |

TABLE 5-continued

| EX. No. | IR (KBr, cm-1) | NMR(ppm) (*:300MHz, non-mark: 270MHz) | M.P. (° .C) |
|---|---|---|---|
| | | 7.56(1H, m), 7.47(1H, d, J=2.2Hz), 7.27 (1H, dd, J=7.9, 4.6Hz), 3.85(2H, s) | |
| 103 | 3000, 1753, 1605, 1508, 1383, 1236, 1149 | *DMSO-d6: 9.15(1H, s), 8.63(1H, s), 8.43 (1H, d, J=1.4Hz), 8.39~8.38(1H, m), 8.25 (1H, d, J=2.2Hz), 8.21(1H, d, J=8.3Hz), 7.76(1H, d, J=7.8Hz), 7.63(1H, dd, J= 8.3, 1.4Hz), 7.51(1H, d, J=2.2Hz), 7.28(1H, dd, J=7.8, 4.7Hz), 4.87(2H, s), 3.88(2H, s) 1.44(9H s) | 230.1–232.0 |
| 104 | 1603, 1578, 1508, 1468, 1389, 1059 | *DMSO-d6: 9.17(1H, s), 8.65~8.61(1H, m), 8.45(1H, d, J=1.6Hz)18.42~8.35(1H, m), 8.28(1H, d, J=2.3Hz), 8.24(1H, d, J= 8.4Hz), 7.80~7.73(1H, m), 7.64(1H, dd, J=8.4, 1.6Hz)17.52(1H, d, J=2.3Hz), 7.28 (1H, dd, J=7.7, 4.7Hz), 4.91(2H, s), 3.88 (2H, s) | 188.9–191.9 |
| 105 | 1589, 1578, 1506, 1389, 1030, 814, 716 | *DMSO-d6: 9.15(1H, s), 8.75(1H, s), 8.64 (1H, s), 8.58~8.56(1H, m), 8.46~8.43 (1H, m), 8.39~8.38(1H, m), 8.34~8.31 (1H, m), 8.20(1H, d, J=8.4Hz), 7.95(1H, d, J=7.7Hz), 7.77(1H, d, J=7.6Hz), 7.69~ 7.67(1H, m), 7.65~7.62(1H, m), 7.46(1H dd, J=7.7, 4.9Hz), 7.29(1H, dd, J=7.6, 5.2Hz), 5.36(2H, s), 3.99(2H, s) | 218.8–223.2 |
| 106 | 1738, 1605, 1506, 1473, 1232, 1055 | *DMSO-d6: 9.18(1H, s), 8.72(1H, s), 8.66~ 8.62(1H, m), 8.61~8.56(1H, m), 8.48~ 8.46(1H, m), 8.39(1H, d, J=4.8Hz), 8.37~ 8.35(1H, m), 8.23(1H, d, J=8.5Hz), 7.96(1H, s).7.78~7.76(1H, m), 7.73~7.68 (1H, m), 7.66(1H, d, J=8.5Hz), 7.29(1H, dd, J=7.7, 4.8Hz), 5.39(2H, s), 5.16(2H, s), 3.89(2H, s), 2.07(3H, s) | 202.7–205.9 |
| 107 | 3167, 1599, 1506, 1471, 1387, 1028, 712 | *DMSO-d6: 9.17(1H, s), 8.67~8.61(2H m), 8.53~8.50(1H, m), 8.41(1H, d, J=1.6 Hz), 8.39(1H, d, J=4.8Hz), 8.34(1H, d, J= 2.2Hz), 8.21(1H, d, J=8.3Hz), 7.93~7.87 (1H, m), 7.77(1H, d, J=7.8Hz), 7.69(1H, d, J=2.2Hz), 7.65(1H, dd, J=8.3, 1.6Hz), 7.29(1H, dd, J=7.8, 4.8Hz), 5.45~5.24 (3H, m), 4.47(2H, s), 3.88(2H, s) | 143.1–146.8 |
| 108 | 1645, 1601, 1578, 1506, 1468, 1389 | *DMSO-d6: 9.20(1H, s), 9.17(1H, s), 9.00 (2H, s), 8.64(1H, d, J=1.7Hz), 8.46(1H, d, J=1.5Hz), 8.39(1H, dd, J=4.5 1.7Hz), 8.36(1H, d, J=2.2Hz), 8.22(1H, d, J=8.1Hz), 7.77(1H, dt, J=7.8, 1.7Hz), 7.72(1H, d, J=2.2Hz), 7.65(1H, dd, J=8.1, 1.5Hz), 7.29(1H, dd, J=7.8, 4.5Hz), 5.40(2H, s) 3.89(2H, s) | 229.2–233.5 |
| 109 | 3055, 1659, 1601, 1579, 1506, 1389, 1059 | *DMSO-d6: 9.16(1H, s), 8.63(1H, d, J=1.6Hz), 8.44(1H, d, J=1.5Hz), 8.39(1H, dd, J=4.7, 1.6Hz), 8.34~8.23(2H, m), 8.20 (1H, d, J=8.4Hz), 7.78~7.75(1H, m), 7.67~ 7.58(2H, m), 7.29(1H, dd, J=8.0, 4.7Hz), 4.67(2H, s), 3.94(2H, s), 3.23~3.14 (2H, m), 1.06(3H, t, J=7.2Hz) | 263.0–266.2 |
| 110 | 1597, 1578, 1506, 1462, 1389, 1057 | *DMSO-d6: 9.13(1H, s), 8.64(1H, s), 8.43– 8.36(2H, m), 8.20(1H, d, J=2.2Hz), 8.19(1H, d, J=8.3Hz), 7.77(1H, d, J=7.8Hz), 7.62(1H, dd, J=8.3, 1.7Hz), 7.54(1H, d, J=2.2Hz), 7.29(1H, dd, J=7.8, 4.7Hz), 4.62 (1H, t, J=5.2Hz), 4.21(2H, t, J=6.4Hz), 3.87(2H, s), 3.65~3.59(2H, m), 2.00~ 190(2H, m) | 221.6–222.8 |
| 111 | 1711, 1601, 1504, 1385, 719 | *DMSO-d6: 9.16(1H, s), 8.63(1H, s), 8.45 (1H, s), 8.38(1H, d, J=4.6Hz), 8.16(1H, d, J=8.1Hz), 8.06(1H, s), 7.87~7.72(5H, m), 7.67~7.61(1H, m), 7.47(1H, s), 7.35~ 7.31(1H, m), 4.26~4.16(2H, m), 3.87 (2H, s), 3.83(2H, t, J=6.8Hz), 2.19~2.08 (2H, m) | 231.9–136.7 |
| 112 | 3444, 3431, 1643, 1601, 1576, 1506, 1462 | *DMSO-d6: 9.24(1H, s), 8.64(1H, s), 8.49 (1H, d, J=1.6Hz), 8.38(1H, d, J=4.7Hz), 8.33~8.27(1H, m), 8.25(1H, d, J=8.4Hz), 7.78(1H, d, J=7.9Hz), 7.65(1H, dd, J=8.4, 1.6Hz), 7.61(1H, d, J=2.4Hz), 7.29(1H, dd, J=7.9, 4.7Hz), 4.21(2H, t, J=6.5Hz), | 253.2 (dec.) |

TABLE 5-continued

| EX. No. | IR (KBr, cm-1) | NMR(ppm) (*:300MHz, non-mark: 270MHz) | M.P. (° .C) |
|---|---|---|---|
| | | 3.87(2H, s), 3.04~2.93(2H, m), 2.19~2.07(2H, m) | |
| 113 | 1593, 1579, 1508, 1473, 1300, 1036 | *DMSO-d6: 8.95(1H, s), 8.41(1H, d, J=1.5Hz), 8.20(1H, d, J=8.3Hz), 8.19(1H, d, J=2.3Hz), 7.61(1H, dd, J=8.3, 1.5Hz), 7.57 (1H, d, J=2.3Hz), 3.96(3H, s), 2.10(3H, s) | 238.4 (dec.) |
| 114 | 1597, 1579, 1450, 1429, 1302, 1209, 1055 | *DMSO-d6: 8.95(1H, s), 8.42(1H, d, J=1.5 Hz), 8.19(1H, d, J=8.3Hz), 7.97(1H, d, J=2.0Hz), 7.59(1H, dd, J=8.3, 1.5Hz), 7.51 (1H, d, J=2.0Hz), 2.09(3H, s) | 300.0 (dec.) |
| 115 | 1603, 1579, 1504, 1427, 1.302 | *DMSO-d6: 8.98(1H, s), 8.77(1H, bs), 8.58 (1H, dd, J=4.9, 1.5Hz), 8.44(1H, d, J=1.3 Hz), 8.33(1H, d, J=2.1Hz), 8.21(1H, d, J=8.3Hz), 7.98~~7.95(1H, m), 7.72(1H, d, J=2.1Hz), 7.63(1H, dd, J=8.3, 1.3Hz), 7.47(1H, dd, J=7.6, 4.9Hz), 5.38(2H, s), 2.11(3H, s) | 203.1 (dec.) |
| 116 | 1597, 1506, 1468, 1383, 1290, 1028, 818 | *DMSO-d6: 8.94(1H, d, J=7.6Hz), 8.49(1H, d, J=1.6Hz), 8.25~8.22(2H, m), 7.65 (1H, dd, J=8.4, 1.6Hz), 7.57(1H, d, J=2.4Hz), 6.38(1H, d, J=7.6Hz), 3.97(3H s) | 279.0 (dec.) |
| 117 | 3000, 1606, 1508, 1450, 1398, 1188, 818 | *DMSO-d6: 8.87(1H, d, J=7.6Hz), 8.44 (1H, d, J=1.5Hz), 8.14(1H, d, J=8.3Hz), 7.93 (1H, d, J=1.9Hz), 7.58(1H, dd, J=8.3, 1.5Hz), 7.45(1H, d, J=1.9Hz), 6.29(1H, d, J=7.6Hz) | 350.0< |
| 118 | 1755, 1601, 1506, 1246, 1153, 814 | *DMSO-d6: 8.93(1H, d, J=7.7Hz), 8.48(1H, d, J=1.7Hz), 8.26(1H, d, J=2.4Hz), 8.22 (1H, d, J=8.3Hz), 7.64(1H, dd, J=8.3, 1.7 Hz), 7.51(1H, d, J=2.4Hz), 6.36(1H, d, J=7.7Hz), 4.90(2H, s), 1.44(9H, s) | 230.3–231.5 |
| 119 | 1647, 1606, 1578, 1504, 1464, 1196, 822 | *DMSO-d6: 13.15(1H, bs), 8.93(1H, d, J=7.7Hz), 8.48(1H, d, J=1.6Hz), 8.26(1H, d, J=2.3Hz), 8.22(1H, d, J=8.4Hz), 7.64 (1H, dd, J=8.4, 1.6Hz), 7.51(1H, d, J=2.3Hz), 6.37(1H, d, J=7.7Hz), 4.93(2H, s) | 350.0 (dec.) |
| 120 | 1605, 1504, 1288, 1194, 1059, 820 | *DMSO-d6: 8.95(1H, d, J=7.6Hz), 8.76 (1H, d, J=1.7Hz), 8.58(1H, dd, J=4.9, 1.7Hz), 8.50(1H, d, J=1.6Hz), 8.36(1H, d, J=2.3 Hz), 8.22(1H, d, J=8.2Hz), 7.99~7.94 (1H, m), 7.70(1H, .d, J=2.3Hz), 7.66(1H, dd, J=8.2, 1.6Hz), 7.49~7.44(1H, m), 6.38 (1H, d.J=7.6Hz), 5.39(2H, s) | 262.0 (dec.) |
| 121 | 1599, 1581, 1506, 1473, 1425, 1230 | *DMSO-d6: 9.12(1H, s), 8.46(1H, d, J=1.5 Hz), 8.24~8.19(2H, m), 7.63(1H, dd, J=8.4, 1.5Hz), 7.57(1H, d, J=2.2Hz), 7.41~7.35(2H, m), 7.29~7.23(2H, m), 7.19~7.13(1H, m), 3.95(3H, s), 3.88(2H, s) | 254.0–258.6 |
| 122 | 1603, 1579, 1512, 1439, 1390, 1308 | *DMSO-d6: 10.10(1H, s), 9.10(1H, s), 8.46(1H, d, J=1.6Hz), 8.20(1H, d, J=8.2Hz), 7.98(1H, d, J=2.2Hz), 7.60(1H, dd, J=8.2, 1.6Hz), 7.49(1H, d, J=2.2Hz), 7.40~7.35(2H, m), 7.29~7.23(2H, m), 7.12(1H, m), 3.88(2H, s) | 350.0 (dec.) |
| 123 | 3435, 1605, 1581, 1508, 1470, 1429, 1385 | *DMSO-d6: 9.14(1H, s), 8.45~8.42(2H, m), 8.24~8.21(3H, m), 7.66~7.60(1H, m), 7.58~7.56(2H, m), 3.94(3H, s), 3.83 (2H, s), 2.22(3H, s) | 285.3–286.4 |
| 124 | 1601, 1576, 1504, 1454, 1389, 1271 | *DMSO-d6: 9.09(1H, s), 8.46~8.38(2H, m), 8.21(1H, d, J=1.9Hz), 8.16(1H, d, J=8.2Hz), 7.96~7.89(1H, m), 7.63~7.54(2H, m), 7.42~7.45(1H, m), 3.82(2H, s), 2.23 (3H, s) | 300.0 |
| 125 | 1605, 1581, 1508, 1470, 1404, 1385 | *DMSO-d6: 9.16(1H, s), 9.02(1H, s), 8.83 (2H, s), 8.42(1H, d, J=1.6Hz), 8.24~8.22(2H, m), 7.64(1H, dd, J=8.3, 1.6Hz), 7.57(1H, d, J=2.4), 3.95(3H, s), 3.88(2H, s) | 266.6–272.0 |
| 126 | 3304, 1603, 1572, 1514, 1450, 1437 | *DMSO-d6: 9.11(1H, s), 9.01(1H, s), 8.82 (2H, s), 8.39(1H, d, J=1.7Hz), 8.17(1H, d, J=8.4Hz), 7.94(1H, d, J=1.9), 7.60(1H, dd, J=8.4, 1.7Hz), 7.44(1H, d, J=1.9), 3.86(2H, s) | 375.0 (dec.) |
| 127 | 3024, 1610, 1510, 1452, 1340, 760 | DMSO-d6: 9.17(1H, s), 8.53(1H, d, J=7.6Hz), (2H, s), 8.39(1H, d, J=1.7Hz), 8.17(1H, 7.8Hz), 81.8(1H, d, J=7.8Hz), 8.11(1H, d, J=7.8Hz), 7.74~7.53(3H, m), 7.49(1H, t, | 167.4–168.1 |

TABLE 5-continued

| EX. No. | IR (KBr, cm-1) | NMR(ppm) (*:300MHz, non-mark: 270MHz) | M.P. (° .C) |
|---|---|---|---|
| 128 | 1643, 1608, 1454, 1333, 754 | J=7.8Hz), 7.39(1H, d, J=7.6Hz), 7.21~7.17(1H, m), 4.07(2H, s)<br>DMSO-d6: 9.22(1H, s), 8.68~8.63(1H, m), 8.52(1H, d, J=8.0Hz), 8.38(1H, d, J=4.8Hz), 8.29(1H, d, J=7.7Hz), 8.15~8.10(2H, m), 7.78(1H, d, J=7.8Hz), 7.70(1H, t, J=8.0Hz), 7.66(1H, t, J=7.7Hz), 7.48(1H, t, J=7.7Hz), 7.28(1H, ddm J=7.8, 4.8 Hz), 3.92(2H, s) | 223.5–224.1 |
| 129 | 3022, 1643 1599, 1454 756 | DMSO-d6: 9.23(1H, s), 8.53(1H, d, J=7.8Hz), 8.45(2H, d, J=5.5Hz), 8.30(1H, d, J=7.8Hz), 8.13(1H, d, J=7.8Hz), 8.12(1H, d, J=7.8Hz), 7.74~7.64(2H, m), 7.49(1H, t, J=7.8Hz), 7.38(2H, d, J=5.6Hz), 3.93(2H, s) | 193.1–194.8 |
| 137 | 3232, 1587, 1512, 1335, 1228, 798, 741 | DMSO-d6: 10.49(1H, bs), 8.93(1H, s), 8.52(1H1d, J=7.6Hz), 8.30(1H1d, J=7.6Hz), 8.15(1H, d, J=7.9Hz), 8.06(1H, d, J=7.9Hz), 7.74~7.62(2H, m)17.48(1H, t, J=7.6 Hz), 6.60~6.58(1H, m), 5.90~5.88(1H, m), 5.82(1H, s), 3.87(2H, s) | 255.1–258.1 |
| 138 | 3273, 1570, 1512, 1335, 1086, 760 | DMSO-d6: 11.63(1H, bs), 9.11(1H, s), 8.54(1H, d, J=7.3Hz), 8.31(1H1d, J=7.6Hz), 8.16~8.10(2H, m), 7.75~7.69(1H, m), 7.69~7.63(1H, m), 7.49(1H, t, J=7.6Hz), 6.95(1H, s), 6.76(1H, s), 3.96(2H, s) | 290.9–292.8 |
| 139 | 1610, 1506, 1452, 1333, 762 | DMSO-d6: 8.93(1H, s), 8.50(1H, d, J=6.9Hz), 8.34~8.25(2H, m), 8.19~8.16(1H, m), 8.02(1H, d, J=8.3Hz), 7.94~7.91(1H, m), 7.85~7.76(1H, m), 7.71(1H, t, J=7.6 Hz), 7.61~7.38(6H, m), 4.39(2H, s) | 196.4–197.2 |
| 140 | 3045, 1643, 1610, 1502, 1452, 1335, 760 | DMSO-d6: 9.24(1H, s), 8.53(1H, d, J=7.6 Hz), 8.31(1H, d, J=7.9Hz), 8.18~8.11(2H, m), 7.84~7.81(4H, m), 7.74~7.57(3H, m), 7.52~7.40(3H, m), 4.10(2H, s) | 165.7–167.1 |
| 141 | 1610, 1510, 1454, 1336, 756 | DMSO-d6: 9.31(1H, s), 9.02(1H, d, J=1.7 Hz), 8.59~8.57(1H, m), 8.31(1H, d, J=7.6 Hz), 8.25(1H, d, J=1.7Hz), 8.19~8.07(2H, m), 7.97(1H, d, J=8.3Hz), 7.92~7.86(1H, m), 7.74~7.65(3H, m), 7.57~7.47(2H, m), 4.12(2H, s) | 231.5–232.4 |
| 142 | 3379, 1608, 1510, 1452, 1109, 758, 744 | DMSO-d6: 10.81(1H, s), 9.00(1H, s), 8.49(1H, d, J=7.3Hz), 8.26(1H, d, J=7.9Hz), 8.15(1H, d, J=7.9Hz), 8.07(1H, d, J=8.3Hz), 7.72~7.69(2H, m), 7.68~7.57(1H, m), 7.47~7.36(1H, m), 7.32(1H, d, J=7.9Hz), 7.20(1H, s), 7.06~6.93(2H, m), 4.02(2H, s) | 153.6–155.6 |
| 143 | 3055, 2924, 1738, 1643, 1610, 1506, 1454, 760 | CDCl3: 8.33(1H, d, J=7.9Hz), 8.23(1H, d, J=7.6Hz), 8.15(1H, s), 8.08(1H, d, J=7.6 Hz), 7.71~7.53(3H, m), 7.41(1H, t, J=7.6 Hz), 2.57~2.54(2H, m), 1.83~1.68(6H, m), 1.32~1.02(5H, m) | oil |
| 144 | 3059, 2997, 1608, 1508, 754 | DMSO-d6: 8.97(1H, s), 8.52(1H, d, J=7.3 Hz), 8.30(1H, d, J=7.6Hz), 8.18(1H, d, J=7.3Hz), 8.16(1H, d, J=7.6Hz), 7.71(1H, t, J=7.6Hz), 7.66(1H, t, J=7.3Hz), 7.48(1H, t, J=7.6Hz), 2.53~2.40(2H, m), 1.24~1.09(1H, m), 0.53~0.47(2H, m), 0.29~0.24(2H, m) | 148.3–151.0 |
| 145 | 1643, 1616, 1452, 762 | DMSO-d6: 9.43(1H, s), 8.59(1H, d, J=6.8 Hz), 8.34(1H, d, J=7.5Hz), 8.32(1H, d, J=7.5Hz), 8.14(1H, d, J=6.8Hz), 7.91~7.88(2H, m), 7.79(1H, t.J=7.5Hz), 7.70~7.63(2H, m), 7.57~7.49(3H, m) | 287.0–289.0 |
| 146 | 3363, 1641, 1564, 1452, 1223, 1171, 760 | DMSO-d6: 9.13(1H, s), 8.54(1H, d, J=7.6 Hz), 8.33(1H, d, J=7.6Hz), 8.31(1H, d, J=7.6Hz), 8.10(1H, d, J=7.6Hz), 7.71(1H, t, J=7.6Hz), 7.66(1H, t, J=7.6Hz), 7.58~7.46(3H, m), 7.30~7.15(3H, m), 5.99~5.93(2H, m) | 202.0–206.3 |
| 147 | 3294, 1601, 1500, 1437, 1317, 758 | DMSO-d6: 9.06(1H, s), 8.59(1H, d, J=7.9 Hz), 8.33(1H, d, J=7.5Hz), 8.29~8.25(2H, m), 7.74(1H, t.J=7.9Hz), 7.64(1H, t, J=7.5Hz), 7.48(1H, t, J=7.5Hz), 7.31~7.26(4H, m), 6.87~6.82(1H, m) | 207.8–210.3 |

TABLE 5-continued

| EX. No. | IR (KBr, cm-1) | NMR(ppm) (*:300MHz, non-mark: 270MHz) | M.P. (° .C) |
|---|---|---|---|
| 148 | 3047, 1639, 1603 1502, 1479, 1452, 1350, 750 | DMSO-d6: 9.31(1H, s), 8.58(1H, d, J=7.3 Hz), 8.33(1H, d, J=7.9Hz), 8.23(1H, d, J=7.9Hz), 8.16(1H, d, J=7.6Hz), 7.74(1H, t, J=7.6Hz), 7.69~7.61(1H, m), 7.54~7.47(1H, m), 7.14(2H, t, J=7.3Hz), 6.83~7.62(3H, m), 3.28(3H, s) | 166.3–170.8 |
| 149 | 3051, 1608, 1321, 1304, 1238, 766, 746 | DMSO-d6: 9.44(1H, s), 8.61(1H, d, J=7.3 Hz), 8.35(1H, d, J=7.9Hz).8.22~8.18(2H, m), 7.79~7.73(1H, m), 7.66(1H, dd, J=7.9, 7.6Hz), 7.51(1H, dd, J=7.6, 7.3Hz), 7.33~7.28(2H, m), 7.28~6.99(3H, m) | 210.0–211.3 |
| 150 | 3051, 1618, 1506, 1450, 1227, 716 | DMSO-d6: 9.71(1H, s), 8.58(1H, d, J=7.6 Hz), 8.33~8.26(2H, m), 8.20(1H, d, J=7.9Hz), 7.78(1H, dd, J=7.9, 7.6Hz), 7.67(1H, dd, J=7.9, 7.6Hz), 7.52(1H, dd, J=7.6, 7.2Hz) | 248.2–250.1 |
| 151 | 1643, 1610, 1566, 1510, 1454, 1227, 762 | DMSO-d6: 8.89(1H, s), 8.54(1H, d, J=7.3 Hz), 8.31(1H, d, J=7.6Hz), 8.27(1H, d, J=8.3Hz), 8.16(1H, d, J=7.9Hz), 7.76~7.70 (1H, m), 7.64(1H, t, J=7.3Hz), 7.52~7.46 (1H, m), 4.93~4.81(1H, m), 1.94~1.53 (2H, m), 0.95(3H, t, J=7.3Hz) | 87.3 (dec.) |
| 152 | 1612, 1572, 1510, 1309, 756 | DMSO-d6: 9.03(1H, s), 8.53(1H, d, J=7.8 Hz), 8.30(1H, d, J=7.8Hz), 8.18~8.10(2H, m), 7.74~7.63(2H, m), 7.48(i H, dd, J= 7.8, 7.3Hz), 2.15(3H, s) | 300.0 (dec.) |
| 153 | 1608, 1504, 1306, 1134, 762 | DMSO-d6: 9.40(1H, s), 8.62(1H, s), 8.56 (1H, d, J=7.3Hz), 8.32(1H, d, J=7.8Hz), 8.20 ~8.12(2H, m), 7.94(1H, s), 7.77~7.66 (2H, m), 7.52(1H, dd, J=7.8, 7.3Hz), 5.34 (2H, s) | 228.8 (dec.) |
| 154 | 1593, 1508, 1464, 1228, 752 | DMSO-d6: 9.14(1H, s), 8.64(1H, d, J=1.6 Hz), 8.38(1H, dd, J=4.8, 1.6Hz) , 8.26(1H, d, J=7.6Hz), 8.18(1H, d, J=2.2Hz), 8.09 (1H, d, J=7.6Hz), 7.77(1H, d, J=7.8Hz), 7.65 1H, t, J=7.6Hz), 7.54(1H, d, J=2.2Hz 7.46(1H, t, J=7.6Hz), 7.28(1H, dd, J=7.8, 4.8Hz), 3.95(3H, s), 3.91(2H, s) | 192.9–193.7 |
| 155 | 3533, 3398, 1568, 1516, 1394, 1319, 1296 | DMSO-d6: 10.07(1H, s), 9.12(1H, s), 8.64 (1H, s), 8.38(1H, bs), 8.24(1H, d, J=7.3 Hz), 8.08(1H, d, J=8.3Hz), 7.96(1H, d, J= 2.0Hz), 7.77(1H, d, J=7.8Hz), 7.64(1H, dd, J=8.3, 7.3Hz), 7.47~7.41(2H, m), 7.30~7.26(1H, m), 3.89(2H, s) | 306.5 (dec.) |
| 156 | 1755, 1599, 1572, 1508, 1458, 1190 | DMSO-d6: 9.14(1H, s), 8.65(1H, s), 8.40~8.38(2H, m), 8.29(1H, d, J=7.8Hz), 8.14 (1H, d, J=7.8Hz), 7.82(1H, d, J=2.0Hz), 7.78(1H, d, J=7.8Hz), 7.69(1H, t, J=7.8Hz), 7.50(1H, dd, J=7.8, 7.3Hz), 7.29(1H, dd, J=7.8, 4.9Hz), 3.92(2H, s), 2.37(3H, s) | 208.5–213.7 |
| 157 | 1753, 1606, 1585, 1508, 1460, 746 | DMSO-d6: 9.12(1H, s), 8.65(1H, d, J=1.5 Hz), 8.38(1H, dd, J=4.9, 1.5Hz), 8.34~8.16(2H, m), 8.07(1H, d, J=8.3Hz), 7.81~7.40(4H, m), 7.28(1H, dd, J=7.8, 4.9Hz), 5.00(2H, s), 4.21(2H, q, J=7.1Hz), 3.90 (2H, s), 1.24(3H, t, J=7.1Hz) | 256.7 (dec.) |
| 158 | 3446, 1718, 1581, 1514, 1460, 1113, 615 | DMSO-d6: 9.14(1H, s), 8.64(1H, s), 8.46~8.16(3H, m), 8.08(1H, d, J=8.3Hz), 7.77 (1H, d, J=7.8Hz), 7.65(1H, t, J=7.8Hz), 7.52~7.38(2H, m), 7.28(1H, dd, J=7.3, 4.9Hz), 4.90(2H, s) 3.91(2H, s) | 182.5–188.1 |
| 159 | 1734, 1597, 1572, 1512, 1340, 1286, 1161 | *DMSO-d6: 9.16(1H, s), 8.67~8.62(1H, m), 8.38(1H, dd, J=4.8, 1.5Hz), 8.28(1H, d, J=7.7Hz), 8.22(1H, d, J=2.2Hz), 8.10 (1H, d, J=7.7Hz), 7.77(1H, d, J=7.7Hz), 7.66(1H, t, J=7.7Hz), 7.53(1H, d, J=2.2Hz), 7.47(1H, t, J=7.7Hz), 7.28(1H, dd, J=7.7, 4.8Hz), 4.19(2H, t, J=6.2Hz), 4.12~4.05(2H, m), 3.91(2H, s), 2.52~2.49(2H, m), 2.08~2.04(2H, m), 1.18(3H, t, J =7.0 Hz) | 94.0–97.0 |
| 160 | 1701, 1601, 1570, 1510, 1458, 1309, 748 | DMSO-d6: 12.20(1H, s), 9.14(1H, s), 8.64 (1H, d, J=2.0Hz), 8.39~8.38(1H, m), 8.26 (1H, d, J=7.3Hz), 8.20(1H, d, J=2.4Hz), 8.09(1H, d, J=7.8Hz), 7.80~7.75(1H, m), | 230.0 (dec.) |

TABLE 5-continued

| EX. No. | IR (KBr, cm-1) | NMR(ppm) (*:300MHz, non-mark: 270MHz) | M.P. (° .C) |
|---|---|---|---|
| | | 7.65(1H, dd, J=7.8, 7.3Hz), 7.52(1H, d, J=2.4Hz), 7.46(1H, t, J=7.3Hz), 7.28(1H, dd, J=7.8, 4.4Hz), 4.18(2H, t.J=6.3Hz), 3.91(2H, s), 2.50~2.46(2H, m), 2.09~2.01(2H, m) | |
| 161 | 1587, 1574, 1512, 1466, 1336, 1315 | DMSO-d6: 8.96(1H, s), 8.28(1H, d, J=7.5 Hz), 8.19(1H, d, J=1.7Hz), 8.09(1H, d, J=8.3Hz), 7.64(1H, dd, J=8.3, 7.3Hz), 7.58 (1H, d, J=1.7Hz), 7.45(1H, dd, J=7.8, 7.3 Hz), 3.97(3H, s), 2.13(3H, s) | 241.5 (dec.) |
| 162 | 3000, 1539 1458, 1159, 783 | DMSO-d6: 8.94(1H, s), 8.23(1H, d, J=7.3 Hz), 8.08(1H, d, J=8.3Hz), 7.96(1H, d, J=2.2Hz), 7.61(1H, dd, J=8.3, 7.3Hz), 7.50 (1H, d, J=2.2Hz), 7.42(1H, dd, J=8.3, 7.3 Hz), 2.12(3H, s) | 324.3 (dec.) |
| 163 | 3500, 1755, 1597, 1572, 1508, 1219 | DMSO-d6: 9.05(1H, s), 8.37(1H, d, J=2.0 Hz), 8.28(1H, d, J=7.8Hz), 8.14(1H, d, J=8.3Hz), 7.86(1H, d, J=2.0Hz), 7.68(1H, dd, J=8.3, 7.3Hz), 7.48(1H, dd, J=7.8, 7.3 Hz), 2.38(3H, s), 2.14(3H, s) | 246.8 (dec.) |
| 164 | 1755, 1597, 1508, 1308, 1186, 787 | DMSO-d6: 8.95(1H, s), 8.37~8.20(2H, m), 8.10~8.07(1H, m), 7.64(1H, dd, J=7.8, 7.3Hz), 7.54(1H, s), 7.45(1H, dd1J=7.8, 7.3Hz), 5.02(2H, s), 4.21(2H, q, J=6.8Hz), 2.12(3H, s), 1.24(3H, t, J=6.8Hz) | 130.9 (dec.) |
| 165 | 3500, 3080, 1734, 1.566, 1475, 1308, 1215, 785 | DMSO-d6: 13.13(1H, bs), 8.96(1H, s), 8.29~8.23(2H, m), 8.08(1H, d, J=8.3Hz), 7.64(1H, m, J=7.3Hz)17.52(1H, d, J=2.0Hz), 7.47~T42(1H, ni), 4.92(2H, s), 2.13 (3H, s) | 261.0 (dec.) |
| 166 | 1649, 1603, 1512, 1466, 1304, 1018 | DMSO-d6: 9.33.(1H, s), 8.60(1H, s), 8.31 (1H, d, J=7.8Hz)18.25(1H, d, J=2.2Hz), 8.15(1H, d, J=T 8Hz), 7.93(1H, s), 7.68 (1H, dd, J=7.8, 7.3Hz), 7.56(1H, d, J=2.2Hz), 7.50(1H, dd, J=7.8, 7.3Hz), 5.34(2H, s), 3.96(3H, s) | 259.7 (dec.) |
| 167 | 3300, 1572, 1508, 1458, 1398, 1304 | DMSO-d6: 10.17(1H, s), 9.28(1H, s), 8.60 (1H, s), 8.25(1H, d, J=7.3Hz), 8.12(1H, d, J=8.3Hz), 7.98(1H, d, J=2.4Hz), 7.93 (1H, s), 7.67~7.62(1H, m), 7.50~7.44 (2H, m), 5.31(2H, s) | 300.0 (dec.) |
| 168 | 1749, 1649, 1612, 1506, 1234, 1223 | DMSO-d6: 9.40(1H, s), 8.62(1H, s), 8.61 (1H, s), 8.30(1H, d, J=7.3Hz), 8.18(1H, d, J=8.3Hz), 7.94(1H, s), 7.84(1H, s), 7.7 5~7.48(2H, m), 5.34(2H, s), 2.37(3H, s) | 224.8 (dec.) |
| 169 | 3035, 1612, 1508, 1203, 1084, 816, 744 | DMSO-d6: 8.93(1H, d, J=7.6Hz), 8.27(1H, d, J=8.1Hz), 8.19(1H, d, J=2.2Hz), 8.12 (1H, d, J=8.1Hz), 7.64(1H, t, J=8.~Hz), 7.54(1H, d, J=2.2Hz), 7.46(1H, t, J=8.1Hz), 6.36(1H, d, J=7.6Hz), 3.97(3H, s) | 226.3–228.4 |
| 170 | 1601, 1516, 1450, 1290, 818, 737 | DMSO-d6: 10.11(1H, s), 8.90(1H, d, J=7.6 Hz), 8.23(1H, d, J=7.3Hz), 8.11(1H, d, J=8.3Hz), 7.96(1H, d, J=2.0Hz), 7.62(1H, dd, J=8.3, 7.3Hz), 7.47~7.42(2H, m), 6.32(1H, d, J=7.6Hz) | 276.9 (dec.) |
| 171 | 1641, 1614, 1601, 1554, 1504, 1288, 818, 741 | DMSO-d6: 9.01(1H, d, J=7.8Hz), 8.66(1H, d, J=1.7Hz), 8.32(i H, d, J=7.6Hz), 8.6 (1H, d, J=8.1Hz), 8.02(1H, d, J=1.7Hz), 7.68(~H, dd, J=8.1, 7.6Hz), 7.50(1H, dd, J=7.6, 7.6Hz), 6.43(i H, d, J=7.8Hz) | 264.6–266.2 |
| 172 | 3059, 2924, 1643, 1612, 1574, 1506, 1452, 1333 | DMSO-d6: 9.04(1H, s), 8.67(1H, d, J=1.8 Hz), 8.34(1H, d, J=7.8Hz), 8.13(1H, d, J=8.3Hz), 8.07(1H, d, J=1.8Hz), 7.69(1H, dd, J=8.3, 7.3Hz), 7.49(1H, dd, J=7.8, 7.3 Hz), 2.14(3H, s) | 278.8–281.0 |
| 173 | 2226, 1618, 1603, 1502, 1471, 1460, 820, 743 | DMSO-d6: 9.09(1H, d, J=7.6Hz), 9.05(1H, s), 8.50(1H, s), 8.38(1H, d, J=8.3Hz), 8.22(1H, d, J=8.3Hz), 7.77~7.71(1H, m), 7.59~7.54(1H, m), 6.52(1H, d, J=7.6Hz) | 300.0< |
| 174 | 3342, 3200, 1664, 1593, 1504, 1288 | DMSO-d6: 9.07~9.04(2H, m), 8.70(1H, s), 8.38~8.35(2H, m), 8.19(1H, d, J=8.3Hz), 7.69(1H, t, J=7.8Hz), 7.64~7.45(2H, m), 6.47(1H, d, J=7.8Hz) | 300.0< |
| 175 | 1714, 1614, 1508, 1194, 1088 | DMSO-d6: 13.35(1H, bs), 9.09(1H, s), 9.06 (1H, d, J=7.8Hz), 8.68(1H, s), 8.45(1H, d, J=7.8Hz), 8.19(1H, d, J=8,3Hz), 7.72~ | 375.0< |

TABLE 5-continued

| EX. No. | IR (KBr, cm-1) | NMR(ppm) (*:300MHz, non-mark: 270MHz) | M.P. (° .C) |
|---|---|---|---|
| | | 7.49(2H, m), 6.48(1H, d, j=7.8Hz) | |
| 176 | 1724, 1645, 1616, 1605, 1506, 1261, 766 | DMSO-d6: 9.08~9.04(2H, m), 8.67(1H, d J=1.5Hz), 8.46(1H, d, J=7.3Hz), 8.19 (1H, d, J=8.3Hz), 7.74~7.68(1H, m), 7.56~ 7.51(1H, m), 6.49(1H, d, J=7.8Hz), 4.00 (3H, s) | 255.9 (dec.) |
| 177 | 1641, 1581, 1508, 1290, 1240, 746 | DMSO-d6: 9.00(1H, d, J=7.6Hz), 8.49(1H, s), 8.30(1H, d, J=7.3Hz), 8.16(1H, d, J= 8.3Hz), 8.09(1H, s), 7.68~7.61(1H, m), 7.48(1H, dd, J=8.3, 7.3Hz), 6.41(1H, d, J= 7.6Hz), 5.53(1H, t, J=5.7Hz), 4.81(2H, d, J=5.7Hz), | 164.3– 169.3 |
| 178 | 1614, 1570, 1506, 1471, 1331, 798, 721 | DMSO-d6: 9.24(1H, s), 8.80(1H, d, J=1.2 Hz), 8.70(1H, s), 8.47(1H, s), 8.34(1H, d, J=7.7Hz), 8.16(1H, d, J=1.2Hz), 812(1H, d, J=7.7Hz), 7.94(1H, d, J=7.7Hz), 7.71 (1H, t, J=7.7Hz), 7.51(1H, t, J=7.7Hz), 7.48~7.37(1H, m), 3.95(2H, s) | 274.7 (dec.) |
| 179 | 3365, 1643, 1560, 1514, 1466, 1313 | DMSO-d6: 9.03(1H, s), 8.63(1H, s), 8.37 (1H, s), 8.14(1H, d, J=7.3Hz), 8.09~ 8.01(1H, m), 7.76(1H, d, J=7.8Hz), 7.72(1H, d, J=2.0Hz), 7.59(1H, t, J=7.3Hz), 7.41 (1H, t, J=7.3Hz), 7.30~7.25(2H, m), 5.62 (2H, s), 3.88(2H, s) | 246.5 (dec.) |
| 180 | 1614, 1552, 1500, 1329, 816, 741 | DMSO-d6: 8.99(1H, d, J=7.3Hz), 8.76(1H, d, J=2.0Hz), 8.30(1H, d, J=7.3Hz), 8.15~ 8.13(1H, m), 8.13(1H, d, J=2.0Hz), 7.67 (1H, dd, J=8.3, 7.3Hz), 7.49(1H, dd, J=7.8, 7.3Hz), 6.42(1H, d, J=7.3Hz) | 294.2 (dec.) |
| 181 | 3370, 1637 1560, 1508, 1466, 1252, 824, 743 | DMSO-d6: 8.82(1H, d, J=7.8Hz), 8.13(1H, d, J=7.8Hz), 8.07(1H, d, J=7.8Hz), 7.72 (1H, d, J=2.0Hz), 7.61~7.55(1H, m), 7.45~ 7.39(1H, m), 7.28(1H, d, J=2.0Hz), 6.25 (1H, d, J=7.8Hz), 5.64(2H, s) | 182.3– 190.3 |
| 182 | 3305, 1595, 1551, 1481, 1458, 1288, 808, 741 | DMSO-d6: 8.82(1H, d, J=7.6Hz), 81.8(1H, d, J=7.8Hz), 8.07(1H, d, J=8.3Hz), 7.80 (1H, s), 7.59(1H, dd, J=7.8, 7.3Hz), 7.45~ 7.40(1H, m), 7.16(1H, s), 6.26(1H, d, J= 7.6Hz), 6.20~6.15(1H, m), 3.20~3.14 (2H, m), 1.71~1.63(2H, m), 1.01(3H, t, J=7.3Hz) | 145.7 (dec.) |
| 183 | 3307, 3050, 1645, 1605, 1250, 816, 740 | DMSO-d6: 10.42(1H, bs), 8.97(1H, d, J=7.8Hz), 8.71(1H, d, J=2.0Hz), 8.31~8.30 (1H, m), 8.25(1H, d, J=7.8Hz), 8.15(1H, d, J=8.3Hz), 7.68~7.41(2H, m), 6.37(1H, d, J=7.8Hz), 2.15(3H, s) | 353.8 (dec.) |
| 184 | 3433, 1645, 1597, 1576, 1504, 1448, 1329 | DMSO-d6: 9.22(1H, s), 8.64~8.58(3H, m), 8.39(1H, dd, J=4.9, 1.5Hz), 8.17~8.09 (2H, m), 7.87~7.71(3H, m), 7.29(1H, dd, J=7.8, 4.9Hz), 3.91(2H, s) | 278.1 (dec.) |
| 185 | 2904, 1593, 1462, 1228, 1065, 758 | DMSO-d6: 9.17(1H, s), 8.65(1H, s), 8.52 (1H, d, J=7.3Hz), 8.38(1H, s), 8.11(1H, d, J=7.8Hz), 8.04(1H, d, J=8.8Hz), 7.92(1H, d, J=2.4Hz), 7.78(1H, d, J=7.8Hz), 7.69 (1H, dd, J=7.8, 7.3Hz), 7.31~7.23(2H, m), 3.97~3.85(5H, m) | 210.1 (dec.) |
| 186 | 3433, 3142, 3091, 1641, 1562, 1500, 1448, 1327 | DMSO-d6: 9.74(1H, s), 9.14(1H, s), 8.70 (1H, s), 8.48~8.45(2H, m), 8.09(1H, d, J=7.8Hz), 7.95~7.91(2H, m), 7.66(1H, dd, J=7.8, 7.8Hz), 7.62(1H, d, J=2.2Hz), 7.44~7.40(1H, m), 7.08(1H, dd, J=8.8, 2.2 Hz), 3.94(2H, s) | 282.4 (dec.) |
| 187 | 1645, 1618, 1510, 1452, 1323, 798 | DMSO-d6: 9.02(1H, d, J=7.8Hz), 8.62~ 8.59(2H, m), 7.17~8.14(2H, m), 7.83(1H, dd, J=8.5, 2.2Hz), 7.78~7.72(1H, m), 6.44(1H, d, J=7.8Hz) | 265.5 (dec.) |
| 188 | 3028, 1643, 1504, 1225, 1036, 810 | DMSO-d6: 8.95(1H, d, J=7.8Hz), 8.53(1H, d, J=7.8Hz), 8.11(1H, d, J=7.8Hz), 8.06 (1H, d, J=9.0Hz), 7.91(1H, d, J=2.6Hz), 7.70(1H, t, J=7.8Hz), 7.23(1H, dd, J=9.0, 2.6Hz), 6.38(1H, d, J=7.8Hz), 3.91(3H, s) | 175.0 (dec.) |
| 189 | 3396, 3101, 1579, 1497, 1450, 1209, 1190 | DMSO-d6: 8.89(1H, d, J=7.8Hz), 8,47(1H, d, J=7.6Hz), 8.12(1H, d, J=7.8Hz), 7.95 (1H, d, J=8.8Hz), 7.71(1H, dd, J=7.8, 7.6 Hz), 7.63(1H, d, J=2.4Hz), 7.07(1H, dd, J= 8.8, 2.4Hz), 6.39(1h, d, J=7.8Hz) | 290.0 (dec.) |

TABLE 5-continued

| EX. No. | IR (KBr, cm-1) | NMR(ppm) (*:300MHz, non-mark: 270MHz) | M.P. (° .C) |
|---|---|---|---|
| 190 | 3039, 1647, 1610, 1581, 1506, 1450 1327 | DMSO-d6: 9.02(1H, s), 8.57(1H, d, J=7.6 Hz), 8.46(1H, s), 8.20~8.13(2H, m), 7.75~ 7.58(2H, m), 2.13(3H, s) | 296.8– 297.7 |
| 191 | 3097, 1649, 1612, 1581, 1506, 1450, 1327, 783 | DMSO-d6: 9.39(1H, s), 8.63~8.60(2H, m), 8.49(1H, d, J=2.0Hz), 8.23~8.16(2H, m), 7.93(1H, s), 7.80~7.72(2H, m), 5.33 (2H, s) | 293.3– 296.9 |
| 192 | 1645, 1599, 1506, 1450, 1309 | CDCl3: 8.49(1H, s), 8.38(1H, d, J=7.8 Hz), 8.24(1H, d, J=8.3Hz), 8.08(1H, d, J=1.8 Hz), 7.74~7.62(2H, m), 7.55(1H, dd, J= 8.3, 1.8Hz), 3.78(4H, dd, J=4.9, 4.4Hz), 3.67(2H, s), 2.65(4H, dd, J=4.9, 4.4Hz) | 231.9– 233.8 |
| 193 | 3047, 1641, 1612, 1556, 1502, 1325, 798 | DMSO-d6: 9.02(1H, d, J=7.8Hz), 8.60(1H, d, J=7.3Hz), 8.48(1H, d, J=2.4Hz), 8.21~ 8.15(2H, m), 7.75~7.72(2H, m), 6.44(1H, d, J=7.8Hz) | 266.6– 269,3 |
| 194 | 1668, 1608, 1504, 1333, 1228, 814 | DMSO-d6: 9.28(1H, s), 8.97(1H, s), 8.69~ 8.66(2H, m), 8.40~8.38(1H, m), 8.30~ 8.21(2H, m), 8.15(1H, d, J=7.8Hz), 7.81~ 7.73(1H, m), 7.29(1H, dd, J=7.8, 4.9Hz), 3.93(2H, s), 2.74(3H, s) | 104.3– 106.1 |
| 195 | 1647, 1614, 1506, 1335, 1257, 1230, 768 | DMSO-d6: 13.13(1H, bs), 9.27(1H, s), 8.92 (1H, s), 8.70~8.66(2H, m), 8.40~8.39 (1H, m), 8.27~8.19(2H, m), 8.15(1H, d, J=7.6Hz), 7.81~7.78(1H, m), 7.74(1H, t, J=7.6Hz), 7.30(1H, dd, J=7.6, 4.6Hz), 3.93(2H, s) | 300.0< |
| 196 | 1672, 1610, 1504, 1425, 1342, 1236, 762 | DMSO-d6: 9.18(1H, s), 8.93(1H, s), 8.63 (1H, d, J=7.7Hz), 8.27-~8.18(2H, m), 8.13 (1H, d, J=7.7Hz), 7.73(1H, t, J=7.7Hz), 7.41(2H, d, J=7.3Hz), 7.28(2H, t, J=7.3Hz), 7.20~7.14(1H, m), 3.91(2H, s), 2.73 (3H, s) | 244.5– 245.3 |
| 197 | 2926, 1707, 1560, 1506, 1246, 1223, 1176, 766 | DMSO-d6: 13.09(1H, bs), 9.17(1H, s), 8.89 (1H, s), 8.64(1H, d, J=7.6Hz), 8.25~ 8.17(2H, m), 8.13(1H, d, J=7.6Hz), 7.72(1H, t, J=7.6Hz), 7.41(2H, d, J=7.3Hz), 7.27 (2H, t, J=7 3Hz), 7.18(1H, t, J=7.3Hz), 3.91(2H, s) | 278.4 (dec.) |
| 198 | 2950, 2880, 1608, 1504, 1338, 1115, 764 | CDCl3: 8.78(1H, d, J=1.5Hz), 8.41(1H, d, J=7.3Hz), 8.34(1H, d, J=7.3Hz), 8.29~ 8.20(1H, m), 8.01(1H, s), 7.78~7.66(1H, m), 7.62(1H, d, J=8.8Hz), 7.45~7.23(5H, m), 4.06(2H, s), 3.93(2H, s), 3.86~ 3.83(4H, m), 2.73~2.62(4H, m) | amorphous |
| 199 | 1643, 1583, 1568, 1508, 325, 764 | *DMSO-d6: 9.14(1H, s), 8.53(1H, d, J= 7.5Hz), 8.30~8.25(1H, m), 8.13~8.06(2H, m), 7.70(1H, t, J=7.5Hz), 7.63(1H, d, J= 8.2Hz), 7.40(2H, d, J=7.6Hz), 7.27(2H, t, J=7.6Hz), 7.16(1H, t, J=7.6Hz), 5.38(1H, d, J=3.7Hz), 5.00~4.80(1H, m), 3.91 (2H, s), 1.44(3H, d, J=6.6Hz) | 145.0– 149.0 |
| 200 | 1676, 1653, 1614, 1504, 1335, 1236, 795 | DMSO-d6: 9.03(1H, d, J=7.6Hz), 8.92(1H, s), 8.65(1H, d, J=7.6Hz), 8.30-~8.23(2H, m), 8.14(1H, d, J=7.6Hz), 7.75(1H, t, J= 7.6Hz), 6.46(1H, d, J=7.6Hz), 2.73(3H, s) | 263.3 (dec.) |
| 201 | 1701, 1589, 1508, 1219, 1188, 768 | DMSO-d6: 13.11(1H, bs), 9.07(1H, d, J= 7.8Hz) , 8.93(1H, s), 8.71(1H, d, J=7.6Hz), 8.25~8.24(2H, m), 8.16(1H, d, J=7.6Hz), 7.76(1H, t, J=7.6Hz), 6.47(1H, d, J=7.8Hz) | 360.0< |
| 202 | 1686, 1643, 1610, 1502, 294, 1194, 1107 | CDCl3: 8.79(1H, d, J=1.0Hz), 8.37~8.28 (4H, m), 7.77~7.69(2H, m), 6.59(1H, d, J=7.8Hz), 3.96(2H, s), 3.81(4H, t, J=4.6 Hz), 2.69(4H, t, J=4.6Hz) | 188.1– 194.0 |
| 203 | 2950, 1643, 1593, 1458, 1271, 789, 716 | *DMSO-d6: 9.18(1H, s), 8.64(1H, d, J=1.7 Hz), 8.38(1H, d, J=4.7, 1.7Hz), 8.16~ 8.12(3H, m), 7.78(1H, d, J=7.8Hz), 7.63 (1H, t, J=7.9), 7.47(1H, t, J=7.9Hz), 7.40 (1H, d, J=9.0Hz), 7.28(1H, dd, J=7.8, 4.7Hz), 4.18(3H, s), 3.90(2H, s) | 207.2 (dec.) |
| 204 | 1643, 1560, 1525, 1446, 1321, 1281, 750 | DMSO-d6: 11.64(1H, bs), 9.14(1H, s), 8.63 (1H, s), 8.46~8.35(1H, m), 8.17~8.10 (2H, m), 7.99(1H, d, J=8.8Hz), 7.86~ 7.72(1H, m), 7.59(1H, t, J=7.1Hz), 7.46(1H, t, J=7.1Hz), 7.28(1H, dd, J=7.6, 4.6Hz) | 339.7 (dec.) |

TABLE 5-continued

| EX. No. | IR (KBr, cm-1) | NMR(ppm) (*:300MHz, non-mark: 270MHz) | M.P. (° .C) |
|---|---|---|---|
| 205 | 1759, 1649, 1612, 1458, 1329, 1192, | 7.15(1H, d, J=8.8Hz), 3.89(2H, s) DMSO-d6: 9.23(1H, s), 8.65(1H, d, J=2.0 Hz), 8.40~8.38(1H, m), 8.20~8.12(2H, m), 8.04(1H, d, J=7.6Hz), 7.78(1H, dt, J=7.8, 2.0Hz), 7.69(1H, t, J=7.6Hz), 7.53~7.47(2H, m), 7.29(1H, dd, J=7.8, 3.9Hz), 3.92(2H, s), 2.58(3H, s) | 247.8 (dec.) |
| 206 | 1645, 1587, 1581, 1460, 1296, 1207, 1111 | DMSO-d6: 9.18(1H, s), 8.64(1H, s), 8.38 (1H, d, J=4.4Hz), 8.24(1H, d, J=7.3Hz), 8.15~8.08(2H, m), 7.78(1H, d, J=7.3Hz), 7.64(1H, dd, J=7.8, 7.3Hz), 7.50(1H, dd, J=7.8, 7.3Hz), 7.32~7.25(2H, m), 5.23 (2H, s), 4.24(2H, q, J=7.0Hz), 3.91(2H, s) 1.26(3H, t, J=7.0Hz) | 231.5 (dec.) |
| 207 | 3050, 1639, 1593, 1460, 1261, 789 | DMSO-d6: 8.92(1H, d, J=7.8Hz), 8.12~8.09(3H, m), 7.58(1H, t, J=8.3Hz), 7.45 (1H, t, J=8.3Hz) , 7.36(1H, d, J=8.8Hz), 6.34 (1H, d, J=7.8Hz), 4.17(3H, s) | 210.8 (dec.) |
| 208 | 1632, 1568, 1446, 1308, 1186, 810 | DMSO-d6: 11.66(1H, s), 8.93(i H, d, J=7.8 Hz), 8.20~8.12(2H, m) , 8.01(1H, d, J=8.8Hz), 7.61~7.42(2H, m), 7.16(1H, d, J=8.3Hz), 6.34(1H, d, J=7.8Hz) | 360.0 (dec.) |
| 209 | 1759, 1651, 1616, 1458, 1194, 746 | *DMSO-d6: 9.03(1H, d, J=7.8Hz), 8.21~8.14(2H, m), 8.05(1H, d, J=7.6Hz), 7.69 (1H, t, J=7.6Hz), 7.53~7.47(2H, m), 6.44 (1H, d, J=7.8Hz), 2.59(3H, s) | 239.6 (dec.) |
| 210 | 1643, 1595, 1570, 1508, 1470, 1338, 1273 | *DMSO-6: 9.17(1H, s), 8.63(1H, d, J=1.5 Hz), 8.45(1H, d, J=8.3Hz), 8.37(1H, dd, J=4.7, 1.7Hz), 8.21(1H, d, J=7.4Hz), 8.09 (1H, d, J=8.2Hz), 7.76(1H, ddd, J=8.0, 1.7, 1.5Hz), 7.57(1H, dd, J=8.2, 7.4Hz), 7.44 (1H, dd, J=7.4, 7.4Hz), 7.27(1H, dd, J=8.0, 4.7Hz), 7.23(1H, d, J=8.3Hz), 3.96 (3H, s), 3.86(2H, s) | 215.1 (dec.) |
| 211 | 1664, 1560, 1504, 1464, 1273, 760 | DMSO-d6: 12.04(1H, s), 9.39(1H, s), 8.66 (1H, s), 8.43~8.40(2H, m), 8.25~8.12 (2H, m), 7.80(1H, d, J=7.8Hz), 7.63~7.54 (1H, m), 7.49(1H, t, J=7.3Hz), 7.31(1H, dd, J=7.8, 4.9Hz), 7.04(1H, d, J=8.3Hz), 3.98(2H, s) | 236.2 (dec.) |
| 212 | 1759, 1645, 1614, 1508, 1456, 1213, 760 | DMSO-d6: 9.23(1H, s), 8.62(1H, s), 8.54 (1H, d, J=7.8Hz), 8.39(1H, d, J=4.9Hz), 8.30(1H, d, J=7.8Hz), 8.15(1H, d, J=8.3Hz), 7.75(1H, d, J=7.8hz), 7.73~7.62(1H, m), 7.58~7.44(1H, m), 7.35(1H, d, J=8.3Hz), 7.29(1H, dd, J=7.8, 4.9Hz), 3.89 (2H, s), 2.37(3H, s) | 240.2 (dec.) |
| 213 | 1637, 1578, 1506, 1466, 1261 | DMSO-d6: 8.90(1H, d, J=7.6Hz), 8.44(1H, d, J=8.3Hz), 8.19(1H, d, J=7.8Hz), 81.0 (1H, d, J=8.3Hz), 7.57~7.51(1H, m), 7.46~7.40(1H, m), 7.24(1H, d, J=8.3Hz), 6.32 (1H, d, J=7.6Hz), 3.98(3H, s) | 57.3–60.6 |
| 214 | 1664, 1491, 1468, 1265, 1219, 829, 733 | DMSO-d6: 12.13(1H, s), 9.20(1H, d, J=7.8Hz) 8.43(1H, d, J=8,3Hz), 8.21(2H, d, J=8.3Hz), 7.60~7.47(2H, m), 7.07(1H, d, J=8.3Hz), 6.57(1H, d, J=7.8Hz) | 238.2 (dec.) |
| 215 | 1761, 1639, 1612, 1504, 1454, 1190, 1026, 744 | DMSO-d6: 9.03(1H, d, J=7.8Hz), 8.56(1H, d, J=8.3Hz), 8.31(1H, d, J=7.8Hz), 8.18 (1H, d, J=7.8Hz), 7.69~7.46(2H, m), 7.37 (1H, d, J=8.3Hz), 6.36(1H, d, J=7.8Hz), 2.38(3H, s) | 178.1 (dec.) |
| 216 | 1643, 1572, 1460, 1286, 1246, 1055, 748 | *DMSO-d6: 8.98(1H, s), 8.62(1H, d, J=1.7 Hz), 8.51(1H, d, J=7.6Hz), 8.41(1H, dd, J=4.6, 1.7Hz), 8.14(1H, d, J=7.9Hz), 7.88 (1H, d, J=7.6Hz), 7.78~7.75(1H, m), 7.71 (1H, t, J=7.6Hz), 7.43(1H, t, J=7.9Hz), 7.33~7.29(2H, m), 4.06(3H, s), 3.96(2H, s) | 214.1–216.3 |
| 217 | 1641, 1558, 1458, 1329, 1286, 764 | *DMSO-d6: 10.87(1H, s), 8.97(1H, s), 8.61 (1H, d, J=1.7Hz), 8.48(1H, d, J=7.7Hz) 8.41(1H, dd, J=4.9, 1.7Hz), 8.14(1H, d, J=7.6Hz), 7.77~7.73(2H, m), 7.70(1H, t, J=7.7Hz), 7.32~7.26(2H, m), 7.08(1H, d, J=7.6Hz), 3.95(2H, s) | 300.0 (dec.) |
| 218 | 1770, 1599, 1572, 1431, 1186, 1146, | *DMSO-d6: 8.66~8.62(1H, m), 8.58(1H, d, J=7.5Hz), 8.45(1H, dd, J=4.7, 1.5Hz), 8.42(1H, s), 8.22~8.17(2H, m), 7.80~ | 180.0–183.6 |

TABLE 5-continued

| EX. No. | IR (KBr, cm-1) | NMR(ppm) (*:300MHz, non-mark: 270MHz) | M.P. (° .C) |
|---|---|---|---|
| | 760 | 7.73(2H, m), 7.51~7.45(2H, m), 7.36(1H, dd, J=7.8. 4.7Hz), 3.97(2H, s), 2.35(3H, s) | |
| 219 | 1751, 1593, 1566, 1431, 1335, 1215, 762 | *DMSO-d6: 9.30(1H, s), 8.61(1H, s), 8.55 (1H, d, J=7.3Hz), 8.39~8.38(1H, m), 8.16(1H, d, J=8.0Hz), 7.95(1H, d, J=7.3Hz), 7.76~7.71(2H, m), 7.42)1H, t, J=8.0Hz), 7.36~7.25(2H, m), 5.14(2H, s), 4.24(2H, q, J=7.2Hz), 3.93(2H, 2), 1.23(3H, t, J=7.2Hz) | 248.1 (dec.) |
| 220 | 1641, 1618, 1497, 1454, 1284, 1188, 1016, 770 | *DMSO-d6: 8.96(1H, d, J=7.9Hz), 8.54(1H, d, J=7.7Hz), 8.13(1H, d, J=7.8Hz), 7.90 (1H, d, J=7.7Hz), 7.73(1H, d, J=7.7Hz), 7.45(1H, d, J=7.8Hz), 7.33(1H, d, J=7.8Hz), 6.38(1H, d, J=7.9Hz), 4.10(3H, s) | 230.4– 232.7 |
| 221 | 1639, 1560, 1502, 1456, 1292, 1188, 775 | *DMSO-d6: 10.95(1H, s), 8.97(1H, d, J= 7.7Hz), 8.49(1H, d, J=7.7Hz), 8.12(1H, d, J=7.7Hz), 7.77~7.68(2H, m), 7.30(1H, t, J=7.9Hz), 7.10(1H, d, J=7.9Hz), 6.37 (1H, d, J=7.7Hz) | 300.0 (dec.) |
| 222 | 1767, 1649, 1626, 1458, 1435, 1184, 771 | *DMSO-d6: 8.70(1H, d, J=7.9Hz), 8.59(1H, d, J=7.7Hz), 8.22(1H, dd, J=6.0, 3.0Hz), 8.16(1H, d, J=7.7Hz), 7.76(1H, t, J=7.7 Hz), 7.52~7.50(2H, m), 6.39(1H, d, J=7.9 Hz), 2.09(3H, s) | 210.1– 212.4 |
| 223 | 1749, 1643, 1622, 1497, 1458, 1234, 773 | *DMSO-d6: 9.12(1H, d, J=7.9Hz), 8.54(1H, d, J=7.6Hz), 8.14(1H, d, J=7.9Hz), 7.93 (1H, d, J=7.6Hz), 7.73(1H, t, J=7.6Hz), 7.44~7.39(1H, m), 7.30(1H, d, J=8.1Hz), 6.40(1H, d, J=7.9Hz), 5.13(2H, s), 4.24 (2H, q, J=7.2Hz), 1.26(3H, t, J=7.2Hz) | 200.2– 202.6 |
| 224 | 1624, 1612, 1514, 1470, 1244, 756 | DMSO-d6: 9.24(1H, s), 8.65(1H, d, J=1.5 Hz), 8.40~8.37(2H, m), 8.17(1H, d, J=8.5 Hz), 8.01(1H, d, J=7.6Hz), 7.81(1H, d, J= 2.3Hz), 7.80~7.75(1H, m), 7.65(1H, t, J=7.6Hz), 7.31~7.27(1H, m), 7.07(1H, dd, J=8.5, 2.3Hz), 3.95(3H, s), 3.91(2H, s) | 207.2 (dec.) |
| 225 | 3050, 1614, 1498, 1448, 1279, 1232, 827 | DMSO-d6: 10.25(1H, bs), 9.11(1H, s), 8.64(1H, d, J=2.0Hz), 8.41~8.28(2H, m), 8.05(1H, d, J=8.4Hz), 7.97(1H, dd, J=7.8, 1.0Hz), 7.82~7.74(1H, m), 7.62(1H, t, J=7.8Hz), 7.47(1H, d, J=2.1Hz), 7.32~ 7.25(1H, m), 6.92(1H, dd, J=8.4, 2.1Hz), 3.90(2H, s) | 335.0 (dec.) |
| 226 | 1755, 1647, 1616, 1510, 1444, 1215, 762 | DMSO-d6: 9.17(1H, s), 8.64(1H, s), 8.53 (1H, d, J=7.7Hz), 8.40~8.38(1H, m), 8.33 (1H, d, J=8,3Hz), 8.11(1H, d, J=7.7Hz), 8.02(1H, d, J=2.0Hz), 7.79~7.68(2H, m), 7.31~7.25(2H, m), 3.90(2H, s), 2.38 (3H, s) | 223.1 (dec.) |
| 227 | 1751, 1610, 1514, 1468, 1230, 1200 | DMSO-d6: 9.20(1H, s), 8.63(1H, d, J=1.5 Hz), 8.42~8.37(2H, m), 8.18(1H, d, J=8.5 Hz), 8.01(1H, d, J=7.8Hz), 7.85(1H, d, J= 2.3Hz), 7.76(1H, d, J=7.8Hz), 7.66(1H, t, J=7.8Hz), 7.28(1H, dd, J=7.8, 4.9Hz), 7.09(1H, dd, J=8.5, 2.3Hz), 4.97(2H, s), 4.22(2H, q, J=7.0Hz), 3.91(2H, s), 1.25 (3H, t, J=7.0Hz) | 128.3– 133.0 |
| 228 | 3080, 3020, 2825, 1649, 1614, 1516, 1232, 791 | *DMSO-d6: 9.02(1H, d, J=7.7Hz), 8.40(1H, d, J=7.5Hz), 8.17(1H, d, J=8.7Hz), 8.01 (1H, d, J=7.5Hz), 7.85(1H, d, J=2.3Hz), 7.66(1H, t, J=7.5Hz), 7.07(1H, dd, J=8.7, 2.3Hz), 6.42(1H, d, J=7.7Hz), 3.93(3H, s) | 254.5 (dec.) |
| 229 | 1628, 1587, 1448, 1215, 797 | DMSO-d6: 10.19(1H, s), 8.91(1H, d, J=7.8 Hz), 8.33(1H, d, J=7.3Hz), 8.06~7.96 (2H, m), 7.63(1H, dd, J=7.8, 7.8Hz), 7.49 (1H, d, J=2.0Hz), 6.94~6.90(1H, m), 6.36 (1H, d, J=7.3Hz) | 375.0 (dec.) |
| 230 | 3053, 1751, 1614, 1508, 1194, 1161, 767 | DMSO-d6: 8.96(1H, d, J=7.8Hz), 8.53(1H, d, J=7.6Hz), 8.33(1H, d, J=8.6Hz), 8.11 (1H, d, J=7.6Hz), 8.06(1H, d, J=2.1Hz), 7.73(1H, t, J=7.6Hz), 7.27(1H, dd, J=8.6, 2.1Hz), 6.43(1H, d, J=7.8Hz), 2.37(3H, s) | 257.2 (dec.) |
| 231 | 1759, 1614 1514, 1209, 1196, 1097, 793 | DMSO-d6: 8.98(1H, d, J=7.8Hz), 8.41(1H, d, J=7.8Hz), 8.17(1H, d, J=8.6Hz), 8.02 (1H, d, J=7.8Hz), 7.88(1H, d, J=2.3Hz), 7.67(1H, t, J=7.8Hz), 7.09(1H, dd, J=8.6, | 163.1– 168.6 |

TABLE 5-continued

| EX. No. | IR (KBr, cm-1) | NMR(ppm) (*:300MHz, non-mark: 270MHz) | M.P. (° .C) |
|---|---|---|---|
| | | 2.3Hz), 6.42(1H, d, J=7.8Hz), 4.95(2H, s), 4.22(2H, q, J=7.2Hz), 1.25(3H, t, J=7.2Hz) | |
| 232 | 1608, 1572 1487, 1458, 1267, 1078, 779 | DMSO-d6: 9.16(1H, s)(1H, s), 8.53(1H, d, J=2.4 Hz), 8.37(1H,dd, J=4.6, 1.5Hz), 8.31(1H, d, J=7.8Hz), 8.04(1H, d, J=7.8Hz), 7.79~ 7.75(1H, m), 7.75~7.53(3H, m), 7.27 (1H, dd, J=7.8, 4.6Hz), 7.06(1H, d, J=7.8Hz), 4.06(3H, s), 3.89(2H, s) | 218.8 (dec.) |
| 233 | 2981, 1597, 1574, 1483, 1454, 1284, 748 | DMSO-d6: 10.79(1H, bs), 9.17(1H, s), 8.65 (1H, s), 8.39~8.32(2H, m), 8.04(1H, d, J=7.7Hz), 7.78(1H, d, J=7.6Hz), 7.66 (1H, t, J=7.7Hz), 7.56(1H, d, J=8.1Hz), 7.46 (1H, t, J=8.1Hz), 7.28(1H, dd, J=7.6, 4.6 Hz), 6.91(1H, d, J=8.1Hz), 3.91(2H, s) | 295.6 (dec.) |
| 234 | 1755, 1614, 1462, 1227, 1200, 754 | (DMS)-d6: 9.24(1H, s), 8.65(1H, d, J=2.0 Hz), 8.39(1H, dd, J=4.9, 1.5Hz), 8.28(1H, d, J=7.9Hz), 8.14(1H, d, J=7.9Hz), 8.05 (1H, d, J=7.9Hz), 7.78(1H, dd, J=7.8, 2.0 Hz), 770(2H, t, J=7.9Hz), 7.31~7.26 (2H, m), 3.92(2H, s), 2.51(3H, s) | 217.3 (dec.) |
| 235 | 1605, 1570, 1508, 1485, 1464, 1279, 1146 | DMSO-d6: 9.14(1H, s), 8.63(1H, d, J=2.0 Hz), 8.38(1H, dd, J=5.0, 1.5Hz), 8.23(1H, d, J=2.4Hz), 8.22~8.08(2H, m), 7.78~ 7.74(1H, m), 7.58(1H, d, J=2.4Hz), 7.53 (1H, ddd, J=9.0, 9.0, 2.5Hz), 7.28(1H, dd, J=7.6, 5.0Hz), 3.95(3H, s), 3.90(2H, s) | 251.4– 255.7 |
| 236 | 1583, 1576, 1564, 1508, 1471, 1389, 1335 | DMSO-d6: 10.10(1H, s), 9.11(1H s), 8.6 4(1H, s), 8.40~8.39(1H m), 8.17(1H, dd, J=8.8, 2.4Hz), 8.10(1 H, dd, J=9.0, 4.1Hz), 7.99(1 H, d, J=2.2Hz), 7.80(1 H, d, J=7.8 Hz), 7.54~7.46(2H, m), 7.50(1H, d J= 2.2Hz), 7.31(1H dd, J=7.8, 4.9Hz), 3.89 (2H, s) | 306.2 (dec.) |
| 237 | 1605, 1574, 1508, 1483, 1336, 1196, 1186 | DMSO-d6: 9.22(1 H, s), 8.64(1 H, s), 8.41~ 8.37(2H, m), 8.21~8.14(2H, m), 7.87 (1H, d, J=2.0Hz), 7.79~7.75(1H, m), 7.57 (1H, ddd, J=9.3, 9.3, 2.4Hz), 7.29(1H, dd, J=7.6, 4.6Hz), 3.91(2H, s), 2.37(3H, s) | 226.8 (dec.) |
| 238 | 2970, 1751, 1481, 1333, 1200, 1142 | DMSO-d6: 9.23(1H, s), 8.64(1H, d, J=2.0 Hz), 8.40~8.38(2H, m), 8.27~8.13(2H, m), 7.85(1H, d, J=2.0Hz), 7.78(1H, dd, J= 5.9, 2.0Hz), 7.58(1H, ddd, J=11.7, 8.8, 2.4Hz), 7.29(1 H, dd, J=7.6, 4.7Hz), 3.91 (2H, s), 2.68(2H, t, J=7.3Hz), 1.80~1.65 (2H, m), 1.03(3H, t, J=7.3Hz) | 221.1– 217.1 |
| 239 | 1649, 1593, 1556, 1506, 1485, 1462, 1275 | DMSO-d6: 8.90(1H, d, J=7.6Hz), 8.20(1H, d, J=2.2Hz), 8.i7~8.02(2H, m), 7.56(1H, d, J=2.2Hz), 7.54~7.46(1 H, m), 6.34 (1H, d, J=7.6Hz) 3.96(3H, s) | 233.3– 239.1 |
| 240 | 1655, 1603, 1477, 1437, 1402, 1277, 1194 | DMSO-d6: 10.20(1 H, s), 8.89(1 H, d, J=7.8 Hz), 8.17~8.11(2H, m), 7.99(1H, d, J= 2.4Hz), 7.53~7.41(2H, m), 6.31(1H, d J= 7.8Hz) | 360.0< |
| 241 | 1761, 1593, 1500, 1190, 841 | DMSO-d6: 9.o1(1H, d, J=7.6Hz), 8.39(1H, d, J=2.0Hz), 8.23~8.17(2H, m), 7.88(1H, d, J=2.0Hz), 7.60~7.52(1H, m), 6.42 (1H, d, J=7.6Hz), 2.39(3H, s) | 267.8 (dec.) |
| 242 | 1751, 1597, 1504, 1487, 1273, 1194, 1151 | DMSO-d6: 9.02(1H, d, J=7.8Hz), 8.40(1H, d, J=2.0Hz), 8.24~8.19(2H, m), 7.85(1H, d, J=2.0Hz), 7.56(1 H, ddd, J=9.3, 9.3, 2.4Hz), 6.42(1H, d, J=7.8Hz), 2.68(2H, t, J=7.3Hz), 1.73(2H, qt, J=7.3, 7.3Hz), 1.04(3H, t, J=7.3Hz) | 194.5 (dec.) |
| 243 | 1608, 1579, 1506, 1477, 1433, 1423, 1333 | DMSO-d6: 9.14(1H, s), 8.63(1H, d, J=0.8 Hz), 8.44(1H, d, J=1.0Hz), 8.38(1H, d, J= 4.9Hz), 8.26(1H, d, J=1.0Hz), 8.11(1H, d, J=8.3Hz), 7.81~7.74(1H, m), 7.71(1H, dd, J=8.2, 0.8Hz), 7.58(1H, d, J=1.0Hz), 7.28(1H, dd, J=8.2, 4.9Hz), 3.95(3H, s), 3.90(2H, s) | 221.7– 225.6 |
| 244 | 3317, 1581, 1510, 1454, 1425, 1392, 1331 | DMSO-d6: 10.15(1H, s), 9.12(1H, s), 8.68 (1H, s), 8.47~8.36(2H, m), 8.10(1H, d, J=8.8Hz), 8.02(1H, s), 7.88(1H, d, J=7.6 Hz), 7.72~7.64(1H, m), 7.54~7.48(1H, m), 7.39(1H, dd, J=7.6, 4.4Hz), 3.91(2H, s) | 300.0< |

TABLE 5-continued

| EX. No. | IR (KBr, cm-1) | NMR(ppm) (*:300MHz, non-mark: 270MHz) | M.P. (° .C) |
|---|---|---|---|
| 245 | 1751, 1606, 1581, 1504, 1477, 1331, 1192 | DMSO-d6: 9.~6(1H, s), 8.63(1H, d, J=2.4 Hz), 8.46(1H, d, J=2.0Hz), 8.38(1H, dd, J=4.7, 1.8Hz), 8.34(1H, d, J=2.4Hz), 8.13 (1H, d, J=8.8Hz), 7.78~7.70(2H, m), 7.56 (1H, d, J=2.4Hz), 7.30~7.25(1H, m), 5.01(2H, s), 4.20(2H, q, J=7.3Hz), 3.90(2H, s), 1.23(3H, t, J=7.3Hz) | 194.4– 197.1 |
| 246 | 3061, 1653, 1606, 1556, 1504, 1475, 1325, 814 | DMSO-d6: 8.94(1H, d, J=8.1Hz), 8.44(1H, d, J=1.8Hz), 8.28(1H, d, J=1.8Hz), 8.16 (1H, d, J=8.6Hz), 7.70(1H, dd, J=8.6, 1.8 Hz), 7.59(1H, d, J=1.8Hz), 6.38(1H, d, J=8.1Hz), 3.96(3H, s) | 261.3– 263.6 |
| 247 | 3078, ~651, 1601, 1508, 1454, 1429, 1400, 1327, 1190 | DMSO-d6: 10.18(1H, bs), 8.91(1H, d, J=7.8Hz), 8.41(1H, s), 8.14(1H, d, J=8.8Hz) 8.02(1H, d, J=2.0Hz), 7.66(i H, d, J=8.8 Hz), 7.49(1H, d, J=2.0Hz), 6.33(1H, d, J=7.8Hz) | 300.0< |
| 248 | 2966, 1597, 1570, 1508, 1452, 1333 | *DMSO-d6: 9.12(1H, s), 8.64(1H, s), 8.38 (1H, d, J=4.7Hz), 8.17(1H, d, J=2.2Hz), 8.13(1H, s), 8.00(1H, d, J=8.3Hz), 7.78~7.75(1H, m), 7.53~7.49(2H, m), 7.28 (1H, dd, J=7.9, 4.7Hz), 3.95(3H, s), 3.90 (2H, s), 2.80(2H, q, J=7.7Hz), 1.30(3H, t, J=7.7Hz) | 143.1– 144.6 |
| 249 | 3446, 1605, 1504, 1433, 1325 | *DMSO-d6: 10.06(1H, s), 9.08(1H, s), 8.62(1H, s), 8.38~8.37(1H, m), 8.08(1H, s), 7.98(1H, d, J=8.4Hz), 7.92(1H, d, J=2.0 Hz), 7.74~7.70(1H, m), 7.48(1H, dd, J=8.4, 1.6Hz), 7.44(1H, d, J=2.0Hz), 7.28 (1H, dd, J=8.0, 4.9Hz), 3.88(2H, s), 2.81~2.78(2H, m), 1.29(3H, t, J=7.5Hz) | 247.0– 249.4 |
| 250 | 1755, 1605, 1587, 1566, 1504, 1323, 1198 | *DMSO-d6: 9.13(1H, s), 8.63(1H, d, J=1.7Hz), 8.37(1H, dd, J=4.9, 1.7Hz), 8.24(1H, d, J=2.3Hz), 8.14(1H, s), 8.00(1H, d, J=8.3Hz), 7.77(1H, d, J=8.0Hz), 7.53~7.49(1H, m), 7.49(1H, d, J=2.2Hz), 7.28(1H, dd, J=8.0, 4.9Hz), 5.01(2H, s), 4.20(2H, q, J=7.2Hz), 3.90(2H, s), 2.80(2H, q, J=7.6Hz), 1.30(3H, t, J=7.6Hz), 1.23(3H, t, J=7.2Hz) | 146.7– 147.5 |
| 251 | 1585, 1566, 1508, 1483, 1327, 1234, 714 | *DMSO-d6: 9.13(1H, s), 8.76(1H, d, J=2.0 Hz), 8.64(1H, d, J=2.1Hz), 8.57(1H, dd, J=5.0, 2.0Hz), 8.38(1H, dd, J=5.0, 2.1Hz), 8.30(1H, d, J=2.2Hz), 8.13(1H, d, J=1.6 Hz), 8.01(1H, d, J=8.3Hz), 7.95(1H, d, J=8.0Hz), 7.77(1H, d, J=8.0Hz), 7.66(1H, d, J=2.2Hz), 7.52(1H, dd, J=8.3, 1.6Hz), 7.47(1H, dd, J=8.0, 5.0HZ), 7.28(1H, d, J=8.0, 5.0Hz), 5.38(2H, s), 3.90(2H, s), 2.80 (2H, q, J=7.6Hz), 1.30(3H, t, J=7.6Hz) | 163.0– 163.4 |
| 252 | 3010, 1589, 1568, 1510, 1489, 1147, 700 | DMSO-d6: 9.09(1H, s), 8.63(IH, d, J=2.0 Hz), 8.38~8.36(1H, m), 8.31(1H, d, J=2.0 Hz), 8.00(1H, d, J=9.3Hz), 7.90(1H, d, J=2.4Hz), 7.78~7.74(1H, m), 7.63(1H, d, J=2.0Hz), 7.54~7.51(2H, m), 7.45~7.22 2(5H, m), 5.32(2H, s), 3.90~3.89(5H, m) | 192.7– 196.4 |
| 253 | 1560, 1485, 1284, 1211, 839 | DMSO-d6: 10.08(1H, bs), 9.05(1H, 5), 8.66~8.58(1H, m), 8.37(1H, dd, J=4.9, 1.5 Hz), 8.00~7.95(2H, m), 7.86(1H, d, J=2.4 Hz), 7.77~7.73(1H, m), 7.46(1H, d, J=2.4 Hz), 7.27(1H, dd, J=7.8, 4.9Hz), 7.21 (1H, dd, J=8.8, 2.4Hz), 3.93~3.81(5H, m) | 287.7 (dec.) |
| 254 | 1724, 1605, 1508, 1308, 1205, 1028 | DMSO-d6: 9.10(1H, s), 8.63(1H, s), 8.38~8.37(1H, m), 8.28(1H, d, J=2.4Hz), 8.01 (1H, d, J=8.8Hz), 7.92(1H, d, J=2.4Hz), 7.76(1H, d, J=7.8Hz), 7.51(1H, d, J=2.4Hz), 7.29~7.23(2H, m), 5.00(2H, s), 4.21 (2H, q, J=7.2Hz)~, 3.90(3H, s), 3.89(2H, s), 1.23(3H, t, J=7.2Hz) | 178.7– 182.7 |
| 255 | 3002, 1608, 1589, 1508, 1485, 1282, 1217, 816 | DMSO-d6: 8.86(1H, d, J=7.6Hz), 8.30(1H, d, J=2.0Hz), 8.02(1H, d, J=8.8Hz), 7.88 (1H, d, J=2.7Hz), 7.63~7.32(6H, m), 7.21 (1H, dd, J=8.8, 2.7Hz), 6.30(1H, d, J=7.6Hz), 5.33(2H, s), 3.90(3H, s) | 159.4 (dec.) |
| 256 | 1585, 1485, 1450, 1281, | DMSO-d6: 10.08(1H, s), 8.83(1H, d, J=7.8 Hz), 8.01(1H, d, J=8.8Hz), 7.96(1H, d, J= | 328.6 (dec.) |

TABLE 5-continued

| EX. No. | IR (KBr, cm-1) | NMR(ppm) (*:300MHz, non-mark: 270MHz) | M.P. (° .C) |
|---|---|---|---|
| | 825 | 2.4Hz), 7.85(1H, d, J=2.4Hz), 7.49~7.42 (1H, m), 7.20(1H, dd, J=8.8, 2.4Hz), 6.26(1H, d, J=7.8Hz), 3.89(3H, s) | |
| 257 | 2950, 1585, 1466, 1288, 1213, 1034, 789 | DMSO-d6: 9.04(1H, s), 8.64(1H, s), 8.38 (1H, d, J=1.5Hz), 8.15(1H, d, J=1.5Hz), 7.96(1H, d, J=8.8Hz), 7.86(1H, d, J=2.0Hz), 7.77(1H, d, J=7.3Hz), 7.51(1H, d, J=1.5 Hz), 7.30~7.19(2H, m), 4.02~3.78(8H, m) | 206.3 (dec.) |
| 258 | 3103, 1558, 1497, 1448, 1327, 1201, 1151 | DMSO-d6: 10.17(1H, s), 9.85(1H, s), 9.05 (1H, s), 8.63(1H, d, J=1.5Hz), 8.38~ 8.30(1H, m), 7.90(1H, d, J=2.0Hz), 7.88(1H, d, J=8.8Hz), 7.77(1H, d, J=7.8Hz), 7.55 (1H, d, J=2.3Hz), 7.46(1H, d, J=2.0Hz), 7.28(1H, dd, J=7.8, 4.9Hz), 7.07(1H, dd, J= 8.8, 2.3Hz), 3.87(2H, s) | 300< |
| 259 | 1759, 1572, 1479, 1209, 1182, 1134 | DMSO-d6: 9.24(1H, s), 8.67~8.64(1H, m), 8.40~8.37(2H, m), 8.18(1H, d, J=8.8Hz), 8.11(1H, d, J=2.0Hz), 7.86(1H, d, J=2.0 Hz), 7.78(1H, d, J=7.8Hz), 7.47(1H, dd, J=8.8, 2.0Hz), 7.31~7.27(1H, m), 3.92 (2H, s), 2.37(3H, s), 2.36(3H, s) | 131.9-137.1 |
| 260 | 3028, 1579 1489, 1219, 1034, 702 | DMSO-d6: 8.98(1H, s), 8.16(1H, d, J=2.2 Hz), 7.97(1H, d, J=9.3Hz), 7.87(1H, d, J= 2.4Hz), 7.53(1H, d, J=2.2Hz), 7.38(2H, d, J=6.8Hz), 7.29~7.18(4H, m), 3.94(3H, s), 3.90(3H, s), 3.89(2H, s) | 182.9–187.0 |
| 261 | 3300, 1558, 1450, 1392, 1319, 1200, 700 | DMSO-d6: 10.20~9.41(2H, m), 8.92(1H, s), 7.89.~7.86(2H, m), 7.54(1H, d, J=2.4 Hz), 7.44(1H, d, J=2.0Hz), 7.38~7.35(2H, m), 7.28~7.23(2H, m), 7.18~7.12(1H, m), 7.03(1H, dd, J=8.8, 2.4Hz), 3.87(2H, s) | 350.0< |
| 262 | 3398, 1647, 1587, 1284, 1200, 1030, 818 | DMSO-d6: 8.82(1H, s), 8.14(1H, d, J=7.6Hz), 7.98(1H, d, J=8.8Hz), 7.84 (1H, d, J=2.6Hz), 7.51(1H, d, J=2.3Hz), 7.18(1H, dd, J=8.8, 2.6Hz), 6.29(1H, d, J= 7.6Hz), 3.96(3H, s), 3.90(3H, s) | 195.0–197.2 |
| 263 | 3066, 1547, 1471, 1452, 1406, 1252 | DMSO-d6: 10.02(1H, s), 9.67(1H, s), 8.77 (1H, d, J=7.4Hz), 7.89(1H, d, J=8.6Hz), 7.87(1H, d, J=2.0Hz), 7.52(1H, d, J=2.3Hz), 7.41(1H, d, J=2.0Hz), 7.01(1H, dd, J= 8.6, 2.3Hz), 6.23(1H, d, J=7.4Hz) | 300.0< |
| 264 | 3064, 1647, 1616, 1597, 1497, 1317, 814 | DMSO-d6: 9.o.1(1H, d, J=7.8Hz), 8.72(1H, d, J=1.9Hz), 8.48(1H, d, J=2.3Hz), 8.20 (1H, d, J=8.9Hz), 8.07(1H, d, J=1.9Hz), 7.74(1H, dd, J=8 9, 2.3Hz), 6.44(1H, d, J=7.8Hz) | 250.0< |
| 265 | 3051, 1643, 1610, 1500, 1321, 700 | DMSO-d6: 9.13(1H, s), 8.67(1H, d, J=2.0 Hz), 8.45(1H, d, J=2.0Hz), 8.14(1H, d, J=8.7Hz), 8.05(1.H, d, J=2.0Hz), 7.73(1H, dd, J=8.7, 2.0Hz), 7.38(2H, d, J=7.3Hz), 7.26(2H, dd, J=7.3, 7.3Hz), 7.16(1H, t, J= 7.3Hz), 3.88(2H, s) | 224.9–226.6 |
| 266 | 3045, 1643, 1614, 1500, 1425, 1323, 802 | DMSO-d6: 9.19(1H, s), 8.67(1H, d, J=2.0 Hz), 8.63(1H, d, J=1.7Hz), 8.46(1H, d, J= 2.0Hz), 8.39(1H, dd, J=4.8, 1.7Hz), 8.14 (1H, d, J=8.9Hz), 8.04(1H, d, J=1.7Hz), 7.78~7.73(2H, m), 7.29(1H, dd, J=7.9, 4.8Hz), 3.89(2H, s) | 255.0–257.2 |
| 267 | 3053, 1647, 1603, 1500, 1323, 1221, 798 | DMSO-d6: 9.20(1H, s), 8.69(1H, d, J=1.8 Hz), 8.47~8.42(3H, m), 8.14(1H, d, J=8.8 Hz), 8.05(1H, d, J=1.8Hz), 7.75(1H, dd, J=8.8, 2.~Hz), 7.36(2H, d, J=5.9Hz), 3.89 (2H, s) | 300.0< |
| 268 | 3053, 1643, 1608, 1497, 1321, 802 | DMSO-d6: 9.07(1H, s), 8.66(1H, d, J=1.8 Hz), 8.45(1H, d, J=2.0Hz), 8.14(1H, d, J= 8.6Hz), 8.04(1 H, d, J=1.8Hz), 7.73(1 H, dd, J=8.6, 2.0Hz), 7.29(2H, d, J=8.6Hz), 6.82(2H, d, J=8.6Hz), 3.80(2H, s), 3.69 (3H, s) | 199.9–202.1 |
| 269 | 3271, 1579 1502, 1323, 1219, 806 | DMSO-d6: 9.08(1H, s), 8.71(1H, d, J=1.8 Hz), 8.49(1H, d, J=1.9Hz), 8.17(1H, d, J= 8.7Hz), 8.07(1H, d, J=1.8Hz), 7.74(1H, dd, d, J=8.7, 1.9Hz), 7.16(2H, d, J=8.6Hz), 6.65(2H, d, J=8.6Hz), 3.76(2H, s) | 300.0< |
| 270 | 3323, 1676, | DMSO-d6: 9.84(1H, s), 9.10(1H, s), 8.69 | 300.0< |

TABLE 5-continued

| EX. No. | IR (KBr, cm-1) | NMR(ppm) (*:300MHz, non-mark: 270MHz) | M.P. (° .C) |
|---|---|---|---|
|  | 1608, 1500, 1323, 808 | (1H, d, J=1.3Hz), 8.47(1 H, d, J=1.7Hz), 8.16(1H, d, J=8.6Hz), 8.06(1H, d, J=1.3Hz), 7.74(1H, dd, J=8.6, 1.7Hz), 7.45(2H, d, J=9.2Hz), 7.28(2H, d, J=9.2Hz), 3.82 (2H, s), 1.99(3H, s) |  |
| 271 | 3462, 3346, 1624, 1500, 1321, 864 | DMSO-d6: 8.95(1H, s), 8.62(1H, d, J=1.7 Hz), 8.41(1H, d, J=2.1Hz), 8.10(1H, d, J= 8.7Hz), 8.01(1H, d, J=1.7Hz), 7.70(1H, dd, J=8.7, 2.1Hz), 7.02(2H, d, J=8.4Hz), 6.47(2H, d, J=8.4Hz), 4.85(2H, bs), 3.69 (2H, s) | 300.0< |
| 272 | 3055, 1614, 1498, 1468, 1335, 1298, 1225 | DMSO-d6: 9.35(1H, d, J=2.2Hz), 9.30(1H, s), 8.91(1H, d, J=1.5Hz), 8.64~8.58 (2H, m), 8.40~8.39(1H, m), 8.32(1H, d, J= 9.3Hz), 8.10(1 H, d, J=2.2Hz), 7.78(1H, d, J=7.8Hz), 7.29(1H, dd, J=7.8, 4.9Hz), 3.91 (2H, s) | 311.3 (dec.) |
| 273 | 3336, 1637, 1579, 1558, 1508, 1489, 1311 | DMSO-d6: 9.04(1H, s), 8.62(1H, s), 8.48 (1H, d, J=1.5Hz), 8.42~8.35(1H, m), 7.97 (1H, d, J=1.5Hz), 7.78(1H, d, J=8.6Hz), 7.75(1H, d, J=7.3Hz), 7.36(1H, d, J=2.1Hz), 7.28(1H dd, J=7.3, 4.9Hz), 6.90(1H, dd, J=8.6, 2.1Hz), 5.42~5.36(2H, m), 3.88(2H, s) | 307.1 (dec.) |
| 274 | 1593, 1560, 1475, 1321, 1265, 1215 | DMSO-d6: 9.82(1H s), 9.11(1H, s), 8.62~ 8.60(2H, m), 8.42~8.36(1H, m), 8.00 (1H, d, J=2.0Hz), 7.92(1H, d, J=8.6Hz), 7.77~7.74(1H, m), 7.65(1H, d, J=2.1Hz), 7.28(1H, dd, J=7.3, 4.9Hz), 7.11(1H, d, J= 8.6, 2.1Hz), 3.88(2H, s) | 343.4 (dec.) |
| 275 | 3307, 3082, 1647, 1585, 1495, 1309, 1190 | DMSO-d6: 9.81(1H, s), 8.91(1H, d, J=7.8 Hz), 8.63(1H, d, J=1.8Hz), 8.01(1H, d, J= 1.8Hz), 7.96(1H, d, J=8.8Hz), 7.66(1H, d, J=2.4Hz), 7.09(1H, dd, J=8.8, 2.4Hz), 6.37(1H, d, J=7.8Hz) | 300.0< |
| 276 | 1647, 1605, 1576, 1502, 1329, 1275, 1236 | DMSO-d6: 9.12(1H, s), 8.63(1H, s), 8.49 (1H, d, J=2.0Hz), 8.39~8.35(2H, m), 8.06~ 7.93(1H, m), 7.81(1H, d, J=2.0Hz), 7.78~7.75(2H, m), 7.31~7.29(1H, m), 3.8 9(2H, s), 2.60(3H, s) | 195.8– 196.1 |
| 277 | 1643, 1601, 1502, 1323, 1273, 1242, 818 | DMSO-d6: 8.95(1H, d, J=7.8Hz), 8.53(1H, d, J=2.0Hz), 8.42~8.40(1H, m), 8.11 (1H, d, J=8.8Hz), 7.99~7.95(1H, m), 7.83~ 7.75(1H, m), 6.39(1H, d, J=7.8Hz), 2.62 (3H, s) | 255.7- 258.9 |

TABLE 6

| Ex. No. | R¹ |
|---|---|
| 1 | —OCH₃ |
| 2 | —OH |
| 3 | —OCH₂CO₂C(CH₃)₃ |
| 4 | —OCH₂CO₂CH(CH₃)₂ |
| 5 | —OCH₂CO₂CH₂CH₃ |

TABLE 6-continued

| Ex. No. | R¹ |
|---|---|
| 6 | —OCH₂CO₂H |
| 7 | —OCH₂CO₂CH₂CH₂CH₃ |
| 8 | —OC(CH₃)₂CO₂CH₂CH₃ |
| 9 | —OC(CH₃)₂CO₂H |
| 10 | —OCH₂CH₂CH₂CO₂CH₂CH₃ |

TABLE 6-continued

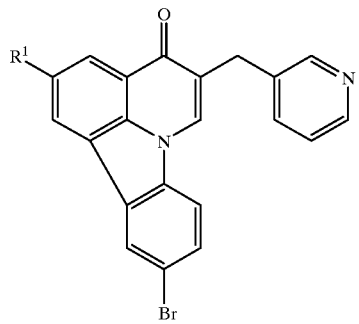

| Ex. No. | R¹ |
|---|---|
| 11 | —OCH$_2$CH$_2$CH$_2$CO$_2$H |
| 12 | —OCH$_2$CO$_2$CH$_2$-phenyl |
| 13 | —OCH$_2$CO$_2$CH$_3$ |
| 14 | —OCH$_2$CO$_2$(CH$_2$)$_4$CH$_3$ |
| 15 | —OCH$_2$CO$_2$(CH$_2$)$_2$N(CH$_3$)$_2$ |
| 16 | —OCH$_2$CO$_2$(CH$_2$)$_2$N(CH$_3$)$_2$ |
| 17 | —OCH=CHCH$_2$CO$_2$H |
| 18 | —OCH$_2$-(pyridin-3-yl) |
| 19 | —OCH$_2$-(pyridin-4-yl) |
| 20 | —OCH$_2$-(pyridin-2-yl) |
| 21 | —OCH$_3$ ester of nicotinic acid |
| 22 | —OCH$_2$-phenyl |
| 23 | —OCH$_2$C(O)-phenyl |
| 24 | 3,5-bis(methylene) pyridine with OCOCH$_3$ |

TABLE 6-continued

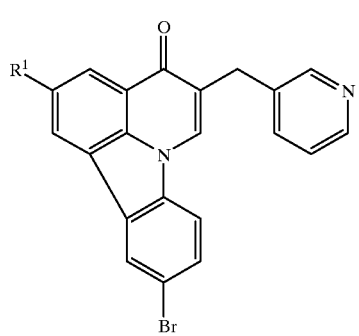

| Ex. No. | R¹ |
|---|---|
| 25 | 3,5-bis(methylene)pyridine with OCH$_3$ and OH |
| 26 | —OCH$_2$CH$_2$CH$_2$OH |
| 27 | —OCH$_2$CH$_2$CH$_2$CH$_2$OH |
| 28 | —OCH$_2$CH$_2$CH$_2$CH$_2$CH$_2$OH |
| 29 | —OCH$_2$(CH$_2$)$_4$CH$_2$OH |
| 30 | —OCH$_2$CH$_2$OCH$_2$CH$_2$OH |
| 31 | —OCH$_2$C(CH$_3$)$_2$CH$_2$OH |
| 32 | —OCH$_2$COCH$_2$CH$_2$OH |
| 33 | —OCH$_2$CH$_3$ |
| 34 | —OCH$_2$CH$_2$CH$_2$CH$_3$ |
| 35 | —OCH$_2$CH$_2$OCH$_3$ |
| 36 | —OCH$_2$CH$_2$OCH$_2$CH$_3$ |
| 37 | —OCH$_2$CH(OCH$_2$CH$_3$)$_2$ |
| 38 | —OCOCH$_3$ |
| 39 | —OCH$_2$COCH$_2$CH$_3$ |
| 40 | —OCH$_2$COCH$_2$CH$_2$CH$_3$ |
| 41 | —OCH$_2$CH(CH)CH$_2$CH$_2$CH$_3$ |
| 42 | —OCH$_2$COC(CH$_3$)$_3$ |
| 43 | —OCH$_2$CONHCH$_2$CH$_3$ |
| 44 | —OCH$_2$CO-morpholinyl |
| 45 | —OCH$_2$CO-piperidinyl-CO$_2$CH$_2$CH$_3$ |
| 46 | —OCH$_2$CO-piperidinyl-CO$_2$H |
| 47 | —OCH$_2$CONHCH$_2$OH |

TABLE 7

[Structure: tricyclic core with R¹ on upper aromatic ring, C=O, R⁴ on pyridinone ring, fused N-phenyl ring with Br substituent]

| Ex. No | R¹ | R⁴ |
|---|---|---|
| 48 | —OCH₃ | —CH₃ |
| 49 | —OH | —CH₃ |
| 50 | —OCH₂CO₂C(CH₃)₃ | —CH₃ |
| 51 | —OCH₂CO₂CH(CH₃)₂ | —CH₃ |
| 52 | —OCH₂CO₂CH₂CH₃ | —CH₃ |
| 53 | —OCH₂CO₂H | —CH₃ |
| 54 | —OCH₂-(pyridin-3-yl) | —CH₃ |
| 55 | —OCH₂(CH₂)₂CH₂OH | —CH₃ |
| 56 | —OCOCH₃ | —CH₃ |
| 57 | —OCH₂CO(CH₂)₂CH₃ | —CH₃ |
| 58 | —OCH₃ | —H |
| 59 | —OH | —H |
| 60 | —OCH₂CO₂C(CH₃)₃ | —H |
| 61 | —OCH₂CO₂CH(CH₃)₂ | —H |
| 62 | —OCH₂CO₂CH₂CH₃ | —H |
| 63 | —OCH₂CO₂H | —H |
| 64 | —OCH₂-(pyridin-3-yl) | —H |
| 65 | —OCH₂-(pyridin-2-yl) | —H |
| 66 | —OCH₂-(phenyl) | —H |
| 67 | —OCH₂CH₂-(pyridin-2-yl) | —H |
| 68 | —O(CH₂)₃-(pyridin-3-yl) | —H |
| 69 | —OCH₂-(5-(CH₂OCOCH₃)-pyridin-3-yl) | —H |
| 70 | —OCH₂-(5-(CH₂OH)-pyridin-3-yl) | —H |
| 71 | —OCH₂-(6-(CH₂OCOCH₃)-pyridin-2-yl) | —H |
| 72 | —OCH₂-(6-(CH₂OH)-pyridin-2-yl) | —H |
| 73 | —OCH₂-(5-(CO₂CH₃)-pyridin-2-yl) | —H |
| 74 | —OCH₂-(pyridin-3-yl) | —H |
| 75 | —OCH₂-(pyrazin-2-yl) | —H |
| 76 | —OCH₂-(1,2,4-oxadiazol-3-yl) | —H |
| 77 | —OCH₂-(1-methylpiperidin-3-yl) | —H |
| 78 | —O(CH₂)₃N(CH₃)₂ | —H |
| 79 | —O(CH₂)₃CH₂OH | —H |
| 80 | —O(CH₂)₄CH₂OH | —H |
| 81 | —O(CH₂)₅CH₂OH | —H |
| 82 | —OCOCH₃ | —H |
| 83 | —OCH₂CO(CH₂)₂CH₃ | —H |

TABLE 7-continued

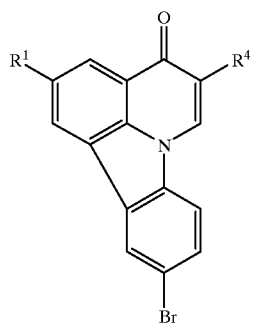

| Ex. No | R¹ | R⁴ |
|---|---|---|
| 84 | —OCH₃ | ethyl-2-pyridyl |
| 85 | —OH | ethyl-2-pyridyl |
| 86 | —OCH₂CO₂C(CH₃)₃ | ethyl-2-pyridyl |
| 87 | —OCH₃ | ethyl-4-pyridyl |
| 88 | —OH | ethyl-4-pyridyl |
| 89 | —OCH₂CO₂C(CH₃)₃ | ethyl-4-pyridyl |
| 90 | —OCH₃ | ethylphenyl |
| 91 | —OH | ethylphenyl |
| 92 | —OCH₃ | ethyl-4-methoxyphenyl |
| 93 | —OH | ethyl-4-hydroxyphenyl |

TABLE 7-continued

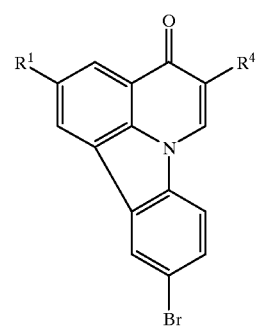

| Ex. No | R¹ | R⁴ |
|---|---|---|
| 94 | —OCH₃ | ethyl-2-furyl |
| 95 | —OCH₃ | ethyl-1,2,4-triazolyl |
| 96 | —OH | ethyl-1,2,4-triazolyl |
| 97 | —OCOCH₃ | ethyl-1,2,4-triazolyl |
| 98 | —OCH₃ | —CO₂CH₂CH₃ |
| 99 | —OCH₃ | —CO₂H |
| 100 | —OCH₃ | acetylmorpholino |

TABLE 8

| Ex. No. | R¹ | R⁴ |
|---|---|---|
| 101 | —OCH₃ | ethyl-3-pyridyl |

TABLE 8-continued

Core structure: R¹ and R⁴ substituted pyrido-fused carbazolone with Br substituent

| Ex. No. | R¹ | R⁴ |
|---|---|---|
| 102 | —OH | 3-ethylpyridine |
| 103 | —OCH₂CO₂C(CH₃)₃ | 3-ethylpyridine |
| 104 | —OCH₂CO₂H | 3-ethylpyridine |
| 105 | —OCH₂-(3-pyridyl) | 3-ethylpyridine |
| 106 | 3,5-disubstituted pyridine: —OCH₂- and —CH₂OCOCH₃ | 3-ethylpyridine |
| 107 | 3,5-disubstituted pyridine: —OCH₂- and —CH₂OH | 3-ethylpyridine |
| 108 | —OCH₂-(5-pyrimidinyl) | 3-ethylpyridine |
| 109 | —OCH₂CONHCH₂CH₃ | 3-ethylpyridine |
| 110 | —O(CH₂)₂CH₂OH | 3-ethylpyridine |
| 111 | N-(3-methoxypropyl)phthalimide | 3-ethylpyridine |
| 112 | —O(CH₂)₂CH₂NH₂ | 3-ethylpyridine |
| 113 | —OCH₃ | —CH₃ |
| 114 | —OH | —CH₃ |
| 115 | —OCH₂-(3-pyridyl) | —CH₃ |
| 116 | —OCH₃ | —H |
| 117 | —OH | —H |
| 118 | —OCH₂CO₂C(CH₃)₃ | —H |
| 119 | —OCH₂CO₂H | —H |
| 120 | —OCH₂-(3-pyridyl) | —H |
| 121 | —OCH₃ | ethylphenyl |
| 122 | —OH | ethylphenyl |
| 123 | —OCH₃ | 3,5-diethylpyridine |
| 124 | —OH | 3,5-diethylpyridine |

TABLE 8-continued

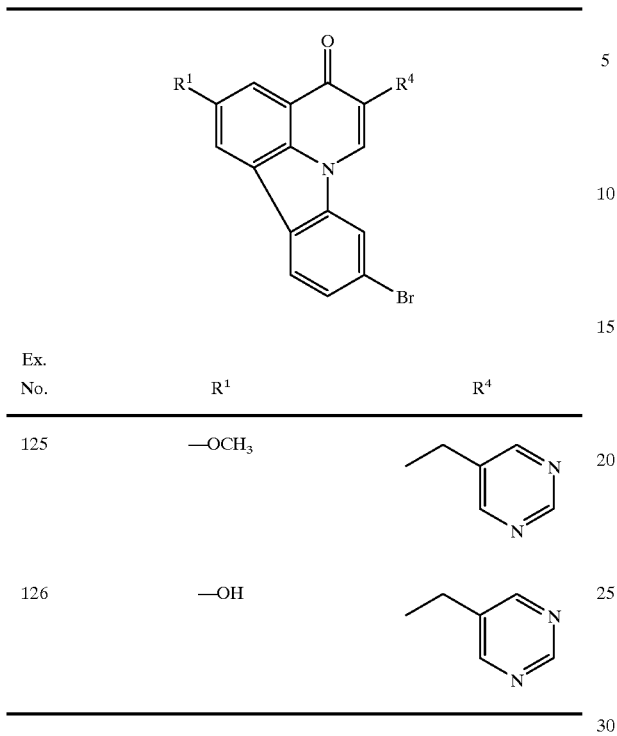

| Ex. No. | R¹ | R⁴ |
|---|---|---|
| 125 | —OCH₃ | (5-pyrimidinyl-methyl) |
| 126 | —OH | (5-pyrimidinyl-methyl) |

TABLE 9

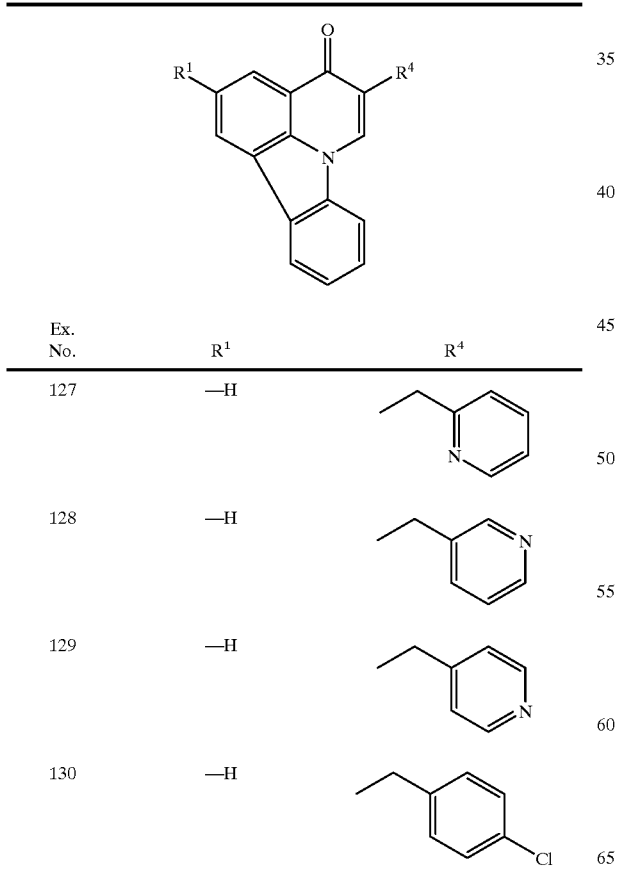

| Ex. No. | R¹ | R⁴ |
|---|---|---|
| 127 | —H | (2-pyridyl-methyl) |
| 128 | —H | (3-pyridyl-methyl) |
| 129 | —H | (4-pyridyl-methyl) |
| 130 | —H | (4-Cl-phenyl-methyl) |

TABLE 9-continued

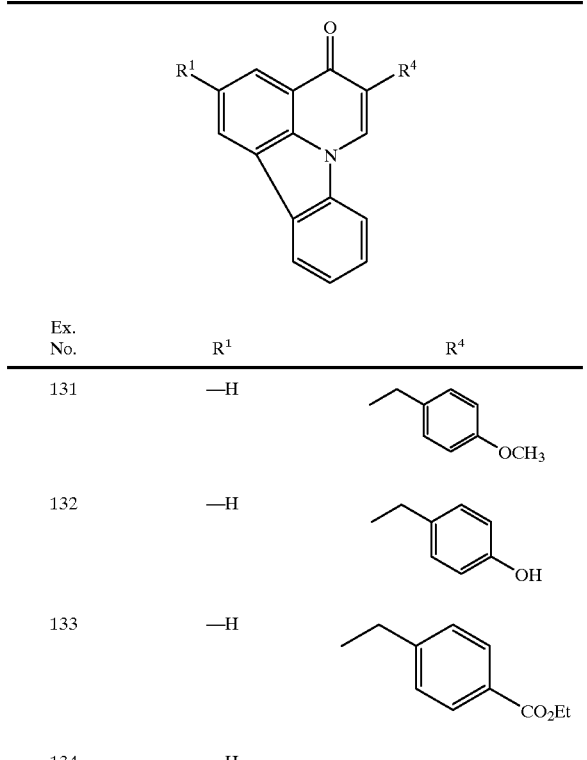

| Ex. No. | R¹ | R⁴ |
|---|---|---|
| 131 | —H | (4-OCH₃-phenyl-methyl) |
| 132 | —H | (4-OH-phenyl-methyl) |
| 133 | —H | (4-CO₂Et-phenyl-methyl) |
| 134 | —H | (4-CO₂H-phenyl-methyl) |
| 135 | —H | (4-NH₂-phenyl-methyl) |
| 136 | —H | (2-thienyl-methyl) |
| 137 | —H | (2-pyrrolyl-methyl) |
| 138 | —H | (2-imidazolyl-methyl) |
| 139 | —H | (1-naphthyl-methyl) |
| 140 | —H | (2-naphthyl-methyl) |

TABLE 9-continued
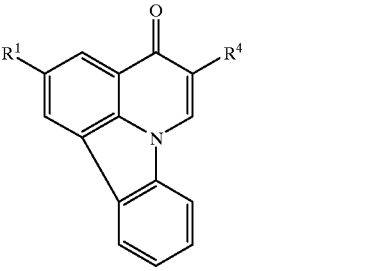
| Ex. No. | R¹ | R⁴ |
|---|---|---|
| 141 | —H | 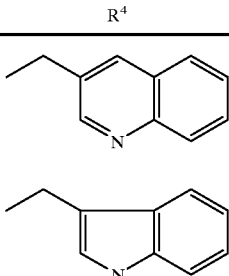 |
| 142 | —H | 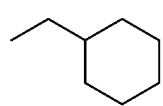 |
| 143 | —H | 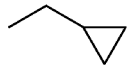 |
| 144 | —H | 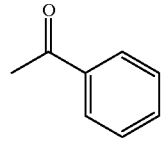 |
| 145 | —H | 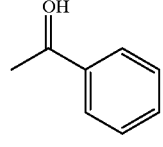 |
| 146 | —H | 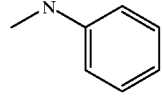 |
| 147 | —H | 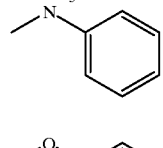 |
| 148 | —H | 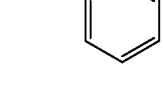 |
| 149 | —H | 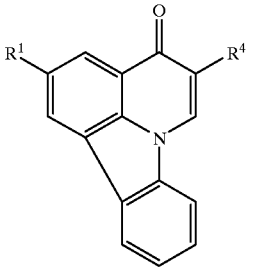 |
| 150 | —H | —Br |
TABLE 9-continued
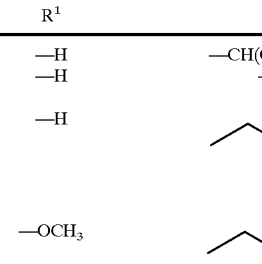
| Ex. No. | R¹ | R⁴ |
|---|---|---|
| 151 | —H | —CH(OH)CH₂CH₃ |
| 152 | —H | —CH₃ |
| 153 | —H | 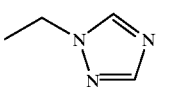 |
| 154 | —OCH₃ | 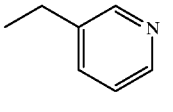 |
| 155 | —OH | 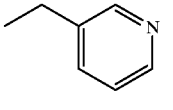 |
| 156 | —OCOCH₃ | 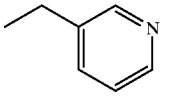 |
| 157 | —OCH₂CO₂CH₂CH₃ | 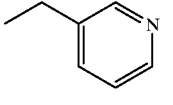 |
| 158 | —OCH₂CO₂H | 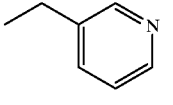 |
| 159 | —O(CH₂)₃CO₂CH₂CH₃ | 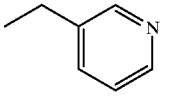 |
| 160 | —O(CH₂)₂CH₂CO₂H | 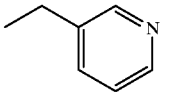 |
| 161 | —OCH₃ | —CH₃ |
| 162 | —OH | —CH₃ |
| 163 | —OCOCH₃ | —CH₃ |
| 164 | —OCH₂CO₂CH₂CH₃ | —CH₃ |
| 165 | —OCH₂CO₂H | —CH₃ |
| 166 | —OCH₃ | 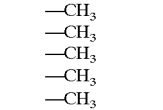 |

TABLE 9-continued
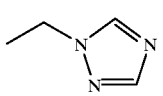
| Ex. No. | R¹ | R⁴ |
|---|---|---|
| 167 | —OH | 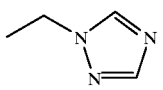 |
| 168 | —OCOCH₃ | 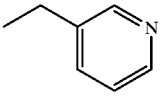 |
| 169 | —OCH₃ | —H |
| 170 | —OH | —H |
| 171 | —Cl | —H |
| 172 | —Cl | —CH₃ |
| 173 | —CN | —H |
| 174 | —CONH₂ | —H |
| 175 | —CO₂H | —H |
| 176 | —CO₂CH₃ | —H |
| 177 | —CH₂OH | —H |
| 178 | —Br | 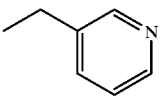 |
| 179 | —NH₂ | 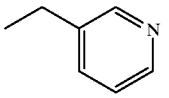 |
| 180 | —Br | —H |
| 181 | —NH₂ | —H |
| 182 | —NHCH₂CH₂CH₃ | —H |
| 183 | —NHCOCH₃ | —H |
TABLE 10
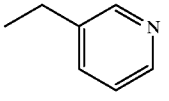
| Ex. No. | R² | R⁴ |
|---|---|---|
| 184 | —Br | 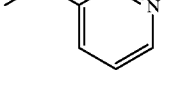 |
| 185 | —OCH₃ | 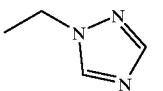 |
| 186 | —OH | 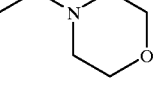 |
| 187 | —Br | —H |
| 188 | —OCH₃ | —H |
| 189 | —OH | —H |
| 190 | —Cl | —CH₃ |
| 191 | —Cl | 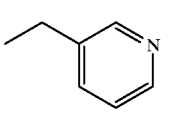 |
| 192 | —Cl | 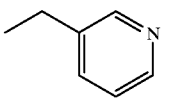 |
| 193 | —Cl | —H |
| 194 | —COCH₃ | 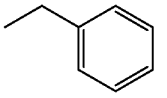 |
| 195 | —CO₂H | 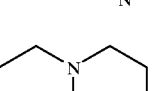 |
| 196 | —COCH₃ | 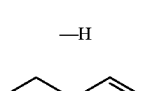 |

TABLE 10-continued
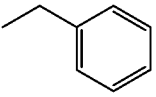
| Ex. No. | R² | R⁴ |
|---|---|---|
| 197 | —CO₂H | 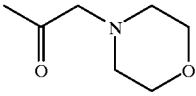 |
| 198 | 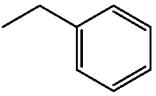 | 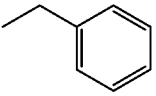 |
| 199 | —CH(OH)CH₃ | 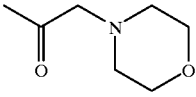 |
| 200 | —COCH₃ | —H |
| 201 | —CO₂H | —H |
| 202 | 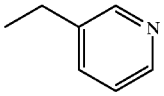 | —H |
TABLE 11
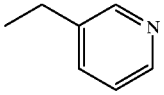
| Ex. No. | R¹ | R⁴ |
|---|---|---|
| 203 | —OCH₃ | 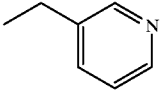 |
| 204 | —OH | 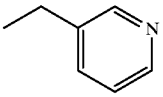 |
TABLE 11-continued
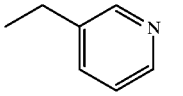
| Ex. No. | R¹ | R⁴ |
|---|---|---|
| 205 | —OCOCH₃ | 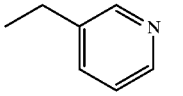 |
| 206 | —OCH₂CO₂CH₂CH₃ | 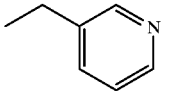 |
| 207 | —OCH₃ | —H |
| 208 | —OH | —H |
| 209 | OCOCH₃ | —H |
TABLE 12
| Ex. No. | R¹ | R⁴ |
|---|---|---|
| 210 | —OCH₃ | (3-pyridylethyl) |
| 211 | —OH | (3-pyridylethyl) |
| 212 | —OCOCH₃ | (3-pyridylethyl) |
| 213 | —OCH₃ | —H |
| 214 | —OH | —H |
| 215 | —OCOCH₃ | —H |

TABLE 13

[Structure: tricyclic pyridinone-indole scaffold with R⁴ at pyridinone position and R² on the benzene ring]

| Ex. No. | R² | R⁴ |
|---|---|---|
| 216 | —OCH₃ | 3-ethylpyridinyl |
| 217 | —OH | 3-ethylpyridinyl |
| 218 | —OCOCH₃ | 3-ethylpyridinyl |
| 219 | —OCH₂CO₂CH₂CH₃ | 3-ethylpyridinyl |
| 220 | —OCH₃ | —H |
| 221 | —OH | —H |
| 222 | —OCOCH₃ | —H |
| 223 | —OCH₂CO₂CH₂CH₃ | —H |

TABLE 14

[Structure: tricyclic scaffold with R² on different position of benzene ring]

| Ex. No. | R² | R⁴ |
|---|---|---|
| 224 | —OCH₃ | 3-ethylpyridinyl |
| 225 | —OH | 3-ethylpyridinyl |

TABLE 14-continued

| Ex. No. | R² | R⁴ |
|---|---|---|
| 226 | —OCOCH₃ | 3-ethylpyridinyl |
| 227 | —OCH₂CO₂CH₂CH₃ | 3-ethylpyridinyl |
| 228 | —OCH₃ | —H |
| 229 | —OH | —H |
| 230 | —OCOCH₃ | —H |
| 231 | —OCH₂CO₂CH₂CH₃ | —H |

TABLE 15

[Structure: tricyclic scaffold with R² on another position]

| Ex. No. | R² | R⁴ |
|---|---|---|
| 232 | —OCH₃ | 3-ethylpyridinyl |
| 233 | —OH | 3-ethylpyridinyl |
| 234 | —OCOCH₃ | 3-ethylpyridinyl |

TABLE 16
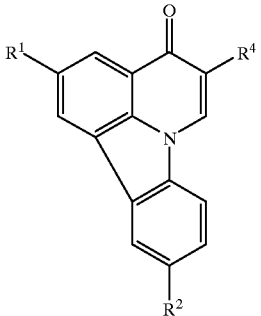
| Ex. No. | R¹ | R² | R⁴ |
|---|---|---|---|
| 235 | —OCH₃ | —F | 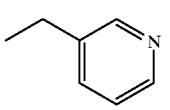 |
| 236 | —OH | —F | 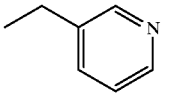 |
| 237 | —OCOCH₃ | —F | 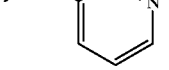 |
| 238 | —OCOCH₂CH₃ | —F | 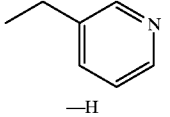 |
| 239 | —OCH₃ | —F | —H |
| 240 | —OH | —F | —H |
| 241 | —OCOCH₃ | —F | —H |
| 242 | —OCOCH₂CH₃ | —F | —H |
| 243 | —OCH₃ | —Cl | 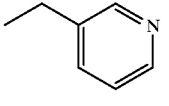 |
| 244 | —OH | —Cl | 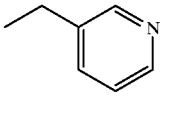 |
| 245 | —OCH₂CO₂CH₂CH₃ | —Cl | 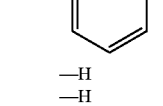 |
| 246 | —OCH₃ | —Cl | —H |
| 247 | —OH | —Cl | —H |
| 248 | —OCH₃ | —CH₂CH₃ | 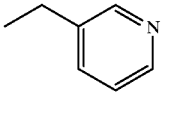 |
| 249 | —OH | —CH₂CH₃ | 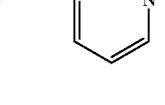 |

TABLE 16-continued
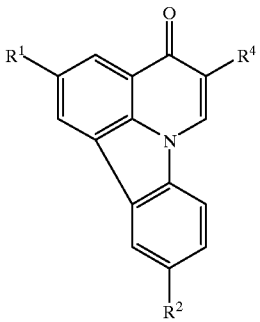
| Ex. No. | R¹ | R² | R⁴ |
|---|---|---|---|
| 250 | —OCH₂CO₂CH₂CH₃ | —CH₂CH₃ | 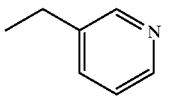 |
| 251 | 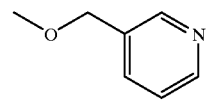 | —CH₂CH₃ | 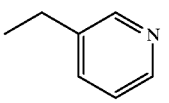 |
| 252 | 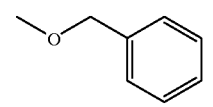 | —OCH₃ | 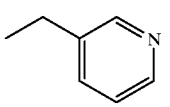 |
| 253 | —OH | —OCH₃ | 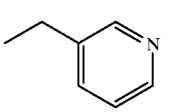 |
| 254 | —OCH₂CO₂CH₂CH₃ | —OCH₃ | 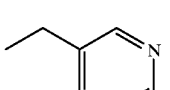 |
| 255 | 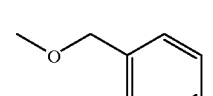 | —OCH₃ | —H |
| 256 | —OH | —OCH₃ | —H |
| 257 | —OCH₃ | —OCH₃ | 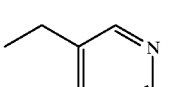 |
| 258 | —OH | —OH | 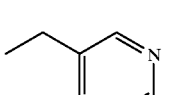 |
| 259 | —OCOCH₃ | —OCOCH₃ | 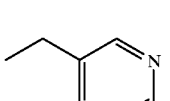 |

TABLE 16-continued
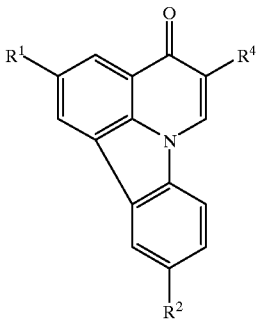
| Ex. No. | R¹ | R² | R⁴ |
|---|---|---|---|
| 260 | —OCH₃ | —OCH₃ | 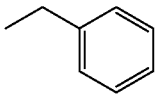 |
| 261 | —OH | —OH | 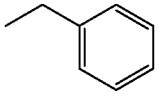 |
| 262 | —OCH₃ | —OCH₃ | —H |
| 263 | —OH | —OH | —H |
| 264 | —Cl | —Cl | —H |
| 265 | —Cl | —Cl | 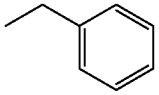 |
| 266 | —Cl | —Cl | 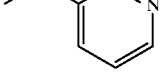 |
| 267 | —Cl | —Cl | 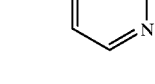 |
| 268 | —Cl | —Cl | 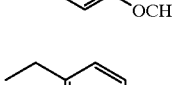 |
| 269 | —Cl | —Cl | 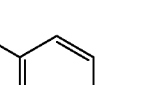 |
| 270 | —Cl | —Cl | 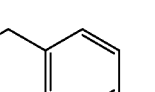 |
| 271 | —Cl | —Cl |  |

TABLE 16-continued
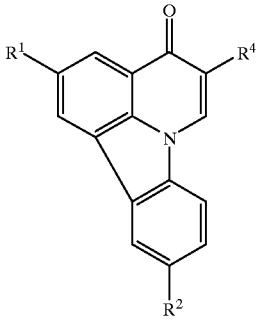
| Ex. No. | R¹ | R² | R⁴ |
|---|---|---|---|
| 272 | —Cl | —NO₂ | 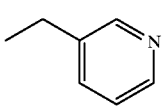 |
| 273 | —Cl | —NH₂ | 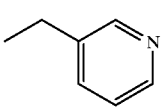 |
| 274 | —Cl | —OH | 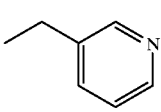 |
| 275 | —Cl | —OH | —H |
| 276 | —CH₃ | —Br | 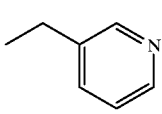 |
| 277 | —CH₃ | —Br | —H |
| TABLE 17 | TABLE 17-continued |
|---|---|
| 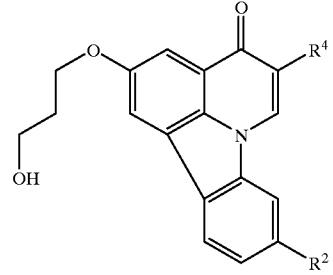 | 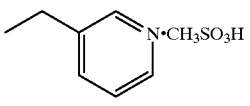 |
| Ex. No. | R² | R⁴ | Ex. No. | R² | R⁴ |
|---|---|---|---|---|---|
| 279 | —Br | 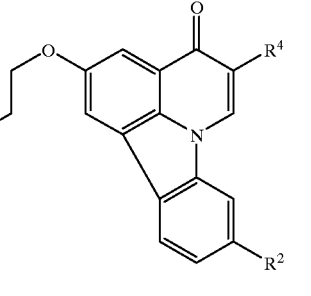 | 280 | —Br | (ethyl-pyridine·HNO₃) |

TABLE 17-continued

| Ex. No. | R² | R⁴ |
|---|---|---|
| 281 | —Br | 3-ethylpyridine·H₂SO₄ |
| 282 | —Br | 3-ethylpyridine·HO₂CCH=CHCO₂H |
| 283 | —Cl | 3-ethylpyridine |
| 284 | —Cl | 3-ethylpyridine·HCl |
| 285 | —Cl | 3-ethylpyridine·CH₃SO₃H |
| 286 | —F | 3-ethylpyridine |
| 287 | —F | 3-ethylpyridine·CH₃SO₃H |
| 288 | —H | 3-ethylpyridine |
| 289 | —CF₃ | 3-ethylpyridine |
| 290 | —CF₃ | 3-ethylpyridine·HCl |
| 291 | —CF₃ | 3-ethylpyridine·CH₃SO₃H |

The following are non-limiting examples of the pharmaceutical formulations containing the compounds of the invention.

| (Formulation 1: Tablet) | |
|---|---|
| Compound of Example 3 | 100 g |
| Lactose | 350 g |
| Potato starch | 120 g |
| Polyvinyl alcohol | 15 g |
| Magnesium stearate | 15 g |

The above-listed ingredients were weighed and then the compound of Example 3, lactose and potato starch were mixed uniformly. An aqueous polyvinyl alcohol solution was added to the mixture and granules were prepared by wet granulation method. The granules were dried, mixed with magnesium stearate and compressed to tablets each weighing 300 mg.

| (Formulation 2: Capsule) | |
|---|---|
| Compound of Example 50 | 50 g |
| Lactose | 435 g |
| Magnesium stearate | 15 g |

The above-listed ingredients were weighed and then mixed uniformly. By means of a capsule-filling machine, the mixture was filled into hard capsules in 300-mg portions to prepare capsules.

| (Formulation 3: Injection) | |
|---|---|
| Compound of Example 105 | 2 g |
| Propylene glycol | 200 g |
| Water for injection | q.s. |

The above-listed ingredients were weighed and then the compound of Example 105 was dissolved in propylene glycol. The sterile water for injection was added to make a total of 1,000 mL; following sterilizing filtration, the solution was put in 5-mL portions into 10-mL ampules, which were fused and sealed to prepare injections.

| (Formulation 4: Suppository) | |
|---|---|
| Compound of Example 110 | 100 g |
| Polyethylene glycol 1500 | 180 g |
| Polyethylene glycol 4000 | 720 g |

The compound of Example 110 was sufficiently ground in a mortar to prepare a fine powder, which was then prepared into suppositories, each of 1 g, by a fusing method.

| (Formulation 5: Powder) | |
|---|---|
| Compound of Example 51 | 200 g |
| Lactose | 790 g |
| Magnesium stearate | 10 g |

The above-listed ingredients were weighed and then mixed uniformly to prepare a 20% powder.

Industrial Applicability

The compounds of the invention which have a pyridocarbazole skeleton exhibit an extremely high isozyme selectivity for inhibiting PDE type V. In addition, the compounds of the invention prove effective in tests with animal models while causing extremely low toxicity and only limited side effects; hence, they are useful as pharmaceuticals both clinically and in animals and expected to be particularly effective in preventing and/or treating pulmonary hypertension, ischemic heart diseases or other diseases against which the cGMP-PDE inhibitory action is effective.

The pharmaceutical compositions of the invention are also effective in treating or preventing pulmonary hypertension, ischemic heart diseases and other diseases against which the cGMP-PDE inhibitory action is effective. "Pulmonary hypertension" is a generic term for the various diseases that manifest hypertension in the pulmonary artery and it includes chronic bronchitis, peripheral lesions in the airway, pulmonary pneumatosis, bronchiectasis, sarcoidosis, sequelae of pulmonary tuberculosis, diffuse interstitial pneumonia, diffuse bronchiolitis, asthma, fibrosis of the lung, collagenosis, pulmonary thromboembolism, pulmonary venous obstruction, pulmonary arteritis and primary pulmonary hypertension, as well as diseases such as cor pulmonale that are in a developed stage of pulmonary hypertension. Patients manifesting pulmonary hypertension suffer from disorders in pulmonary circulation due to the obstruction of pulmonary vessels and experience cyanosis and dyspnea. They often complain of palpitation and pectoralgia, as well as coughing. The pharmaceutical compositions of the invention are effective against these symptoms. The term "ischemic heart diseases" as used herein refers to all diseases that occur as the result of disorders in coronary circulation due to various causes and it covers angina of effort, resting angina, unstable angina, variant angina pectoris, acute heart failure, chronic heart failure, myocardial infarction, cardiac edema and arrhythmia.

Further, the pharmaceutical compositions of the invention increase the cGMP level markedly and are also applicable to arteriosclerosis, post-PTCA restenosis and thrombosis (caused by, for example, injury of vascular walls, arterio sclerosis, arterits and platelet aggregation). In addition, aside from those listed above, the "diseases against which the cGMP-PDE inhibitory action is effective" include the following against which increased cGMP levels are believed to be effective: asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence), peripheral circulatory disorders, peripheral vascular diseases, cerebral circulatory disorders (e.g., cerebral infarction), brain dysfunction, dementia, allergic diseases (e.g. atopic dermatitis and allergic rhinitis) and hypertension. The pharmaceutical compositions of the invention are also applicable to these diseases, among which asthma, chronic obstructive pulmonary diseases (e.g. bronchitis and pulmonary pneumatosis), glomerular diseases including glomerular nephritis and diabetic nephropathy, renal failure, nephritic edema, diseases in urinary organs and genital system (e.g. prostatomegaly, impotence and incontinence) are worth particular mention. "Renal failure" refers to those pathologic and clinical symptoms which are manifested by defective function of the kidneys, i.e., the decrease in glomerular filtration rate (GFR) due to various etiological factors. In chronic renal failure, some glomeruli give a sclerotic image but the progress of the sclerosis to less affected glomeruli would bring the renal failure to a developed phase. As a result, various excreted substances will accumulate in the body to cause "uremia". Polyuria and nocturia also occur due to disordered concentrating ability. If inappropriate Na and water loading accompanies renal failure, reduced GFR prevents sufficient compensation, causing edema, pulmonary edema, congestive heart failure, hypertension, etc. The pharmaceutical compositions of the invention are also effective against these symptoms.

Using the production processes of the invention, one can produce compounds having a pyridocarbazole skeleton which exhibit a PDE type V inhibitory action featuring an extremely high selectivity in enzyme inhibition.

What is claimed is:

1. A method for preventing or treating ischemic heart disease, said method comprising;
    administering to a person in need thereof, an effective amount of a compound represented by the following formula (I) or a pharmaceutically acceptable salt thereof as active ingredient, and a pharmaceutically acceptable carrier thereof:

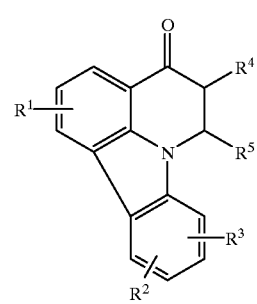

(I)

where $R^1$ represents a hydrogen atom, a halogen atom, a cyano group, an optionally protected carboxyl group, an optionally protected carboxymethyl group, an alkoxycarbonyl group having 1–4 carbon atoms, a carbamoyl group, an acetylamino group, a 3-carboxy-1-propenyl group, a 2-hydroxypentyloxy group, a 2,2-diethyoxyethoxy group, an optionally protected hydroxyl group, an optionally protected mercapto group, a straight- or branched-chain alkanoyloxy group having 1–4 carbon atoms, a carbonyloxy group substituted by a phenyl group or a pyridyl group, a straight- or branched-chain alkyl group having 1–4 carbon atoms which may be substituted by one hydroxyl group, an amino group which may be mono- or disubstituted by an alkyl group having 1–4 carbon atoms, an alkylthio group having 1–3 carbon atoms which may be monosubstituted by any group selected from the group consisting of a hydroxyl group, a carboxyl group, a phenyl group and a pyridyl group, or represented by the following formula (XXI):

 (XXI)

(where Z represents a hydrogen atom, a carboxyl group, an alkoxy group having 1 or 2 carbon atoms which may be substituted by one hydroxyl group, an alkoxycarbonyl group having 1–6 carbon atoms, a carbamoyl group which may be mono- or disubstituted by a hydroxymethyl group or an alkyl group having 1 or 2 carbon atoms, an alkanoyl group having 1–4 carbon atoms which may be substituted by one hydroxyl group or mercapto group, a piperidinylcarbonyl group which may be substituted by one carboxyl group or alkoxycarbonyl group having 1 or 2 carbon atoms, a morpholylcarbonyl group, a hydroxyl group, a mercapto group, an amino group, a phenyl group, a pyridyl group which may be monosubstituted by a hydroxymethyl group or an acetoxymethyl group or an alkyl group having 1–4 carbon atoms or an alkoxycarbonyl group having 1 or 2 carbon atoms, a pyrazinyl group, a pyrimidinyl group, a furyl group, a thienyl group, an oxadiazolyl group or a 4-methoxyphenoxy group; n is 1–6); $R^2$ represents a hydrogen atom, a halogen atom, an optionally protected hydroxyl group, an optionally protected mercapto group, an optionally protected amino group, a cyano group, a nitro group, a trifluoromethyl group, a trifluoromethoxy group, an optionally substituted carboxylgroup, a 4-morpholylacetyl group, a straight- or branched-chain alkanoyloxy group having 1–4 carbon atoms, a straight- or branched-chain alkanoyl group having 1–4 carbon atoms, a straight- or branched-chain alkyl group having 1–4 carbon atoms, an alkylthio group having 1–3 carbon atoms which may be monosubstituted by any group selected from the group consisting of a hydroxyl group, a carboxyl group, a phenyl group and pyridyl group or a straight- or branched-chain alkoxy group having 1–4 carbon atoms which may be substituted by one alkoxycarbonyl group having 1–4 carbon atoms; $R^3$ represents a hydrogen atom, a halogen atom, an optionally protected hydroxyl group or a straight- or branched-chain alkoxy group having 1–4 carbon atoms; $R^4$ represents a hydrogen atom, a halogen atom, an optionally protected carboxyl group, a phenoxy group, an anilino group, a N-methylanilino group, a 4-morpholylcarbonyl group, an alkyl group having 1 or 2 carbon atoms which may be substituted by a cyclic alkyl group having 3–6 carbon atoms, a benzyl group which may be mono- or disubstituted in the phenyl portion by any group selected from the group consisting of a halogen atom, a hydroxyl group, a mercapto group, an alkoxy group having 1 or 2 carbon atoms, an alkylthio group having 1 or 2 carbon atoms, an alkoxycarbonyl group having 1–4 carbon atoms, an acetylamino group, a carboxyl group and an amino group, a pyridylmethyl group which may be substituted by an alkyl group having 1–4 carbon atoms, a morpholylmethyl group, a triazolylmethyl group, a furylmethyl group, a thienylmethyl group, a pyrimidinylmethyl group, a pyrazinylmethyl group, a pyrrolylmethyl group, an imidazolylmethyl group, a quinolylmethyl group, an indolylmethyl group, a naphthylmethyl group, a benzoyl group, an α-hydroxybenzyl group or an alkoxycarbonyl group having 1 or 2 carbon atoms; $R^5$ represents a hydrogen atom or a methyl group with the proviso that; when $R^1$, $R^2$, $R^3$ and $R^5$ are a hydrogen atom at the same time, $R^4$ is not a hydrogen atom, a benzyl group, a 4-diethylaminobenzyl group or a furylmethyl group.

2. The method of claim 1, wherein administration is effected orally.

3. The method of claim 1, wherein administration is effected transmucomembranously.

4. The method of claim 1, wherein the compound is given a daily dose in the range of approximately 1 to 500 mg/adult.

* * * * *